US008551981B2

(12) United States Patent
Calderwood et al.

(10) Patent No.: US 8,551,981 B2
(45) Date of Patent: Oct. 8, 2013

(54) FURO[3,2-D]PYRIMIDINE COMPOUNDS

(75) Inventors: David J. Calderwood, Framingham, MA (US); Noel S. Wilson, Kenosha, WI (US); Philip Cox, Grayslake, IL (US); Michael Z. Hoemann, Marlborough, MA (US); Bruce Clapham, Lindenhurst, IL (US); Anil Vasudevan, Union Grove, WI (US); Clara I. Villamil, Glenview, IL (US); Bin Li, Ashland, MA (US); Gagandeep Somal, Framingham, MA (US); Kelly D. Mullen, Charlton, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/268,387

(22) Filed: Oct. 7, 2011

(65) Prior Publication Data
US 2012/0122846 A1 May 17, 2012

Related U.S. Application Data

(60) Provisional application No. 61/391,157, filed on Oct. 8, 2010, provisional application No. 61/503,368, filed on Jun. 30, 2011.

(51) Int. Cl.
| | |
|---|---|
| A61K 31/519 | (2006.01) |
| A61K 31/5375 | (2006.01) |
| A61K 31/55 | (2006.01) |
| A61K 31/497 | (2006.01) |
| A61K 31/496 | (2006.01) |
| A61K 31/397 | (2006.01) |
| A61K 31/505 | (2006.01) |
| C07D 491/048 | (2006.01) |
| C07D 239/00 | (2006.01) |
| C07D 265/36 | (2006.01) |
| C07D 241/02 | (2006.01) |
| C07D 403/14 | (2006.01) |
| C07D 205/04 | (2006.01) |

(52) U.S. Cl.
USPC .............. 514/210.21; 514/211.15; 514/230.5; 514/252.11; 514/252.16; 514/255.05; 514/260.1; 540/600; 544/70; 544/105; 544/230; 544/278

(58) Field of Classification Search
USPC ............... 514/210.21, 211.15, 230.5, 252.11, 514/252.16, 255.05, 260.1; 540/600; 544/70, 544/105, 230, 278
See application file for complete search history.

(56) References Cited

U.S. PATENT DOCUMENTS

| | | | |
|---|---|---|---|
| 5,877,178 A | 3/1999 | Gangjee | |
| 7,384,949 B2 | 6/2008 | Gillespie et al. | |
| 2005/0153989 A1 | 7/2005 | Grotzfeld et al. | |

FOREIGN PATENT DOCUMENTS

| | | | |
|---|---|---|---|
| WO | WO-0132632 A2 | 5/2001 | |
| WO | WO-03/080064 A1 | 10/2003 | |
| WO | WO-2005/010009 A1 | 2/2005 | |
| WO | WO-2005023806 A2 | 3/2005 | |
| WO | WO-2005026126 A1 | 3/2005 | |
| WO | WO-2006030031 A1 | 3/2006 | |
| WO | WO-2006104945 A2 | 10/2006 | |
| WO | WO-2006128129 A2 | 11/2006 | |
| WO | WO-2006128172 A2 | 11/2006 | |
| WO | WO-2007114323 A1 | 10/2007 | |
| WO | WO-2011079230 A2 | 6/2011 | |
| WO | WO-2011162515 A2 | 12/2011 | |

OTHER PUBLICATIONS

Gangjee et al., "Antiangiogenic and Antitumor Agents: Design, Synthesis, and Evaluation of Novel 2-amino-4-(3-bromoaniliino)-6-benzylsubstituted Pyrrolo[2,3-d]pyrimidines as Inhibitors of Receptor Tyrosine Kinases," Bioorg. Med. Chem. (2003) 11:5155-5170.

Lazarovici et al., Cross talk between the cardiovascular and nervous systems: neurotrophic effects of vascular endothelial growth factor (VEGF) and angiogenic effects of nerve growth factor (NGF)-implications in drug development, Curr. Pharm. Des. (2006) 12(21):2609-2622. Abstract only.

Belenkil et al., "Synthesis of heterocycles based on products of addition of polyhaloalkanes to unsaturated systems. 4. Synthesis of substituted furo[2,3-d]pyrimidines," Chemical Abstracts (1994) 120(13):1175, Abstract #164091c.

Dave et al., "Reaction of nitriles under acidic conditions. Part I. A general method of synthesis of condense pyrimidines," J. Heterocyclic Chemistry (1980) 17(7):1497-1500.

Rao et al., "Synthesis of Triple Helix Forming Oligonucleotides containing 2'-deoxyformycin A," Chemical Abstracts (1994) 121(13):1073, Abstract #158087k.

(Continued)

Primary Examiner — Samantha Shterengarts
(74) Attorney, Agent, or Firm — McCarter & English, LLP; Elizabeth A. Hanley; Yu Lu

(57) ABSTRACT

The present invention is directed to novel compounds of Formula (I)

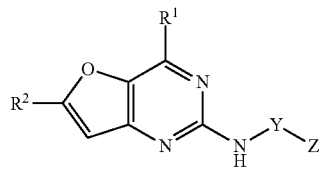

Formula (I)

pharmaceutically acceptable salts, biologically active metabolites, pro-drugs, racemates, enantiomers, diastereomers, solvates and hydrates thereof wherein the variables are defined as herein. The compounds of Formula (I) are useful as kinase inhibitors and as such would be useful in treating certain conditions and diseases, especially inflammatory conditions and diseases and proliferative disorders and conditions, for example, cancers.

29 Claims, No Drawings

(56) References Cited

OTHER PUBLICATIONS

Rajagopalan et al., "Synthesis of 4-hydroxy-, 4-chloro-, 4-amino- and 4-substituted aminoisoxazolo[5,4-d]pyrimidines," *Tetrahedron* (1967) 23:3541-3543.

Shishoo et al., "Reaction of nitriles under acidic conditions. Part VI. Synthesis of condensed 4-chloro and 4-aminopyrimidines from ortho-aminonitriles," *J. Heterocyclic Chemistry* (1990) 27(2):19-126.

Taylor et al., "The Synthesis of 4-aminoisoxazolo[5,4-d]pyrimidines," *J. Organic Chemistry*, (1964) 29(8):2116-2120.

Temnikova et al., "Reaction of metal derivatives of compounds containing a labile hydrogen atom with a-halo ketones. II. Conversion of substituted a-halodeoxybenzoins to 2-amino-3-cyano-4,5-diarylfurans," *Chemical Abstracts* (1967) 67(9):4116-4117, Abstract #43778k.

Yu et al., "Reaction of Metallic compounds containing a labile hydrogen atom with a-halo ketones. IV. Properties of 2-amino-3-cyanofurans," *Chemical Abstracts* (1968) 68(22):9357, Abstract #96786p.

FURO[3,2-D]PYRIMIDINE COMPOUNDS

CROSS REFERENCE TO RELATED APPLICATION

This application claims priority to U.S. Provisional Application Ser. No. 61/391,157 filed on Oct. 8, 2010 and U.S. Provisional Application Ser. No. 61/503,368 filed Jun. 30, 2011, the contents of which are incorporated herein.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, Syk, PKC or Aurora kinases.

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); the fusion kinases, such as BCR-Abl, focal adhesion kinase (FAK), Fes, Lck and Syk; receptor tyrosine kinases such as platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Spleen tyrosine kinase (Syk) (*J. Bio. Chem.*, 1991, 266, 15790) is a non-receptor tyrosine kinase that plays a key role in immunoreceptor signaling in a host of inflammatory cells including B cells, mast cells, macrophages and neutrophils. Syk is related to zeta associated protein 70 (ZAP-70) but also demonstrates similarity with JAK, Src and Tec family kinases.

Syk plays a critical and specific role in B-cell receptor (BCR) signaling on auto-reactive B cells and in FcR signaling on mast cells, macrophages, osteoclasts and neutrophils. (See *Immunology Today*, 2002, 21(3), 148 and *Current Opinion in Immunology* 2002, 14(3), 341). Syk plays a key role in the activation mediated by Fc receptors of sentinel cells (mast cells and macrophages) and effector cells (neutrophils, basophils and eosinophils). The importance of Syk in rheumatoid arthritis is substantiated by data demonstrating the importance of Fc receptors (FcR) function and immune complexes in disease pathogenesis. Syk also mediates the activation of B cells through the BCR, which results in their expansion and the production of antispecific immunoglobulins. Therefore any disease that revolves around antibody-Fc receptor interactions may be modulated by Syk suppression. Thus a Syk inhibitor is likely to dampen both the initiation of the disease by blocking BCR signaling and the effector phase of the disease by blocking FcR signaling on macrophages, neutrophils and mast cells. Furthermore, blocking Syk would provide the added benefit of inhibiting osteoclast maturation and therefore attenuate bone erosions, joint destruction and generalized osteopenia associated with rheumatoid arthritis. Moreover, Syk acts upstream close to the receptors at the initiation of complex signaling events and thus its inhibition influences all responses elicited by the activating agent. In mast cells for example, inhibition of Syk blocks the early release of a number of granule contents, as well as the subsequent production and secretion of lipid mediators and cytokines. Syk inhibitors can thus impart multiple beneficial effects as each of these mediators play distinct roles in the integrated inflammatory response.

Inhibiting Syk should impact several critical nodes of the inflammatory cascade resulting in an effective and rapid suppression of the deleterious responses. Inhibiting Syk may be useful in treating a host of inflammatory and allergic diseases—for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting Syk as a treatment of autoimmune and allergic disorders, see *Expert Opin. Invest. Drugs*, 2004, 13(7), 743.

Taken together, Syk inhibitors provide a broad modality to treat a host of inflammatory diseases and immunological disorders.

SUMMARY OF THE INVENTION

In a first embodiment the invention provides a compound of Formula (I)

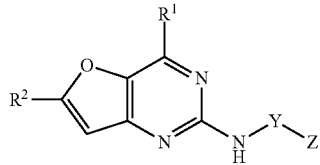

Formula (I)

pharmaceutically acceptable salts, biologically active metabolites, pro-drugs, racemates, enantiomers, diastereomers, solvates and hydrates thereof wherein $R^1$ is $N(R^a)(R^b)$, $-CH(R^a)(R^b)$, $-C(R^a)=CH(R^b)$, $-C\equiv C(R^b)$, $-OR^b$, $-C(O)R^b$, $-C(O)N(R^a)-R^b-$, $-N(R^a)C(O)-R^b-$, or $-SR^b$; wherein $R^a$ is H, optionally substituted $(C_1-C_6)$alkyl, optionally substituted $(C_2-C_6)$alkenyl, or optionally substituted $(C_2-C_6)$alkynyl; and $R^b$ is optionally substituted $(C_1-C_6)$alkyl, optionally substituted $(C_2-C_6)$alkenyl, optionally substituted $(C_3-C_6)$cycloalkyl, optionally substituted $(C_1-C_6)$alkylene-optionally substituted $(C_3-C_6)$cycloalkyl, optionally substituted bridged saturated or partially unsaturated $(C_5-C_{12})$cycloalkyl, optionally substituted $(C_6-C_{10})$aryl, optionally substituted saturated or partially unsaturated bridged $(C_2-C_{10})$heterocyclyl, optionally substituted saturated or partially unsaturated $(C_1-C_{10})$heterocyclyl, -optionally substituted $(C_1-C_6)$alkylene-optionally substituted saturated or partially unsaturated $(C_1-C_{10})$heterocyclyl, optionally substituted $(C_1-C_{10})$heteroaryl, -optionally substituted $(C_1-C_6)$alkylene-optionally substituted $(C_1-C_{10})$heteroaryl; or $R^a$ and $R^b$ together form an optionally substituted saturated or partially unsaturated $(C_3-C_{12})$carbocyclic ring, an optionally substituted saturated or partially unsaturated ($C_2$-$C_{10}$) heterocyclic ring, optionally substituted ($C_1$-$C_{10}$)heteroaryl ring, an optionally substituted saturated or partially unsaturated ($C_5$-$C_{12}$)spirocarbocyclic ring, an optionally substituted saturated or partially unsaturated ($C_5$-$C_{10}$)spiroheterocyclic ring, an optionally substituted saturated or partially unsaturated ($C_5$-$C_{12}$)carbocyclic bridged ring or an optionally substituted saturated or partially unsaturated ($C_2$-$C_{10}$) heteroclic bridged ring;

$R^2$ is H, deuterium, —N($R^a$)($R^b$), halo, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)($R^b$), —C(O)$R^a$, —N($R^a$)S(O)$_2$—, —S(O)$_2$N($R^a$)—, —CF$_3$, —OCF$_3$, optionally substituted —($C_1$-$C_6$)alkyl, optionally substituted ($C_2$-$C_6$)alkenyl, or optionally substituted —($C_2$-$C_6$)alkynyl;

Y is optionally substituted ($C_6$-$C_{10}$)arylene, optionally substituted ($C_1$-$C_6$)heterocyclylene, or optionally substituted ($C_1$-$C_{10}$)heteroarylene; and Z is H, halogen, —CN, —C(O)N($R^c$)($R^d$), —C(O)$R^d$, —N($R^c$)($R^d$), —N($R^c$)C(O)($R^d$), —O$R^c$, —S(O)$_2R^c$, —S(O)$_2$—N($R^c$)($R^d$), optionally substituted ($C_1$-$C_3$)-alkyl, -optionally substituted ($C_1$-$C_3$)alkylene-optionally substituted heterocyclyl, optionally substituted ($C_3$-$C_6$)cycloalkyl, optionally substituted ($C_6$-$C_{10}$)aryl, ($C_1$-$C_{10}$)heteroaryl, optionally substituted heterocyclyl or -optionally substituted ($C_1$-$C_3$)alkyl-optionally substituted heterocycyl;

wherein $R^c$ and $R^d$ are independently H, optionally substituted ($C_1$-$C_6$)alkyl, optionally substituted ($C_3$-$C_6$)cycloalkyl, optionally substituted heterocyclyl or optionally substituted heteroaryl; or $R^c$ and $R^d$, together with the atom to which they are attached, can form an optionally substituted saturated cycloalkyl or optionally substituted saturated heterocyclyl ring.

In a second embodiment the invention provides a compound according to the first embodiment wherein Y is optionally substituted benzo[b]azepinyl, optionally substituted benzo[b][1,4]oxazinyl, optionally substituted benzo[b][1,4]thiazinyl, optionally substituted benzo[c]thiophenyl, optionally substituted benzo[d]imidazolyl, optionally substituted benzo[d]isothiazolyl, optionally substituted benzo[d]isoxazolyl, optionally substituted benzo[d]oxazolyl, optionally substituted benzo[d]thiazolyl, optionally substituted chromanyl, optionally substituted chromenyl, optionally substituted ($C_3$-$C_6$)cycloalkylene, optionally substituted dihydrobenzo[b]azepinyl, optionally substituted dihydrobenzo[b][1,4]dioxinyl, optionally substituted dihydroindenyl, optionally substituted dihydroisoquinolinyl, optionally substituted dihydroquinolinyl, optionally substituted imidazo[1,2-a]pyridinyl, optionally substituted indazolyl, optionally substituted indolinyl, optionally substituted indolyl, optionally substituted isoindolinyl, optionally substituted isoquinolinyl, optionally substituted isothiazolyl, optionally substituted morpholine, optionally substituted naphthalene optionally substituted oxoindolinyl, optionally substituted phenyl, optionally substituted piperazinyl, optionally substituted piperidinyl, optionally substituted pyrrolidinyl, optionally substituted pyrazolyl, optionally substituted pyridinyl, optionally substituted pyrido[3,2-b][1,4]oxazinyl, optionally substituted pyrido[3,2-d][1,4]oxazinyl, optionally substituted quinolinyl, optionally substituted tetrahydrofuran, optionally substituted tetrahydroindole, optionally substituted tetrahydroisoquinolinyl, optionally substituted tetrahydro-1,6-naphthyridinyl, optionally substituted tetrahydroquinolinyl, optionally substituted thiomorpholinyl, optionally substituted tetrahydropyranyl, optionally substituted thiazolyl, optionally substituted thiomorpholinyl or optionally substituted tropanyl.

In a third embodiment the invention provides a compound according to any of the foregoing embodiments wherein Y is optionally substituted benzo[b]azepinyl, optionally substituted benzo[d]imidazolyl, optionally substituted benzo[b][1,4]oxazinyl, optionally substituted benzo[d]isothiazolyl, optionally substituted benzo[d]oxazolyl, optionally substituted benzo[b][1,4]thiazinyl, optionally substituted benzo[d]thiazolyl, optionally substituted benzo[c]thiophenyl, optionally substituted chromanyl, optionally substituted chromenyl, optionally substituted dihydrobenzo[b]azepinyl, optionally substituted dihydrobenzo[b][1,4]dioxinyl, optionally substituted dihydroisoquinolinyl, optionally substituted dihydroquinolinyl, optionally substituted imidazo[1,2-a]pyridinyl, optionally substituted indazolyl, optionally substituted indolinyl, optionally substituted isoquinolinyl, optionally substituted oxoindolinyl, optionally substituted phenyl, optionally substituted pyrazolyl, optionally substituted pyridinyl, optionally substituted pyrido[3,2-b][1,4]oxazinyl, optionally substituted quinolinyl, optionally substituted tetrahydroisoquinolinyl, or optionally substituted tetrahydro-1,6-naphthyridinyl.

In a fourth embodiment the invention provides a compound according to any of the foregoing embodiments wherein Z is H, —CN, —N($R^c$)($R^d$), —C(O)N(H)-optionally substituted ($C_1$-$C_3$)alkylene, —C(O)N(H)($C_3$-$C_6$)cylcoalkyl, —C(O)N(CH$_3$)$_2$, —C(O)-optionally substituted ($C_1$-$C_3$)alkyl, —C(O)-morpholinyl, —N(H)morpholinyl, —N(H)C(O)-optionally substituted ($C_1$-$C_3$)alkyl, —N(H)C(O)CH$_2$-morpholinyl, —N(CH$_3$)C(O)-optionally substituted ($C_1$-$C_3$)alkyl, —O-optionally substituted ($C_1$-$C_3$)alkyl, —S(O)$_2$-optionally substituted ($C_1$-$C_3$)alkyl, —S(O)$_2$—N(H) optionally substituted ($C_1$-$C_4$)alkyl, —S(O)$_2$NH$_2$, —S(O)$_2$N(H)-pyridinyl, optionally substituted ($C_1$-$C_3$)alkyl, optionally substituted ($C_3$-$C_6$)cycloalkyl, optionally substituted imidazolyl, optionally substituted morpholinyl, optionally substituted phenyl, optionally substituted piperazinyl, optionally substituted pyridinyl, optionally substituted triazolyl, -optionally substituted ($C_1$-$C_3$)alkylene-optionally substituted azetidinyl, -optionally substituted ($C_1$-$C_3$)alkylene-optionally substituted indolinyl, -optionally substituted ($C_1$-$C_3$) alkylene-optionally substituted isoindolinyl, -optionally substituted ($C_1$-$C_3$)alkylene-optionally substituted morpholinyl, -optionally substituted ($C_1$-$C_3$)alkylene-optionally substituted piperazinyl, -optionally substituted ($C_1$-$C_3$)alkylene-optionally substituted piperidinyl, -optionally substituted ($C_1$-$C_3$)alkylene-optionally substituted pyrrolidinyl, -optionally substituted ($C_1$-$C_3$)alkylene-optionally substituted thiomorpholinyl, -optionally substituted ($C_1$-$C_3$)alkylene-optionally substituted tetrahydropyranyl, -optionally substituted ($C_1$-$C_3$)alkylene-optionally substituted tetrahydrofuranyl, -optionally substituted ($C_1$-$C_3$)alkylene-optionally substituted tetrahydroindolyl, -optionally substituted ($C_1$-$C_3$)alkylene-optionally substituted thiomorpholinyl, -optionally substituted ($C_1$-$C_3$)alkylene-optionally substituted tropanyl, optionally substituted azaindolyl, optionally substituted benzo(b)thienyl, optionally substituted benzo[b][1,4]oxazinyl, optionally substituted benzimidazoly, optionally substituted benzofuranyl, optionally substituted benzoxazolyl, optionally substituted benzothiazolyl, optionally substituted benzothiadiazolyl, optionally substituted benzoxadiazolyl, optionally substituted furanyl, optionally substituted imidazolyl, optionally substituted imidazopyridinyl, optionally substituted indolyl, optionally substituted indazolyl, optionally substituted isoxazolyl, optionally substituted isothiazolyl, optionally substituted oxadiazolyl, optionally substituted oxazolyl, optionally substituted purinyl, optionally substituted pyranyl, optionally substituted pyrazinyl, optionally substituted pyrazolyl, optionally substituted pyridazinyl, optionally substituted pyridinyl, optionally substituted pyrimidinyl, optionally substituted pyrrolyl, optionally substituted pyrrolo[2,3-d]pyrimidinyl, optionally substituted pyrazolo[3,4-d]pyrimidinyl, optionally substituted quinolinyl, optionally substituted quinazolinyl, optionally substituted tetrahydroquinolinyl, optionally substituted triazolyl, optionally substituted thiazolyl, optionally substituted tetrazolyl, optionally substituted thiadiazolyl, or optionally substituted thienyl.

In a fifth embodiment the invention provides a compound according to any of the foregoing embodiments wherein Z is H, —CN, —N($R^c$)($R^d$), —C(O)N(H)-optionally substituted ($C_1$-$C_3$)alkylene, —C(O)N(H)-optionally substituted ($C_3$-$C_6$)cycloalkylene, —C(O)-optionally substituted ($C_1$-$C_3$) alkyl, —C(O)-morpholinyl, —N(H)C(O)-optionally substituted ($C_1$-$C_3$)alkyl, —N($CH_3$)C(O)-optionally substituted ($C_1$-$C_3$)alkyl, —$R^c$, —S(O)$_2$-optionally substituted ($C_1$-$C_3$) alkyl, —S(O)$_2$—N(H) optionally substituted ($C_1$-$C_4$)alkyl, —S(O)$_2$N$H_2$, —S(O)$_2$N(H)-pyridinyl, optionally substituted ($C_1$-$C_3$)alkyl, optionally substituted morpholinyl, optionally substituted piperazinyl, optionally substituted pyridinyl, -optionally substituted ($C_1$-$C_3$)alkylene-optionally substituted morpholinyl, -optionally substituted ($C_1$-$C_3$)alkylene-optionally substituted piperazinyl, optionally substituted imidazolyl, or optionally substituted pyridinyl.

In a sixth embodiment the invention provides a compound according to any of the foregoing embodiments wherein Z can be optionally substituted by one or more substituents independently selected from CN, halogen, N($R^c$)($R^d$), —O$R^c$, —C(O)$R^c$, —C(O)O$R^c$, —C(O)N($R^c$)($R^d$), —N($R^c$)C(O)($R^d$), —$CF_3$, —OC(O)$R^c$, —N($R^c$)S(O)$_2R^d$, —O$CF_3$, oxo, S($R^c$), —S(O)($R^c$), —S(O)$_2$($R^c$), —S(O)$_2$N($R^c$)($R^d$), and optionally substituted —($C_1$-$C_6$)alkyl.

In a seventh embodiment the invention provides a compound according to the first through fourth embodiments wherein $R^a$ and $R^b$ together form

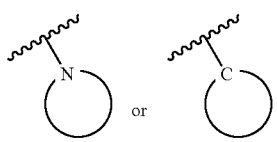

forming an optionally substituted 4 to 10 membered monocyclic, bicyclic or spirocyclic saturated, unsaturated or partially unsaturated ring containing 0 to 4 heteroatoms selected from N, O and S.

In an eighth embodiment the invention provides a compound according to the seventh embodiment wherein $R^1$ is optionally substituted azepinyl, optionally substituted azetidinyl, optionally substituted diazaspiro[3.5]nonanyl, optionally substituted diazaspiro[4.5]decanyl, optionally substituted diazaspiro[5.5]undecanyl, optionally substituted dihydroimidazo[1,5-a]pyrazinyl, optionally substituted dihydroimidazo[4,5-c]pyridinyl, optionally substituted dihydroisoquinolinyl, optionally substituted morpholinyl, optionally substituted piperazinyl, optionally substituted piperidinyl, optionally substituted pyrrolidinyl, or tetrahydropyrrolo[3,4-c]pyridinyl.

In a ninth embodiment the invention provides a compound according to the eighth embodiment wherein $R^1$ is optionally substituted by one or more substituents selected from halogen, —CN, —C(N$H_2$)(=NOH), —C(O)N($R^c$)($R^d$), —N($R^c$)($R^d$), —O$R^c$, —S(O)$_2R^c$, optionally substituted ($C_1$-$C_4$)alkyl, —$CH_2$—NH-optionally substituted heterocyclyl, or optionally substituted heteroaryl.

In a tenth embodiment the invention provides a compound according to the ninth embodiment wherein Y is optionally substituted benzo[b][1,4]oxazinyl, optionally substituted benzo[b][1,4]thiazinyl, optionally substituted dihydroisoquinolinyl, optionally substituted dihydroquinolinyl, optionally substituted indazolyl, optionally substituted indolinyl, optionally substituted phenyl, optionally substituted quinolinyl, or optionally substituted tetrahydroquinolinyl.

In an eleventh embodiment the invention provides a compound according to the tenth embodiment wherein Z is H, F, —N(H)C(O)-optionally substituted ($C_1$-$C_3$)alkyl, —N($CH_3$)C(O)-optionally substituted ($C_1$-$C_3$)alkyl, —S(O)$_2$-optionally substituted ($C_1$-$C_3$)alkyl, —S(O)$_2$—N(H) optionally substituted ($C_1$-$C_4$)alkyl, —S(O)$_2$N$H_2$, optionally substituted ($C_1$-$C_3$)alkyl, optionally substituted morpholinyl, or optionally substituted piperazinyl.

In a twelfth embodiment the invention provides a compound according to any of the foregoing embodiments wherein the compound is 4-(4-((2,2-difluoroethylamino)methyl)piperidin-1-yl)-N-(3-methyl-1H-indazol-6-yl)furo[3,2-d]pyrimidin-2-amine;

4-(3,4-dihydroisoquinolin-2 (1H)-yl)-N-(1H-indazol-6-yl) furo[3,2-d]pyrimidin-2-amine;

4-(4-(aminomethyl)-4-methylpiperidin-1-yl)-N-(1H-indazol-6-yl)furo[3,2-d]pyrimidin-2-amine;

N-(4-(4-(3,4-dihydroisoquinolin-2(1H)-yl)furo[3,2-d]pyrimidin-2-ylamino)phenyl)-N-methylacetamide;

2,2-dimethyl-6-(4-(4-((2-(methylsulfonyl)ethylamino)methyl)piperidin-1-yl)furo[3,2-d]pyrimidin-2-ylamino)-2H-benzo[b][1,4]oxazin-3(4H)-one;

3,3-dimethyl-6-(4-(4-((2-(methylsulfonyl)ethylamino)methyl)piperidin-1-yl)furo[3,2-d]pyrimidin-2-ylamino)indolin-2-one;

N-(3-methoxypropyl)-4-(4-(4-((methylamino)methyl)piperidin-1-yl)furo[3,2-d]pyrimidin-2-ylamino)benzene sulfonamide;

2-methyl-2-(4-(4-(4-((methylamino)methyl)piperidin-1-yl) furo[3,2-d]pyrimidin-2-ylamino)phenyl)propanenitrile;

6-(4-(2,7-diazaspiro[4.4]nonan-2-yl)furo[3,2-d]pyrimidin-2-ylamino)-2,2-dimethyl-2H-benzo[b][1,4]oxazin-3(4H)-one;

6-(4-(2,8-diazaspiro[4.5]decan-8-yl)furo[3,2-d]pyrimidin-2-ylamino)-2,2-dimethyl-2H-benzo[b][1,4]oxazin-3(4H)-one;

6-(4-(2,7-diazaspiro[4.5]decan-2-yl)furo[3,2-d]pyrimidin-2-ylamino)-2,2-dimethyl-2H-benzo[b][1,4]oxazin-3(4H)-one;

6-(4-(1,7-diazaspiro[3.5]nonan-7-yl)furo[3,2-d]pyrimidin-2-ylamino)-2,2-dimethyl-2H-benzo[b][1,4]oxazin-3(4H)-ones;

6-(4-(2,9-diazaspiro[5.5]undecan-9-yl)furo[3,2-d]pyrimidin-2-ylamino)-2,2-dimethyl-2H-benzo[b][1,4]oxazin-3 (4H)-one;

6-(4-(4,4-bis(aminomethyl)piperidin-1-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(1-oxa-4,9-diazaspiro[5.5] undecan-9-yl)furo[3,2-d]pyrimidin-2-amine;

N-(3-methyl-1H-indazol-6-yl)-4-(4-((2-(methylsulfonyl) ethylamino)methyl)piperidin-1-yl)furo[3,2-d]pyrimidin-2-amine;

7-(4-(4-(aminomethyl)piperidin-1-yl)furo[3,2-d]pyrimidin-2-ylamino)-3,4-dihydroquinolin-2 (1H)-one;

6-(4-(4-(1-aminoethyl)piperidin-1-yl)furo[3,2-d]pyrimidin-2-ylamino)-2,2-dimethyl-2H-benzo[b][1,4]oxazin-3(4H)-one;

7-(4-(4-(aminomethyl)piperidin-1-yl)furo[3,2-d]pyrimidin-2-ylamino)quinolin-2(1H)-one;

6-(4-(3-(aminomethyl)-3-methylpyrrolidin-1-yl)furo[3,2-d]pyrimidin-2-ylamino)-2,2-dimethyl-2H-benzo[b][1,4]oxazin-3 (4H)-one;

6-(4-(4-(aminomethyl)-4-ethylpiperidin-1-yl)furo[3,2-d]pyrimidin-2-ylamino)-2,2-dimethyl-2H-benzo[b][1,4]oxazin-3 (4H)-one;

6-(4-(4-(aminomethyl)-4-(cyclopropylmethyl)piperidin-1-yl)furo[3,2-d]pyrimidin-2-ylamino)-2,2-dimethyl-2H-benzo[b][1,4]oxazin-3 (4H)-one;

(4-{4-[(4-aminotetrahydro-2H-thiopyrane1,1-dioxide)-methyl]-piperidin-1-yl}-furo[3,2-d]pyrimidin-2-yl)-(3-methyl-1H-indazol-6-yl)-amine;

N-(3-methyl-1H-indazol-6-yl)-4-(4-((tetrahydro-2H-pyran-4-ylamino)methyl)piperidin-1-yl)furo[3,2-d]pyrimidin-2-amine;

6-(4-(3-(aminomethyl)-4-methylpyrrolidin-1-yl)furo[3,2-d]pyrimidin-2-ylamino)-2,2-dimethyl-2H-benzo[b][1,4]oxazin-3(4H)-one;

6-(4-(4,4-bis(aminomethyl)piperidin-1-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(1-oxa-4,9-diazaspiro[5.5]undecan-9-yl)furo[3,2-d]pyrimidin-2-amine;

6-(4-(4-(aminomethyl)-4-(hydroxymethyl)piperidin-1-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(4-((methylamino)methyl)piperidin-1-yl)furo[3,2-d]pyrimidin-2-amine;

N-(1-methyl-1H-indazol-5-yl)-4-(4-((methylamino)methyl)piperidin-1-yl)furo[3,2-d]pyrimidin-2-amine;

(R)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)piperidine-4-carboxamide;

(S)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)piperidine-3-carboxamide;

4-(4-(4-(methylsulfonyl)piperazin-1-yl)furo[3,2-d]pyrimidin-2-ylamino)benzenesulfonamide;

4-(4-(4-(aminomethyl)piperidin-1-yl)furo[3,2-d]pyrimidin-2-ylamino)benzenesulfonamide;

1-(4-(2-(4-(methylsulfonyl)phenylamino)furo[3,2-d]pyrimidin-4-yl)piperazin-1-yl)ethanone;

4-(4-(4-acetylpiperazin-1-yl)furo[3,2-d]pyrimidin-2-ylamino)benzenesulfonamide;

N-((1-(2-(4-sulfamoylphenylamino)furo[3,2-d]pyrimidin-4-yl)piperidin-4-yl)methyl)acetamide;

4-(4-(4-(hydroxymethyl)piperidin-1-yl)furo[3,2-d]pyrimidin-2-ylamino)benzenesulfonamide;

4-(4-(3-aminopyrrolidin-1-yl)furo[3,2-d]pyrimidin-2-ylamino)benzenesulfonamide;

4-(3-(aminomethyl)pyrrolidin-1-yl)-N-(3-methyl-1H-indazol-6-yl)furo[3,2-d]pyrimidin-2-amine;

4-(4-aminoazepan-1-yl)-N-(3-methyl-1H-indazol-6-yl)furo[3,2-d]pyrimidin-2-amine;

6-(4-(4-aminoazepan-1-yl)furo[3,2-d]pyrimidin-2-ylamino)-2,2-dimethyl-2H-benzo[b][1,4]oxazin-3(4H)-one;

4-(4-(aminomethyl)-4-methylpiperidin-1-yl)-N-(3-methyl-1H-indazol-6-yl)furo[3,2-d]pyrimidin-2-amine;

6-(4-(4-(aminomethyl)-4-methylpiperidin-1-yl)furo[3,2-d]pyrimidin-2-ylamino)-3,3-dimethylindolin-2-one;

6-(4-(4-(aminomethyl)-4-methylpiperidin-1-yl)furo[3,2-d]pyrimidin-2-ylamino)-2,2-dimethyl-2H-benzo[b][1,4]oxazin-3(4H)-one;

6-(4-(4-aminoazepan-1-yl)furo[3,2-d]pyrimidin-2-ylamino)-3,3-dimethylindolin-2-one;

(R)-6-(4-(2,7-diazaspiro[4.5]decan-2-yl)furo[3,2-d]pyrimidin-2-ylamino)-2,2-dimethyl-2H-benzo[b][1,4]oxazin-3(4H)-one;

2,2-dimethyl-6-(4-(tetrahydro-1H-pyrrolo[3,4-c]pyridin-5(6H,7H,7aH)-yl)furo[3,2-d]pyrimidin-2-ylamino)-2H-benzo[b][1,4]oxazin-3(4H)-one;

6-(4-(2,9-diazaspiro[5.5]undecan-9-yl)furo[3,2-d]pyrimidin-2-ylamino)-3,3-dimethylindolin-2-one;

6-(4-(2,8-diazaspiro[4.5]decan-8-yl)furo[3,2-d]pyrimidin-2-ylamino)-3,3-dimethylindolin-2-one;

N-(3-methoxy-4-morpholinophenyl)-4-(2,9-diazaspiro[5.5]undecan-9-yl)furo[3,2-d]pyrimidin-2-amine;

N-(1-methyl-1H-indazol-5-yl)-4-(2,8-diazaspiro[4.5]decan-8-yl)furo[3,2-d]pyrimidin-2-amine;

N-(3-chloro-4-morpholinophenyl)-4-(2,9-diazaspiro[5.5]undecan-9-yl)furo[3,2-d]pyrimidin-2-amine;

N-(3-methyl-4-morpholinophenyl)-4-(2,9-diazaspiro[5.5]undecan-9-yl)furo[3,2-d]pyrimidin-2-amine;

N-(1-methyl-1H-indazol-5-yl)-4-(2,9-diazaspiro[5.5]undecan-9-yl)furo[3,2-d]pyrimidin-2-amine;

N-(3-chloro-4-morpholinophenyl)-4-(2,8-diazaspiro[4.5]decan-8-yl)furo[3,2-d]pyrimidin-2-amine;

N-(3-methoxy-4-morpholinophenyl)-4-(2,8-diazaspiro[4.5]decan-8-yl)furo[3,2-d]pyrimidin-2-amine;

N-(3-methyl-1H-indazol-6-yl)-4-(2,9-diazaspiro[5.5]undecan-9-yl)furo[3,2-d]pyrimidin-2-amine;

N-(3-methyl-4-morpholinophenyl)-4-(2,8-diazaspiro[4.5]decan-8-yl)furo[3,2-d]pyrimidin-2-amine;

N-(3-methyl-1H-indazol-6-yl)-4-(2,8-diazaspiro[4.5]decan-8-yl)furo[3,2-d]pyrimidin-2-amine;

4-(azetidin-1-yl)-N-(3-methyl-1H-indazol-6-yl)furo[3,2-d]pyrimidin-2-amine;

(Z)—N'-hydroxy-1-(2-(3-methyl-1H-indazol-6-ylamino)furo[3,2-d]pyrimidin-4-yl)piperidine-4-carboximidamide;

4-(6,7-dihydro-3H-imidazo[4,5-c]pyridin-5 (4H)-yl)-N-(3-methyl-1H-indazol-6-yl)furo[3,2-d]pyrimidin-2-amine;

1-(4-(4-(4-(4-((methylamino)methyl)piperidin-1-yl)furo[3,2-d]pyrimidin-2-ylamino)phenyl)piperazin-1-yl)ethanone;

1-(4-(4-(4-(4-(aminomethyl)piperidin-1-yl)furo[3,2-d]pyrimidin-2-ylamino)phenyl)piperazin-1-yl)ethanone;

6-(4-(4-(aminomethyl)piperidin-1-yl)furo[3,2-d]pyrimidin-2-ylamino)-3,4-dihydroquinolin-2 (1H)-one;

6-(4-(4-(aminomethyl)piperidin-1-yl)furo[3,2-d]pyrimidin-2-ylamino)-2,2-dimethyl-2H-benzo[b][1,4]oxazin-3 (4H)-one;

N-(4-(4-(4-(aminomethyl)piperidin-1-yl)furo[3,2-d]pyrimidin-2-ylamino)phenyl)butyramide;

4-(4-(aminomethyl)piperidin-1-yl)-N-(1H-indazol-6-yl)furo[3,2-d]pyrimidin-2-amine;

N2-(3-chloro-4-morpholinophenyl)-N4-(piperidin-4-ylmethyl)furo[3,2-d]pyrimidine-2,4-diamine;

4-(4-(aminomethyl)piperidin-1-yl)-N-(3-chloro-4-morpholinophenyl)furo[3,2-d]pyrimidin-2-amine;

N-(1H-indazol-6-yl)-4-(3-((methylamino)methyl)pyrrolidin-1-yl)furo[3,2-d]pyrimidin-2-amine;

4-(3-(aminomethyl)pyrrolidin-1-yl)-N-(1H-indazol-6-yl) furo[3,2-d]pyrimidin-2-amine;

4-(3-(aminomethyl)-5,6-dihydroimidazo[1,5-a]pyrazin-7 (8H)-yl)-N-(1H-indazol-6-yl)furo[3,2-d]pyrimidin-2-amine;

4-(4-((2,2-difluoroethylamino)methyl)piperidin-1-yl)-N-(1H-indazol-6-yl)furo[3,2-d]pyrimidin-2-amine;

4-(4-((2-fluoroethylamino)methyl)piperidin-1-yl)-N-(1H-indazol-6-yl)furo[3,2-d]pyrimidin-2-amine;

N-(1H-indazol-6-yl)-4-(4-((oxetan-3-ylamino)methyl)piperidin-1-yl)furo[3,2-d]pyrimidin-2-amine;

N-(4-(4-(4-((2,2-difluoroethylamino)methyl)piperidin-1-yl) furo[3,2-d]pyrimidin-2-ylamino)phenyl)-N-methylacetamide;

4-(4-(4-(aminomethyl)piperidin-1-yl)furo[3,2-d]pyrimidin-2-ylamino)-N-(3-methoxypropyl)benzenesulfonamide;

4-(4-(aminomethyl)piperidin-1-yl)-N-(1-methyl-1H-indazol-5-yl)furo[3,2-d]pyrimidin-2-amine;

N-(1H-indazol-6-yl)-4-(3-((methylamino)methyl)-5,6-dihydroimidazo[1,5-a]pyrazin-7(8H)-yl)furo[3,2-d]pyrimidin-2-amine;

6-(4-(4-((2,2-difluoroethylamino)methyl)piperidin-1-yl) furo[3,2-d]pyrimidin-2-ylamino)-2,2-dimethyl-2H-benzo [b][1,4]oxazin-3(4H)-one;

N-(1H-indazol-6-yl)-4-(4-((2-(methylsulfonyl)ethylamino) methyl)piperidin-1-yl)furo[3,2-d]pyrimidin-2-amine;

4-(4-(aminomethyl)piperidin-1-yl)-N-(3-methyl-1H-indazol-6-yl)furo[3,2-d]pyrimidin-2-amine;

6-(4-(3,4-dihydroisoquinolin-2(1H)-yl)furo[3,2-d]pyrimidin-2-ylamino)-2,2-dimethyl-2H-benzo[b][1,4]oxazin-3 (4H)-one;

4-(4-aminoazepan-1-yl)-N-(1H-indazol-6-yl)furo[3,2-d]pyrimidin-2-amine;

2,2-dimethyl-6-(4-(4-((methylamino)methyl)piperidin-1-yl) furo[3,2-d]pyrimidin-2-ylamino)-2H-benzo[b][1,4]oxazin-3(4H)-one;

N-(1H-indazol-6-yl)-4-(4-((methylamino)methyl)piperidin-1-yl)furo[3,2-d]pyrimidin-2-amine;

6-(4-(4-((2,2-difluoroethylamino)methyl)piperidin-1-yl) furo[3,2-d]pyrimidin-2-ylamino)-3,3-dimethylindolin-2-one;

3,3-dimethyl-6-(4-(4-((methylamino)methyl)piperidin-1-yl) furo[3,2-d]pyrimidin-2-ylamino)indolin-2-one;

2,2-dimethyl-6-(4-(3-((methylamino)methyl)pyrrolidin-1-yl)furo[3,2-d]pyrimidin-2-ylamino)-2H-benzo[b][1,4]oxazin-3(4H)-one;

4-(4-(aminomethyl)-4-fluoropiperidin-1-yl)-N-(1H-indazol-6-yl)furo[3,2-d]pyrimidin-2-amine;

4-(4-(4-((2,2-difluoroethylamino)methyl)piperidin-1-yl) furo[3,2-d]pyrimidin-2-ylamino)-N-(3-methoxypropyl) benzenesulfonamide;

4-(4-(4-((2,2-difluoroethylamino)methyl)piperidin-1-yl)-N-(1-methyl-1H-indazol-5-yl)furo[3,2-d]pyrimidin-2-amine;

6-(4-(4-((2-fluoroethylamino)methyl)piperidin-1-yl)furo[3, 2-d]pyrimidin-2-ylamino)-2,2-dimethyl-2H-benzo[b][1, 4]oxazin-3(4H)-one;

6-(4-(4-((2-fluoroethylamino)methyl)piperidin-1-yl)furo[3, 2-d]pyrimidin-2-ylamino)-3,3-dimethylindolin-2-one;

1-(2-(2,2-dimethyl-3-oxo-3,4-dihydro-2H-benzo[b][1,4]oxazin-6-ylamino)furo[3,2-d]pyrimidin-4-yl)piperidine-3-carboxamide;

7-(4-(4-(aminomethyl)piperidin-1-yl)furo[3,2-d]pyrimidin-2-ylamino)-4-methylquinolin-2(1H)-one;

7-(4-(4-((2,2-difluoroethylamino)methyl)piperidin-1-yl) furo[3,2-d]pyrimidin-2-ylamino)-3,4-dihydroquinolin-2 (1H)-one;

7-(4-(4-((2,2-difluoroethylamino)methyl)piperidin-1-yl) furo[3,2-d]pyrimidin-2-ylamino)quinolin-2(1H)-one;

7-(4-(4-((2,2-difluoroethylamino)methyl)piperidin-1-yl) furo[3,2-d]pyrimidin-2-ylamino)-4-methylquinolin-2 (1H)-one;

6-(4-(4-((2,2-difluoroethylamino)methyl)piperidin-1-yl) furo[3,2-d]pyrimidin-2-ylamino)-2H-benzo[b][1,4]oxazin-3 (4H)-one;

N-(3-chloro-4-morpholinophenyl)-4-(4-((2,2-difluoroethylamino)methyl)piperidin-1-yl)furo[3,2-d]pyrimidin-2-amine;

7-(4-(4-((2,2-difluoroethylamino)methyl)piperidin-1-yl) furo[3,2-d]pyrimidin-2-ylamino)-3,3-dimethyl-3,4-dihydroquinolin-2(1H)-one;

7-(4-(4-((2,2-difluoro ethylamino)methyl)piperidin-1-yl) furo[3,2-d]pyrimidin-2-ylamino)-3-methylquinolin-2 (1H)-one;

6-(4-(4-((2,2-difluoroethylamino)methyl)piperidin-1-yl) furo[3,2-d]pyrimidin-2-ylamino)-2,2-difluoro-2H-benzo [b][1,4]oxazin-3(4H)-one;

6-(4-(4-(1-(2,2-difluoroethylamino)ethyl)piperidin-1-yl) furo[3,2-d]pyrimidin-2-ylamino)-2,2-dimethyl-2H-benzo [b][1,4]oxazin-3 (4H)-one;

6-(4-(4-(1-(2,2-difluoroethylamino)ethyl)piperidin-1-yl) furo[3,2-d]pyrimidin-2-ylamino)-3,3-dimethylindolin-2-one;

4-(4-((2,2-difluoroethylamino)methyl)piperidin-1-yl)-N-(3-fluoro-4-morpholinophenyl)furo[3,2-d]pyrimidin-2-amine;

7-(4-(4-((2,2-difluoroethylamino)methyl)piperidin-1-yl) furo[3,2-d]pyrimidin-2-ylamino)-3-methyl-3,4-dihydroquinolin-2(1H)-one;

6-(4-(4-((2,2-difluoroethylamino)methyl)-4-methylpiperidin-1-yl)furo[3,2-d]pyrimidin-2-ylamino)-2,2-dimethyl-2H-benzo[b][1,4]oxazin-3(4H)-one;

1-(2-(2,2-dimethyl-3-oxo-3,4-dihydro-2H-benzo[b][1,4]oxazin-6-ylamino)furo[3,2-d]pyrimidin-4-yl)pyrrolidine-3-carboxamide;

6-(4-(4-(hydroxymethyl)-4-methylpiperidin-1-yl)furo[3,2-d]pyrimidin-2-ylamino)-2,2-dimethyl-2H-benzo[b][1,4] oxazin-3 (4H)-one;

6-(4-(4-hydroxy-4-methylpiperidin-1-yl)furo[3,2-d]pyrimidin-2-ylamino)-2,2-dimethyl-2H-benzo[b][1,4]oxazin-3 (4H)-one;

6-(4-(4-hydroxy-4-methylpiperidin-1-yl)furo[3,2-d]pyrimidin-2-ylamino)-2,2-dimethyl-2H-benzo[b][1,4]oxazin-3 (4H)-one;

6-(4-(4-hydroxy-4-(hydroxymethyl)piperidin-1-yl)furo[3,2-d]pyrimidin-2-ylamino)-2,2-dimethyl-2H-benzo[b][1,4] oxazin-3(4H)-one;

6-(4-(3-hydroxypiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-hydroxypiperidin-1-yl)furo[3,2-d] pyrimidin-2-ylamino)-2,2-dimethyl-2H-benzo[b][1,4]oxazin-3(4H)-one;

6-(4-(4-((2,2-difluoroethylamino)methyl)piperidin-1-yl) furo[3,2-d]pyrimidin-2-ylamino)-2,2-dimethyl-2H-benzo [b][1,4]thiazin-3(4H)-one;

4-(aminomethyl)-1-(2-(3-methyl-1H-indazol-6-ylamino) furo[3,2-d]pyrimidin-4-yl)piperidin-4-ol;

6-(4-((3S,4S)-4-(aminomethyl)-3-hydroxypiperidin-1-yl) furo[3,2-d]pyrimidin-2-ylamino)-2,2-dimethyl-2H-benzo [b][1,4]oxazin-3(4H)-one;

6-(4-(4-(aminomethyl)-4-hydroxypiperidin-1-yl)furo[3,2-d] pyrimidin-2-ylamino)-3,3-dimethylindolin-2-one;

2,2-dimethyl-6-(4-(4-((methylamino)methyl)piperidin-1-yl)furo[3,2-d]pyrimidin-2-ylamino)-2H-benzo[b][1,4]thiazin-3(4H)-one;

6-(4-(3,9-diazaspiro[5.5]undecan-3-yl)furo[3,2-d]pyrimidin-2-ylamino)-2,2-dimethyl-2H-benzo[b][1,4]oxazin-3(4H)-one;

4-(4-(2-aminoethyl)piperidin-1-yl)-N-(3-methyl-1H-indazol-6-yl)furo[3,2-d]pyrimidin-2-amine;

4-(4-(2,2-difluoroethylamino)azepan-1-yl)-N-(3-methyl-1H-indazol-6-yl)furo[3,2-d]pyrimidin-2-amine;

1-(2-(2,2-dimethyl-3-oxo-3,4-dihydro-2H-benzo[b][1,4]oxazin-6-ylamino)furo[3,2-d]pyrimidin-4-yl)-4-(2-hydroxyethyl)piperidine-4-carbonitrile;

2,2-dimethyl-6-(4-(4-(((3,3,3-trifluoropropylamino)methyl)piperidin-1-yl)furo[3,2-d]pyrimidin-2-ylamino)-2H-benzo[b][1,4]oxazin-3(4H)-one;

6-(4-(4-(aminomethyl)-4-methoxypiperidin-1-yl)furo[3,2-d]pyrimidin-2-ylamino)-2,2-dimethyl-2H-benzo[b][1,4]oxazin-3(4H)-one;

6-(4-((3S,4S)-4-amino-3-hydroxyazepan-1-yl)furo[3,2-d]pyrimidin-2-ylamino)-2,2-dimethyl-2H-benzo[b][1,4]oxazin-3(4H)-one;

6-(4-(3-((2,2-difluoroethylamino)methyl)pyrrolidin-1-yl)furo[3,2-d]pyrimidin-2-ylamino)-3,3-dimethylindolin-2-one;

6-(4-(3-(hydroxymethyl)pyrrolidin-1-yl)furo[3,2-d]pyrimidin-2-ylamino)-2,2-dimethyl-2H-benzo[b][1,4]oxazin-3(4H)-one;

3,3-dimethyl-6-(4-(4-((3,3,3-trifluoropropylamino)methyl)piperidin-1-yl)furo[3,2-d]pyrimidin-2-ylamino)indolin-2-one;

N-(3-methyl-1H-indazol-6-yl)-4-(4-((3,3,3-trifluoropropylamino)methyl)piperidin-1-yl)furo[3,2-d]pyrimidin-2-amine;

6-(4-(4-(aminomethyl)-4-(2-hydroxyethyl)piperidin-1-yl)furo[3,2-d]pyrimidin-2-ylamino)-2,2-dimethyl-2H-benzo[b][1,4]oxazin-3(4H)-one;

(3S,4S)-4-(aminomethyl)-1-(2-(3-methyl-1H-indazol-6-ylamino)furo[3,2-d]pyrimidin-4-yl)piperidin-3-ol;

6-(4-(3-hydroxypyrrolidin-1-yl)furo[3,2-d]pyrimidin-2-ylamino)-2,2-dimethyl-2H-benzo[b][1,4]oxazin-3(4H)-one;

6-(4-(4-hydroxypiperidin-1-yl)furo[3,2-d]pyrimidin-2-ylamino)-2,2-dimethyl-2H-benzo[b][1,4]oxazin-3(4H)-one;

1-(4-(4-(4-(4-((dimethylamino)methyl)piperidin-1-yl)furo[3,2-d]pyrimidin-2-ylamino)phenyl)piperazin-1-yl)ethanone;

4-(4-(aminomethyl)piperidin-1-yl)-N-(4-(piperazin-1-yl)phenyl)furo[3,2-d]pyrimidin-2-amine;

1-(4-(4-(4-(4-((dimethylamino)methyl)-4-methylpiperidin-1-yl)furo[3,2-d]pyrimidin-2-ylamino)phenyl)piperazin-1-yl)ethanone;

1-(4-(4-(4-(3-(hydroxymethyl)-5,6-dihydroimidazo[1,5-a]pyrazin-7(8H)-yl)furo[3,2-d]pyrimidin-2-ylamino)phenyl)piperazin-1-yl)ethanone;

1-(4-(4-(4-(5,6-dihydroimidazo[1,5-a]pyrazin-7(8H)-yl)furo[3,2-d]pyrimidin-2-ylamino)phenyl)piperazin-1-yl)ethanone;

1-(4-(4-(4-(3-((dimethylamino)methyl)-5,6-dihydroimidazo[1,5-a]pyrazin-7(8H)-yl)furo[3,2-d]pyrimidin-2-ylamino)phenyl)piperazin-1-yl)ethanone;

1-(4-(4-(4-(3-methyl-5,6-dihydroimidazo[1,5-a]pyrazin-7(8H)-yl)furo[3,2-d]pyrimidin-2-ylamino)phenyl)piperazin-1-yl)ethanone;

ethyl 2-(1-(2-(4-(piperazin-1-yl)phenylamino)furo[3,2-d]pyrimidin-4-yl)piperidin-4-yl)acetate;

ethyl 2-(1-(2-(4-(4-acetylpiperazin-1-yl)phenylamino)furo[3,2-d]pyrimidin-4-yl)piperidin-4-yl)acetate;

ethyl 2-(1-(2-(4-(N-methylacetamido)phenylamino)furo[3,2-d]pyrimidin-4-yl)piperidin-4-yl)acetate;

ethyl 2-(1-(2-(4-butyramidophenylamino)furo[3,2-d]pyrimidin-4-yl)piperidin-4-yl)acetate;

1-(4-(4-(4-(4-hydroxy-4-(pyrrolidin-1-ylmethyl)piperidin-1-yl)furo[3,2-d]pyrimidin-2-ylamino)phenyl)piperazin-1-yl)ethanone;

1-(4-(4-(4-(3-((dimethylamino)methyl)pyrrolidin-1-yl)furo[3,2-d]pyrimidin-2-ylamino)phenyl)piperazin-1-yl)ethanone;

(S)-1-(4-(4-(4-(3-aminopiperidin-1-yl)furo[3,2-d]pyrimidin-2-ylamino)phenyl)piperazin-1-yl)ethanone;

ethyl 2-(1-(2-(2-oxo-1,2,3,4-tetrahydroquinolin-6-ylamino)furo[3,2-d]pyrimidin-4-yl)piperidin-4-yl)acetate;

ethyl 2-(1-(2-(2,2-dimethyl-3-oxo-3,4-dihydro-2H-benzo[b][1,4]oxazin-6-ylamino)furo[3,2-d]pyrimidin-4-yl)piperidin-4-yl)acetate;

ethyl 2-(1-(2-(3-chloro-4-morpholinophenylamino)furo[3,2-d]pyrimidin-4-yl)piperidin-4-yl)acetate;

ethyl 2-(1-(2-(3-oxo-3,4-dihydro-2H-benzo[b][1,4]oxazin-6-ylamino)furo[3,2-d]pyrimidin-4-yl)piperidin-4-yl)acetate;

1-(4-(4-(4-(4-(pyridin-3-yl)piperazin-1-yl)furo[3,2-d]pyrimidin-2-ylamino)phenyl)piperazin-1-yl)ethanone;

ethyl 2-(1-(2-(1H-indazol-6-ylamino)furo[3,2-d]pyrimidin-4-yl)piperidin-4-yl)acetate;

1-(6-(4-(4-(aminomethyl)piperidin-1-yl)furo[3,2-d]pyrimidin-2-ylamino)-5-methoxyindolin-1-yl)-2-(dimethylamino)ethanone;

4-(4-(aminomethyl)piperidin-1-yl)-N-(4-(4-isopropylpiperazin-1-yl)-2-methoxyphenyl)furo[3,2-d]pyrimidin-2-amine;

4-(1-benzylpyrrolidin-3-yl)-N-(1H-indazol-6-yl)furo[3,2-d]pyrimidin-2-amine;

N-(1H-indazol-6-yl)-4-(piperazin-1-yl)furo[3,2-d]pyrimidin-2-amine;

3-((1-(2-(1H-indazol-6-ylamino)furo[3,2-d]pyrimidin-4-yl)piperidin-4-yl)methyl)oxazolidin-2-one;

N-(1H-indazol-6-O-4-(4-((2,2,2-trifluoroethylamino)methyl)piperidin-1-yl)furo[3,2-d]pyrimidin-2-amine;

4-(3-(2-aminoethyl)azetidin-1-yl)-N-(1H-indazol-6-yl)furo[3,2-d]pyrimidin-2-amine;

N-(1H-indazol-6-yl)-4-(3-((methylamino)methyl)piperidin-1-yl)furo[3,2-d]pyrimidin-2-amine;

4-(3-(aminomethyl)piperidin-1-yl)-N-(1H-indazol-6-yl)furo[3,2-d]pyrimidin-2-amine;

4-(3-(2-aminoethyl)piperidin-1-yl)-N-(1H-indazol-6-yl)furo[3,2-d]pyrimidin-2-amine;

4-(2-(2-aminoethyl)morpholino)-N-(1H-indazol-6-yl)furo[3,2-d]pyrimidin-2-amine;

4-(2-(aminomethyl)azetidin-1-yl)-N-(1H-indazol-6-yl)furo[3,2-d]pyrimidin-2-amine;

N-(1H-indazol-6-yl)-4-(4-(((3-methyloxetan-3-yl)methylamino)methyl)piperidin-1-yl)furo[3,2-d]pyrimidin-2-amine;

1-(4-(4-(4-(2-hydroxy-2-methylpropyl)piperazin-1-yl)furo[3,2-d]pyrimidin-2-ylamino)phenyl)piperazin-1-yl)ethanone;

(R)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)piperidine-4-carboxamide;

(S)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)
piperidine-3-carboxamide;
4-(4-(4-(methylsulfonyl)piperazin-1-yl)furo[3,2-d]pyrimidin-2-ylamino)benzenesulfonamide;
4-(4-(4-(aminomethyl)piperidin-1-yl)furo[3,2-d]pyrimidin-2-ylamino)benzenesulfonamide;
1-(4-(2-(4-(methylsulfonyl)phenylamino)furo[3,2-d]pyrimidin-4-yl)piperazin-1-yl)ethanone;
4-(4-(4-acetylpiperazin-1-yl)furo[3,2-d]pyrimidin-2-ylamino)benzenesulfonamide;
N-((1-(2-(4-sulfamoylphenylamino)furo[3,2-d]pyrimidin-4-yl)piperidin-4-yl)methyl)acetamide;
4-(4-(4-(hydroxymethyl)piperidin-1-yl)furo[3,2-d]pyrimidin-2-ylamino)benzenesulfonamide;
4-(4-(3-aminopyrrolidin-1-yl)furo[3,2-d]pyrimidin-2-ylamino)benzenesulfonamide;
1-(4-(4-(4-(4-((methylamino)methyl)piperidin-1-yl)furo[3,2-d]pyrimidin-2-ylamino)phenyl)piperazin-1-yl)ethanone;
1-(4-(4-(4-(4-((dimethylamino)methyl)piperidin-1-yl)furo[3,2-d]pyrimidin-2-ylamino)phenyl)piperazin-1-yl)ethanone;
1-(4-(4-(4-(4-(aminomethyl)piperidin-1-yl)furo[3,2-d]pyrimidin-2-ylamino)phenyl)piperazin-1-yl)ethanone;
4-(4-(aminomethyl)piperidin-1-yl)-N-(4-(piperazin-1-yl)phenyl)furo[3,2-d]pyrimidin-2-amine;
6-(4-(4-(aminomethyl)piperidin-1-yl)furo[3,2-d]pyrimidin-2-ylamino)-3,4-dihydroquinolin-2(1H)-one;
6-(4-(4-(aminomethyl)piperidin-1-yl)furo[3,2-d]pyrimidin-2-ylamino)-2,2-dimethyl-2H-benzo[b][1,4]oxazin-3(4H)-one;
N-(4-(4-(4-(aminomethyl)piperidin-1-yl)furo[3,2-d]pyrimidin-2-ylamino)phenyl)-N-methylacetamide;
1-(4-(4-(4-(((dimethylamino)methyl)-4-methylpiperidin-1-yl)furo[3,2-d]pyrimidin-2-ylamino)phenyl)piperazin-1-yl)ethanone;
1-(4-(4-(4-(3-(hydroxymethyl)-5,6-dihydroimidazo[1,5-a]pyrazin-7(8H)-yl)furo[3,2-d]pyrimidin-2-ylamino)phenyl)piperazin-1-yl)ethanone;
1-(4-(4-(4-(5,6-dihydroimidazo[1,5-a]pyrazin-7(8H)-yl)furo[3,2-d]pyrimidin-2-ylamino)phenyl)piperazin-1-yl)ethanone;
1-(4-(4-(4-((dimethylamino)methyl)-5,6-dihydroimidazo[1,5-a]pyrazin-7(8H)-yl)furo[3,2-d]pyrimidin-2-ylamino)phenyl)piperazin-1-yl)ethanone;
N-(4-(4-(4-(aminomethyl)piperidin-1-yl)furo[3,2-d]pyrimidin-2-ylamino)phenyl)butyramide;
4-(4-(aminomethyl)piperidin-1-yl)-N-(1H-indazol-6-yl)furo[3,2-d]pyrimidin-2-amine;
1-(4-(4-(4-(4-(2-hydroxy-2-methylpropyl)piperazin-1-yl)furo[3,2-d]pyrimidin-2-ylamino)phenyl)piperazin-1-yl)ethanone;
1-(4-(4-(4-(3-methyl-5,6-dihydroimidazo[1,5-a]pyrazin-7(8H)-yl)furo[3,2-d]pyrimidin-2-ylamino)phenyl)piperazin-1-yl)ethanone;
ethyl 2-(1-(2-(4-(piperazin-1-yl)phenylamino)furo[3,2-d]pyrimidin-4-yl)piperidin-4-yl)acetate;
ethyl 2-(1-(2-(4-(4-acetylpiperazin-1-yl)phenylamino)furo[3,2-d]pyrimidin-4-yl)piperidin-4-yl)acetate;
ethyl 2-(1-(2-(4-(N-methylacetamido)phenylamino)furo[3,2-d]pyrimidin-4-yl)piperidin-4-yl)acetate;
ethyl 2-(1-(2-(4-butyramidophenylamino)furo[3,2-d]pyrimidin-4-yl)piperidin-4-yl)acetate;
1-(4-(4-(4-(4-hydroxy-4-(pyrrolidin-1-ylmethyl)piperidin-1-yl)furo[3,2-d]pyrimidin-2-ylamino)phenyl)piperazin-1-yl)ethanone;
1-(4-(4-(4-(3-((dimethylamino)methyl)pyrrolidin-1-yl)furo[3,2-d]pyrimidin-2-ylamino)phenyl)piperazin-1-yl)ethanone;
(S)-1-(4-(4-(4-(3-aminopiperidin-1-yl)furo[3,2-d]pyrimidin-2-ylamino)phenyl)piperazin-1-yl)ethanone;
4-(4-(aminomethyl)piperidin-1-yl)-N-(3-chloro-4-morpholinophenyl)furo[3,2-d]pyrimidin-2-amine;
ethyl 2-(1-(2-(2-oxo-1,2,3,4-tetrahydroquinolin-6-ylamino)furo[3,2-d]pyrimidin-4-yl)piperidin-4-yl)acetate;
ethyl 2-(1-(2-(2,2-dimethyl-3-oxo-3,4-dihydro-2H-benzo[b][1,4]oxazin-6-ylamino)furo[3,2-d]pyrimidin-4-yl)piperidin-4-yl)acetate;
ethyl 2-(1-(2-(3-chloro-4-morpholinophenylamino)furo[3,2-d]pyrimidin-4-yl)piperidin-4-yl)acetate;
ethyl 2-(1-(2-(3-oxo-3,4-dihydro-2H-benzo[b][1,4]oxazin-6-ylamino)furo[3,2-d]pyrimidin-4-yl)piperidin-4-yl)acetate;
1-(4-(4-(4-(pyridin-3-yl)piperazin-1-yl)furo[3,2-d]pyrimidin-2-ylamino)phenyl)piperazin-1-yl)ethanone;
4-tert-butyl-N-(1-(2-(5-(morpholine-4-carbonyl)pyridin-2-ylamino)furo[3,2-d]pyrimidin-4-yl)piperidin-3-yl)benzamide bis(2,2,2-trifluoroacetate); or
ethyl 2-(1-(2-(1H-indazol-6-ylamino)furo[3,2-d]pyrimidin-4-yl)piperidin-4-yl)acetate;
and pharmaceutically acceptable salts thereof.

In a thirteenth embodiment the invention provides a compound according to the seventh embodiment wherein $R^1$ is optionally substituted azepinyl, optionally substituted diazaspiro[4.5]decanyl, optionally substituted diazaspiro[5.5]undecanyl, optionally substituted 1-oxa-4,9-diazaspiro[5.5]undecanyl, optionally substituted piperidinyl, or optionally substituted pyrrolidinyl.

In a fourteenth embodiment the invention provides a compound according to the thirteenth embodiment wherein Y is optionally substituted benzo[b][1,4]oxazinyl, optionally substituted benzo[b][1,4]thiazinyl, optionally substituted dihydroquinolinyl, optionally substituted indazolyl, optionally substituted indolinyl, optionally substituted indolyl, optionally substituted phenyl, or optionally substituted quinolinyl In a fifteenth embodiment the invention provides a compound according to the fourteenth embodiment wherein Z is H, —C(O)N(CH$_3$)$_2$, —N(H)C(O)—(C$_1$-C$_3$)alkyl, (C$_1$-C$_3$)alkyl, —S(O)$_2$N(H) optionally substituted (C$_1$-C$_3$)alkyl, optionally substituted morpholinyl, or optionally substituted piperazinyl.

In a sixteenth embodiment the invention provides a compound according to the fifteenth embodiment wherein the compound is 4-(4-((2,2-difluoroethylamino)methyl)piperidin-1-yl)-N-(3-methyl-1H-indazol-6-yl)furo[3,2-d]pyrimidin-2-amine;
4-(4-(aminomethyl)-4-methylpiperidin-1-yl)-N-(1H-indazol-6-yl)furo[3,2-d]pyrimidin-2-amine;
2,2-dimethyl-6-(4-(4-((2-(methylsulfonyl)ethylamino)methyl)piperidin-1-yl)furo[3,2-d]pyrimidin-2-ylamino)-2H-benzo[b][1,4]oxazin-3 (4H)-one;
3,3-dimethyl-6-(4-(4-((2-(methylsulfonyl)ethylamino)methyl)piperidin-1-yl)furo[3,2-d]pyrimidin-2-ylamino)indolin-2-one;
N-(3-methoxypropyl)-4-(4-(4-((methylamino)methyl)piperidin-1-yl)furo[3,2-d]pyrimidin-2-ylamino)benzenesulfonamide;
2-methyl-2-(4-(4-(4-((methylamino)methyl)piperidin-1-yl)furo[3,2-d]pyrimidin-2-ylamino)phenyl)propanenitrile;
6-(4-(2,8-diazaspiro[4.5]decan-8-yl)furo[3,2-d]pyrimidin-2-ylamino)-2,2-dimethyl-2H-benzo[b][1,4]oxazin-3(4H)-one;

6-(4-(2,9-diazaspiro[5.5]undecan-9-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(4-((2-(methylsulfonyl)ethylamino)methyl)piperidin-1-yl)furo[3,2-d]pyrimidin-2-amine;

7-(4-(4-(aminomethyl)piperidin-1-yl)furo[3,2-d]pyrimidin-2-ylamino)-3,4-dihydroquinolin-2 (1H)-one;

6-(4-(4-(1-aminoethyl)piperidin-1-yl)furo[3,2-d]pyrimidin-2-ylamino)-2,2-dimethyl-2H-benzo[b][1,4]oxazin-3(4H)-one;

7-(4-(4-(aminomethyl)piperidin-1-yl)furo[3,2-d]pyrimidin-2-ylamino)quinolin-2(1H)-one;

6-(4-(4-(aminomethyl)-4-ethylpiperidin-1-yl)furo[3,2-d]pyrimidin-2-ylamino)-2,2-dimethyl-2H-benzo[b][1,4]oxazin-3 (4H)-one;

6-(4-(4-(aminomethyl)-4-(cyclopropylmethyl)piperidin-1-yl)furo[3,2-d]pyrimidin-2-ylamino)-2,2-dimethyl-2H-benzo[b][1,4]oxazin-3 (4H)-one;

(4-{-[(4-aminotetrahydro-2H-thiopyrane1,1-dioxide)-methyl]-piperidin-1-yl}furo[3,2-d]pyrimidin-2-yl)-(3-methyl-1H-indazol-6-yl)-amine;

N-(3-methyl-1H-indazol-6-yl)-4-(1-oxa-4,9-diazaspiro[5.5]undecan-9-yl)furo[3,2-d]pyrimidin-2-amine;

N-(3-methyl-1H-indazol-6-yl)-4-(4-((methylamino)methyl)piperidin-1-yl)furo[3,2-d]pyrimidin-2-amine;

N-(1-methyl-1H-indazol-5-yl)-4-(4-((methylamino)methyl)piperidin-1-yl)furo[3,2-d]pyrimidin-2-amine;

4-(4-aminoazepan-1-yl)-N-(3-methyl-1H-indazol-6-yl)furo[3,2-d]pyrimidin-2-amine;

4-(4-(aminomethyl)-4-methylpiperidin-1-yl)-N-(3-methyl-1H-indazol-6-yl)furo[3,2-d]pyrimidin-2-amine;

6-(4-(4-(aminomethyl)-4-methylpiperidin-1-yl)furo[3,2-d]pyrimidin-2-ylamino)-3,3-dimethylindolin-2-one;

6-(4-(4-(aminomethyl)-4-methylpiperidin-1-yl)furo[3,2-d]pyrimidin-2-ylamino)-2,2-dimethyl-2H-benzo[b][1,4]oxazin-3(4H)-one;

(R)-6-(4-(2,7-diazaspiro[4.5]decan-2-yl)furo[3,2-d]pyrimidin-2-ylamino)-2,2-dimethyl-2H-benzo[b][1,4]oxazin-3 (4H)-one;

6-(4-(2,9-diazaspiro[5.5]undecan-9-yl)furo[3,2-d]pyrimidin-2-ylamino)-3,3-dimethylindolin-2-one;

6-(4-(2,8-diazaspiro[4.5]decan-8-yl)furo[3,2-d]pyrimidin-2-ylamino)-3,3-dimethylindolin-2-one;

N-(3-methoxy-4-morpholinophenyl)-4-(2,9-diazaspiro[5.5]undecan-9-yl)furo[3,2-d]pyrimidin-2-amine;

N-(1-methyl-1H-indazol-5-yl)-4-(2,8-diazaspiro[4.5]decan-8-yl)furo[3,2-d]pyrimidin-2-amine;

N-(3-chloro-4-morpholinophenyl)-4-(2,9-diazaspiro[5.5]undecan-9-yl)furo[3,2-d]pyrimidin-2-amine;

N-(1-methyl-1H-indazol-5-yl)-4-(2,9-diazaspiro[5.5]undecan-9-yl)furo[3,2-d]pyrimidin-2-amine;

N-(3-chloro-4-morpholinophenyl)-4-(2,8-diazaspiro[4.5]decan-8-yl)furo[3,2-d]pyrimidin-2-amine;

N-(3-methyl-1H-indazol-6-yl)-4-(2,9-diazaspiro[5.5]undecan-9-yl)furo[3,2-d]pyrimidin-2-amine;

N-(3-methyl-4-morpholinophenyl)-4-(2,8-diazaspiro[4.5]decan-8-yl)furo[3,2-d]pyrimidin-2-amine;

N-(3-methyl-1H-indazol-6-yl)-4-(2,8-diazaspiro[4.5]decan-8-yl)furo[3,2-d]pyrimidin-2-amine;

(Z)—N'-hydroxy-1-(2-(3-methyl-1H-indazol-6-ylamino)furo[3,2-d]pyrimidin-4-yl)piperidine-4-carboximidamide;

1-(4-(4-(4-(4-((methylamino)methyl)piperidin-1-yl)furo[3,2-d]pyrimidin-2-ylamino)phenyl)piperazin-1-yl)ethanone;

1-(4-(4-(4-(4-(aminomethyl)piperidin-1-yl)furo[3,2-d]pyrimidin-2-ylamino)phenyl)piperazin-1-yl)ethanone;

6-(4-(4-(aminomethyl)piperidin-1-yl)furo[3,2-d]pyrimidin-2-ylamino)-3,4-dihydroquinolin-2(1H)-one;

N-(4-(4-(4-(aminomethyl)piperidin-1-yl)furo[3,2-d]pyrimidin-2-ylamino)phenyl)butyramide;

4-(4-(aminomethyl)piperidin-1-yl)-N-(1H-indazol-6-yl)furo[3,2-d]pyrimidin-2-amine;

4-(3-(aminomethyl)pyrrolidin-1-yl)-N-(1H-indazol-6-yl)furo[3,2-d]pyrimidin-2-amine;

4-(4-((2,2-difluoroethylamino)methyl)piperidin-1-yl)-N-(1H-indazol-6-yl)furo[3,2-d]pyrimidin-2-amine;

4-(4-((2-fluoroethylamino)methyl)piperidin-1-yl)-N-(1H-indazol-6-yl)furo[3,2-d]pyrimidin-2-amine;

N-(1H-indazol-6-yl)-4-(4-((oxetan-3-ylamino)methyl)piperidin-1-yl)furo[3,2-d]pyrimidin-2-amine;

4-(4-(aminomethyl)piperidin-1-yl)furo[3,2-d]pyrimidin-2-ylamino)-N-(3-methoxypropyl)benzenesulfonamide;

4-(4-(aminomethyl)piperidin-1-yl)-N-(1-methyl-1H-indazol-5-yl)furo[3,2-d]pyrimidin-2-amine;

6-(4-(4-((2,2-difluoroethylamino)methyl)piperidin-1-yl)furo[3,2-d]pyrimidin-2-ylamino)-2,2-dimethyl-2H-benzo[b][1,4]oxazin-3 (4H)-one;

N-(1H-indazol-6-yl)-4-(4-((2-(methylsulfonyl)ethylamino)methyl)piperidin-1-yl)furo[3,2-d]pyrimidin-2-amine;

N-(1H-indazol-6-yl)-4-(4-((methylamino)methyl)piperidin-1-yl)furo[3,2-d]pyrimidin-2-amine;

6-(4-(4-((2,2-difluoro ethylamino)methyl)piperidin-1-yl)furo[3,2-d]pyrimidin-2-ylamino)-3,3-dimethylindolin-2-one;

(diexo)-3-(2-(3,3-dimethyl-2-oxoindolin-6-ylamino)furo[3,2-d]pyrimidin-4-ylamino)bicyclo[2.2.1]hept-5-ene-2-carboxamide;

3,3-dimethyl-6-(4-(4-((methylamino)methyl)piperidin-1-yl)furo[3,2-d]pyrimidin-2-ylamino)indolin-2-one;

6-(4-(4-((2-fluoroethylamino)methyl)piperidin-1-yl)furo[3,2-d]pyrimidin-2-ylamino)-2,2-dimethyl-2H-benzo[b][1,4]oxazin-3 (4H)-one;

6-(4-(4-((2-fluoroethylamino)methyl)piperidin-1-yl)furo[3,2-d]pyrimidin-2-ylamino)-3,3-dimethylindolin-2-one;

7-(4-(4-((2,2-difluoroethylamino)methyl)piperidin-1-yl)furo[3,2-d]pyrimidin-2-ylamino)-3,4-dihydroquinolin-2(1H)-one;

7-(4-(4-((2,2-difluoroethylamino)methyl)piperidin-1-yl)furo[3,2-d]pyrimidin-2-ylamino)-4-methylquinolin-2(1H)-one;

6-(4-(4-((2,2-difluoroethylamino)methyl)piperidin-1-yl)furo[3,2-d]pyrimidin-2-ylamino)-2H-benzo[b][1,4]oxazin-3 (4H)-one;

N-(3-chloro-4-morpholinophenyl)-4-(4-((2,2-difluoroethylamino)methyl)piperidin-1-yl)furo[3,2-d]pyrimidin-2-amine;

6-(4-(4-(2-hydroxyethyl)piperidin-1-yl)furo[3,2-d]pyrimidin-2-ylamino)-2,2-dimethyl-2H-benzo[b][1,4]oxazin-3 (4H)-one;

4-(aminomethyl)-1-(2-(3-methyl-1H-indazol-6-ylamino)furo[3,2-d]pyrimidin-4-yl)piperidin-4-ol;

6-(4-((3S,4S)-4-(aminomethyl)-3-hydroxypiperidin-1-yl)furo[3,2-d]pyrimidin-2-ylamino)-2,2-dimethyl-2H-benzo[b][1,4]oxazin-3 (4H)-one;

6-(4-(4-(aminomethyl)-4-hydroxypiperidin-1-yl)furo[3,2-d]pyrimidin-2-ylamino)-3,3-dimethylindolin-2-one;

2,2-dimethyl-6-(4-(4-((methylamino)methyl)piperidin-1-yl)furo[3,2-d]pyrimidin-2-ylamino)-2H-benzo[b][1,4]thiazin-3(4H)-one;

1-(2-(2,2-dimethyl-3-oxo-3,4-dihydro-2H-benzo[b][1,4]oxazin-6-ylamino)furo[3,2-d]pyrimidin-4-yl)-4-(2-hydroxyethyl)piperidine-4-carbonitrile;
6-(4-(4-(aminomethyl)-4-methoxypiperidin-1-yl)furo[3,2-d]pyrimidin-2-ylamino)-2,2-dimethyl-2H-benzo[b][1,4]oxazin-3 (4H)-one;
3,3-dimethyl-6-(4-(4-((3,3,3-trifluoropropylamino)methyl)piperidin-1-yl)furo[3,2-d]pyrimidin-2-ylamino)indolin-2-one;
6-(4-(4-(aminomethyl)-4-(2-hydroxyethyl)piperidin-1-yl)furo[3,2-d]pyrimidin-2-ylamino)-2,2-dimethyl-2H-benzo[b][1,4]oxazin-3 (4H)-one;
(3S,4S)-4-(aminomethyl)-1-(2-(3-methyl-1H-indazol-6-ylamino)furo[3,2-d]pyrimidin-4-yl)piperidin-3-ol;
6-(4-(cyclopropylamino)furo[3,2-d]pyrimidin-2-ylamino)-N,N-dimethyl-1H-indazole-3-carboxamide;
6-(4-(4-hydroxypiperidin-1-yl)furo[3,2-d]pyrimidin-2-ylamino)-2,2-dimethyl-2H-benzo[b][1,4]oxazin-3(4H)-one;
N-propyl-4-(4-(2,2,2-trifluoroethylamino)furo[3,2-d]pyrimidin-2-ylamino)benzamide;
N2-(3-chloro-4-(4-methylpiperazin-1-yl)phenyl)-N4-cyclopropylfuro[3,2-d]pyrimidine-2,4-diamine;
N4-allyl-N2-(4-(methylsulfonyl)phenyl)furo[3,2-d]pyrimidine-2,4-diamine;
N2-(3-chloro-4-morpholinophenyl)-N4-cyclopropylfuro[3,2-d]pyrimidine-2,4-diamine;
4-(4-(cyclopropylamino)furo[3,2-d]pyrimidin-2-ylamino)benzenesulfonamide;
4-(4-(cyclopropylamino)furo[3,2-d]pyrimidin-2-ylamino)benzenesulfonamide bis(2,2,2-trifluoroacetate);
4-(4-(cyclopropylamino)furo[3,2-d]pyrimidin-2-ylamino)-N-propylbenzamide;
N*4*-cyclopropyl-N*2*-(2,2-dioxo-2,3-dihydro-1H-2lambda*6*-benzo[c]thiophen-5-yl)-furo[3,2-d]pyrimidine-2,4-diamine;
N4-cyclopropyl-N2-(4-(morpholinomethyl)phenyl)furo[3,2-d]pyrimidine-2,4-diamine;
1-(4-(4-(4-(cyclopropylamino)furo[3,2-d]pyrimidin-2-ylamino)phenyl)piperazin-1-yl)ethanone;
N*4*-cyclopropyl-N*2*-(1,1-dioxo-2,3-dihydro-1H-1lambda*6*-benzo[d]isothiazol-6-yl)-uro[3,2-d]pyrimidine-2,4-diamine-2;
6-(4-cyclopropylamino-furo[3,2-d]pyrimidin-2-ylamino)-1,1-dioxo-1,2-dihydro-1lambda*6*-benzo[d]isothiazol-3-one;
N4-cyclopropyl-N2-(1H-indazol-6-yl)furo[3,2-d]pyrimidine-2,4-diamine;
4-(4-(cyclobutylamino)furo[3,2-d]pyrimidin-2-ylamino)benzenesulfonamide 2,2,2-trifluoroacetate;
N4-cyclopropyl-N2-(1-methyl-1H-pyrazol-4-yl)furo[3,2-d]pyrimidine-2,4-diamine;
(1R,2S)-2-(2-(4-sulfamoylphenylamino)furo[3,2-d]pyrimidin-4-ylamino)cyclopentanecarboxamide;
6-(4-(cyclopropylamino)furo[3,2-d]pyrimidin-2-ylamino)-3,4-dihydroquinolin-2(1H)-one;
(1R,2R,3S,4S)-3-(2-(4-sulfamoylphenylamino)furo[3,2-d]pyrimidin-4-ylamino)bicyclo[2.2.1]hept-5-ene-2-carboxamide;
N-(4-(4-(cyclobutylamino)furo[3,2-d]pyrimidin-2-ylamino)phenyl)-N-methylacetamide;
N-(4-(4-(cyclobutylamino)furo[3,2-d]pyrimidin-2-ylamino)phenyl)butyramide;
N2-(3-chloro-4-morpholinophenyl)-N4-cyclobutylfuro[3,2-d]pyrimidine-2,4-diamine;
N4-cyclobutyl-N2-(1H-indazol-6-yl)furo[3,2-d]pyrimidine-2,4-diamine;
6-(4-(cyclopropylamino)furo[3,2-d]pyrimidin-2-ylamino)-2,2-dimethyl-2H-benzo[b][1,4]oxazin-3(4H)-one;
N-(4-(4-(cyclopropylamino)furo[3,2-d]pyrimidin-2-ylamino)phenyl)-N-methylacetamide;
N4-allyl-N2-(quinolin-4-yl)furo[3,2-d]pyrimidine-2,4-diamine;
N2-(3-chloro-4-morpholinophenyl)-N4-(piperidin-4-ylmethyl)furo[3,2-d]pyrimidine-2,4-diamine;
6-(4-(piperidin-4-ylmethylamino)furo[3,2-d]pyrimidin-2-ylamino)-2H-benzo[b][1,4]oxazin-3(4H)-one;
N-(4-(4-(piperidin-4-ylmethylamino)furo[3,2-d]pyrimidin-2-ylamino)phenyl)butyramide;
N4-cyclopropyl-N2-(isoquinolin-1-yl)furo[3,2-d]pyrimidine-2,4-diamine;
6-(4-(cyclobutylamino)furo[3,2-d]pyrimidin-2-ylamino)-3,4-dihydroquinolin-2(1H)-one;
N4-cyclopropyl-N2-(4-(piperazin-1-yl)phenyl)furo[3,2-d]pyrimidine-2,4-diamine;
N2-(1H-indazol-6-yl)-N4-(piperidin-4-ylmethyl)furo[3,2-d]pyrimidine-2,4-diamine;
N4-cyclobutyl-N2-(4-(piperazin-1-yl)phenyl)furo[3,2-d]pyrimidine-2,4-diamine;
6-(4-(cyclobutylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2H-benzo[b][1,4]oxazin-3(4H)-one;
7-(4-(cyclobutylamino)furo[3,2-d]pyrimidin-2-ylamino)-1H-benzo[d][1,3]oxazin-2(4H)-one;
N4-cyclopropyl-N2-(1-methyl-1H-indazol-5-yl)furo[3,2-d]pyrimidine-2,4-diamine;
N4-cyclopropyl-N2-(1-methyl-1H-indazol-3-yl)furo[3,2-d]pyrimidine-2,4-diamine;
4-(4-(cyclopropylamino)furo[3,2-d]pyrimidin-2-ylamino)-N-(3-methoxypropyl)benzamide;
4-(4-(cyclopropylamino)furo[3,2-d]pyrimidin-2-ylamino)-N-(3-methoxypropyl)benzenesulfonamide;
N4-cyclopropyl-N2-(imidazo[1,2-a]pyridin-3-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
2,2-dimethyl-6-(4-(2,2,2-trifluoroethylamino)furo[3,2-d]pyrimidin-2-ylamino)-2H-benzo[b][1,4]oxazin-3(4H)-one;
6-(4-(piperidin-4-ylmethylamino)furo[3,2-d]pyrimidin-2-ylamino)-3,4-dihydroquinolin-2(1H)-one;
2,2-dimethyl-6-(4-(piperidin-4-ylmethylamino)furo[3,2-d]pyrimidin-2-ylamino)-2H-benzo[b][1,4]oxazin-3(4H)-one;
N-methyl-N-(4-(4-(piperidin-4-ylmethylamino)furo[3,2-d]pyrimidin-2-ylamino)phenyl)acetamide;
N4-cyclopropyl-N2-(isoquinolin-4-yl)furo[3,2-d]pyrimidine-2,4-diamine;
N4-cyclopropyl-N2-(quinolin-4-yl)furo[3,2-d]pyrimidine-2,4-diamine;
N4-cyclopropyl-N2-(1-methyl-1H-indazol-6-yl)furo[3,2-d]pyrimidine-2,4-diamine; or
N2-(3-chloro-4-morpholinophenyl)-N4-(2,2,2-trifluoroethyl)furo[3,2-d]pyrimidine-2,4-diamine In a seventeenth embodiment the invention provides a compound according to the fourth embodiment wherein $R^1$ is $N(R^a)(R^b)$, $-C(R^a)=CH(R^b)$, or $-OR^b$; wherein $R^a$ is H or optionally substituted $(C_1-C_6)$alkyl; and
$R^b$ is optionally substituted $(C_1-C_6)$alkyl, optionally substituted $(C_2-C_6)$alkenyl, optionally substituted $(C_3-C_6)$cycloalkyl, optionally substituted bridged saturated or partially unsaturated $(C_5-C_{12})$cycloalkyl, or optionally substituted $(C_1-C_{10})$heteroaryl.

In an eighteenth embodiment the invention provides a compound according to the seventeenth embodiment wherein $R^b$ is optionally substituted $(C_1-C_6)$alkyl, optionally substituted $(C_2-C_6)$alkenyl, optionally substituted cyclopropyl, optionally substituted cyclobutyl, optionally substituted cyclopentyl, optionally substituted cyclohexyl, optionally substituted benzo[b][1,4]oxazinyl, optionally substituted bicyclo[2.2.1]heptanyl, optionally substituted bicyclo[2.2.1]heptenyl, optionally substituted indazolyl, optionally substituted oxetanyl, optionally substituted piperidinyl, —CH$_2$-optionally substituted azetidinyl, —CH$_2$-optionally substituted imidazolyl, —CH$_2$-optionally substituted piperidinyl, —CH$_2$-optionally substituted pyridinyl, In a nineteenth embodiment the invention provides a compound according to the eighteenth embodiment wherein Y is optionally substituted benzo[b]azepinyl, optionally substituted benzo[d]imidazolyl, optionally substituted benzo[b][1,4]oxazinyl, optionally substituted benzo[d]isothiazolyl, optionally substituted benzo[d]oxazolyl, optionally substituted benzo[b][1,4]thiazinyl, optionally substituted benzo[d]thiazolyl, optionally substituted benzo[c]thiophenyl, optionally substituted chromanyl, optionally substituted chromenyl, optionally substituted dihydrobenzo[b]azepinyl, optionally substituted dihydroquinolinyl, optionally substituted imidazo[1,2-a]pyridinyl, optionally substituted indazolyl, optionally substituted indolinyl, optionally substituted isoquinolinyl, optionally substituted phenyl, optionally substituted pyrazolyl, optionally substituted quinolinyl, optionally substituted tetrahydroisoquinolinyl, or optionally substituted tetrahydro-1,6-naphthyridinyl.

In a twentieth embodiment the invention provides a compound according to the nineteenth embodiment wherein Z is H, —CN, —N(H)-tetrahydropyranyl, —C(O)N(H)-optionally substituted $(C_1-C_3)$alkylene, —C(O)N(H)-optionally substituted $(C_3-C_6)$cycloalkylene, —C(O)-morpholinyl, —N(H)C(O)-optionally substituted $(C_1-C_3)$alkyl, —N(CH$_3$)C(O)-optionally substituted $(C_1-C_3)$alkyl, —O-optionally substituted $(C_1-C_3)$alkyl, —S(O)$_2$-optionally substituted $(C_1-C_3)$alkyl, —S(O)$_2$—N(H) optionally substituted $(C_1-C_4)$alkyl, —S(O)$_2$NH$_2$, —S(O)$_2$N(H)-pyridinyl, optionally substituted $(C_1-C_3)$alkyl, optionally substituted morpholinyl, optionally substituted piperazinyl, optionally substituted pyridinyl, -optionally substituted $(C_1-C_3)$alkylene-optionally substituted morpholinyl, or optionally substituted pyridinyl.

In a twenty-first embodiment the invention provides a compound according to the twentieth embodiment wherein the compound is
N4-cyclopropyl-N2-(3-methyl-1H-indazol-6-yl)furo[3,2-d]pyrimidine-2,4-diamine;
2,2-dimethyl-6-(4-((3-methyloxetan-3-yl)methylamino)furo[3,2-d]pyrimidin-2-ylamino)-2H-benzo[b][1,4]oxazin-3(4H)-one;
N4-cyclopropyl-N2-(3-(pyridin-4-yl)-1H-indazol-6-yl)furo[3,2-d]pyrimidine-2,4-diamine;
6-(4-(cyclopropylamino)furo[3,2-d]pyrimidin-2-ylamino)-1H-indazole-3-carbonitrile;
N-cyclopropyl-6-(4-(cyclopropylamino)furo[3,2-d]pyrimidin-2-ylamino)-1H-indazole-3-carboxamide;
N4-allyl-N4-methyl-N2-(3-methyl-1H-indazol-6-yl)furo[3,2-d]pyrimidine-2,4-diamine;
7-(4-(2,2-difluoroethylamino)furo[3,2-d]pyrimidin-2-ylamino)-3,4-dihydroquinolin-2(1H)-one;
3-(2-(2,2-dimethyl-3-oxo-3,4-dihydro-2H-benzo[b][1,4]oxazin-6-ylamino)furo[3,2-d]pyrimidin-4-ylamino)propanamide;
6-(4-(2,2-difluoroethylamino)furo[3,2-d]pyrimidin-2-ylamino)-2,2-dimethyl-2H-benzo[b][1,4]oxazin-3(4H)-one;
N4-cyclopropyl-N2-(4-methyl-1H-indazol-6-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
N4-cyclopropyl-N2-(3-(tetrahydro-2H-pyran-4-ylamino)-1H-indazol-6-yl)furo[3,2-d]pyrimidine-2,4-diamine;
(S)-7-(4-(cyclopropylamino)furo[3,2-d]pyrimidin-2-ylamino)-3-methyl-3,4-dihydroquinolin-2(1H)-one;
(R)-7-(4-(cyclopropylamino)furo[3,2-d]pyrimidin-2-ylamino)-3-methyl-3,4-dihydroquinolin-2(1H)-one;
N4-cyclopropyl-N2-(1H-indazol-6-yl)furo[3,2-d]pyrimidine-2,4-diamine 2,2,2-trifluoroacetate;
N-propyl-4-(4-(2,2,2-trifluoroethylamino)furo[3,2-d]pyrimidin-2-ylamino)benzamide;
N2-(3-chloro-4-(4-methylpiperazin-1-yl)phenyl)-N4-cyclopropylfuro[3,2-d]pyrimidine-2,4-diamine;
N4-allyl-N2-(4-(methylsulfonyl)phenyl)furo[3,2-d]pyrimidine-2,4-diamine;
N2-(3-chloro-4-morpholinophenyl)-N4-cyclopropylfuro[3,2-d]pyrimidine-2,4-diamine;
4-(4-(cyclopropylamino)furo[3,2-d]pyrimidin-2-ylamino)benzenesulfonamide;
4-(4-(cyclopropylamino)furo[3,2-d]pyrimidin-2-ylamino)benzenesulfonamide bis(2,2,2-trifluoroacetate);
4-(4-(cyclopropylamino)furo[3,2-d]pyrimidin-2-ylamino)-N-propylbenzamide;
N*4*-cyclopropyl-N*2*-(2,2-dioxo-2,3-dihydro-1H-2lambda*6*-benzo[c]thiophen-5-yl)-furo[3,2-d]pyrimidine-2,4-diamine;
N4-cyclopropyl-N2-(4-(morpholinomethyl)phenyl)furo[3,2-d]pyrimidine-2,4-diamine;
1-(4-(4-(4-(cyclopropylamino)furo[3,2-d]pyrimidin-2-ylamino)phenyl)piperazin-1-yl)ethanone;
N*4*-cyclopropyl-N*2*-(1,1-dioxo-2,3-dihydro-1H-1lambda*6*-benzo[d]isothiazol-6-yl)-uro[3,2-d]pyrimidine-2,4-diamine;
6-(4-cyclopropylamino-furo[3,2-d]pyrimidin-2-ylamino)-1,1-dioxo-1,2-dihydro-1lambda*6*-benzo[d]isothiazol-3-one;
4-(4-(cyclobutylamino)furo[3,2-d]pyrimidin-2-ylamino)benzenesulfonamide;
N4-cyclopropyl-N2-(1-methyl-1H-pyrazol-4-yl)furo[3,2-d]pyrimidine-2,4-diamine;
(1R,2S)-2-(2-(4-sulfamoylphenylamino)furo[3,2-d]pyrimidin-4-ylamino)cyclopentanecarboxamide;
6-(4-(cyclopropylamino)furo[3,2-d]pyrimidin-2-ylamino)-3,4-dihydroquinolin-2(1H)-one;
(1R,2R,3S,4S)-3-(2-(4-sulfamoylphenylamino)furo[3,2-d]pyrimidin-4-ylamino)bicyclo[2.2.1]hept-5-ene-2-carboxamide;
N4-((1R,3S)-3-aminocyclopentyl)-N2-(3-methyl-1H-indazol-6-yl)furo[3,2-d]pyrimidine-2,4-diamine;
N4-((1S,3R)-3-aminocyclopentyl)-N2-(3-methyl-1H-indazol-6-yl)furo[3,2-d]pyrimidine-2,4-diamine;
2,2-dimethyl-6-(4-(methylamino)furo[3,2-d]pyrimidin-2-ylamino)-2H-benzo[b][1,4]oxazin-3(4H)-one;
6-(4-(isopropylamino)furo[3,2-d]pyrimidin-2-ylamino)-2,2-dimethyl-2H-benzo[b][1,4]oxazin-3(4H)-one;
7-(4-(cyclopropylamino)furo[3,2-d]pyrimidin-2-ylamino)-3,4-dihydroquinolin-2(1H)-one;
7-(4-(cyclopropylamino)furo[3,2-d]pyrimidin-2-ylamino)-3-methyl-3,4-dihydroquinolin-2(1H)-one;
N2-(3-methyl-1H-indazol-6-yl)-N4-(4,5,6,7-tetrahydro-1H-indazol-6-yl)furo[3,2-d]pyrimidine-2,4-diamine;

N4-(3,3-difluorocyclobutyl)-N2-(3-methyl-1H-indazol-6-yl)furo[3,2-d]pyrimidine-2,4-diamine;
N4-(3,3-difluorocyclobutyl)-N2-(3-methyl-1H-indazol-6-yl)furo[3,2-d]pyrimidine-2,4-diamine;
N4-cyclobutyl-N2-(3-methyl-1H-indazol-6-yl)furo[3,2-d]pyrimidine-2,4-diamine;
7-(4-(cyclobutylamino)furo[3,2-d]pyrimidin-2-ylamino)-3,4-dihydroquinolin-2(1H)-one;
6-(4-(cyclobutylamino)furo[3,2-d]pyrimidin-2-ylamino)-3,3-dimethylindolin-2-one;
7-(4-(cyclobutylamino)furo[3,2-d]pyrimidin-2-ylamino)-3,3-dimethyl-3,4-dihydroquinolin-2(1H)-one;
7-(4-(cyclobutylamino)furo[3,2-d]pyrimidin-2-ylamino)-3-methyl-3,4-dihydroquinolin-2(1H)-one;
7-(4-(isobutylamino)furo[3,2-d]pyrimidin-2-ylamino)-3,4-dihydroquinolin-2(1H)-one;
N2-(3-methyl-1H-indazol-6-yl)-N4-propylfuro[3,2-d]pyrimidine-2,4-diamine;
7-(4-(propylamino)furo[3,2-d]pyrimidin-2-ylamino)-3,4-dihydroquinolin-2(1H)-one;
3,3-dimethyl-7-(4-(propylamino)furo[3,2-d]pyrimidin-2-ylamino)-3,4-dihydroquinolin-2(1H)-one;
8-(4-(propylamino)furo[3,2-d]pyrimidin-2-ylamino)-4,5-dihydro-1H-benzo[b]azepin-2(3H)-one;
2-methyl-2-(4-(4-(propylamino)furo[3,2-d]pyrimidin-2-ylamino)phenyl)propanenitrile;
7-(4-(isobutylamino)furo[3,2-d]pyrimidin-2-ylamino)-3,3-dimethyl-3,4-dihydroquinolin-2(1H)-one;
8-(4-(isobutylamino)furo[3,2-d]pyrimidin-2-ylamino)-4,5-dihydro-1H-benzo[b]azepin-2(3H)-one;
2-(4-(4-(isobutylamino)furo[3,2-d]pyrimidin-2-ylamino)phenyl)-2-methylpropanenitrile;
N-(4-(4-(cyclobutylamino)furo[3,2-d]pyrimidin-2-ylamino)phenyl)-N-methylacetamide;
N-(4-(4-(cyclobutylamino)furo[3,2-d]pyrimidin-2-ylamino)phenyl)butyramide;
N2-(3-chloro-4-morpholinophenyl)-N4-cyclobutylfuro[3,2-d]pyrimidine-2,4-diamine;
N4-cyclobutyl-N2-(1H-indazol-6-yl)furo[3,2-d]pyrimidine-2,4-diamine;
N-(4-(4-(cyclopropylamino)furo[3,2-d]pyrimidin-2-ylamino)phenyl)-N-methylacetamide;
6-(4-(cyclobutylamino)furo[3,2-d]pyrimidin-2-ylamino)-3,4-dihydroquinolin-2(1H)-one;
N4-cyclopropyl-N2-(4-(piperazin-1-yl)phenyl)furo[3,2-d]pyrimidine-2,4-diamine;
N4-cyclobutyl-N2-(4-(piperazin-1-yl)phenyl)furo[3,2-d]pyrimidine-2,4-diamine;
6-(4-(cyclobutylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2H-benzo[b][1,4]oxazin-3(4H)-one;
N4-cyclopropyl-N2-(1-methyl-1H-indazol-5-yl)furo[3,2-d]pyrimidine-2,4-diamine;
4-(4-(cyclopropylamino)furo[3,2-d]pyrimidin-2-ylamino)-N-(3-methoxypropyl)benzamide;
4-(4-(cyclopropylamino)furo[3,2-d]pyrimidin-2-ylamino)-N-(3-methoxypropyl)benzenesulfonamide;
2,2-dimethyl-6-(4-(2,2,2-trifluoroethylamino)furo[3,2-d]pyrimidin-2-ylamino)-2H-benzo[b][1,4]oxazin-3(4H)-one;
N4-cyclopropyl-N2-(1-methyl-1H-indazol-6-yl)furo[3,2-d]pyrimidine-2,4-diamine;
N2-(3-chloro-4-morpholinophenyl)-N4-(2,2,2-trifluoroethyl)furo[3,2-d]pyrimidine-2,4-diamine;
N-(4-(4-(1H-indazol-6-ylamino)furo[3,2-d]pyrimidin-2-ylamino)phenyl)butyramide;
N4-cyclopropyl-N2-(1H-indol-6-yl)furo[3,2-d]pyrimidine-2,4-diamine;
N4-(3-aminopropyl)-N2-(1H-indazol-6-yl)furo[3,2-d]pyrimidine-2,4-diamine;
N4-(4-aminobutyl)-N2-(1H-indazol-6-yl)furo[3,2-d]pyrimidine-2,4-diamine;
N4-cyclopropyl-N2-(1H-indazol-5-yl)furo[3,2-d]pyrimidine-2,4-diamine;
N4-cyclopropyl-N2-(1-isopropyl-1H-indazol-5-yl)furo[3,2-d]pyrimidine-2,4-diamine;
6-(4-(cyclopropylamino)furo[3,2-d]pyrimidin-2-ylamino)-2H-benzo[b][1,4]thiazin-3(4H)-one;
N4-cyclopropyl-N2-(4-morpholinophenyl)furo[3,2-d]pyrimidine-2,4-diamine;
6-(4-(cyclopropylamino)furo[3,2-d]pyrimidin-2-ylamino)benzo[d]oxazol-2(3H)-one;
5-(4-(cyclopropylamino)furo[3,2-d]pyrimidin-2-ylamino)-1H-benzo[d]imidazol-2(3H)-one;
5-(4-(cyclopropylamino)furo[3,2-d]pyrimidin-2-ylamino)-2,3-dihydro-1H-inden-1-one;
N-(3-(4-(cyclopropylamino)furo[3,2-d]pyrimidin-2-ylamino)phenyl)acetamide;
3-(4-(cyclopropylamino)furo[3,2-d]pyrimidin-2-ylamino)benzenesulfonamide;
5-(4-(cyclopropylamino)furo[3,2-d]pyrimidin-2-ylamino)benzo[d]oxazol-2(3H)-one;
6-(4-(cyclopropylmethylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-dimethyl-2H-pyrido[3,2-b][1,4]oxazin-3(4H)-one;
6-(4-(cyclopropylamino)furo[3,2-d]pyrimidin-2-ylamino)indolin-2-one;
(3-(4-(cyclopropylamino)furo[3,2-d]pyrimidin-2-ylamino)phenyl)methanol;
N4-cyclopropyl-N2-(6-morpholinopyridin-3-yl)furo[3,2-d]pyrimidine-2,4-diamine;
6-(4-(cyclopropylamino)furo[3,2-d]pyrimidin-2-ylamino)-2,2-dimethyl-2H-benzo[b][1,4]thiazin-3(4H)-one;
N4-cyclopropyl-N2-(4-(thiomorpholine 1,1 dioxide)phenyl)furo[3,2-d]pyrimidine-2,4-diamine;
N2-(1H-benzo[d]imidazol-6-yl)-N4-cyclopropylfuro[3,2-d]pyrimidine-2,4-diamine;
N4-cyclopropyl-N2-(3-fluoro-4-(4-methylpiperazin-1-yl)phenyl)furo[3,2-d]pyrimidine-2,4-diamine;
7-(4-(cyclopropylamino)furo[3,2-d]pyrimidin-2-ylamino)-4-methylquinolin-2(1H)-one;
7-(4-(cyclopropylamino)furo[3,2-d]pyrimidin-2-ylamino)quinolin-2(1H)-one;
2,2-dimethyl-6-(4-(1-methylcyclopropylamino)furo[3,2-d]pyrimidin-2-ylamino)-2H-benzo[b][1,4]oxazin-3(4H)-one;
6-(4-(1-(hydroxymethyl)cyclopropylamino)furo[3,2-d]pyrimidin-2-ylamino)-2,2-dimethyl-2H-benzo[b][1,4]oxazin-3(4H)-one;
6-(4-(ethylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-difluoro-2H-benzo[b][1,4]oxazin-3(4H)-one;
7-(4-(cyclopropylamino)furo[3,2-d]pyrimidin-2-ylamino)-3,3-dimethyl-3,4-dihydroquinolin-2(1H)-one;
2-(4-(4-(cyclopropylamino)furo[3,2-d]pyrimidin-2-ylamino)phenyl)-2-methylpropanenitrile;
N4-cyclopropyl-N2-(1,2,3,4-tetrahydroisoquinolin-6-yl)furo[3,2-d]pyrimidine-2,4-diamine;
N4-cyclopropyl-N2-(4-isopropoxyphenyl)furo[3,2-d]pyrimidine-2,4-diamine;

N4-cyclopropyl-N2-(2-methylbenzo[d]thiazol-6-yl)furo[3,2-d]pyrimidine-2,4-diamine;
N4-cyclopropyl-N2-(2-methylquinolin-6-yl)furo[3,2-d]pyrimidine-2,4-diamine;
N4-cyclopropyl-N2-(4-isopropoxy-3-methylphenyl)furo[3,2-d]pyrimidine-2,4-diamine;
N2-(3-chloro-4-isopropoxyphenyl)-N4-cyclopropylfuro[3,2-d]pyrimidine-2,4-diamine;
N4-cyclopropyl-N2-(3-fluoro-4-isopropoxyphenyl)furo[3,2-d]pyrimidine-2,4-diamine;
7-(4-(cyclopropylamino)furo[3,2-d]pyrimidin-2-ylamino)-3-(hydroxymethyl)quinolin-2(1H)-one;
N4-cyclopropyl-N2-(2,2-dimethylchroman-6-yl)furo[3,2-d]pyrimidine-2,4-diamine;
7-(4-(cyclopropylamino)furo[3,2-d]pyrimidin-2-ylamino)-2H-chromen-2-one;
N4-cyclopropyl-N2-(2,3-dihydrobenzo[b][1,4]dioxin-6-yl)furo[3,2-d]pyrimidine-2,4-diamine;
N2-(benzo[d]oxazol-6-yl)-N4-cyclopropylfuro[3,2-d]pyrimidine-2,4-diamine;
N2-(4-(2H-1,2,3-triazol-2-yl)phenyl)-N4-cyclopropylfuro[3,2-d]pyrimidine-2,4-diamine;
7-(4-(cyclopropylamino)furo[3,2-d]pyrimidin-2-ylamino)-4,5-dihydro-1H-benzo[b]azepin-2(3H)-one;
1-(7-(4-(cyclopropylamino)furo[3,2-d]pyrimidin-2-ylamino)-4,5-dihydro-1H-benzo[d]azepin-3(2H)-yl)ethanone;
N4-cyclopropyl-N4-methyl-N2-(3-methyl-1H-indazol-6-yl)furo[3,2-d]pyrimidine-2,4-diamine;
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]hept-5-ene-2-carboxamide;
(diexo)-3-(2-(3,3-dimethyl-2-oxoindolin-6-ylamino)furo[3,2-d]pyrimidin-4-ylamino)bicyclo[2.2.1]hept-5-ene-2-carboxamide;
(diexo)-3-(2-(3-methyl-1H-indazol-6-ylamino)furo[3,2-d]pyrimidin-4-ylamino)bicyclo[2.2.1]hept-5-ene-2-carboxamide;
6,6'-(furo[3,2-d]pyrimidine-2,4-diylbis(azanediyl))bis(2,2-dimethyl-2H-benzo[b][1,4]oxazin-3(4H)-one);
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]heptane-2-carboxamide;
6-(4-(tert-butylamino)furo[3,2-d]pyrimidin-2-ylamino)-2,2-dimethyl-2H-benzo[b][1,4]oxazin-3(4H)-one;
6-(4-(diethylamino)furo[3,2-d]pyrimidin-2-ylamino)-2,2-dimethyl-2H-benzo[b][1,4]oxazin-3(4H)-one;
6-(4-(isobutylamino)furo[3,2-d]pyrimidin-2-ylamino)-3,3-dimethylindolin-2-one;
3,3-dimethyl-6-(4-(propylamino)furo[3,2-d]pyrimidin-2-ylamino)indolin-2-one;
8-(4-(cyclopropylamino)furo[3,2-d]pyrimidin-2-ylamino)-4,5-dihydro-1H-benzo[b]azepin-2(3H)-one;
N4-cyclopropyl-N2-(4-fluoro-3-methyl-1H-indazol-6-yl)furo[3,2-d]pyrimidine-2,4-diamine;
N4-cyclopropyl-N2-(4-(4-(methylsulfonyl)piperazin-1-yl)phenyl)furo[3,2-d]pyrimidine-2,4-diamine;
N2-(4-(1H-imidazol-1-yl)phenyl)-N4-cyclopropylfuro[3,2-d]pyrimidine-2,4-diamine;
6-(4-(cyclopropylethynyl)furo[3,2-d]pyrimidin-2-ylamino)-3,3-dimethylindolin-2-one;
N2-(benzo[d]isoxazol-6-yl)-N4-cyclopropylfuro[3,2-d]pyrimidine-2,4-diamine;
7-(4-(cyclopropylamino)furo[3,2-d]pyrimidin-2-ylamino)-3-methylquinolin-2(1H)-one;
6-(4-(cyclopropylamino)furo[3,2-d]pyrimidin-2-ylamino)-2,2-dimethyl-2H-benzo[b][1,4]oxazin-3(4H)-one;
6-(4-(cyclobutylamino)furo[3,2-d]pyrimidin-2-ylamino)-2H-benzo[b][1,4]oxazin-3(4H)-one;
6-(4-(cyclopropylamino)furo[3,2-d]pyrimidin-2-ylamino)-3,3-dimethylindolin-2-one;
3,3-dimethyl-6-(4-(2-methylcyclopropylamino)furo[3,2-d]pyrimidin-2-ylamino)indolin-2-one;
N2-(3-methyl-1H-indazol-6-yl)-N4-(pyridin-3-ylmethyl)furo[3,2-d]pyrimidine-2,4-diamine;
6-(4-(2,2-difluoroethylamino)furo[3,2-d]pyrimidin-2-ylamino)-3,3-dimethylindolin-2-one;
N4-(2,2-difluoroethyl)-N2-(3-methyl-1H-indazol-6-yl)furo[3,2-d]pyrimidine-2,4-diamine;
6-(4-(cyclopropylamino)furo[3,2-d]pyrimidin-2-ylamino)-N,N-dimethyl-1H-indazole-3-carboxamide;
4-(4-(cyclopropylamino)furo[3,2-d]pyrimidin-2-ylamino)benzonitrile;
N4-cyclopropyl-N2-(4-methoxyphenyl)furo[3,2-d]pyrimidine-2,4-diamine;
(6-(4-(cyclopropylamino)furo[3,2-d]pyrimidin-2-ylamino)-1H-indazol-3-yl)(morpholino)methanone;
6-(4-(cyclopropylamino)furo[3,2-d]pyrimidin-2-ylamino)-N-(2-hydroxyethyl)-1H-indazole-3-carboxamide;
2-(4-(4-(cyclopropylamino)furo[3,2-d]pyrimidin-2-ylamino)phenyl)acetonitrile;
4-(4-(cyclopropylamino)furo[3,2-d]pyrimidin-2-ylamino)-N-(pyridin-2-yl)benzenesulfonamide;
N4-cyclopropyl-N2-(4-(pyridin-4-yl)phenyl)furo[3,2-d]pyrimidine-2,4-diamine;
8-(4-cyclobutoxyfuro[3,2-d]pyrimidin-2-ylamino)-4,5-dihydro-1H-benzo[b]azepin-2(3H)-one;
4-cyclobutoxy-N-(3-methyl-1H-indazol-6-yl)furo[3,2-d]pyrimidin-2-amine;
7-(4-cyclobutoxyfuro[3,2-d]pyrimidin-2-ylamino)-3,4-dihydroquinolin-2(1H)-one;
N4-allyl-N2-(quinolin-4-yl)furo[3,2-d]pyrimidine-2,4-diamine;
6-(4-(piperidin-4-ylmethylamino)furo[3,2-d]pyrimidin-2-ylamino)-2H-benzo[b][1,4]oxazin-3(4H)-one;
N-(4-(4-(piperidin-4-ylmethylamino)furo[3,2-d]pyrimidin-2-ylamino)phenyl)butyramide;
N4-cyclopropyl-N2-(isoquinolin-1-yl)furo[3,2-d]pyrimidine-2,4-diamine;
N2-(1H-indazol-6-yl)-N4-(piperidin-4-ylmethyl)furo[3,2-d]pyrimidine-2,4-diamine;
N4-cyclopropyl-N2-(1-methyl-1H-indazol-3-yl)furo[3,2-d]pyrimidine-2,4-diamine;
N4-cyclopropyl-N2-(imidazo[1,2-a]pyridin-3-yl)furo[3,2-d]pyrimidine-2,4-diamine;
6-(4-(piperidin-4-ylmethylamino)furo[3,2-d]pyrimidin-2-ylamino)-3,4-dihydroquinolin-2(1H)-one;
2,2-dimethyl-6-(4-(piperidin-4-ylmethylamino)furo[3,2-d]pyrimidin-2-ylamino)-2H-benzo[b][1,4]oxazin-3(4H)-one;
N-methyl-N-(4-(4-(piperidin-4-ylmethylamino)furo[3,2-d]pyrimidin-2-ylamino)phenyl)acetamide;
N4-cyclopropyl-N2-(isoquinolin-4-yl)furo[3,2-d]pyrimidine-2,4-diamine;
N4-cyclopropyl-N2-(quinolin-4-yl)furo[3,2-d]pyrimidine-2,4-diamine;
1-(4-(4-(4-((1H-imidazol-2-yl)methylamino)furo[3,2-d]pyrimidin-2-ylamino)phenyl)piperazin-1-yl)ethanone;
N4-cyclopropyl-N2-(2-methyl-2H-indazol-6-yl)furo[3,2-d]pyrimidine-2,4-diamine;
N4-cyclopropyl-N2-(3-methyl-1H-indazol-5-yl)furo[3,2-d]pyrimidine-2,4-diamine;
N4-(3-amino-2,2-dimethylpropyl)-N2-(1H-indazol-6-yl)furo[3,2-d]pyrimidine-2,4-diamine;

N4-((1r,4r)-4-aminocyclohexyl)-N2-(3-methyl-1H-indazol-6-yl)furo[3,2-d]pyrimidine-2,4-diamine;
(R)—N2-(3-methyl-1H-indazol-6-yl)-N4-(piperidin-3-yl)furo[3,2-d]pyrimidine-2,4-diamine;
N2-(3-methyl-1H-indazol-6-yl)-N4-(oxetan-3-yl)furo[3,2-d]pyrimidine-2,4-diamine;
6-(4-(cyclopropylamino)furo[3,2-d]pyrimidin-2-ylamino)-4-methyl-2H-benzo[b][1,4]oxazin-3(4H)-one;
N4-cyclopropyl-N2-(3-(pyridin-4-yl)phenyl)furo[3,2-d]pyrimidine-2,4-diamine;
2,2-dimethyl-6-(4-(piperidin-3-ylmethylamino)furo[3,2-d]pyrimidin-2-ylamino)-2H-benzo[b][1,4]oxazin-3(4H)-one;
N4-cyclopropyl-N2-(3-morpholinophenyl)furo[3,2-d]pyrimidine-2,4-diamine;
(S)—N2-(3-methyl-1H-indazol-6-yl)-N4-(piperidin-3-yl)furo[3,2-d]pyrimidine-2,4-diamine;
N4-cyclopropyl-N2-(5,6,7,8-tetrahydro-1,6-naphthyridin-3-yl)furo[3,2-d]pyrimidine-2,4-diamine;
N-(4-(4-(cyclopropylamino)furo[3,2-d]pyrimidin-2-ylamino)-2-methoxyphenyl)-2-morpholinoacetamide; or
6-(4-(cyclopropylamino)furo[3,2-d]pyrimidin-2-ylamino)-2H-pyrido[3,2-b][1,4]oxazin-3(4H)-one.

In a twenty-second embodiment the invention provides a compound according to the seventeenth embodiment wherein $R^1$ is $N(R^a)(R^b)$, or —$OR^b$; wherein
$R^a$ is H or optionally substituted $(C_1-C_6)$alkyl; and
$R^b$ is optionally substituted $(C_1-C_6)$alkyl, optionally substituted $(C_3-C_6)$cycloalkyl, optionally substituted bridged saturated or partially unsaturated $(C_5-C_{12})$cycloalkyl, or optionally substituted $(C_1-C_{10})$heteroaryl.

In a twenty-third embodiment the invention provides a compound according to the twenty-second embodiment wherein
$R^a$ is H; and
$R^b$ is optionally substituted $(C_1-C_6)$alkyl, optionally substituted cyclopropyl, optionally substituted cyclobutyl, optionally substituted bicycle[2.2.1]heptenyl, optionally substituted bicycle[2.2.1]heptanyl, or optionally substituted indazolyl.

In a twenty-fourth embodiment the invention provides a compound according to the twenty-third embodiment wherein Y is optionally substituted benzo[b]azepinyl, optionally substituted benzo[b][1,4]oxazinyl, optionally substituted benzo[b][1,4]thiazinyl, optionally substituted benzo[c]thiophenyl, optionally substituted dihydroquinolinyl, optionally substituted indazolyl, optionally substituted indolinyl, optionally substituted phenyl, optionally substituted quinolinyl, or optionally substituted tetrahydroisoquinolinyl.

In a twenty-fifth embodiment the invention provides a compound according to the twenty-fourth embodiment wherein Z is H, —CN, —C(O)N(H)-optionally substituted cyclopropyl, —C(O)-optionally substituted $(C_1-C_3)$alkyl, —N(H)C(O)-optionally substituted $(C_1-C_3)$alkyl, —S(O)$_2$NH$_2$, optionally substituted $(C_1-C_3)$alkyl, optionally substituted morpholinyl, optionally substituted piperazinyl, —CH$_2$-optionally substituted morpholinyl, or optionally substituted pyridinyl.

In a twenty-sixth embodiment the invention provides a compound according to the twenty-fifth embodiment wherein the compound is
N4-cyclopropyl-N2-(3-methyl-1H-indazol-6-yl)furo[3,2-d]pyrimidine-2,4-diamine;
N4-cyclopropyl-N2-(3-(pyridin-4-yl)-1H-indazol-6-yl)furo[3,2-d]pyrimidine-2,4-diamine;
6-(4-(cyclopropylamino)furo[3,2-d]pyrimidin-2-ylamino)-1H-indazole-3-carbonitrile;
N-cyclopropyl-6-(4-(cyclopropylamino)furo[3,2-d]pyrimidin-2-ylamino)-1H-indazole-3-carboxamide;
N4-cyclopropyl-N2-(4-methyl-1H-indazol-6-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
(S)-7-(4-(cyclopropylamino)furo[3,2-d]pyrimidin-2-ylamino)-3-methyl-3,4-dihydroquinolin-2(1H)-one;
(R)-7-(4-(cyclopropylamino)furo[3,2-d]pyrimidin-2-ylamino)-3-methyl-3,4-dihydroquinolin-2(1H)-one;
N4-cyclopropyl-N2-(1H-indazol-6-yl)furo[3,2-d]pyrimidine-2,4-diamine 2,2,2-trifluoroacetate;
N2-(3-chloro-4-(4-methylpiperazin-1-yl)phenyl)-N4-cyclopropylfuro[3,2-d]pyrimidine-2,4-diamine;
N2-(3-chloro-4-morpholinophenyl)-N4-cyclopropylfuro[3,2-d]pyrimidine-2,4-diamine;
4-(4-(cyclopropylamino)furo[3,2-d]pyrimidin-2-ylamino)benzenesulfonamide;
4-(4-(cyclopropylamino)furo[3,2-d]pyrimidin-2-ylamino)benzenesulfonamide bis(2,2,2-trifluoroacetate);
N*4*-cyclopropyl-N*2*-(2,2-dioxo-2,3-dihydro-1H-2lambda*6*-benzo[c]thiophen-5-yl)-furo[3,2-d]pyrimidine-2,4-diamine;
N4-cyclopropyl-N2-(1H-indazol-6-yl)furo[3,2-d]pyrimidine-2,4-diamine 2,2,2-trifluoroacetate;
(1R,2R,3S,4S)-3-(2-(4-sulfamoylphenylamino)furo[3,2-d]pyrimidin-4-ylamino)bicyclo[2.2.1]hept-5-ene-2-carboxamide;
7-(4-(cyclopropylamino)furo[3,2-d]pyrimidin-2-ylamino)-3,4-dihydroquinolin-2(1H)-one;
7-(4-(cyclopropylamino)furo[3,2-d]pyrimidin-2-ylamino)-3-methyl-3,4-dihydroquinolin-2(1H)-one;
N4-cyclobutyl-N2-(3-methyl-1H-indazol-6-yl)furo[3,2-d]pyrimidine-2,4-diamine;
7-(4-(cyclobutylamino)furo[3,2-d]pyrimidin-2-ylamino)-3,4-dihydroquinolin-2(1H)-one;
6-(4-(cyclobutylamino)furo[3,2-d]pyrimidin-2-ylamino)-3,3-dimethylindolin-2-one;
7-(4-(cyclobutylamino)furo[3,2-d]pyrimidin-2-ylamino)-3-methyl-3,4-dihydroquinolin-2(1H)-one;
N2-(3-methyl-1H-indazol-6-yl)-N4-propylfuro[3,2-d]pyrimidine-2,4-diamine;
7-(4-(propylamino)furo[3,2-d]pyrimidin-2-ylamino)-3,4-dihydroquinolin-2(1H)-one;
2-methyl-2-(4-(4-(propylamino)furo[3,2-d]pyrimidin-2-ylamino)phenyl)propanenitrile;
N2-(3-chloro-4-morpholinophenyl)-N4-cyclobutylfuro[3,2-d]pyrimidine-2,4-diamine;
N4-cyclobutyl-N2-(1H-indazol-6-yl)furo[3,2-d]pyrimidine-2,4-diamine;
N-(4-(4-(4-(aminomethyl)piperidin-1-yl)furo[3,2-d]pyrimidin-2-ylamino)phenyl)-N-methylacetamide;
6-(4-(cyclobutylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2H-benzo[b][1,4]oxazin-3(4H)-one;
N4-cyclopropyl-N2-(1-methyl-1H-indazol-5-yl)furo[3,2-d]pyrimidine-2,4-diamine;
N2-(3-chloro-4-morpholinophenyl)-N4-(2,2,2-trifluoroethyl)furo[3,2-d]pyrimidine-2,4-diamine;
N-(4-(4-(1H-indazol-6-ylamino)furo[3,2-d]pyrimidin-2-ylamino)phenyl)butyramide;
N4-(4-aminobutyl)-N2-(1H-indazol-6-yl)furo[3,2-d]pyrimidine-2,4-diamine;
6-(4-(cyclopropylamino)furo[3,2-d]pyrimidin-2-ylamino)-2H-benzo[b][1,4]thiazin-3(4H)-one;

7-(4-(cyclopropylamino)furo[3,2-d]pyrimidin-2-ylamino)-4-methylquinolin-2(1H)-one;

7-(4-(cyclopropylamino)furo[3,2-d]pyrimidin-2-ylamino)quinolin-2(1H)-one;

6-(4-(ethylamino)furo[3,2-d]pyrimidin-2-ylamino)-2,2-dimethyl-2H-benzo[b][1,4]oxazin-3(4H)-one;

6-(4-(cyclopropylamino)furo[3,2-d]pyrimidin-2-ylamino)-2,2-difluoro-2H-benzo[b][1,4]oxazin-3(4H)-one;

7-(4-(cyclopropylamino)furo[3,2-d]pyrimidin-2-ylamino)-3,3-dimethyl-3,4-dihydroquinolin-2 (1H)-one;

2-(4-(4-(cyclopropylamino)furo[3,2-d]pyrimidin-2-ylamino)phenyl)-2-methylpropanenitrile;

2-(4-(4-(cyclopropylamino)furo[3,2-d]pyrimidin-2-ylamino)phenyl)-2-methylpropanenitrile;

7-(4-(cyclopropylamino)furo[3,2-d]pyrimidin-2-ylamino)-3-(hydroxymethyl)quinolin-2(1H)-one;

7-(4-(cyclopropylamino)furo[3,2-d]pyrimidin-2-ylamino)-2H-chromen-2-one;

7-(4-(cyclopropylamino)furo[3,2-d]pyrimidin-2-ylamino)-4,5-dihydro-1H-benzo[b]azepin-2(3H)-one;

1-(7-(4-(cyclopropylamino)furo[3,2-d]pyrimidin-2-ylamino)-4,5-dihydro-1H-benzo[d]azepin-3 (2H)-yl)ethanone;

(diexo)-3-(2-(3,3-dimethyl-2-oxoindolin-6-ylamino)furo[3,2-d]pyrimidin-4-ylamino)bicyclo[2.2.1]hept-5-ene-2-carboxamide;

(diexo)-3-(2-(3-methyl-1H-indazol-6-ylamino)furo[3,2-d]pyrimidin-4-ylamino)bicyclo[2.2.1]hept-5-ene-2-carboxamide;

6,6'-(furo[3,2-d]pyrimidine-2,4-diylbis(azanediyl))bis(2,2-dimethyl-2H-benzo[b][1,4]oxazin-3 (4H)-one);

(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]heptane-2-carboxamide, Acetic Acid;

6-(4-(isobutylamino)furo[3,2-d]pyrimidin-2-ylamino)-3,3-dimethylindolin-2-one;

3,3-dimethyl-6-(4-(propylamino)furo[3,2-d]pyrimidin-2-ylamino)indolin-2-one;

8-(4-(cyclopropylamino)furo[3,2-d]pyrimidin-2-ylamino)-4,5-dihydro-1H-benzo[b]azepin-2(3H)-one;

N4-cyclopropyl-N2-(4-(4-(methylsulfonyl)piperazin-1-yl)phenyl)furo[3,2-d]pyrimidine-2,4-diamine;

N2-(benzo[d]isoxazol-6-yl)-N4-cyclopropylfuro[3,2-d]pyrimidine-2,4-diamine;

7-(4-(cyclopropylamino)furo[3,2-d]pyrimidin-2-ylamino)-3-methylquinolin-2(1H)-one;

6-(4-(cyclopropylamino)furo[3,2-d]pyrimidin-2-ylamino)-2,2-dimethyl-2H-benzo[b][1,4]oxazin-3(4H)-one;

6-(4-(cyclopropylamino)furo[3,2-d]pyrimidin-2-ylamino)-3,3-dimethylindolin-2-one;

3,3-dimethyl-6-(4-(2-methylcyclopropylamino)furo[3,2-d]pyrimidin-2-ylamino)indolin-2-one;

6-(4-(2,2-difluoroethylamino)furo[3,2-d]pyrimidin-2-ylamino)-3,3-dimethylindolin-2-one;

N4-(2,2-difluoroethyl)-N2-(3-methyl-1H-indazol-6-yl)furo[3,2-d]pyrimidine-2,4-diamine;

6-(4-(cyclopropylamino)furo[3,2-d]pyrimidin-2-ylamino)-N,N-dimethyl-1H-indazole-3-carboxamide;

(6-(4-(cyclopropylamino)furo[3,2-d]pyrimidin-2-ylamino)-1H-indazol-3-yl)(morpholino)methanone;

2-(4-(4-(cyclopropylamino)furo[3,2-d]pyrimidin-2-ylamino)phenyl)acetonitrile;

8-(4-cyclobutoxyfuro[3,2-d]pyrimidin-2-ylamino)-4,5-dihydro-1H-benzo[b]azepin-2(3H)-one;

4-cyclobutoxy-N-(3-methyl-1H-indazol-6-yl)furo[3,2-d]pyrimidin-2-amine; or 7-(4-cyclobutoxyfuro[3,2-d]pyrimidin-2-ylamino)-3,4-dihydroquinolin-2(1H)-one.

In a twenty-seventh embodiment the invention provides a method of treating a patient having a condition which is mediated by protein kinase activity, said method comprising the step of administering to the patient a therapeutically effective amount of a compound according to any of the foregoing embodiments or a pharmaceutically acceptable salt, pro-drug or biologically active metabolite thereof.

In a twenty-eighth embodiment the invention provides a method according to the twenty-seventh embodiment wherein the protein kinase is selected from the group consisting of Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, Syk, PKC and Aurora kinases.

In a twenty-ninth embodiment the invention provides a method according to the twenty-seventh embodiment wherein the condition is selected from cancer, cardiovascular disorders, central nervous system disorders, immunological disorders, an ocular condition, a cancer, rheumatoid arthritis, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, a diabetic condition, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, senile chorea, senile dementia of Lewy body type, shock, skin allograft, skin changes syndrome, vitritis, restenosis, ischemia/reperfusion injury, ischemic stroke, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, primary sclerosing cholangitis, psoriasis type 1, psoriasis type 2, idiopathic leucopaenia, autoimmune neutropaenia, renal disease NOS, glomerulonephritides, microscopic vasulitis of the kidneys, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example retinopathy of prematurity, choroidal neovascularization due to age-related macular degeneration, infantile hemangiomas in human beings, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

In a thirtieth embodiment the invention provides a method according to the twenty-ninth embodiment wherein the cancer is a solid tumor, a sarcoma, fibrosarcoma, osteoma, melanoma, retinoblastoma, rhabdomyosarcoma, glioblastoma, neuroblastoma, teratocarcinoma, an hematopoietic malignancy, malignant ascites, Kaposi's sarcoma, Hodgkin's disease, lymphoma, myeloma, leukemia, hematopoietic cancers, malignancies.

In a thirty-first embodiment the invention provides a method according to the twenty-ninth embodiment wherein the cardiovascular disorder is acute myocardial infarction, acute coronary syndrome, chronic heart failure, myocardial infarction, atherosclerosis, viral myocarditis, cardiac allograft rejection, valvular heart diseases, vascular occlusion, carotid obstructive disease, regular narrow QRS tachycardia, renovascular hypertension, restrictive cardiomyopathy, or sepsis-associated cardiac dysfunction.

In a thirty-second embodiment the invention provides a method according to the twenty-ninth embodiment wherein the central nervous system disorder is meningococcal meningitis, Alzheimer's disease or Parkinson's disease.

In a thirty-third embodiment the invention provides a method according to the twenty-ninth embodiment wherein the immunological disorder is rheumatoid arthritis, asthma, allergic asthma, osteoarthritis, juvenile arthritis, juvenile rheumatoid arthritis, ankylosing spondylitis, psoriasis, psoriatic arthritis, Crohn's Disease, ulcerative colitis, or inflammatory bowel disease.

In a thirty-fourth embodiment the invention provides a method according to the twenty-ninth embodiment wherein the ocular condition is ocular or macular edema, ocular neovascular disease, scleritis, radial keratotomy, uveitis, myopia, optic pits, chronic retinal detachment, post-laser treatment complications, conjunctivitis, Stargardt's disease, Eales disease, retinopathy, or macular degeneration.

In a thirty-fifth embodiment the invention provides a method according to the twenty-ninth embodiment wherein the diabetic condition is insulin-dependent diabetes mellitus glaucoma, diabetic retinopathy, diabetes, diabetes mellitus, insulin dependent diabetes mellitus, or microangiopathy.

In a thirty-sixth embodiment the invention provides a pharmaceutical composition comprising a compound of Formula (I) and a pharmaceutically acceptable carrier or excipient.

DETAILED DESCRIPTION OF THE INVENTION

Protein kinases are a broad and diverse class of over 500 enzymes that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

Spleen tyrosine kinase (Syk) is a 72 kDa non-receptor protein tyrosine kinase that functions as a key signaling regulator in most hematopoietic cells. Its closest homolog is zeta-associated protein 70 (ZAP-70). Like ZAP-70, full-length Syk carries two N-terminal SH2 domains. These domains allow Syk to bind di-phosphorylated immunoreceptor tyrosine-based activation motifs (ITAMS) on the intercellular portion of a variety of receptors involved in immune regulation. Upon activation and recruitment to immunoreceptors, Syk phosphorylates a variety of cellular proteins including Linker for Activator of T-cells (LAT), B-cell Linker (BLNK), Vav, Bruton's Tyrosine Kinase, Gab, Bcap, SH2-domain containing Leukocyte Protein-76 (SLP-76) and Phospholipase Cγ.

In B-cells, Syk is essentially involved in B-cell Receptor (BCR) signal initiation, leading to development and survival of B lymphocytes in both bone marrow and periphery (Cheng et al. 1995, *Nature* 378:3003; Turner et al. 1995 *Nature* 378: 298). It is activated by the Src-family kinase Lyn after Syk binds to doubly phosphorylated ITAMs on Igα/β chains on the BCR. The downstream effects of BCR engagement include $Ca^{2+}$ flux, mitogen-activated protein (MAP) kinase activation & Akt activation. Signaling through the BCR is critical for development and survival of B lymphocytes in both bone marrow and periphery.

In mast cells and basophils, Syk is a critical component of FcεR1 signaling where downstream effects of activation include degranulation, release of cytokines such a tumor necrosis factor α and interleukin-6 and release of lipid mediators such as LTC4 (Costello et al. 1996 *Oncogene* 13:2595). Similar Syk-dependent signaling is driven by IgG-antigen crosslinking via Fcγ receptors in macrophages, neutrophils & dendritic cells (Kiefer et al. 1998 *Mol Cell Biol* 18: 4209; Sedlik et al. 2003 *J. Immun.* 170:846). In macrophages, Syk activity is believed to regulate phagocytosis of opsonized foreign (and self) antigens via the FcγR, and Syk is important for antigen presentation from and maturation of dendritic cells. A role for Syk has been proposed for osteoclast maturation and in DAP12 receptor signaling in these cell types involved in bone metabolism. Reviews of these finding can be found in *Expert Opin. Invest. Drugs,* 2004, 13(7), 743 and *Expert Opin. Invest. Drugs,* 2008, 17(5), 641.

Therefore, Syk inhibition offers an opportunity to affect multiple cell types involved in inflammation, and it could be predicted to serve as therapy for autoimmune diseases including rheumatoid arthritis, asthma, systemic lupus erythematosus (SLE), and multiple sclerosis.

The Jak family kinases (Jak1, Jak2, Jak3 and Tyk2) are cytoplasmic tyrosine kinases that associate with membrane bound cytokine receptors. Cytokine binding to their receptor initiates Jak kinase activation via trans and autophosphorylation processes. The activated Jak kinases phosphorylate residues on the cytokine receptors creating phosphotyrosine binding sites for SH2 domain containing proteins such as Signal Transduction Activators of Transcript (STAT) factors and other signal regulators transduction such as SOCS proteins and SHIP phosphatases. Activation of STAT factors via this process leads to their dimerization, nuclear translocation and new mRNA transcription resulting in expression of immunocyte proliferation and survival factors as well as additional cytokines, chemokines and molecules that facilitate cellular trafficking (see *Journal of Immunology,* 2007, 178, p. 2623). Jak kinases transduce signals for many different cytokine families and hence potentially play roles in diseases with widely different pathologies including but not limited to the following examples. Both Jak1 and Jak3 control signaling of the so-called common gamma chain cytokines (IL2, IL4, IL7, IL9, IL15 and IL21), hence simultaneous inhibition of either Jak1 or Jak3 could be predicted to impact Th1 mediated diseases such as rheumatoid arthritis via blockade of IL2, IL7 and IL15 signaling and Th2 mediated diseases such as asthma or atopic dermatitis via IL4 and IL9 signaling blockade. Jak1 and Tyk2 mediate signaling of IL13 (see *Int. Immunity,* 2000, 12, p. 1499). Hence, blockade of these may also be predicted to have a therapeutic effect in asthma. These two kinases are also thought to mediate Type I interferon signaling; their blockade could therefore be predicted to reduce the severity of systemic lupus erythematosus (SLE). Tyk2 and Jak2 mediate signaling of IL12 and IL23.

Jak2 is also activated in a wide variety of human cancers such as prostate, colon, ovarian and breast cancers, melanoma, leukemia and other haematopoietic malignancies. In addition, somatic point mutation of the Jak2 gene has been identified to be highly associated with classic myeloproliferative disorders (MPD) and infrequently in other myeloid disorders. Constitutive activation of Jak2 activity is also caused by chromosomal translocation in hematopoeitic malignancies. Accordingly, the identification of small-molecule compounds that inhibit, regulate and/or modulate the signal transduction of kinases, particularly Jak2, is desirable as a means to treat or prevent diseases and conditions associated with cancers.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG. PKCtheta is a member of the nPKC sub-family (Baier, G., et al., *J. Biol. Chem.,* 1993, 268, 4997). It has a restricted expression pattern, found predominantly in T cells and skeletal muscle (Mischak, H. et al., *FEBS Lett.,* 1993, 326, p. 51), with some expression reported in mast cells (Liu, Y. et al., *J. Leukoc. Biol.,* 2001, 69, p. 831) and endothelial cells (Mattila, P. et al., *Life Sci.,* 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., *Nature,* 1997, 385, 83), placing it in proximity with other signaling enzymes that mediate T cell activation processes. In another study (Baier-Bitterlich, G. et al., *Mol. Cell. Biol.,* 1996, 16, 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., *J. Exp. Med.,* 2004, 199, p. 743; Marsland, B. J. et al., *J. Exp. Med.,* 2004, 200, p. 181). Evidence also exists that PKCtheta participates in the IgE receptor (FcεR1)-mediated response of mast cells (Liu, Y. et al., *J. Leukoc. Biol.*, 2001, 69, p. 831).

The studies cited above and other studies confirm the critical role of PKCtheta in T cells activation and in mast cell (MC) signaling. Thus an inhibitor of PKCtheta would be of therapeutic benefit in treating immunological disorders and other diseases mediated by the inappropriate activation of T cells and MC signaling.

Many of the kinases, whether a receptor or non-receptor tyrosine kinase or a serine/threonine (S/T) kinase have been found to be involved in cellular signaling pathways involved in numerous pathogenic conditions, including immunomodulation, inflammation, or proliferative disorders such as cancer.

Many autoimmune diseases and diseases associated with chronic inflammation, as well as acute responses, have been linked to excessive or unregulated production or activity of one or more cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of rheumatoid arthritis, asthma, allergic asthma, osteoarthritis, juvenile arthritis, juvenile rheumatoid arthritis, ankylosing spondylitis, an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma, edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-IRA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1R1, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SC10-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1βmonoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, p38 or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1R1, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I), can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I), may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RI, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874, D2E7 (U.S. Pat. No. 6,090,382; HUMIRA™), and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by ($C_1$-$C_4$)alkyl, ($C_1$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino ($C_2$-$C_3$) alkyl.

Other exemplary pro-drugs release an alcohol of Formula (I) wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_{12}$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

As used herein, the term "($C_5$-$C_{12}$)carbocyclic bridged ring" means a saturated or unsaturated, bicyclic or polycyclic bridged hydrocarbon group having two or three $C_3$-$C_{10}$ cycloalkyl rings. Non bridged cycloalkyls are excluded. Bridged cycloalkyls may include moieties such as bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "($C_2$-$C_{10}$)heterocyclic bridged ring" means bicyclic or polycyclic aza-bridged hydrocarbon groups and may include azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, and azabicyclo[3.3.1]nonanyl.

The term "heterocyclic", "heterocyclyl" or "heterocyclylene", as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 4 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b; 2',3'-d]pyridinyl, 6H-3-thia-2,5,6-triaza-as-indacenyl or 1,6-dihydroimidazo[4,5-d]pyrrolo[2,3-b]pyridine.

As used herein, "alkyl" or "alkylene" include straight chained or branched hydrocarbons which are completely saturated. Examples of alkyls are methyl, ethyl, propyl, isopropyl, butyl, pentyl, hexyl and isomers thereof. As used herein, "alkenyl", "alkenylene", "alkynylene" and "alkynyl" means $C_2$-$C_8$ and includes straight chained or branched hydrocarbons which contain one or more units of unsaturation, one or more double bonds for alkenyl and one or more triple bonds for alkynyl.

As used herein, "aryl" or "arylene" groups include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that is completely saturated or has one or more unsaturated bonds but does not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: $(C_1-C_8)$alkyl groups, $(C_2-C_8)$alkenyl groups, $(C_2-C_8)$alkynyl groups, $(C_3-C_{10})$cycloalkyl groups, halogen (F, Cl, Br or I), halogenated $(C_1-C_8)$alkyl groups (for example but not limited to —$CF_3$), —O—$(C_1-C_8)$alkyl groups, —OH, —S—$(C_1-C_8)$alkyl groups, —SH, —NH$(C_1-C_8)$alkyl groups, —N$((C_1-C_8)$alkyl$)_2$ groups, —$NH_2$, —C(O)$NH_2$, —C(O)NH$(C_1-C_8)$alkyl groups, —C(O)N$((C_1-C_8)$alkyl$)_2$, —NHC(O)H, —NHC(O) $(C_1-C_8)$alkyl groups, —NHC(O) $(C_3-C_8)$cycloalkyl groups, —N$((C_1-C_8)$alkyl$)$C(O)H, —N$((C_1-C_8)$alkyl$)$C(O)$(C_1-C_8)$alkyl groups, —NHC(O)$NH_2$, —NHC(O)NH$(C_1-C_8)$alkyl groups, —N$((C_1-C_8)$alkyl$)$C(O)$NH_2$ groups, —NHC(O)N$((C_1-C_8)$alkyl$)_2$ groups, —N$((C_1-C_8)$alkyl$)$C(O)N$((C_1-C_8)$alkyl$)_2$ groups, —N$((C_1-C_8)$alkyl$)$C(O)NH$((C_1-C_8)$alkyl), —C(O)H, —C(O)$(C_1-C_8)$alkyl groups, —CN, —$NO_2$, —S(O)$(C_1-C_8)$alkyl groups, —S(O)$_2$$(C_1-C_8)$alkyl groups, —S(O)$_2$N$((C_1-C_8)$alkyl$)_2$ groups, —S(O)$_2$NH$(C_1-C_8)$alkyl groups, —S(O)$_2$NH$(C_3-C_8)$cycloalkyl groups, —S(O)$_2$$NH_2$ groups, —NHS(O)$_2$$(C_1-C_8)$alkyl groups, —N$((C_1-C_8)$alkyl$)$S(O)$_2$$(C_1-C_8)$alkyl groups, —$(C_1-C_8)$alkyl-O—$(C_1-C_8)$alkyl groups, —O—$(C_1-C_8)$alkyl-O—$(C_1-C_8)$alkyl groups, —C(O)OH, —C(O)O$(C_1-C_8)$alkyl groups, NHOH, NHO$(C_1-C_8)$alkyl groups, —O-halogenated $(C_1-C_8)$alkyl groups (for example but not limited to —$OCF_3$), —S(O)$_2$-halogenated $(C_1-C_8)$alkyl groups (for example but not limited to —S(O)$_2$$CF_3$), —S-halogenated $(C_1-C_8)$alkyl groups (for example but not limited to —$SCF_3$), —$(C_1-C_6)$ heterocycle (for example but not limited to pyrrolidine, tetrahydrofuran, pyran or morpholine), —$(C_1-C_6)$ heteroaryl (for example but not limited to tetrazole, imidazole, furan, pyrazine or pyrazole), -phenyl, —NHC(O)O—$(C_1-C_6)$alkyl groups, —N$((C_1-C_6)$alkyl$)$C(O)O—$(C_1-C_6)$alkyl groups, —C(=NH)—$(C_1-C_6)$alkyl groups, —C(=NOH)—$(C_1-C_6)$alkyl groups, or —C(=N—O—$(C_1-C_6)$alkyl$)$-$(C_1-C_6)$alkyl groups.

As used herein, many moieties or substituents are termed as being either "saturated or partially unsaturated." When a moiety is modified by one of these terms, unless otherwise noted, it denotes that one or more bonds of the moiety may be unsaturated.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a co-solvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

ABBREVIATIONS aa Amino acids
Ac Acyl or acetate
AcOH Glacial acetic acid
t-AmOH tert-Amyl alcohol
ATP Adenosine triphosphate
Boc t-Butoxycarbonyl
$Boc_2O$ Di-tert-butyl dicarbonate
BOP-Cl Bis(2-oxo-3-oxazolidinyl)phosphinic chloride
t-BuOH tert-Butanol
BSA Bovine serum albumin
$Bu_4NI$ Tetrabutylammonium iodide
Cbz Carboxybenzyl
CDI Carbonyldiimidazole
CT Computed tomography
d Doublet
dba Dibenzylideneacetone
DBU 1,8-Diazabicyclo[5.4.0]undec-7-ene.
DCE 1,2-Dichloroethane
DCI N,N'-carbonyldiimidazole
DCM Dichloromethane (methylene chloride)
dd Doublet of doublets
DIBAL-H Diisobutylaluminum hydride
DIEA N,N-Diisopropylethylamine
DMA Dimethylacetamide
DMAP N,N-Dimethylaminopyridine
DME 1,2-Dimethoxyethane
DMEM Dulbecco's Modified Eagle Medium
DMF N,N-Dimethylformamide
DMSO Dimethyl sulfoxide
DNP-HSA Dinitrophenyl-human serum albumin
DTT Dithiothreitol
dppf 1,1'-Bis(diphenylphosphino)ferrocene
EDC.HCl 1-[3-(dimethylamino)propyl]-3-ethylcarbodiimide hydrochloride
EDTA Ethylene diamine tetraacetic acid
EPO Erythropoetin
equiv Equivalent(s)
EtOAc Ethyl acetate
$Et_2O$ Diethyl ether
EtOH Ethanol
FBS Fetal bovine serum
FLAG DYKDDDDK peptide sequence
Fmoc Fluorenylmethyloxycarbonyl
g Gram(s)
GM-CSF Granulocyte-macrophage colony-stimulating factor
GST Glutathione S-transferase
h Hour(s)
HATU O-(7-azabenzotriazol-1-yl)-N,N,N',N'-tetramethyluronium hexafluorophosphate
HEPES N2-Hydroxyethylpiperazine-N2-ethanesulfonic acid
HOBt 1-Hydroxybenzotriazole
HPLC High-pressure liquid chromatography
HPMC Hydroxypropyl methylcellulose
IBCF Isobutyl chloroformate
i.d. Intradermal
IFA Incomplete Freunds Adjuvant
IPA Isopropyl alcohol
KHMDS Potassium bis(trimethylsilyl)amide
KOAc Potassium acetate
KOt-Bu Potassium tert-butoxide
LAH Lithium aluminum hydride
LC/MS Liquid chromatography/mass spectrometry
LDA Lithium diisopropylamide
LiHMDS Lithium bis(trimethylsilyl)amide
m Multiplet
M Molar
MeCN Acetonitrile
MeOH Methyl alcohol
min Minute(s)
mmol Millimole
MOPS 3-(N-morpholino)-propanesulfonic acid
MOPSO 3-(N-morpholino)-2-hydroxypropanesulfonic acid
MS Mass spectrometry
MsCl Methanesulfonyl chloride
MsOH Methanesulfonic acid
n- Normal (nonbranched)
N Normal
NaHMDS Sodium bis(trimethylsilyl)amide
NaOEt Sodium ethoxide
NaOMe Sodium methoxide
n-BuLi n-Butyl lithium
NaOt-Bu Sodium tert-butoxide
$NH_4OAc$ Ammonium acetate
NMP N-Methylpyrrolidinone
NMR Nuclear magnetic resonance
OD Optical density
or Optical rotation
OVA Ovalbumin
PBS Phosphate buffered saline
$Pd_2dba_3$ Tris(dibenzylideneacetone)dipalladium(0)
$Pd(OAc)_2$ Palladium(II) acetate
Pet ether Petroleum Ether
pH $-\log [H^+]$
pNAG Nitrophenyl-N-acetyl-β-D-glucosaminide
$Pd(PPh_3)_4$ tetrakis(triphenylphosphine)palladium(0)
$Pd(PPh_3)_2Cl_2$ Bis(triphenylphosphine)palladium(II) chloride
$PPh_3$ Triphenylphosphine
ppm Parts per million
PPTS Pyridinium p-toluenesulfonate
PrOH n-Propanol
psi Pounds per square inch
p-TSA p-Toluenesulfonic acid
rcf Relative centrifugal force
RP-HPLC Reverse-phase high-pressure liquid chromatography
RPM Revolutions per minute
$R_t$ Retention time
rt Room temperature
RuPhos 2-Dicyclohexylphosphino-2',6'-diisopropoxybiphenyl
s Singlet
SEM 2-(Trimethylsilyl)ethoxymethyl
SEMCl 2-(Trimethylsilyl)ethoxymethyl Chloride
SFC Supercritical fluid chromatography
SLM Standard liters per minute
SPE Solid phase extraction
t Triplet
t- Tertiary
TBDMSCl tert-Butyldimethylchlorosilane
TBDMSOTf tert-Butyldimethylsilyl triflate
TEA Triethylamine
tert- Tertiary tert-Butyl X-Phos 2-Di-tert-butylphosphino-2',4',6'-triisopropylbiphenyl
TESCl Triethylchlorosilane
TFA Trifluoroacetic acid
THF Tetrahydrofuran
THP Tetrahydropyran
TIPS Triisopropylsilyl
TLC Thin layer chromatography
TMS Trimethylsilyl
TMSCl Trimethylchlorosilane
TsCl p-Toluenesulfonyl Chloride
USP United States Pharmacopeia
UV Ultraviolet
wt % Weight percent
Xantphos 4,5-Bis(diphenylphosphino)-9,9-dimethylxanthene
X-Phos 2-Dicyclohexylphosphino-2',4',6'-triisopropylbiphenyl Assays In Vitro Syk Kinase Activity Measured by Time-Resolved Fluorescence Resonance Energy Transfer (trFRET)

Purified Syk catalytic domain (aa 356-635 with a C-terminal His-tag purified in-house by immobilized metal ion affinity chromatography; 0.14 nM final) was mixed with peptide substrate (biotin-TYR1, Sequence: Biotin-(Ahx)-GAEEE-IYAAFFA-COOH, 0.2 µM final) at varying inhibitor concentrations in reaction buffer: 50 mM MOPSO pH 6.5, 10 mM $MgCl_2$, 2 mM $MnCl_2$, 2.5 mM DTT, 0.01% BSA, 0.1 mM $Na_3VO_4$ and 0.001 mM ATP. After about 60 min incubation at rt, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.6 µg/mL SAXL (Phycolink streptavidin-allophycocyanin acceptor, cat #PJ25S, Prozyme, San Leandro, Calif.). The developed reaction was incubated in the dark either at about 4° C. for about 14 h or for about 60 min at rt, then read via a time-resolved fluorescence detector (Rubystar, BMG) using a 337 nm laser for excitation and monitoring emission wavelengths at 665 nm. Within the linear range of the assay, the observed signal at 665 nm was directly related to phosphorylated product and can be used to calculate the $IC_{50}$ values. For the purpose of the Tables and Examples below, the Syk $IC_{50}$ of each compound, which can be determined using the assay method described herein using the Syk catalytic domain (aa 356-635 with a C-terminal His-tag purified in-house by immobilized metal ion affinity chromatography), is expressed as follows; A=a compound with a Syk $IC_{50}$ less than 0.1 µM, B=a compound with a Syk $IC_{50}$ within the range of 0.1 to 1.0 µM, C=a compound with a Syk $IC_{50}$ within the range of 1.0 to 10.0 µM and D=a compound with a Syk $IC_{50}$ greater than 10 µM.

Purchased Syk full-length enzyme (Millipore cat #14-314; more details in Table 1) was also used to evaluate enzyme potency. Additional kinase assays used to assess selectivity were performed using a similar protocol (see Table 1). Additional purified enzymes Jak1 enzyme (aa 845-1142; expressed in SF9 cells as a GST fusion and purified by glutathione affinity chromatography); Lck (aa 62-509; purified in-house by DEAE ion-exchange and ATP-sepharose affinity chromatography), and ITK (aa 354-620 with His tag, purified in-house by immobilized metal ion affinity and mono Q ion exchange chromatography) were expressed in SF9 cells. Other enzymes used are available from commercial sources. Enzymes were mixed with biotinylated substrates at varying concentrations of inhibitor in different reaction buffers (see Table 1). After about 60 min incubation at rt, the reaction was quenched by addition of EDTA and developed by addition of revelation reagents (final approximate concentrations: 30 mM HEPES pH 7.0, 0.06% BSA, 0.006% Tween-20, 0.24 M KF, varying amounts of donor europium labeled antibodies and acceptor streptavidin labeled allophycocyanin (SAXL)). The developed reactions were incubated in the dark at about 4° C. for about 14 h or for about 60 min at rt, then read in a time-resolved fluorescence detector (Rubystar, BMG Labtech) as described above.

TABLE 1

Specific conditions (per 40 µL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| Jak1 | aa 845-1142 | Biotin-TYR2 | MOPSO | 5 | 2 µM | 0.001 | 5 | 60 | 8 ng/well PT66K, 0.39 µg/well SAXL |
| Jak2 | Millipore cat# 14-640 | Biotin-TYR1 | MOPSO | 2.5 | 2 µM | 0.001 | 5 | 60 | 8 ng/well PT66K, 0.078 µg/well SAXL |
| Jak3 | Millipore cat# 14-629 | Biotin-TYR2 | MOPSO | 1 | 2 µM | 0.001 | 5 | 60 | 8 ng/well PT66K, 0.078 µg/well SAXL |
| MARK2/EMK | Invitrogen cat# 3878 | KinEASE S1 | MOPS | 0.4 | 1 µM | 0.01 | 5 | 60 | 15 ng/well EuSTK, 0.34 µg/well SAXL |

TABLE 1-continued

Specific conditions (per 40 μL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| ITK | aa354-620 | Biotin-TYR1 | MOPSO | 25 | 4 μM | 0.01 | 5 | 60 | 10 ng/well PT66K, 0.078 μg/well SAXL |
| Lck | aa 62-509 | Biotin-TYR1 | MOPSO | 2.1 | 4 μM | 0.01 | 5 | 60 | 10 ng/well PT66K, 0.078 μg/well SAXL |
| Syk (catalytic domain) | aa 356-635 | Biotin-TYR1 | MOPSO | 0.2 | 0.2 μM | 0.001 | 5 | 60 | 10 ng/well PT66K, 0.078 μg/well SAXL |
| Syk (full-length) | Millipore cat #14-314 | Biotin-TYR1 | MOPSO | 3 | 0.1 μM | 0.01 | 5 | 60 | 11.3 ng/well PT66K, 0.075 μg/well SAXL |

Reaction Buffers:
MOPSO buffer contains: 50 mM MOPSO pH 6.5, 10 mM $MgCl_2$, 2 mM $MnCl_2$, 2.5 mM DTT, 0.01% BSA, and 0.1 mM $Na_3VO_4$
HEPES buffer contains: 50 mM HEPES pH 7.1, 2.5 mM DTT, 10 mM $MgCl_2$, 2 mM $MnCl_2$, 0.01% BSA, and 0.1 mM $Na_3VO_4$
MOPS buffer contains: 20 mM MOPS pH 7.2, 10 mM $MgCl_2$, 5 mM EGTA, 5 mM Beta-phosphoglycerol, 1 mM $Na_3VO_4$, 0.01% Triton-X-100 and 1 mM DTT
Substrates:
Biotin-TYR1-peptide sequence: Biotin-(Ahx)-GAEEEIYAAFFA-COOH
Biotin-TYR2-peptide sequence: Biotin-(Ahx)-AEEEYFFLFA-amide
KinEASE S1 peptides were purchased from Cisbio (cat #62ST0PEB, Bedford, MA)
Detection Reagents:
PT66K was purchased from Cisbio (cat #61T66KLB, Bedford, MA)
EuSTK was purchased from Cisbio (cat #62ST0PEB, Bedford, MA)
SAXL was purchased from Prozyme (cat #PJ25S, San Leandro, CA)

Human T-Blasts IL-2 pSTAT5 Cellular Assay
Materials:

Phytohemaglutinin T-blasts were prepared from Leukopacks purchased from Biological Specialty Corporation, Colmar, Pa. 18915, and cryopreserved in 5% DMSO/media prior to assay. For this assay the cells were thawed in assay medium with the following composition: RPMI 1640 medium (Gibco 11875093) with 2 mM L-glutamine (Gibco 25030-081), 10 mM HEPES (Gibco 15630-080), 100 μg/mL Pen/Strep (Gibco 15140-122), and 10% heat inactivated FBS (Gibco 10438026). Other materials used in the assay: DMSO (Sigma D2650), 96-well dilution plates (polypropylene) (Corning 3365), 384-well assay plates (grey, ½ area, 96 well) (PerkinElmer 6005350), D-PBS (Gibco 14040133), IL-2 (R&D 202-IL-10 (10 μg)), Alphascreen pSTAT5 kit (Perkin Elmer TGRS5S10K) and Alphascreen protein A kit (Perkin Elmer 6760617M).
Methods:

T-Blasts were thawed and cultured for about 3 days in media with IL-2 and then for an additional 24 h in media without IL-2 prior to assay. Test compounds or controls were dissolved and serially diluted in 100% DMSO. DMSO stocks were subsequently diluted 1:50 in cell culture media to create the 4× compound stocks (containing 2% DMSO). Cells were plated in 384 well grey plates at $1\times10^5/5$ μL/well in 5 μL media followed by addition of 5 μL of 4× test compound in duplicate. Cells were incubated with compound for about 0.5 h at about 37° C. Next, 2.5 μL of IL-2 stock was added at 20 ng/mL final concentration. IL-2 was stored as a 10 μg/mL stock solution, as specified by the manufacturer, at about −20° C. in aliquots and diluted 1:50 with assay media (to 80 ng/mL) just prior to use. The contents of the wells were mixed by carefully tapping sides of plate(s) several times followed by incubation at about 37° C. for about 20 min. The assay was terminated by adding 2.5 μL of 5× AlphaScreen lysis buffer and shaking on an orbital shaker for about 10 min at rt. AlphaScreen acceptor bead mix and donor bead mix were reconstituted following Perkin Elmer's protocol. A mixture of equal volumes of the acceptor beads and donor beads was prepared and 21 μL/well of mixed beads was added to the assay plates. The plates were covered with foil then shaken on orbital shaker for about 16 h on low at about 25° C. Plates were read on an EnVision reader following Perkin Elmer's AlphaScreen protocol instructions with excitation=680 nm, emmission=570 nm. Within the linear range of the assay, the observed signal at 570 nm was directly related to pSTAT5 concentration and can be used to calculate the $IC_{50}$ values.

TF-1 IL-6 pSTAT3 Cellular Assay
Materials:

TF-1 cells (ATCC #CRL-2003). Culture medium: RPMI medium (Gibco 21870) with 2 mM L-glutamine (Gibco 25030-081), 10 mM HEPES (Gibco 15630-080), 100 μg/mL Pen/Strep (Gibco 15140-122), 10% heat inactivated FBS (Gibco 10437-028), and 2 ng/mL GM-CSF (R&D 215-GM-010). Other materials used in this assay: DMSO (Sigma D2650), 96-well dilution plates (polypropylene) (Corning 3365), 384-well assay plates (grey, ½ area, 96 well) (Perkin Elmer 6005350), D-PBS (Gibco 14040133), IL-6 (R&D 206-

IL/CF-050 (50 µg)), AlphaScreen pSTAT3 kit (Perkin Elmer TGRS3S10K) and AlphaScreen protein A kit (Perkin Elmer 6760617M).
Methods:

Prior to the assay, cells were cultured for about 18 h in the culture medium without GM-CSF. Test compounds or controls were dissolved and serially diluted in 100% DMSO. DMSO stocks were subsequently diluted 1:50 in cell culture media to create the 4× compound stocks (containing 2% DMSO). Cells were plated in 384 well grey plates at $1 \times 10^5/5$ µL/well in 5 µL media followed by addition of 2.5 µL of the 4× test compound stock in duplicate. Cells were incubated with compound for about 0.5 h at about 37° C. followed by addition of 2.5 µL of 400 ng/mL IL-6. IL-6 was stored in 10 µg/mL aliquots using endotoxin free D-PBS (0.1% BSA) at about −20° C. Prior to assay IL-6 was diluted to 400 ng/mL in culture media and applied (2.5 µL/well) to all wells, except to negative control wells where 2.5 µL/well of media is added. The contents of the wells were mixed carefully by tapping the side of the plate several times. Plates were incubated at about 37° C. for about 30 min. Cells were lysed by adding 2.5 µL of 5× AlphaScreen cell lysis buffer to all wells, shaken for about 10 min at rt then assayed. Alternatively, assay plates were frozen at about −80° C. and thawed later at rt. Using the pSTAT3 SureFire Assay kit (Perkin Elmer #TGRS3S10K), AlphaScreen acceptor bead mix and donor bead mix were reconstituted following Perkin Elmer's protocol. A mixture of equal volumes of the acceptor beads and donor beads was prepared and 21 µL/well of mixed beads was added to the assay plates. The plates were covered with foil then shaken on an orbital shaker for about 16 h on low at about 25° C. Plates were read on an EnVision reader following Perkin Elmer's AlphaScreen protocol instructions with excitation=680 nm, emmission=570 nm. Within the linear range of the assay, the observed signal at 570 nm was directly related to pSTAT3 concentration and can be used to calculate the $IC_{50}$ values.

UT7/EPO pSTAT5 Cellular Assay
Materials:

UT7/EPO cells were passaged with erythropoietin (EPO), split twice per week and fresh culture medium was thawed and added at time of split. Culture Medium: DMEM medium (Gibco 11960-044) with 2 mM L-glutamine (Gibco 25030-081), 10 mM HEPES (Gibco 15630-080), 100 U/mL Pen/Strep (Gibco 15140-122), 10% heat inactivated FBS (Gibco 10437-028), EPO (5 µL/mL=7.1 µL of a 7 µg/mL stock per mL of medium). Assay media: DMEM, 2 mM L-glutamine, 5% FBS, 10 mM HEPES. Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 µg)), AlphaScreen pSTAT5 kit (Perkin Elmer TGRS5S10K) and AlphaScreen protein A kit (Perkin Elmer 6760617M).
Methods:

Cells were cultured for about 16 h without EPO prior to running assay. Test compounds or controls were dissolved and serially diluted in 100% DMSO. DMSO stocks were subsequently diluted 1:50 in cell culture media to create the 4× compound stocks (containing 2% DMSO). Using a Corning white 96 well, ½ area plate, cells were plated at $2 \times 10^5/10$ µL/well in 10 µL media followed by addition of 5 µL of 4× test compound stock in duplicate. Cells were incubated with compound for about 0.5 h at about 37° C. After incubation, 5 µL of EPO was added to afford a final concentration of 1 nM EPO. The contents of the wells were mixed by carefully tapping sides of the plate several times followed by incubation at about 37° C. for about 20 min. 5 µL of 5× AlphaScreen lysis buffer were added followed by shaking on an orbital shaker for about 10 min at rt. 30 µL/well of acceptor beads were added after reconstitution following Perkin Elmer's AlphaScreen protocol, covered with foil and shaken on an orbital shaker for about 2 min on high, then about 2 h on low. Donor beads were reconstituted following Perkin Elmer's AlphaScreen protocol instructions followed by addition of 12 µL/well, covered with foil and shaken on an orbital shaker for about 2 min on high, about 2 h on low. Plates were read on an EnVision reader following Perkin Elmer's AlphaScreen protocol instructions with excitation=680 nm, emmission=570 nm. Within the linear range of the assay, the observed signal at 570 nm was directly related to pSTAT5 concentration and can be used to calculate the $IC_{50}$ values.

Antigen-Induced Degranulation of RBL-2H3Cells:

RBL-2H3 cells were maintained in T75 flasks at about 37° C. and 5% $CO_2$, and passaged every 3-4 days. To harvest cells, 20 mL of PBS was used to rinse the flask once, and then 3 mL of Trypsin-EDTA was added and incubated at about 37° C. for about 2 min. Cells were transferred to a tube with 20 mL medium, spun down at 1000 RPM at rt for about 5 min and resuspended at $1 \times 10^6$ cells/mL. Cells were sensitized by adding DNP-specific mouse IgE (Sigma #D8406) to a final concentration of 0.1 µg/mL. 50 µL of cells were added to each well of a 96 well flat bottom plate ($50 \times 10^3$ cells/well) and incubated overnight at about 37° C. in 5% $CO_2$. The next day, compounds were prepared in 100% DMSO at 10 mM. Each compound was then serially diluted 1:4 six times in 100% DMSO. Each compound dilution was then diluted 1:20 and then 1:25, both dilutions in Tyrode's buffer (HBSS with Ca++ and Mg++ (Gibco #14025)+20 mM Hepes (Gibco #15630)+0.2 mg/mL BSA (Sigma #8527)+5.6 mM glucose (Sigma G8270). Media was aspirated from the cell plates and the cells were rinsed twice with 100 µL of Tyrode's buffer (prewarmed to about 37° C.). 50 µL of compounds diluted in Tyrode's buffer were added to each well and the plates were incubated for about 15 min at about 37° C. in 5% $CO_2$. 50 µL of 0.2 µg/mL DNP-HSA (Bioresearch Technologies, Inc. #D-5059-100) in Tyrode's buffer was then added to each well and the plates were incubated for about 30 min at about 37° C. in 5% $CO_2$. The final concentration of the various components in the incubation mix are 0.002-10 µM compounds, 0.1% DMSO, and 0.1 µg/mL DNP-HSA. As one control, Tyrode's buffer with DNP-HSA was added to a set of wells containing 0.2% DMSO without compounds to determine maximum stimulated release. As a second control, Tyrode's buffer without DNP-HSA was added to a set of wells containing 0.2% DMSO without compounds to determine unstimulated release. At the end of the 30 min incubation, 100 µL of freshly prepared 1 mM 4-methylumbelliferyl N-acetyl-β-D-glucosaminide (MUG; Sigma #M2133) was then added to each well and the plates are incubated for about 45 min at about 37° C. in 5% $CO_2$. The plates were then read on an EnVision plate reader with excitation=355 nm, emission=460 nm. Within the linear range of the assay, the observed signal at 460 nm was directly related to MUG reaction product production and can be used to calculate the $IC_{50}$ values.

Ramos Calcium Flux Assay
Materials:

Ramos cells (ATCC # CRL-1596) were maintained at about 37° C. and 5% $CO_2$ in T150 flasks. Culture medium: RPMI medium (Invitrogen #21870-075) supplemented with 10% heat-inactivated FBS (Invitrogen #10438-026) and 1% Pen/Strep (Invitrogen #15140-122). Assay Buffer: HBSS (Invitrogen: #14025-092) with 40 mM Hepes (Invitrogen #15630-080), 0.1% Bovine Serum Albumin (BSA) (Sigma #A8577), 2.5 mM Probenecid (Invitrogen #P36400) and 10 mM Glucose (Sigma #G-7528). Other materials used in this assay: DMSO (Sigma D8418), 96-well dilution plates (polypropylene) (Corning #3365), 96-well assay plates (Corning #3603), FLIPR Calcium 5 Assay Bulk Kit (Molecular Devices #R8186), and Donkey anti-human IgM Affinity Purified Fab2 (Jackson ImmunoResearch Laboratories #709-006-073), FLIPR TETRA machine (Molecular Devices).

Methods:

Cells were seeded at 5e5 cells per mL in culture medium about 16-18 h before assay. On the day of the assay, cells were centrifuged at 1000 rpm for 5 min, resuspended in culture medium and counted. An appropriate volume of cell suspension was set at a concentration of $2 \times 10^6$ cells/mL in regular culture medium and plated in assay plates at $2 \times 10^5$ cells/well (100 μL/well). A stock solution of Calcium 5 dye was prepared by adding 10 mL of assay buffer per vial of dye from the bulk kit. A 2× dye solution was prepared by adding 1 mL of dye stock solution to 9 mL of assay buffer, added to assay plates (100 μL/well) and incubated for about 1 h at about 37° C. and 5% $CO_2$. DMSO compound stocks were prepared by dissolving and serially diluting test compounds or controls in 100% DMSO. Immediately before compound testing, DMSO compound stocks were diluted 1:33 in assay buffer to make a 6× compound stock (2% DMSO). Using the FLIPR Tetra machine, 6× compound stock was transferred to the assay plate (50 μL/well, 0.33% final DMSO) and potential calcium flux was monitored for about 3.5 min following compound addition (Excitation wavelength: 470/495 nm; Emission wavelength: 515/575 nm; read interval: 1 second, # of reads: 60; # of reads before dispensing: 10; $2^{nd}$ interval read: 6 seconds, # of reads: 30). Compounds were incubated for 30 min at rt. A 6× stimulus solution was made fresh before addition to cells by diluting 1.3 mg/mL anti-IgM antibody stock solution to 60 μg/mL in assay buffer. After compound incubation, the FLIPR Tetra machine transferred 6× stimulus solution to cells (50 μL/well, anti-IgM antibody final 10 ug/mL) and calcium flux was monitored for 3.5 min following antibody addition (Excitation wavelength: 470/495 nm; Emission wave length: 515/575 nm; $1^{st}$ read interval: 2 second, # of reads: 60; # of reads before dispensing: 10; $2^{nd}$ interval read: 6 seconds, # of reads: 80). The $IC_{50}$ values for compounds tested were then calculated based on percent of inhibition of anti-IGM antibody induced calcium flux.

Acute in vivo measurement of Fcγ receptor signaling inhibition of the compounds is measured using the:

Reverse Passive Arthus Model

On day 0 OVA was made up at a concentration of 17 mg/mL, in PBS by rocking gently until a solution was formed. 2% Evans Blue solution (Sigma Aldrich, cat# E2129) was then added to double the volume for a final concentration of 8.5 mg/mL of OVA and 1% Evans Blue dye. Anti-OVA antibody (Abazyme), stock concentration 10 mg/mL, was thawed and a 4 mg/mL solution was made with PBS. Compounds were made up in 0.5% HPMC with 0.02% Tween 80, and vortexed for about 15 seconds followed by homogenization for a minimum of about 2 min at 28,000 RPM until there was a fine particulate suspension with no clumps of compound. Rats were weighed and dosed with compound at a pre-determined time based on compound $T_{max}$ determined in pharmacokinetic studies. Animals were then placed under general anesthesia with a 5% isoflourane and oxygen mixture and shaved. Using a 0.5 cc insulin syringe two sites were injected i.d., 1 site with 100 μL of 4.0 mg/mL of anti-OVA antibody, and 1 site with 100 μL of sterile PBS. Each injection site was circled with a permanent marker to mark the site. Immediately following i.d. injections, animals were injected with 200 μL of the OVA (10 mg/kg)/1% Evans Blue mixture, i.v., using a 0.5 cc insulin syringe. About 4 h post injection animals were euthanized, bled via cardiac puncture and blood was put into plasma separation tubes. Blood samples were stored on ice until centrifugation (within about 2 h of collection). Each injection site was removed with a disposable biopsy punch (Acuderm Acu-Punch Disposable 12 mm), cut into four pieces and placed in a pre-labeled 2 mL eppendorf tube. One mL of DMF (99%) was added to each biopsy tube and they were placed in a heat block at about 50° C. for about 24 h. After incubation, 100 μL of each sample was transferred to a 96 well flat bottom plate and read at 620 nm on a plate reader using the Softmax software. Background was removed by subtracting the OD from the PBS injected site from the OD of the anti-OVA injected site for each individual animal. Plasma samples were spun down in a microcentrifuge (Eppendorf 5415R) for about 5 min at 16.1 rcf. 200 μL of plasma was placed in a 1.7 mL eppendorf tube for drug level measurements and tubes were stored at about −80° C. until evaluation.

Collagen Induced Arthritis (CIA)

Type II Collagen (CII), derived from bovine nasal septum (Elastin Products, cat# CN276) was solubilized in 0.01M AcOH (150 μL AcOH USP grade, J. T. Baker, order#9522-03, and 250 mL Milli Q Water) to give a concentration of 4 mg/mL. The vial was covered with aluminum foil and placed on a rocker at about 4° C. overnight. The collagen stock solution was diluted 1:1 with incomplete Freunds adjuvant (IFA) (Difco labs, cat#263910) and an emulsion was made in glass Hamilton luer lock syringes (SGE Syringe Perfection VWR cat#007230), to a final concentration of 2 mg/mL. Female Lewis rats, weighing approximately 150 g, (Charles River Laboratories) were anesthetized in an anesthesia chamber using isoflurane (5%) and oxygen. Anesthesia was maintained using a nose cone during the injections. Rats were shaved at the base of the tail and 600 μg of collagen was delivered in three 100 μL i.d. injections on the rump of the rat (n=9 per group). A negative control group was immunized with a 1:1 emulsion of 0.01 M AcOH and IFA (n=6). Animals were boosted on day 6 of the study in the same manner as the immunization. Compound dosing began 10 days after the initial immunization when first signs of disease were observed. Compounds were formulated in an inert vehicle such as 0.5% HPMC (Sigma, cat# H3785)/0.02% Tween 80 (Sigma, cat#4780) in water) and dosed orally once or twice a day for at least 9 days. Baseline paw volume was taken on day 7, prior to disease onset, using a water displacement pleythsmograph (Vgo Basile North America Inc. PA 19473, Model#7140). Rats were lightly anesthetized with an inhalant anesthetic (isoflurane) and both hind paws were dipped into the plethysmograph and the paw volume was recorded. The rats were scored 3 times a week from day 10-18 after immunization. On day 18 after immunization, all rats were exsanguinated by cardiac puncture under isoflurane anesthesia, and the hind paws were collected to assess the impact on bone erosion using micro-CT scans (SCANCO Medical, Southeastern, Pa., Model # μCT 40) at a voxel size of 18 μm, a threshold of 400, sigma-gauss 0.8, support-gauss 1.0. Bone volume and density was determined for a 360 μm (200 slice) vertical section encompassing the tarsal section of the paw. The 360 μm section was analyzed from the base of the metatarsals to the top of the tibia, with the lower reference point fixed at the tibiotalar junction. Drug exposure was determined from plasma using LC/MS.

The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using the synthetic transformations illustrated in Schemes I and II. Starting materials are commercially available, may be prepared by the procedures described herein, by literature procedures, or by procedures that would be well known to one skilled in the art of organic chemistry.

Methods for preparing furo[3,2-d]pyrimidine-2,4-diamine compounds 5 of the invention are illustrated in Scheme I. In Scheme I, commercially available 2,4-dichlorofuro[3,2-d]pyrimidine (ArkPharm) 1 may be reacted with an amine 2 (Scheme I, step a) as described in General Procedure A to give a 2-chlorofuro[3,2-d]pyrimidin-4-amine 3 that is substituted with an $R^a$ and $R^b$ substituent. Subsequent reaction with a primary amine 4 (Scheme I, step b) using Buchwald coupling conditions as described by General Procedure B would give a furo[3,2-d]pyrimidine-2,4-diamine 5. Alternatively, this transformation can be accomplished with a 2-chlorofuro[3,2-d]pyrimidin-4-amine 3, a primary amine 4 and an acid source, such as TFA, HCl or AcOH with or without heating to give a furo[3,2-d]pyrimidine-2,4-diamine 5. The amines 2 and/or 4 are either commercially available or can be prepared by methods known to one skilled in the art (see, for example, Larock, R. C. "Comprehensive Organic Transformations: A Guide to Functional Group Preparations, $2^{nd}$ edition", 1999, Wiley-VCH or the General Procedures below). Further functionalization of any of the intermediates, for instance compounds 2, 3 and/or 4 in Scheme I, and/or the furo[3,2-d]pyrimidine-2,4-diamine compounds 5 can be performed with appropriate functionality on $R^a$, $R^b$ and/or $R^3$, if desired, using reactions known to one skilled in the art (see, for example, Larock, R. C. [referenced above] or the General Procedures below). For example, formation of amides or sulfonamides can be achieved by reaction of a primary or secondary amine with either acid halides or carboxylic acids or alternatively a sulfonyl chloride (see, for example, General Procedures D, E.1 and E.2). Additionally, amides could be prepared by the saponification of esters to a carboxylic acid (see, for example, General Procedure AI) and then subsequent reaction with primary or secondary amines by the methods described above for amide formation. Amino alcohols can be cyclized to carbamates (see, for example, General Procedures AL). Amines can be prepared in many ways known to one skilled in the art. For example nitro groups can be reduced to primary amines (see, for example, General Procedures I) Amines can be formed by conversion of alcohols to mesylates (see, for example, General Procedures V) which can then be substituted with amines (see, for example, General Procedures U) directly or converted to the azide which is then reduced (see, for example, General Procedures F) to provide an amine. Alternately, alcohols can be oxidized to the ketone or aldehyde (see, for example, General Procedure P) which may then be converted by reductive amination with a primary or secondary amine (see, for example, General Procedure H) to give amines. Additionally, nitriles may be converted to amines by reduction (see, for example, General Procedure AE). Nitriles may be obtained from aldehydes (see, for example, General Procedure AA). Alcohols may be obtained from reduction of an ester to provide the alcohol (see, for example, General Procedure W). Additionally, alcohols may be obtained by the reaction of ketones or aldehydes with Grignard reagents (see, for example WO2010138487, Reagent Preparation 5) or also by reduction of ketones or aldehydes with reducing agents (see, for example WO20110092475, Intermediate 39a or *European Journal of Organic Chemistry* 2009, (9), 1372). Aryl or heteroaryls bearing a halide may be coupled with an aryl or heteroaryl boronate or boronic acid (see, for example, General Procedure Z). Intermediates or final compounds may be further functionalized by alkylation a to a nitrile (see, for example, General Procedure AF or *Bioorganic & Medicinal Chemistry Letters* 2010, 20(2), 608) or ester (for example a fluorination, General Procedure X or WO 2008108957).

Additionally, carbamates may be alkylated (see, for example, General Procedures L). For Scheme I, in certain cases intermediates or in the synthesis of starting materials 2 and 4 may require protection using conditions such as those described in Greene, T. W. and Wuts, P. G. M. [referenced above]. For example, a Boc (see, for example, General procedure O) or Cbz (see, for example, General procedure O) group can be used to form a protected amine Heteroaryl nitrogens can be protected with Boc (see, for example, General procedure O), tosyl (see, for example, General Procedure AJ), SEM (see, for example, General Procedure N), or THP (see, for example, General Procedure AB). Alcohols may be protected as ethers (see, for example, *Journal of Medicinal Chemistry* 2008, 51(20), 6538 or 2011, 54(3), 869) or as silyl ethers (see, for example, General Procedure AH). Also, deprotection of compounds 5, as well as intermediates 2, 3 and/or 4 containing a protected primary or secondary amine to yield unprotected compounds can be performed using conditions such as those described in Greene, T. W. and Wuts, P. G. M. "Protective Groups in Organic Synthesis, $3^{rd}$ Edition", 1999, Wiley-Interscience or in General Procedures C, G, J, K, S, T, AN or AC. For example, a protecting group such as a Boc can be removed from a protected amine to yield the unprotected amine (see, for example, General Procedure C or Example #3, Step E) and the deprotected compounds 5 may then be reacted further as described above. Additionally, a cyclic carbamate can be hydrolyzed to give an aminoalcohol using conditions described in General Procedure AM. Also, deprotection of compounds 5 as well as intermediates 2, 3 and/or 4 containing a silyl protected alcohol to yield unprotected compounds can be performed using conditions such as those described in Greene, T. W. and Wuts, P. G. M. [referenced above] or General Procedure R. In some cases, the deprotection of multiple protecting groups of a different nature may be removed simultaneously as described in General Procedures Q, AD, AG, and AK. For example, deprotection of a protected diamine compound containing both a Boc group and a SEM group can be performed using General Procedure Q to give the unprotected diamine (for example, see Example #5, Step E).

Scheme I:

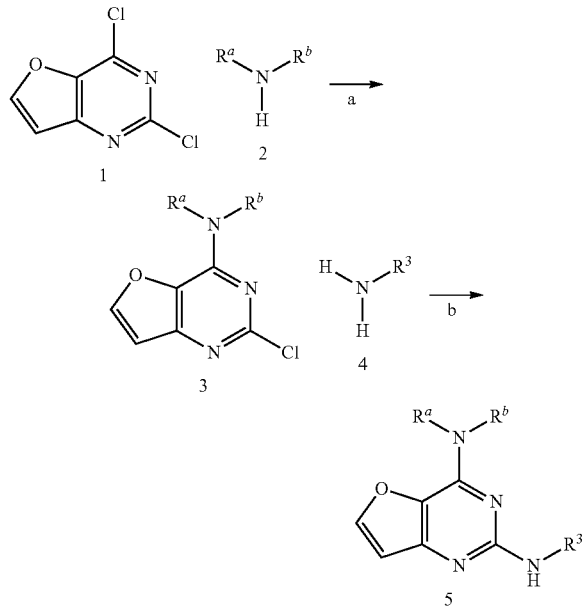

Methods for preparing 4-alkoxy-2-aminofuro[3,2-d]pyrimidine compounds 8 of the invention are illustrated in Scheme II. In Scheme II, commercially available 2,4-dichlorofuro[3,2-d]pyrimidine (ArkPharm) 1 may be reacted with an alcohol 6 (Scheme II, step a) as described in General Procedure Y to give a 2-chloro-4-alkoxyfuro[3,2-d]pyrimidine 7 that is substituted with an $R^a$ substituent. Subsequent reaction with a primary amine 4 (Scheme II, step b) using Buchwald coupling conditions as described by General Procedure B would give a 4-alkoxy-2-aminofuro[3,2-d]pyrimidine 8. The alcohols 6 and/or amines 4 are either commercially available or can be prepared by methods known to one skilled in the art (see, for example, Larock, R. C. [referenced above] or the General Procedures below). Further functionalization of any of the intermediates (for instance Compounds 6, 7 and/or 4 in Scheme II) and/or the 4-alkoxy-2-aminofuro[3,2-d]pyrimidine compounds 8 can be performed with appropriate functionality on $R^a$ and/or $R^3$, if desired, using reactions known to one skilled in the art (see, for example, Larock, R. C. [referenced above] or the General Procedures below) as described for Scheme I in the paragraph above. Additionally, in certain cases intermediates or in the synthesis of starting materials 4 and 6 may require protection using conditions such as those described in Greene, T. W. and Wuts, P. G. M. [referenced above] as described for Scheme I in the paragraph above.

Scheme II:

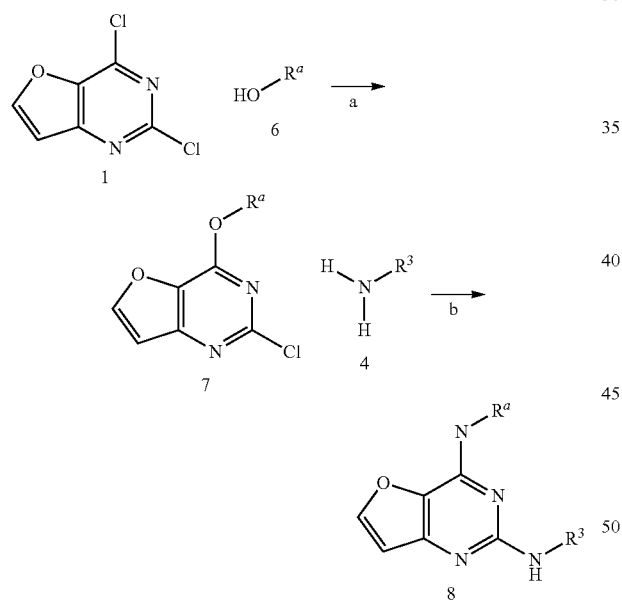

If desired, chiral separation of any of the chiral compounds in Schemes I and II may be done using methods known to one skilled in the art such as chiral SFC (for example, General Procedure M), chiral preparative HPLC, or crystallization of diastereomeric salts.

GENERAL PROCEDURES AND EXAMPLES

The general synthetic schemes that were utilized to construct the majority of compounds disclosed in this application are described below in Schemes 1-41. These schemes are provided for illustrative purposes only and are not to be construed as limiting the scope of the invention.

Scheme 1. Nucleophilic displacement of an aryl halide with an amine (General Procedure A)

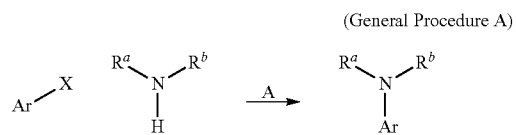

Scheme 2. Buchwald reaction of an aryl halide with an aniline
(General Procedure A)

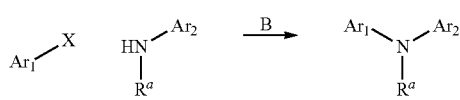

Scheme 3. Removal of a Boc group from an N-Boc amine or heteroaromatic
(General Procedure C)

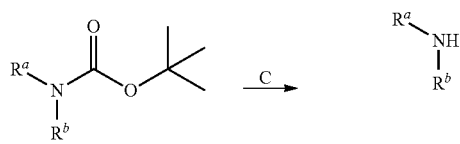

Scheme 4. Formation of a sulfonamide from an amine and a sulfonyl chloride
(General Procedure D)

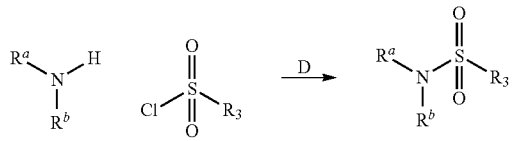

Scheme 5. Formation of an amide from an amine and an acid halide or anhydride
(General Procedure E.1)

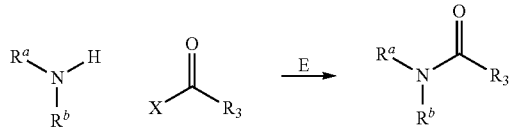

Scheme 6. Formation of an amide from an amine and a carboxylic acid (General Procedure E.2)

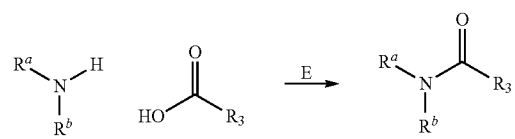

Scheme 7. Reduction of an azide to an amine (General Procedure F)

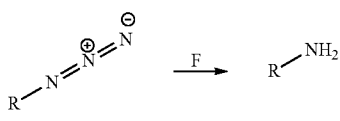

Scheme 8. Removal of a benzyl group from an N-benzyl amine (General Procedure G)

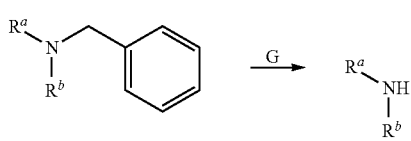

Scheme 9. Reductive amination of an aldehyde or ketone with a primary or secondary amine (General Procedure H)

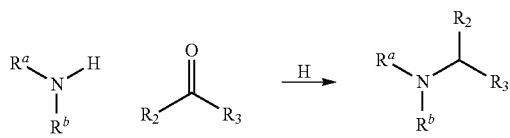

Scheme 10. Reduction of a nitro group to an amine (General Procedure I)

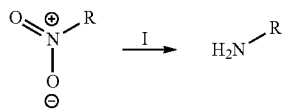

Scheme 11. Reduction of a SEM group from an N-SEM heteroaromatic (General Procedure J)

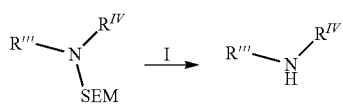

Scheme 12. Removal of a Cbz group from an N-Cbz amine (General Procedure K)

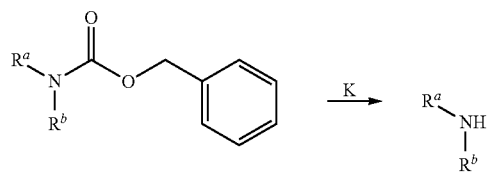

Scheme 13. Alkylation of a Carbamate (General Procedure L)

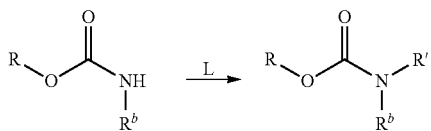

Scheme 14. Chiral separation (General Procedure M)

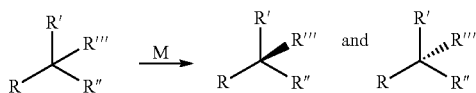

Scheme 15. Preparation of an N-SEM heteroaromatic (General Procedure N)

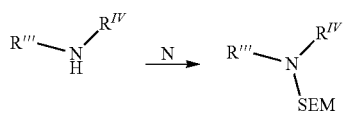

Scheme 16. Formation of a carbamate from an amine and a chloroformate or dicarbonate (General Procedure O)

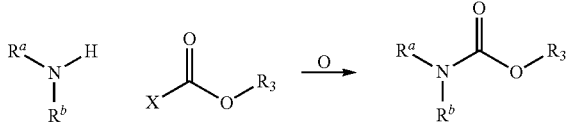

Scheme 17. Oxidation of an alcohol to an aldehyde or ketone (General Procedure P)

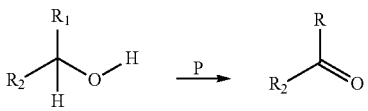

Scheme 18. Removal of a Boc group from an N-Boc amine or heteroaromatic and a SEM group from an N'-SEM heteroaromatic (General Procedure Q)

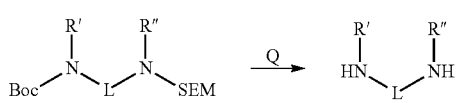

Scheme 19. Removal of a silyl group from an O-silyl ether (General Procedure R)

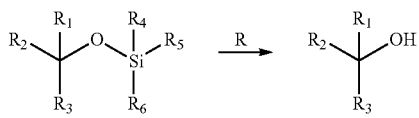

Scheme 20. Removal of a 2,4-dimethoxybenzyl group from an N-2,4-dimethoxybenzylamine (General Procedure S)

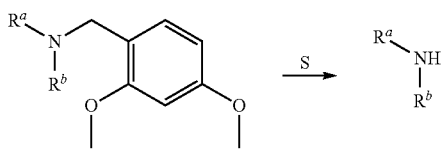

Scheme 21. Hydrolysis of a phthalamide to an amine (General Procedure T)

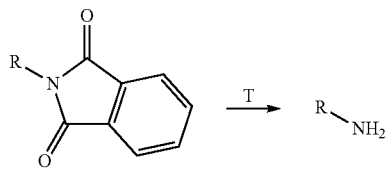

Scheme 22. Substitution of a mesylate with an amine nucleophile (General Procedure U)

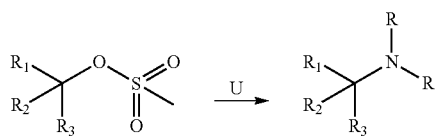

Scheme 23. Formation of a mesylate from an alcohol (General Procedure V)

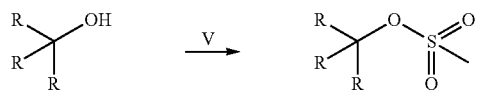

Scheme 24. Reduction of an ester to an alcohol (General Procedure W)

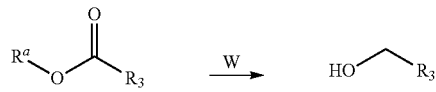

Scheme 25. Nucleophilic fluorination at the α-position of an ester (General Procedure X)

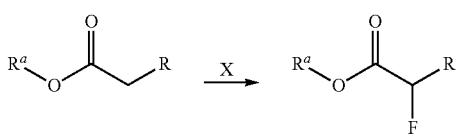

Scheme 26. Nucleophilic displacement of an aryl halide with an alcohol (General Procedure Y)

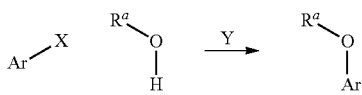

Scheme 27. Suzuki Reaction of an aryl or heteroaryl halide with an aryl or heteroaryl boronic acid or boronate (General Procedure Z)

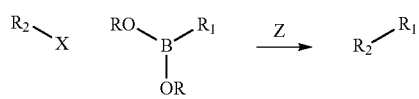

Scheme 28. Conversion of an aldehyde to a nitrile (General Procedure AA)

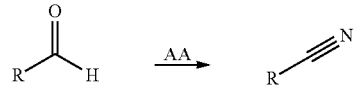

Scheme 29. Formation of an N-THP heteroaromatic (General Procedure AB)

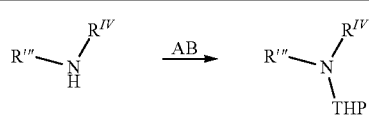

Scheme 30. Removal of a THP group from an N-THP heteroaromatic (General Procedure AC)

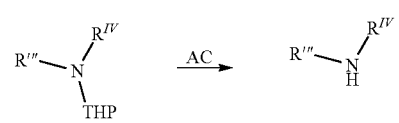

Scheme 31. Removal of a Boc group from an N-Boc amine or heteroaromatic and a silyl group from an O-silyl ether (General Procedure AD)

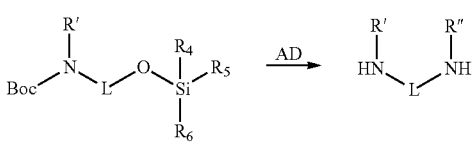

Scheme 32. Reduction of a nitrile to an amine
(General Procedure AE)

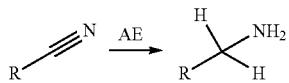

Scheme 33. Alkylation α to a nitrile
(General Procedure AF)

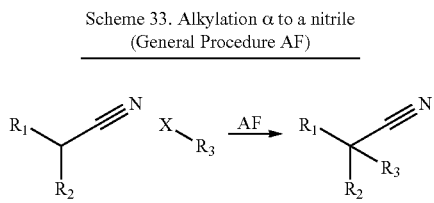

Scheme 34. Removal of a Boc group from an N-Boc amine or heteroaromatic and an acyl group from an N'-acryl amine
(General Procedure AG)

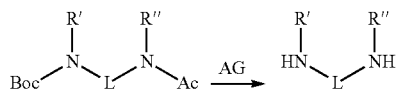

Scheme 35. Formation of a O-silyl ether
(General Procedure AH)

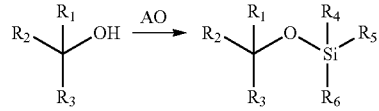

Scheme 36. Hydrolysis of an ester to a carboxylic acid
(General Procedure AI)

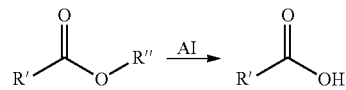

Scheme 37. Formation of an N-tosyl heteroaromatic
(General Procedure AJ)

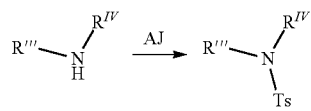

Scheme 38. Removal of a Boc group from an N-Boc amine or heteroaromatic and a tosyl group from an N'-tosyl heteroaromatic
(General Procedure AK)

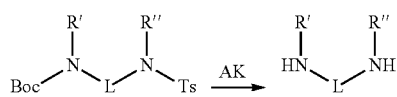

Scheme 40. Hydrolysis of a cyclic carbamate to an aminoalchohol
(General Procedure AL)

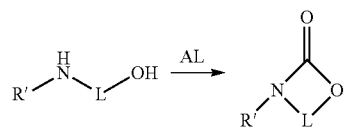

Scheme 40. Hydrolysis of cyclic carbamate to an aminoalcohol
(General Procedure AM)

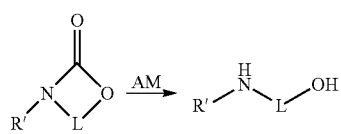

Scheme 41. Removal of a benzylidine from a benzophenone imine
(General Procedure AN)

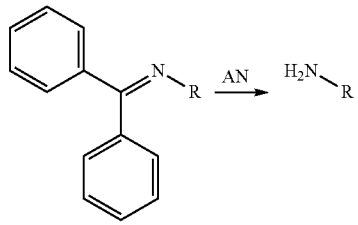

| LIST OF GENERAL PROCEDURES | |
|---|---|
| General Procedure A | Nucleophilic displacement of an aryl halide with an amine |
| General Procedure B | Buchwald reaction of an aryl halide with an aniline |
| General Procedure C | Removal of a Boc group from an N-Boc amine or heteroaromatic |
| General Procedure D | Formation of a sulfonamide from an amine and a sulfonyl chloride |
| General Procedure E.1 | Formation of an amide from an amine and an acid halide or anhydride |

LIST OF GENERAL PROCEDURES

| | |
|---|---|
| General Procedure E.2 | Formation of an amide from an amine and a carboxylic acid |
| General Procedure F | Reduction of an azide to an amine |
| General Procedure G | Removal of a benzyl group from an N-benzyl amine |
| General Procedure H | Reductive amination of an aldehyde or ketone with a primary or secondary amine |
| General Procedure I | Reduction of a nitro group to an amine |
| General Procedure J | Removal of a SEM group from an N-SEM heteroaromatic |
| General Procedure K | Removal of a Cbz group from an N-Cbz amine |
| General Procedure L | Alkylation of a Carbamate |
| General Procedure M | Chiral separation |
| General Procedure N | Preparation of an N-SEM heteroaromatic |
| General Procedure O | Formation of a carbamate from an amine and a chloroformate or dicarbonate |
| General Procedure P | Oxidation of an alcohol to an aldehyde or ketone |
| General Procedure Q | Removal of a Boc group from an N-Boc amine or heteroaromatic and a SEM group from an N'-SEM heteroaromatic |
| General Procedure R | Removal of a silyl group from a O-silyl ether |
| General Procedure S | Removal of a 2,4-dimethoxybenzyl group from an N-2,4-dimethoxybenzylamine |
| General Procedure T | Hydrolysis of a phthalamide to an amine |
| General Procedure U | Substitution of a mesylate with an amine nucleophile |
| General Procedure V | Formation of a mesylate from an alcohol |
| General Procedure W | Reduction of an ester to an alcohol |
| General Procedure X | Nucleophilic fluorination at the α-position of an ester |
| General Procedure Y | Nucleophilic displacement of an aryl halide with an alcohol |
| General Procedure Z | Suzuki reaction of an aryl or heteroaryl halide with an aryl or heteroaryl boronic acid or boronate |
| General Procedure AA | Conversion of an aldehyde to a nitrile |
| General Procedure AB | Formation of an N-THP heteroaromatic |
| General Procedure AC | Removal of a THP group from an N-THP heteroaromatic |
| General Procedure AD | Removal of a Boc group from an N-Boc amine or heteroaromatic and a silyl group from a O-silyl ether |
| General Procedure AE | Reduction of a nitrile to an amine |
| General Procedure AF | Alkylation α to a nitrile |
| General Procedure AG | Removal of a Boc group from an N-Boc amine or heteroaromatic and a acyl group from an N'-acyl amine |
| General Procedure AH | Formation of an O-silyl ether |
| General Procedure AI | Hydrolysis of an ester to a carboxylic acid |
| General Procedure AJ | Formation of an N-tosyl heteroramatic |
| General Procedure AK | Removal of a Boc group from an N-Boc amine or heteroaromatic and a tosyl group from an N'-tosyl heteroaromatic |
| General Procedure AL | Formation of a cyclic carbamate from an aminoalcohol |
| General Procedure AM | Hydrolysis of a cyclic carbamate to an aminoalcohol |
| General Procedure AN | Removal of a benzylidine from a benzophenone imine |

The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Example #C.1 as a non-limiting illustration. Example #C.1 is 4-(4-(4-(aminomethyl)piperidin-1-yl)furo[3,2-d]pyrimidin-2-ylamino)benzenesulfonamide diacetate, which was prepared from tert-butyl (1-(2-(4-sulfamoylphenylamino)furo[3,2-d]pyrimidin-4-yl)piperidin-4-yl)methylcarbamate using General Procedure C as represented in Scheme A.

Scheme A

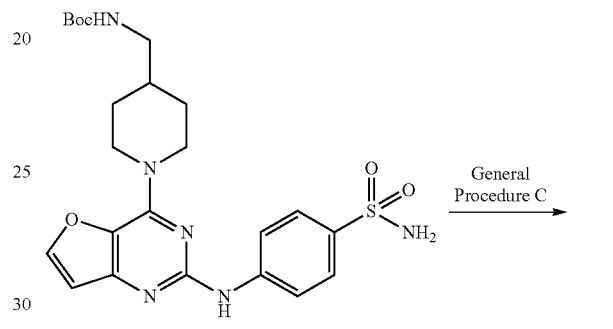

Precursor to Example #C.1

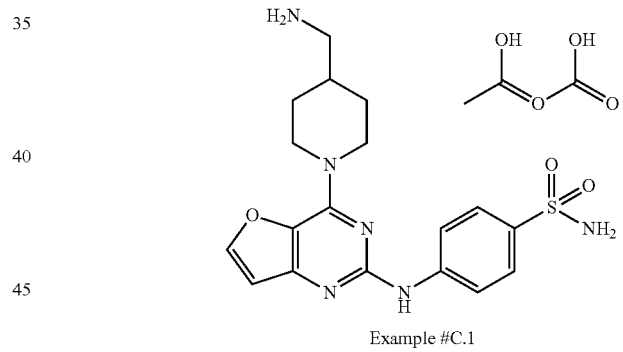

Example #C.1

The precursor to Example #C.1, tert-butyl (1-(2-(4-sulfamoylphenylamino)furo[3,2-d]pyrimidin-4-yl)piperidin-4-yl)methylcarbamate, was prepared as shown in Scheme B. 2,4-Dichlorofuro[3,2-d]pyrimidine [Ark Pharm] and tert-butyl piperidin-4-ylmethylcarbamate [Astatech] are reacted following conditions given in General Procedure A to give tert-butyl (1-(2-chlorofuro[3,2-d]pyrimidin-4-yl)piperidin-4-yl)methylcarbamate. The intermediate is then reacted with 4-aminobenzenesulfonamide using the conditions described in General Procedure B to give the precursor to Example #C.1. The reaction sequence detailed above is translated in the preparations and examples section to "prepared using A from 2,4-dichlorofuro[3,2-d]pyrimidine [ArkPharm] with tert-butyl piperidin-4-ylmethylcarbamate [Astatech] and B with 4-aminobenzenesulfonamide."

Scheme B

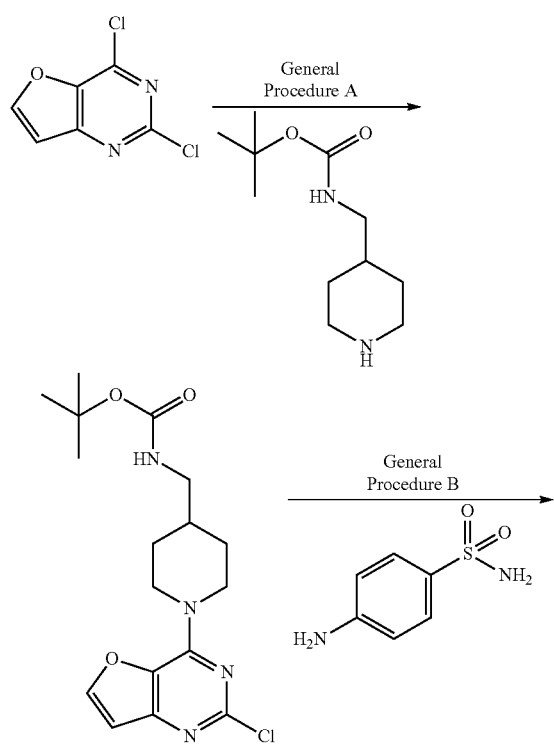

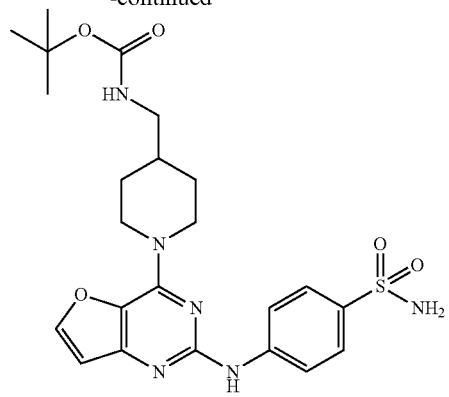

Precursor to Example #C.1

Analytical Methods

Analytical data is included within the procedures below, in the illustrations of the general procedures, or in the tables of examples. Unless otherwise stated, all $^1$H NMR data were collected on a Varian Mercury Plus 400 MHz, a Varian Inova 600 MHz instrument, a Varian Inova 500 MHz, a Bruker AVIII 400, or a Bruker AVIII 300 MHz instrument and chemical shifts are quoted in parts per million (ppm). LC/MS and HPLC data is referenced to the table of LC/MS and HPLC conditions using the lower case method letter provided in Table 2.

TABLE 2

LC/MS and HPLC methods

| Method | Conditions |
|---|---|
| a | LC/MS: Analytical LC-MS was performed on a Finnigan Navigator mass spectrometer and Agilent 1100 HPLC system running Xcalibur 1.2, Open-Access 1.3 and custom login software, or on a Thermo MSQ-Plus mass spectrometer and Agilent 1200 HPLC system running Xcalibur 2.0.7, Open-Access 1.4, and custom login software. The mass spectrometer was operated under positive APCI ionization conditions. The HPLC system comprised an Agilent Quaternary pump, degasser, column compartment, autosampler and diode-array detector, with a Polymer Labs ELS-2100 evaporative light-scattering detector. The column used was a Phenomenex Luna Combi-HTS C8(2) 5 μm 100 Å (2.1 mm × 50 mm), at a temperature of 55° C. "TFA method": A gradient of 10-100% MeCN (A) and 0.1% TFA in water (B) was used, at a flow rate of 2.0 mL/min (0-0.1 min 10% A, 0.1-2.6 min 10-100% A, 2.6-2.9 min 100% A, 2.9-3.0 min 100-10% A. 0.5 min post-run delay). |
| b | PrepHPLC: HTP Waters Prep-HPLC Purification, small scale (10 mg-300 mg): Samples were purified by preparative HPLC on a Waters Sunfire C8 5 μm column (30 mm × 75 mm). A gradient of MeOH (A) and 0.1% TFA in water or 10 mM NH$_4$OH in water (B) was used, at a flow rate of 50 mL/min (0-0.5 min 0% A, 0.5-7.0 min linear gradient 0-90% A, 7.1-10.0 min 95% A, 10.0-12.0 min linear gradient 95-10% A). Samples were injected in 1.5 mL DMSO:MeOH (1:1). A custom purification system was used, consisting of the following modules: Waters LC4000 preparative pump; Waters 996 diode-array detector; Waters 717+ autosampler; Waters SAT/IN module; Gilson 506C interface box; and two Gilson FC204 fraction collectors. The system was controlled using Waters Millennium 32 software, automated using an Abbott developed Visual Basic application for fraction collector control and fraction tracking. Fractions were collected based upon UV signal threshold. Selected fractions were subsequently analyzed by flow injection analysis mass spectrometry using positive APCI ionization on a Finnigan aQa using 70:30 MeOH:10 mM NH$_4$OH in water a flow rate of 0.8 mL/min. The Finnigan aQa was controlled using Navigator 1.2 software and a Gilson 215 liquid handler for fraction injection controlled by an Abbott developed Visual Basic application. |

TABLE 2-continued

LC/MS and HPLC methods

| Method | Conditions |
|---|---|
| c | LC/MS: The column used for the chromatography is a 4.6 × 50 mm MAC-MOD Halo C18 column (2.7 μm particles). The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. Detection methods are diode array (DAD) and evaporative light scattering (ELSD) detection as well as pos/neg electrospray ionization. |
| d | LC/MS: The column used was an XBridge C18, 4.6 × 50 mm, 3.5 um (2.1 mm × 50 mm), at a temperature of 50° C. A gradient of 5-95% MeCN (A) and 10 mM of $NH_4HCO_3$ in water (B) was used, at a flow rate of 2.3 mL/min (0-0.2 min 5% A, 0.2-1.9 min 5-95% A, 1.9-3.3 min 95% A, 3.3-3.4 min 95-5% A). |
| e | LC/MS: The column used was an XBridge C18, 4.6 × 50 mm, 3.5 um (2.1 mm × 50 mm), at a temperature of 50° C. A gradient of 5-95% 0.05% TFA in MeCN (A) and 0.05% TFA in water (B) was used, at a flow rate of 2.3 mL/min (0-0.2 min 5% A, 0.2-1.9 min 5-95% A, 1.9-3.2 min 95% A, 3.2-3.3 95-5% A). |
| f | LC/MS: The column used was an XBridge C18, 4.6 × 50 mm, 3.5 um (2.1 mm × 50 mm), at a temperature of 50° C. A gradient of 5-95% MeCN (A) and 10 mM of $NH_4HCO_3$ in water (B) was used, at a flow rate of 1.8 mL/min (0-0.2 min 5% A, 0.2-1.8 min 5-95% A, 1.8-3.6 min 95% A, 3.6-3.7 95-5% A). |
| g | LC/MS: The column used was a SunFire C18, 4.6 × 50 mm, 3.5 um (2.1 mm × 50 mm), at a temperature of 50° C. A gradient of 5-95% 0.05% TFA in MeCN (A) and 0.05% TFA in water (B) was used, at a flow rate of 2.5 mL/min (0-0.2 min 5% A, 0.2-1.9 min 5-95% A, 1.9-3.2 min 95% A, 3.2-3.3 95-5% A). |
| h | LC/MS: The column used was an XBridge C18, 4.6 × 50 mm, 3.5 um (2.1 mm × 50 mm), at a temperature of 50° C. A gradient of 5-95% MeCN (A) and 10 mM of $NH_4HCO_3$ in water (B) was used, at a flow rate of 2.1 mL/min (0-0.2 min 5% A, 0.2-1.9 min 5-95% A, 1.9-3.3 min 95% A, 3.3-3.4 95-5% A). |
| i | LC/MS: The column used was an XBridge C18, 4.6 × 50 mm, 3.5 um (2.1 mm × 50 mm), at a temperature of 50° C. A gradient of 5-95% 0.01% TFA in MeCN (A) and 0.01% TFA in water (B) was used, at a flow rate of 2.3 mL/min (0-0.2 min 5% A, 0.2-1.9 min 5-95% A, 1.9-3.2 min 95% A, 3.2-3.3 95-5% A). |
| j | LC/MS: The column used was an XBridge C18, 4.6 × 50 mm, 3.5 um (2.1 mm × 50 mm), at a temperature of 50° C. A gradient of 5-95% MeCN (A) and 10 mM of $NH_4HCO_3$ in water (B) was used, at a flow rate of 2.1 mL/min (0-0.2 min 5% A, 0.2-1.9 min 5-95% A, 1.9-3.0 min 95% A, 3.0-3.1 95-5% A). |
| k | LC/MS: The column used was a Zorbax SB-C18 Rapid Resolution HT, 4.6 × 30 mm, 1.8 um (2.1 mm × 50 mm), at a temperature of 45° C. A gradient of 5-95% 0.01% TFA in MeCN (A) and 0.01% TFA in water (B) was used, at a flow rate of 3.0 mL/min (0-0.1 min 5% A, 0.1-0.8 min 5-95% A, 0.8-1.7 min 95% A, 1.7-1.8 95-5% A). |
| l | LC/MS: Mobile Phase: A: Water(0.01% TFA) B: MeCN (0.01% TFA) Gradient: 5% for 0.1 min, increase to 95% B within 0.7 min, 95% B for 0.9 min, back to 5% B within 0.01 min Flow Rate: 3.0 mL/min Column: Zorbax SB-C18 Rapid Resolution HT, 4.6 × 30 mm, 1.8 um Column Temperature: 45 C, UV 214 and 254 nm |
| m | LC/MS: The column used was an XBridge C18, 4.6 × 50 mm, 3.5 um (2.1 mm × 50 mm), at a temperature of 50° C. A gradient of 5-95% MeCN (A) and 10 mM of $NH_4HCO_3$ in water (B) was used, at a flow rate of 1.81 mL/min (0-0.2 min 5% A, 0.2-1.4 min 5-95% A, 1.4-3.0 min 95% A, 3.0-3.1 95-5% A). |
| n | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$ in water, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| o | Prep HPLC: The gradient was 30-55% B over 8 min, hold at 100% B for 6 min (30 mL/min flow rate). Mobile phase A was water (0.05% $NH_4HCO_3$) and mobile phase B was HPLC grade MeCN. The column used for the chromatography was an XBridge Prep C18 column, 5 um. Detection method was UV (214/254 nM detection). |
| p | Prep HPLC: The gradient was 20-50% B over 8.7 min, hold at 100% B for 3.6 min (30 mL/min flow rate). Mobile phase A was water (0.05% $NH_4HCO_3$) and mobile phase B was HPLC grade MeCN. The column used for the chromatography was a 19 × 250 mM XBridge Prep C18 OBD column, 10 um. Detection method was UV (214/254 nM detection). |

TABLE 2-continued

LC/MS and HPLC methods

| Method | Conditions |
|---|---|
| q | Prep HPLC: The gradient was 25-50% B over 8 min, hold at 100% B for 6 min (30 mL/min flow rate). Mobile phase A was water (0.05% NH$_4$HCO$_3$) and mobile phase B was HPLC grade MeCN. The column used for the chromatography was an XBridge Prep C18 column, 5 um. Detection method was UV (214/254 nM detection). |
| r | Prep HPLC: The gradient was 20-60% B over 8.7 min, hold at 100% B for 3.6 min (30 mL/min flow rate). Mobile phase A was water (0.01N NH$_4$HCO$_3$) and mobile phase B was HPLC grade MeCN. The column used for the chromatography was a 19 × 250 mM XBridge Prep C18 OBD column, 10 um. Detection method was UV (214 and 254 nM detection). |
| s | UPLC-MS: Analytical UPLC-MS was performed on a Waters SQD mass spectrometer and Acquity UPLC system running MassLynx 4.1 and Openlynx 4.1 software. The SQD mass spectrometer was operated under positive APCI ionization conditions. The column used was a Waters BEH C8, 1.7 μm (2.1 mm × 30 mm) at a temperature of 55° C.<br>"TFA method": A gradient of 10-100% MeCN (A) and 0.1% TFA in water (B) was used, at a flow rate of 1.0 mL/min (0-0.1 min 10% A, 0.1-1.1 min 10-100% A, 1.1-1.3 min 100% A, 1.3-1.4 min 100-10% A). |
| t | Prep HPLC: Instrument Gilson 281 (PHG008) Column Waters X-bridge OBD C18 19 × 250 mm, 10 um Mobile Phase A water (10 mM NH$_4$HCO$_3$) B MeCN Gradient 25-80% B in 8 min, stop at 15 min Flow Rate (mL/min) 30.00 Detector Wavalength (nm) 214\254 |
| u | LC/MS: The gradient was 5-60% B in 0.75 min then 60-95% B to 1.15 min with a hold at 95% B for 0.75 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| v | Prep HPLC: Instrument waters 2767 PHW003 Column Boston C18 10 μm 21 × 250 mm Mobile Phase A: water (0.05% NH$_4$HCO$_3$); B: MeCN Gradient 25-50% B in 8 min, stop at 14 min Flow Rate (mL/min) 30.00 Detector Wavalength (nm) 214 and 254 |
| w | Prep HPLC: Instrument: Waters 2767; Column: YMC-Triart C18 150 × 20 mm S-5 μm. 12 nm; Mobile Phase: A: water (0.05% NH$_4$CO$_3$), B: MeCN; Gradient: 40-70% B in 8 min; Flow Rate (mL/min): 20.00; Detector Wavelength (nm): 214 and 254 |
| x | Prep HPLC/MS: The gradient was a hold at 14.5% B over 2.50 min followed by 14.5-19% B over 0.50 min, 19-82% B for 6 min, a hold at 82% B for 0.1 min, and 82-95.5% B over 1.5 min (25 mL/min flow rate). Mobile phase A was 50 mM NH$_4$OAc (pH 4.5) and mobile phase B was HPLC grade MeCN. The column used for the chromatography was a 19 × 50 mm Waters Atlantis T3 OBD C18 column (5 um particles), detection methods are Photodiode array DAD and Waters ZQ 2000 mass spectrometer. |

TABLE 3

Chiral Separation Methods

| Method | Conditions |
|---|---|
| 1 | Preparative: Isocratic 75% A for 2.5 min cycle time (60 g/min flow rate, back pressure 100 Bar). Mobile phase A was supercritical CO$_2$, mobile phase B was HPLC grade MeOH with 0.1% diethylamine added. The column used for the chromatography was a ChiralPak OJ-H (Daicel), 20 × 250 mm column (5 μm particles) with a column temperature of 35° C. Detection method was UV, wavelength (nm): 214. |
| 2 | Preparative: Isocratic 70% A (70 mL/min flow rate, back pressure 100 Bar). Mobile phase A was supercritical CO$_2$, mobile phase B was HPLC grade MeOH with 0.5% diethylamine added. The column used for the chromatography was a ChiralPak AS-H (Daicel), 30 × 250 mm column (5 μm particles) with a column temperature of 35° C. Detection method was UV, wavelength (nm): 214. |
| 3 | Analytical: Isocratic 70% A (2.1 mL/min flow rate, back pressure 100 Bar). Mobile phase A was supercritical CO$_2$, mobile phase B was HPLC grade MeOH with 0.1% diethylamine added. The column used for the chromatography was a ChiralPak AS-H (Daicel), 4.6 × 250 mm column (5 μm particles) with a column temperature of 40.8° C. Detection method was PDA, monitoring from wavelength (nm): 214-359. |

General Purification Methods

For the general procedures, the final compounds may be purified by any technique or combination of techniques known to one skilled in the art. Some examples that are not limiting include column chromatography with a solid phase (i.e. silica gel, alumina, etc.) and a solvent (or combination of solvents) that elutes the desired compounds (i.e. hexanes, heptane, EtOAc, DCM, MeOH, EtOH, MeCN, water, etc.); preparatory TLC with a solid phase (i.e. silica gel, alumina etc.) and a solvent (or combination of solvents) that elutes the desired compounds (i.e. hexanes, heptane, EtOAc, DCM, MeOH, EtOH, MeCN, water, etc.); reverse phase HPLC (see Table 2 for some non-limiting conditions); recrystallization from an appropriate solvent (i.e. MeOH, EtOH, IPA, EtOAc, toluene, etc.) or combination of solvents (i.e. EtOAc/heptane, EtOAc/MeOH, etc.); chiral LC with a solid phase and an appropriate solvent (i.e. EtOH/heptane, MeOH/heptane, IPA/heptane, etc. with or without a modifier such as diethylamine, TFA, etc.) to elute the desired compound; chiral SFC with a solid phase and CO$_2$ with an appropriate modifier (i.e. MeOH, EtOH, IPA with or without additional modifier such as diethylamine, TFA, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, IPA, PrOH, etc.); extractions by dissolving a compound in a liquid and washing with an appropriately immiscible liquid (i.e. DCM/water, EtOAc/water, DCM/saturated NaHCO₃, EtOAc/saturated NaHCO₃, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. J. Org. Chem. 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, 2$^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, 4$^{th}$ Edition", 1993; Skoog, D. A. and Leary, J. J. "Principles of Instrumental Analysis, 4$^{th}$ Edition" 1992; Subramanian, G. "Chiral Separation Techniques 3$^{rd}$ Edition" 2007; Kazakevich, Y. and Lobrutto, R. "HPLC for Pharmaceutical Scientists" 2007. Final or intermediate compounds prepared via any of the following General Procedures can be optionally purified using one or more of the purification methods described above.

PREPARATIONS AND EXAMPLES

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 9.0.7, CambridgeSoft® Chemistry E-Notebook 9.0.127, or AutoNom 2000. Compounds designated as salts (e.g. hydrochloride, acetate) may contain more than one molar equiv of the salt.

Preparation #1.
6-Amino-1,2-benzisothiazol-3(2H)-one-1,1-dioxide

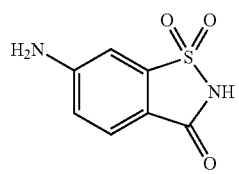 [SMILES: Nc1ccc2c(c1)S(=O)(=O)NC2=O]

Step A: 5-Nitro-2-methyl-phenylsulfonyl chloride

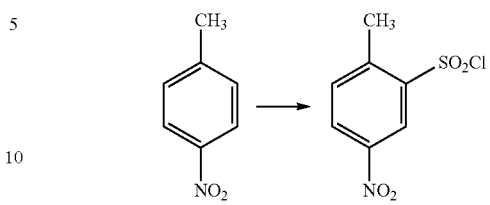

Chlorosulfonic acid (50 mL, 750 mmol) was added within about 30 min dropwise to a solution of p-nitrotoluene (13.7 g, 100 mmol) in CHCl₃ (50 mL) under ice cooling. After addition, the mixture was refluxed for about 6 h, cooled, the mixture poured into ice water (500 mL) and extracted with CHCl₃ (3×300 mL). The CHCl₃ layer was washed with water (2×200 mL) and dried with Na₂SO₄. Evaporation of CHCl₃ gave 5-nitro-2-methyl-phenylsulfonyl chloride (18.4 g, 78%): ¹H NMR (DMSO-d₆) δ: 8.92 (d, J=2.4 Hz, 1H), 8.46 (dd, J=2.4 Hz, 1H), 7.66 (s, 1H), 2.92 (s, 3H).

Step B: 2-Methyl-5-nitrobenzenesulfonamide

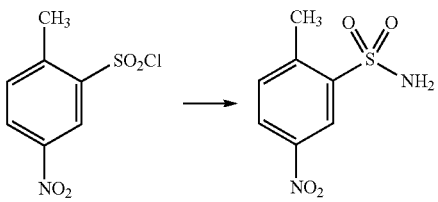

A solution of 2-methyl-5-nitrobenzenesulfonyl chloride (10.0 g, 43.7 mmol) and Et₂O (300 mL) under N₂ was cooled to about 0° C. and concentrated. NH₄OH (40 mL) was added. After stirring for about 42 h, the mixture was filtered and then diluted with DCM (600 mL). The organic layer was separated and dried over MgSO₄. The solution was then concentrated under reduced pressure to afford 2-methyl-5-nitrobenzenesulfonamide (9.2 g, 100%). ¹H NMR (DMSO-d₆) δ: 8.60 (d, J=2.4 Hz, 1H), 8.34 (dd, J=8.0, 2.4 Hz, 1H), 7.77 (br s, 2H), 7.70 (d, J=8.4 Hz, 1H), 2.71 (s, 3H).

Step C: 6-Nitro-1,1-dioxo-1,2-dihydro-1lambda*6*-benzo[d]isothiazol-3-one

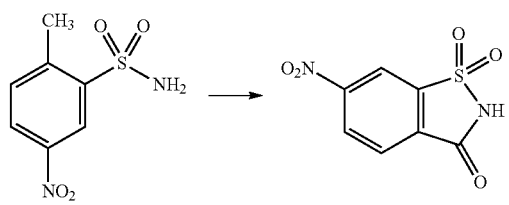

To a solution of CrO₃ (20.8 g, 208 mmol) in water (150 mL) was slowly added concentrated sulfuric acid (190 mL). To the resulting mixture was added 2-methyl-5-nitrobenzenesulfonamide (10.0 g, 46.3 mmol) and the mixture was stirred at rt for about 42 h. The mixture was filtered and the filter cake was washed with water (100 mL). The solid was dissolved in 10% aqueous NaHCO$_3$, filtered and the filtrate acidified with 2 N HCl (pH=1). The precipitate was collected by filtration and washed with water (2×50 mL) to provide 6-nitro-1,1-dioxo-1,2-dihydro-1lambda*6*-benzo[d]isothiazol-3-one (7.2 g, 68%). $^1$H NMR (DMSO-d$_6$) δ: 8.42-8.53 (m, 2H), 8.00 (s, 1H), 3.70 (br s, 1H).

Step D:
6-Amino-1,2-benzisothiazol-3(2H)-one-1,1-dioxide

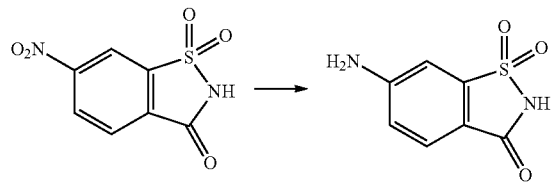 [SMILES: O=C1NS(=O)(=O)c2cc([N+](=O)[O-])ccc21 ; Nc1ccc2c(c1)S(=O)(=O)NC2=O]

To a solution of 6-nitro-1,1-dioxo-1,2-dihydro-1lambda*6*-benzo[d]isothiazol-3-one (11.4 g, 50.0 mmol) and cyclohexene (25.4 mL, 250 mmol) in EtOH (100 mL) was added 5% Pd—C (35 g) at about 0° C. The mixture was refluxed overnight with stirring and then cooled to rt, filtered through Celite® several times until the filtrate became clear. The filtrate was concentrated under reduced pressure. The material was dissolved in saturated aqueous NaHCO$_3$ (200 mL), filtered and to the filtrate was added concentrated hydrochloric acid (pH=7). The precipitate was collected by filtration and washed with water (2×50 mL) to provide 6-amino-1,2-benzisothiazol-3(2H)-one-1,1-dioxide (8.0 g, 68%): $^1$H NMR (DMSO-d$_6$) δ: 7.61 (s, 1H), 7.59 (s, 1H), 6.95 (d, J=2.0 Hz, 2H), 6.91 (d, J=2.4 Hz, 1H), 6.89 (d, J=2.0 Hz, 1H).

Preparation #2. 1,1-Dioxo-2,3-dihydro-1H-1lambda*6*-benzo[d]isothiazol-6-ylamine

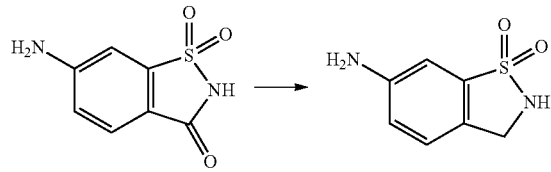 [SMILES: Nc1ccc2c(c1)S(=O)(=O)NC2=O ; Nc1ccc2c(c1)S(=O)(=O)NC2]

To a solution of 6-amino-1,2-benzisothiazol-3(2H)-one-1,1-dioxide (7.0 g, 35 mmol, Preparation #1) in concentrated HCl (80 mL) was added zinc dust (19.0 g, 292 mmol), in portions over about 30 min while maintaining the temperature below about 70° C. The mixture was stirred at rt for about 3 h. The mixture was basified with a solution of saturated aqueous NaHCO$_3$ (50 mL), then with solid NaHCO$_3$ (pH=7). The mixture was added to EtOAc (100 mL), filtered and the filtrate was extracted with EtOAc (3×150 mL). The organic phases were combined, washed with brine (3×150 mL), dried over MgSO$_4$, filtered and concentrated under reduced pressure to give a solid. The residue from filtration was triturated with EtOAc (2×200 mL) and filtered. The organic phases were combined, dried over MgSO$_4$, filtered and concentrated under reduced pressure to give a solid. All the solids were dissolved in MeOH, combined and then concentrated to give 1,1-dioxo-2,3-dihydro-1H-1lambda*6*-benzo[d]isothiazol-6-ylamine (5.7 g, 88%): $^1$H NMR (DMSO-d$_6$) δ 7.54 (s, 1H), 7.14 (d, J=8.5 Hz, 1H), 6.83 (dd, J=2.5, 2.0 Hz, 1H), 6.79 (d, J=1.5 Hz, 1H), 5.81 (s, 2H), 4.18 (s, 2H).

Preparation #3. 4-Amino-N-propylbenzamide

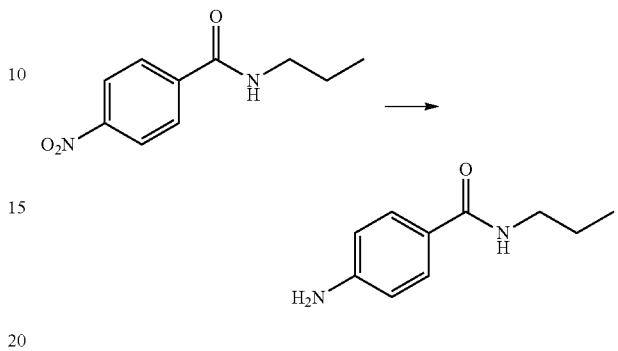

4-Nitro-N-propylbenzamide (3.31 g, 15.9 mmol) was dissolved in EtOAc (125 mL) and EtOH (125 mL) and passed through the H-Cube® at 1 mL/min equipped with a 10% Pd/C catcart (ThalesNano), at full hydrogen and temperature set to about 50° C. The solvent was stripped off and the solid was dried overnight in a vacuum oven set at about 50° C. to provide 4-amino-N-propylbenzamide (2.58 g, 91%): $^1$H NMR (DMSO-d$_6$) δ 7.93 (t, J=5.48 Hz, 1H); 7.54 (d, J=8.57 Hz, 2H); 6.51 (d, J=8.67 Hz, 2H) 5.54 (br s, 2H) 3.13 (m, 2H) 1.47 (sextet, J=7.29 Hz, 2H) 0.85 (t, J=8.49 Hz, 3H).

Preparation #4: Benzyl 4-(aminomethyl)-4-cyanopiperidine-1-carboxylate

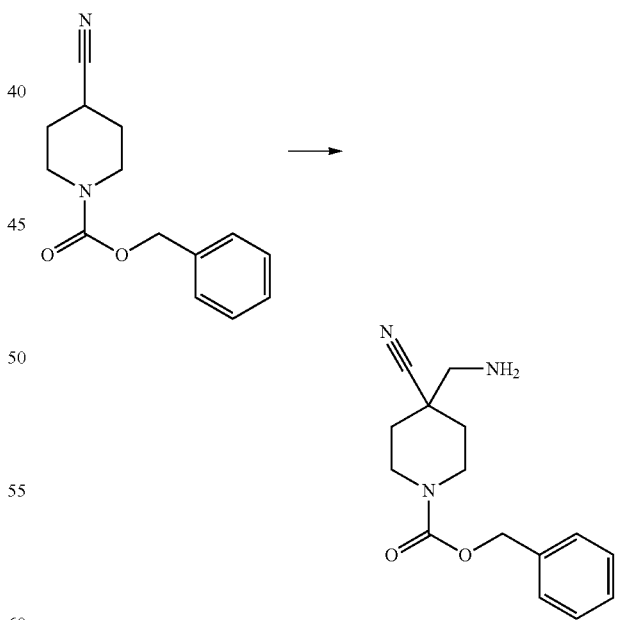

To a mixture of benzyl 4-cyanopiperidine-1-carboxylate (1.0 g, 4.0 mmol, Oakwood) in THF (50 mL) at about −78° C. was added LiHMDS (1.0 M solution in THF, 6.14 mL, 6.14 mmol) dropwise via syringe. The mixture was stirred for about 1 h. Paraformaldehyde (0.25 g, 8.2 mmol) was added in one portion and the mixture was stirred overnight at rt. The mixture was concentrated in vacuo and the residue was purified by preparative TLC (1:1 EtOAc/pet ether) to give benzyl 4-cyano-4-(hydroxymethyl)piperidine-1-carboxylate (0.45 g, 35%): LC/MS (Table 2, Method k) R$_t$=0.60 min; MS m/z: 274 (M+H)$^+$.

Preparation #5: 2-Chloro-4-(cyclopropylethynyl)furo[3,2-d]pyrimidine

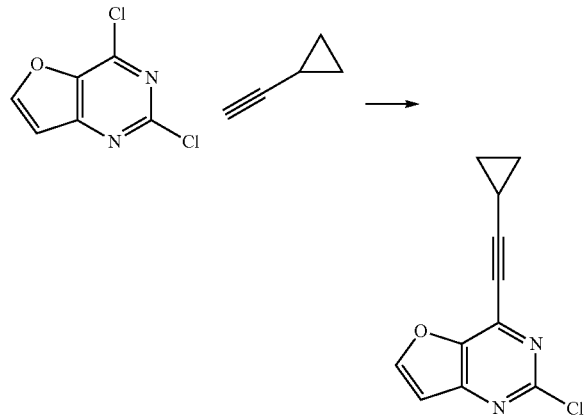

To a flask was added 2,4-dichlorofuro[3,2-d]pyrimidine (0.30 g, 1.6 mmol, ArkPharm), PPh$_3$ (0.008 g, 0.03 mmol) in THF (1.2 mL) and TEA (1.764 mL). The mixture was placed under vacuum and purged with N$_2$ three times, then Pd(PPh$_3$)$_2$Cl$_2$ (0.011 g, 0.016 mmol) and CuI (0.006 g, 0.03 mmol) were added. The mixture was placed under vacuum and purged with N$_2$ three times and then ethynylcyclopropane (0.161 mL, 1.905 mmol) was added. The mixture was placed under vacuum and purged with N$_2$ and then the mixture was stirred at rt for about 18 h. The mixture was filtered and the filter cake was washed with EtOAc (3×20 mL). The filtrate was concentrated under reduced pressure and the residue was deposited on silica gel and purified by column chromatography (12 g silica gel, 0 to 30% EtOAc/heptane) to give 2-chloro-4-(cyclopropylethynyl)furo[3,2-d]pyrimidine (0.090 g, 26%): LC/MS (Table 2, Method c) R$_t$=2.11 min; MS m/z 219 (M+H)$^+$.

Preparation #6: Methyl 6-nitro-1-((2-(trimethylsilyl)ethoxy)methyl)-1H-indazole-3-carboxylate

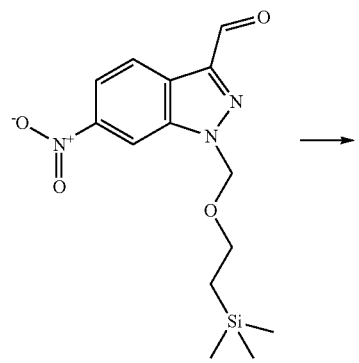

-continued

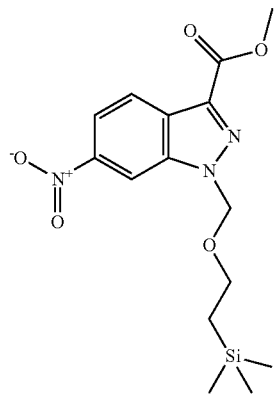

6-Nitro-1-((2-(trimethylsilyl)ethoxy)methyl)-1H-indazole-3-carbaldehyde (1.72 g, 5.35 mmol, Preparation #N.1) was added to a solution of 2-methyl-2-butene (2.0 M in THF, 26.8 mL, 53.5 mmol) and t-BuOH (48.2 mL) under N$_2$. A solution of sodium dihydrogen phosphate (3.35 g, 27.9 mmol) and sodium chlorite (1.50 g, 16.6 mmol) in water (16.1 mL) was added and the mixture was stirred at rt for about 3 h. The mixture was concentrated under reduced pressure. DCM (50 mL) and aqueous 1 N HCl (20 mL) were added and the layers separated. The aqueous layer was extracted with DCM (15 mL). The combined organic layers were washed with brine (10 mL), dried over Na$_2$CO$_3$, filtered, and concentrated under vacuum. The solid was dissolved in a mixture of THF (64.3 mL) and MeOH (16.1 mL). (Trimethylsilyl)diazomethane (2 M in Et$_2$O, 4.01 mL, 8.03 mmol) was added drop-wise. After about 2 h, AcOH (1 mL) was added and the mixture was stirred for about 14 h. The mixture was concentrated under reduced pressure. DCM (100 mL) was added and the mixture was washed with an aqueous solution of saturated NaHCO$_3$ (25 mL) and the layers separated. The organic layer was washed with brine (10 mL), dried over Na$_2$CO$_3$, filtered and concentrated in vacuo. The residue was purified by column chromatography (80 g silica gel) eluting with 10 to 20% EtOAc/heptane to provide methyl 6-nitro-1-((2-(trimethylsilyl)ethoxy)methyl)-1H-indazole-3-carboxylate (1.66 g, 88%): LC/MS (Table 2, Method c) R$_t$=2.99 min.; MS m/z: 352 (M+H)$^+$, 369 (M+H$_2$O)$^+$.

General Procedure A: Nucleophilic Displacement of an Aryl Halide with an Amine

To a solution of an aryl halide and an appropriate organic solvent (such as 1,4-dioxane, DME, n-butanol, THF or DMF, preferably 1,4-dioxane) is added an amine (1 to 5 equiv, preferably 1 equiv) and a base (such as TEA, DIEA, K$_2$CO$_3$, preferably TEA; 1 to 5 equiv, preferably 1 equiv). The resulting mixture is stirred at about 20 to 150° C. (preferably about 25° C.) for a period of about 1 h to 24 h (preferably about 4 to 16). The mixture is optionally concentrated in vacuo or under a warm nitrogen stream to give the intermediates or targeted compound or optionally filtered through a media (such as SiCO$_3$ or Celite®) which is rinsed with an appropriate solvent (such as EtOAc, 1,4-dioxane, THF, MeCN, DCM, Et$_2$O, MeOH, EtOH, DMSO, 1:1 MeOH/DMSO, 2:1 MeOH/DMSO) and then optionally concentrated in vacuo or under a warm nitrogen stream to give the targeted compound.

Illustration of General Procedure A

Preparation #A.1:
2-Chloro-N-cyclopropylfuro[3,2-d]pyrimidin-4-amine

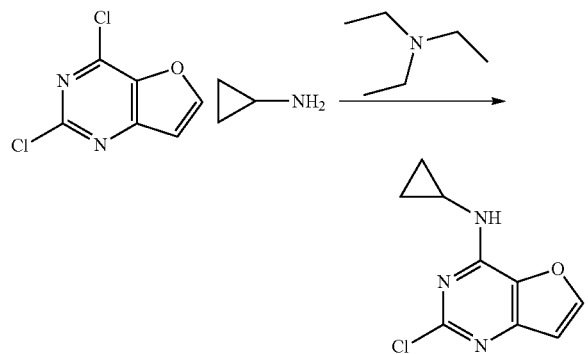

A vial was charged with 2,4-dichlorofuro[3,2-d]pyrimidine (0.50 g, 2.6 mmol, Ark Pharm), TEA (0.369 mL, 2.65 mmol), 1,4-dioxane (20 mL) and cyclopropylamine (0.186 mL, 2.65 mmol). The mixture was stirred at rt for about 5 h and then passed through a 5.0 g SiCO$_3$ SPE cartridge, (MeOH eluent) and concentrated under reduced pressure. The residue was purified by silica gel chromatography with a gradient of 0 to 50% EtOAc/hexanes to give 2-chloro-N-cyclopropylfuro[3,2-d]pyrimidin-4-amine (0.5 g, 90%). $^1$H NMR (CDCl$_3$): δ 7.77 (s, 1H); 6.80 (s, 1H), 5.51 (s, 1H) 3.07 (m, 1H) 0.96 (q, J=5 Hz, 15 Hz, 2H) 0.70, (q, J=5 Hz, 15 Hz, 2H).

General Procedure B: Buchwald Reaction of an Aryl Halide with an Aniline

A mixture of an aryl halide (1.0 equiv), an aniline (1 to 2.2 equiv, preferably 1 to 1.2 equiv), a palladium catalyst (such as Pd$_2$dba$_3$, Pd(OAc)$_2$, preferably Pd$_2$dba$_3$ 0.01 to 1.0 equiv, preferably 0.04 to 0.1 equiv), a ligand (such as X-phos, Xanthphos or tert-butyl-X-phos, preferably tert-butyl-X-phos or X-Phos, 0.01 to 2.0 equiv, preferably 0.04 to 0.1 equiv) and a base (such as K$_2$CO$_3$, Na$_2$CO$_3$, Cs$_2$CO$_3$, K$_3$PO$_4$, NaOt-Bu, KOt-Bu, KOAc, KOH, preferably K$_2$CO$_3$; 1 to 5 equiv, preferably 1 to 3 equiv) are added to a solvent (such as 1,4-dioxane, t-BuOH, preferably t-BuOH). The mixture is degassed under an inert atmosphere (such as nitrogen or argon, preferably nitrogen) and heated with conventional heating at about 80 to 100° C. (preferably about 85 to 95° C.) for about 2 to 24 h (preferably about 16 h). The mixture is cooled to rt. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH, DMSO, 1:1 MeOH/DMSO or 2:1 MeOH/DMSO, preferably MeOH/DMSO) and then the filtrate is optionally concentrated in vacuo or under a warm nitrogen stream to give a residue.

Illustration of General Procedure B

Example #B.1

N$^2$-(3-Chloro-4-(4-methylpiperazin-1-yl)phenyl)-N$^4$-cyclopropylfuro[3,2-d]pyrimidine-2,4-diamine

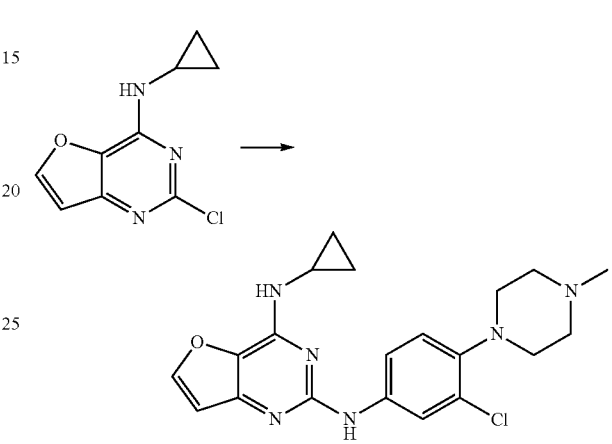

To a vial was added 2-chloro-N-cyclopropylfuro[3,2-d]pyrimidin-4-amine (0.099 g, 0.476 mmol, Preparation #A.1), 3-chloro-4-(4-methylpiperazin-1-yl)aniline (0.118 g, 0.523 mmol, Art-Chem), X-Phos (0.0136 g, 0.029 mmol), K$_2$CO$_3$ (0.079 g, 0.571 mmol), and Pd$_2$dba$_3$ (0.026 g, 0.029 mmol). t-BuOH (2 mL) was then added and tube was sealed. The tube was evacuated and purged with nitrogen (3×), and stirred overnight at about 85° C. The mixture was filtered, the filter pad was washed with EtOAc and then the solvent was removed in vacuo. The crude material was added to a silica gel column and was eluted with MeOH/DCM (2% to 10%). The sample was further purified by preparative reverse phase HPLC (Table 2, Method b). The collected fractions were dissolved in DCM (10 mL) and washed with saturated aqueous NaHCO$_3$, (10 mL) and separated using a Biotage phase separator column. The filtrate was concentrated to provide N$^2$-(3-chloro-4-(4-methylpiperazin-1-yl)phenyl)-N$^4$-cyclopropylfuro[3,2-d]pyrimidine-2,4-diamine (0.082 g, 43%): LC/MS (Table 2, Method a) R$_t$=1.04 min; MS m/z 399.2 (M+H)$^+$. Syk IC$_{50}$=B

TABLE B.1

Examples prepared from an aniline with 2-chloro-N-cyclopropylfuro[3,2-d]pyrimidin-4-amine (Preparation #A.1) using General Procedure B

| Aniline | Product | Ex. # | R$_t$ min (Table 2, Method) | m/z ESI+ (M + H)$^+$ | Syk IC$_{50}$ |
|---|---|---|---|---|---|
| 3-Chloro-4-morpholin-4-yl-phenylamine [Maybridge] | | B.1.1 | 1.42 (a) | 386 | A |

TABLE B.1-continued

*Examples prepared from an aniline with 2-chloro-N-cyclopropylfuro[3,2-d]pyrimidin-4-amine (Preparation #A.1) using General Procedure B*

| Aniline | Product | Ex. # | $R_t$ min (Table 2, Method) | m/z ESI+ $(M + H)^+$ | Syk $IC_{50}$ |
|---|---|---|---|---|---|
| 4-Aminobenzenesulfonamide | | B.1.2 | 0.52 (a) | 346 | B |
| 4-Amino-N-propylbenzamide (Preparation #3) | | B.1.3 | 1.18 (a) | 352 | B |
| 2,2-Dioxo-1,3-dihydrobenzo[c]thiophene-5ylamine [Maybridge] | | B.1.4 | 0.91 (a) | 357 | B |
| 4-(Morpholinomethyl)aniline [Maybridge] | | B.1.5 | 0.33 (a) | 366 | B |
| 1-(4-(4-Aminophenyl)piperazin-1-yl)ethanone [Alfa Aesar] | | B.1.6 | 0.94 (a) | 393 | B |
| 1,1-Dioxo-2,3-dihydro-1H-1lambda*6*-benzo[d]isothiazol-6-ylamine (Preparation #2) | | B.1.7 | 0.92 (a) | 358 | C |

TABLE B.1-continued

Examples prepared from an aniline with 2-chloro-N-cyclopropylfuro[3,2-d]pyrimidin-4-amine (Preparation #A.1) using General Procedure B

| Aniline | Product | Ex. # | $R_t$ min (Table 2, Method) | m/z ESI+ $(M + H)^+$ | Syk $IC_{50}$ |
|---|---|---|---|---|---|
| 6-Amino-1,2-benzisothiazol-3(2H)-one-1,1-dioxide (Preparation #1) | | B.1.8 | 0.83 (a) | 372 | B |
| 1H-Indazol-6-amine | | B.1.9 | 1.08 (a) | 307 | A |
| 1-Methyl-1H-pyrazol-4-amine [Oakwood] | | B.1.10 | 0.53 (a) | 271 | B |
| 6-Amino-3,4-dihydroquinolin-2(1H)-one [Tyger] | | B.1.11 | 0.90 (a) | 336 | B |

TABLE B.2

Examples prepared from a heteroaryl chloride with 4-Aminobenzenesulfonamide using General Procedure B

| Heteroaryl Chloride | Product | Ex. # | $R_t$ min (Table 2, Method) | m/z ESI+ $(M + H)^+$ | Syk $IC_{50}$ |
|---|---|---|---|---|---|
| (R)-1-(2-Chlorofuro[3,2-d]pyrimidin-4-yl)pyrrolidine-2-carboxamide (prepared using A from 2,4-dichlorofuro[3,2-d]pyrimidine [ArkPharm] with D-prolinamide [Oakwood]) | | B.2.1 | 0.24 (a) | 403 | D |

TABLE B.2-continued

Examples prepared from a heteroaryl chloride with 4-Aminobenzenesulfonamide using General Procedure B

| Heteroaryl Chloride | Product | Ex. # | $R_t$ min (Table 2, Method) | m/z ESI+ $(M + H)^+$ | Syk $IC_{50}$ |
|---|---|---|---|---|---|
| 1-(2-Chlorofuro[3,2-d]pyrimidin-4-yl)piperidine-4-carboxamide (prepared using A from 2,4-dichlorofuro[3,2-d]pyrimidine [ArkPharm] with isonipecotamide) | | B.2.2 | 0.29 (a) | 417 | C |
| (S)-1-(2-Chlorofuro[3,2-d]pyrimidin-4-yl)pyrrolidine-2-carboxamide (prepared using A from 2,4-dichlorofuro[3,2-d]pyrimidine [ArkPharm] with L-prolinamide) | | B.2.3 | 0.25 (a) | 403 | D |
| 1-(2-Chlorofuro[3,2-d]pyrimidin-4-yl)piperidine-3-carboxamide (prepared using A from 2,4-dichlorofuro[3,2-d]pyrimidine [ArkPharm] with nipecotamide [Acros]) | | B.2.4 | 0.35 (a) | 417 | B |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | | B.2.5 | 0.97 (a) | 360 | B |
| (1-(2-Chlorofuro[3,2-d]pyrimidin-4-yl)piperidin-4-yl)methanol (prepared using A from 2,4-dichlorofuro[3,2-d]pyrimidine [ArkPharm] with piperidin-4-ylmethanol) | | B.2.6 | 0.58 (a) | 404 | C |

TABLE B.2-continued

Examples prepared from a heteroaryl chloride with 4-Aminobenzenesulfonamide using General Procedure B

| Heteroaryl Chloride | Product | Ex. # | $R_t$ min (Table 2, Method) | m/z ESI+ $(M + H)^+$ | Syk $IC_{50}$ |
|---|---|---|---|---|---|
| cis-2-(2-Chlorofuro[3,2-d]pyrimidin-4-ylamino)cyclopentane-carboxamide (prepared using A from 2,4-dichlorofuro[3,2-d]pyrimidine [ArkPharm] with cis-2-amino-1-cyclopentanecarbox-amide [Acros]) | | B.2.7 | 0.47 | 417 | C |
| 2-Chloro-4-(4-(methylsulfonyl)piper-azin-1-yl)furo[3,2-d]pyrimidine [Preparation #D.1] | | B.2.8 | 0.44 (a) | 453 | C |
| 1-(4-(2-Chlorofuro[3,2-d]pyrimidin-4-yl)piperazin-1-yl)ethanone [Preparation #E.1.1] | | B.2.9 | 0.37 (a) | 417 | D |
| 3-exo-(2-Chlorofuro[3,2-d]pyrimidin-4-ylamino)bicyclo[2.2.1]hept-5-ene-2-carboxamide (prepared using A from 2,4-dichlorofuro[3,2-d]pyrimidine [ArkPharm] with 3-exo-aminobicyclo[2.2.1]hept-5-ene-2-exo-carboxamide [Bioblocks]) | | B.2.10 | 0.88 (a) | 441 | A |

TABLE B.3

Examples prepared from a heteroaryl chloride with 4-(methylsulfonyl)aniline [Oakwood] using General Procedure B

| Heteroaryl Chloride | Product | Example # | $R_t$ min (Table 2, Method) | m/z ESI+ $(M + H)^+$ | Syk $IC_{50}$ |
|---|---|---|---|---|---|
| 1-(4-(2-Chlorofuro[3,2-d]pyrimidin-4-yl)piperazin-1-yl)ethanone [Preparation #E.1.1] | | B.3.1 | 0.61 (a) | 416 | C |

TABLE B.4

Examples prepared from an aniline with 2-chloro-N-(2,2,2-trifluoroethyl)furo[3,2-d]pyrimidin-4-amine (prepared using General Procedure A with 2,2,2-trifluoroethanamine) using General Procedure B

| Aniline | Product | Example # | $R_t$ min (Table 2, Method) | m/z ESI+ $(M + H)^+$ | Syk $IC_{50}$ |
|---|---|---|---|---|---|
| 4-Amino-N-propylbenzamide [Preparation #3] | | B.4.1 | 2.10 (c) | 394 | B |

TABLE B.5

Examples prepared from a heteroaryl chloride with an aniline using General Procedure B

| Heteroaryl Chloride | Aniline | Product | Example # | $R_t$ min (Table 2, Method) | m/z ESI+ $(M + H)^+$ | Syk $IC_{50}$ |
|---|---|---|---|---|---|---|
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | N-(4-Aminophenyl)-N-methylacetamide | | B.5.1 | 1.91 (d) | 352 | B |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 3-Chloro-4-morpholino-aniline [Akos] | | B.5.2 | 2.19 (d) | 400 | A |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | N-(4-Aminophenyl)butyramide [Preparation #3] | | B.5.3 | 1.98 (d) | 366 | C |
| 2-Chloro-N-cyclopropylfuro[3,2-d]pyrimidin-4-amine (Preparation #A.1) | N-(4-Aminophenyl)-N-methylacetamide | | B.5.4 | 1.80 (d) | 338 | B |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 6-Amino-3,4-dihydroquinolin-2(1H)-one [Akos] | | B.5.5 | 1.82 (h) | 350 | B |
| 2-Chloro-N-cyclobutylfuro[3,2-d]pyrimidin-4-amine(prepared using A from 2,4-dichlorofuro[3,2-d]pyrimidine [ArkPharm] with cyclobutylamine) | 6-Amino-2,2-dimethyl-2H-benzo[b][1,4]oxazin-3(4H)-one [ArkPharm] | | B.5.6 | 1.67 (i) | 380 | B |
| 2-Chloro-N-cyclopropylfuro[3,2-d]pyrimidin-4-amine (Preparation #A.1) | 6-Amino-2H-benzo[b][1,4]oxazin-3(4H)-one [ArkPharm] | | B.5.7 | 1.78 (d) | 338 | B |
| 2-Chloro-N-cyclopropylfuro[3,2-d]pyrimidin-4-amine (Preparation #A.1) | 1-Methyl-1H-indazol-5-amine [ArkPharm] | | B.5.8 | 1.85 (h) | 321 | A |

TABLE B.5-continued

Examples prepared from a heteroaryl chloride with an aniline using General Procedure B

| Heteroaryl Chloride | Aniline | Product | Example # | R_t min (Table 2, Method) | m/z ESI+ (M+H)+ | Syk IC_50 |
|---|---|---|---|---|---|---|
| 2-Chloro-N-cyclopropylfuro[3,2-d]pyrimidin-4-amine (Preparation #A.1) | 4-Amino-N-(3-methoxypropyl)benzamide [Matrix] | 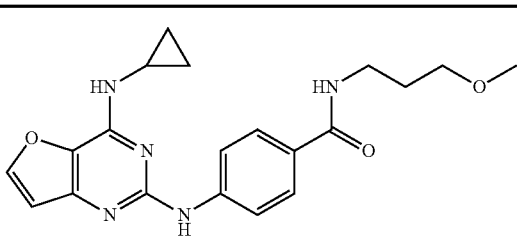 | B.5.9 | 1.81 (h) | 382 | B |
| 2-Chloro-N-cyclopropylfuro[3,2-d]pyrimidin-4-amine (Preparation #A.1) | 4-Amino-N-(3-methoxypropyl)benzenesulfonamide [Akos] | 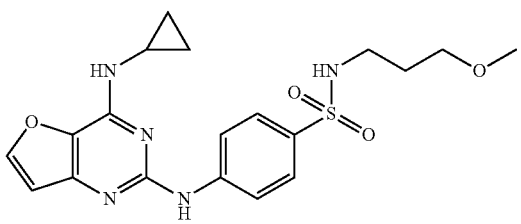 [SMILES: COCCCNS(=O)(=O)c1ccc(Nc2nc(NC3CC3)c3occc3n2)cc1] | B.5.10 | 1.88(h) | 418 | B |
| 2-Chloro-N-(2,2,2-trifluoroethyl)furo[3,2-d]pyrimidin-4-amine (prepared using A from 2,4-dichlorofuro[3,2-d]pyrimidine [ArkPharm] with 2,2,2-trifluoroethanamine) | 6-Amino-2,2-dimethyl-2H-benzo[b][1,4]oxazin-3(4H)-one [ArkPharm] | 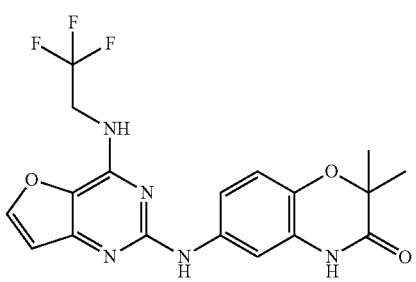 [SMILES: CC1(C)Oc2ccc(Nc3nc(NCC(F)(F)F)c4occc4n3)cc2NC1=O] | B.5.11 | 1.96 (h) | 508 | B |
| 2-Chloro-N-cyclopropylfuro[3,2-d]pyrimidin-4-amine (Preparation #A.1) | 1-Methyl-1H-indazol-6-amine [ArkPharm] | 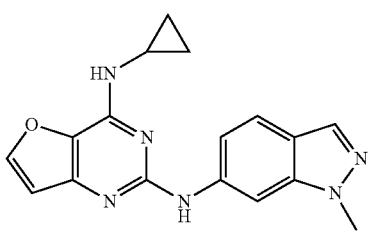 [SMILES: Cn1ncc2ccc(Nc3nc(NC4CC4)c4occc4n3)cc21] | B.5.12 | 1.88 (h) | 321 | B |
| 2-Chloro-N-(2,2,2-trifluoroethyl)furo[3,2-d]pyrimidin-4-amine (prepared using A from 2,4-dichlorofuro[3,2-d]pyrimidine [ArkPharm] with 2,2,2-trifluoroethanamine) | 3-Chloro-4-morpholinoaniline (Akos) | 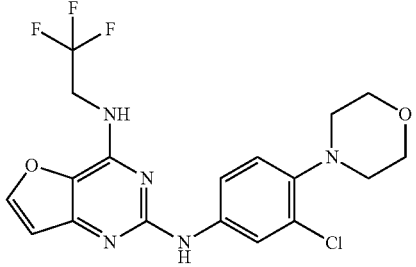 [SMILES: FC(F)(F)CNc1nc(Nc2ccc(N3CCOCC3)c(Cl)c2)nc2ccoc12] | B.5.13 | 2.09 (h) | 428 | A |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| N-((1-(2-Chlorofuro[3,2-d]pyrimidin-4-yl)piperidin-4-yl)methyl)-2,2-difluoroethanamine (Preparation #H.1) | 6-Amino-2,2-dimethyl-2H-benzo[b][1,4]oxazin-3(4H)-one [ArkPharm] | | B.5.14 | 1.50 (c) | 485 | B |
| 2-Chloro-N-cyclopropylfuro[3,2-d]pyrimidin-4-amine (Preparation #A.1) | 1-Isopropyl-1H-indazol-5-amine [ECA International] | | B.5.15 | 1.89 (c) | 349 | B |
| 2-Chloro-4-(3,4-dihydroisoquinolin-2(1H)-yl)furo[3,2-d]pyrimidine (prepared using A from 2,4-dichlorofuro[3,2-d]pyrimidine [ArkPharm] with 1,2,3,4-tetrahydroisoquinoline) | 6-Amino-2,2-dimethyl-2H-benzo[b][1,4]oxazin-3(4H)-one [ArkPharm] | | B.5.16 | 2.54 (c) | 442 | B |
| 2-Chloro-N-cyclopropylfuro[3,2-d]pyrimidin-4-amine (Preparation #A.1) | 6-Amino-2H-benzo[b][1,4]thiazin-3(4H)-one [Specs] | | B.5.17 | 1.88 (c) | 382 | A |
| 2-Chloro-N-cyclopropylfuro[3,2-d]pyrimidin-4-amine (Preparation #A.1) | 4-Morpholino-aniline | | B.5.18 | 1.65 (c) | 352 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk $IC_{50}$ |
|---|---|---|---|---|---|---|
| 2-Chloro-N-cyclopropylfuro[3,2-d]pyrimidin-4-amine (Preparation #A.1) | 6-Aminobenzo[d]oxazol-2(3H)-one [Asinex] | | B.5.19 | 1.48 (c) | 324 | B |
| 2-Chloro-N-cyclopropylfuro[3,2-d]pyrimidin-4-amine (Preparation #A.1) | 5-Amino-1H-benzo[d]imidazol-2(3H)-one [Pfaltz & Bauer] | | B.5.20 | 1.18 (c) | 323 | B |
| 2-Chloro-N-cyclopropylfuro[3,2-d]pyrimidin-4-amine (Preparation #A.1) | 5-Amino-2,3-dihydro-1H-inden-1-one [Maybridge] | | B.5.21 | 1.83 (c) | 321 | B |
| N-((1-(2-Chlorofuro[3,2-d]pyrimidin-4-yl)piperidin-4-yl)methyl)-2,2-difluoroethanamine (Preparation #H.1) | N-(4-Aminophenyl)-N-methylacetamide | | B.5.22 | 1.77 (c) | 459 | B |
| 2-Chloro-N-cyclopropylfuro[3,2-d]pyrimidin-4-amine (Preparation #A.1) | N-(3-Aminophenyl)acetamide | | B.5.23 | 1.64 (c) | 324 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)$^+$ | Syk IC$_{50}$ |
|---|---|---|---|---|---|---|
| 2-Chloro-N-cyclopropylfuro[3,2-d]pyrimidin-4-amine (Preparation #A.1) | 3-Aminobenzenesulfonamide [Alfa Aesar] | | B.5.24 | 1.80 (c) | 346 | B |
| 2-Chloro-N-cyclopropylfuro[3,2-d]pyrimidin-4-amine (Preparation #A.1) | 5-Aminobenzo[d]oxazol-2(3H)-one [Enamine] | | B.5.25 | 1.60 (c) | 324 | B |
| 2-Chloro-N-cyclopropylfuro[3,2-d]pyrimidin-4-amine (Preparation #A.1) | 5-Amino-1-methyl-1H-benzo[d]imidazol-2(3H)-one (WO 2007/028445, Intermediate 10) | | B.5.26 | 1.61 (c) | 337 | B |
| 2-Chloro-N-cyclopropylfuro[3,2-d]pyrimidin-4-amine (Preparation #A.1) | 6-Amino-2,2-dimethyl-2H-pyrido[3,2-b][1,4]oxazin-3(4H) one [ArkPharm] | | B.5.27 | 2.66 (h) | 477 | B |
| 2-Chloro-N-cyclopropylfuro[3,2-d]pyrimidin-4-amine (Preparation #A.1) | 6-Aminoindolin-2-one [ArkPharm] | | B.5.28 | 1.71 (h) | 322 | B |
| 2-Chloro-N-cyclopropylfuro[3,2-d]pyrimidin-4-amine (Preparation #A.1) | (3-Aminophenyl)methanol | | B.5.29 | 1.56 (c) | 297 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| 2-Chloro-N-cyclopropylfuro[3,2-d]pyrimidin-4-amine (Preparation #A.1) | 6-Morpholino-pyridin-3-amine [Alfa Aesar] | | B.5.30 | 1.62 (c) | 353 | B |
| 2-Chloro-N-cyclopropylfuro[3,2-d]pyrimidin-4-amine (Preparation #A.1) | 6-Amino-2,2-dimethyl-2H-benzo[b][1,4]thiazin-3(4H)-one (*Bioorg. Med. Chem.* 2000, 8, 393, Compound 4) | | B.5.31 | 2.11 (c) | 382 | A |
| 2-Chloro-N-cyclopropylfuro[3,2-d]pyrimidin-4-amine (Preparation #A.1) | 4-(4-Aminophenyl)thiomorpholine 1,1 dioxide [TCI] | | B.5.32 | 1.46 (c) | 400 | A |
| 2-Chloro-N-(cyclopropylmethyl)furo[3,2-d]pyrimidin-4-amine (prepared using A from 2,4-dichlorofuro[3,2-d]pyrimidine [ArkPharm] with cyclopropylmethanamine [Fluka]) | 6-Amino-2,2-dimethyl-2H-benzo[b][1,4]oxazin-3(4H)-one [ArkPharm] | | B.5.33 | 1.98 (h) | 380 | B |
| 2-Chloro-N-cyclopropylfuro[3,2-d]pyrimidin-4-amine (Preparation #A.1) | 3-Fluoro-4-(4-methylpiperazin-1-yl)aniline [Matrix] | | B.5.34 | 1.25 (c) | 383 | B |
| 2-Chloro-N-cyclopropylfuro[3,2-d]pyrimidin-4-amine (Preparation #A.1) | 7-Amino-4-methylquinolin-2(1H)-one | | B.5.35 | 1.78 (h) | 348 | A |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 2-Chloro-N-cyclopropylfuro[3,2-d]pyrimidin-4-amine (Preparation #A.1) | 7-Aminoquinolin-2(1H)-one [ArkPharm] | | B.5.36 | 1.73 (h) | 334 | A |
| 2-Chloro-N-(1-methylcyclopropyl)furo[3,2-d]pyrimidin-4-amine (prepared using A from 2,4-dichlorofuro[3,2-d]pyrimidine [ArkPharm] with 1-methylcyclopropanamine [WuXi]) | 6-Amino-2,2-dimethyl-2H-benzo[b][1,4]oxazin-3(4H)-one [ArkPharm] | | B.5.37 | 2.06 (h) | 380 | B |
| (1-(2-Chlorofuro[3,2-d]pyrimidin-4-ylamino)cyclopropyl)methanol (prepared using A from 2,4-dichlorofuro[3,2-d]pyrimidine [ArkPharm] with (1-aminocyclopropyl)methanol [Sinova]) | 6-Amino-2,2-dimethyl-2H-benzo[b][1,4]oxazin-3(4H)-one [ArkPharm] | | B.5.38 | 1.76 (h) | 397 | B |
| 2-Chloro-N-ethylfuro[3,2-d]pyrimidin-4-amine (prepared using A from 2,4-dichlorofuro[3,2-d]pyrimidine [ArkPharm] with ethanamine) | 6-Amino-2,2-dimethyl-2H-benzo[b][1,4]oxazin-3(4H)-one [ArkPharm] | | B.5.39 | 1.90 (h) | 354 | B |
| 2-Chloro-N-cyclopropylfuro[3,2-d]pyrimidin-4-amine (Preparation #A.1) | 6-Amino-2,2-difluoro-2H-benzo[b][1,4]oxazin-3(4H)-one [WO 2008/024634, Intermediate D] | | B.5.40 | 2.13 (c) | 374 | A |
| 2-Chloro-N-cyclopropylfuro[3,2-d]pyrimidin-4-amine (Preparation #A.1) | 7-Amino-3,3-dimethyl-3,4-dihydroquinolin-2(1H)-one [*Bioorganic & Medicinal Chemistry* 2000, 8, 393, Compound 16] | | B.5.41 | 1.94 (j) | 364 | A |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 2-Chloro-N-cyclopropylfuro[3,2-d]pyrimidin-4-amine (Preparation #A.1) | 2-(4-Aminophenyl)-2-methylpropanenitrile [ArkPharm] | | B.5.42 | 2.07 (j) | 334 | A |
| 2-Chloro-N-cyclopropylfuro[3,2-d]pyrimidin-4-amine (Preparation #A.1) | 4-Isopropoxyaniline [TCI] | | B.5.43 | 2.13 (h) | 325 | B |
| 2-Chloro-N-cyclopropylfuro[3,2-d]pyrimidin-4-amine (Preparation #A.1) | 2-Methylbenzo[d]thiazol-6-amine [Akos] | | B.5.44 | 1.96 (h) | 338 | B |
| 2-Chloro-N-cyclopropylfuro[3,2-d]pyrimidin-4-amine (Preparation #A.1) | 2-Methylquinolin-6-amine [Akos] | | B.5.45 | 1.91 (h) | 332 | B |
| 2-Chloro-N-cyclopropylfuro[3,2-d]pyrimidin-4-amine (Preparation #A.1) | 4-Isopropoxy-3-methylaniline [Ryan Scientific] | | B.5.46 | 2.22 (h) | 339 | B |
| 2-Chloro-N-cyclopropylfuro[3,2-d]pyrimidin-4-amine (Preparation #A.1) | 3-Chloro-4-isopropoxyaniline [Matrix] | | B.5.47 | 2.25 (j) | 359 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| 2-Chloro-N-cyclopropylfuro[3,2-d]pyrimidin-4-amine (Preparation #A.1) | 3-Fluoro-4-isopropoxy-aniline [Oakwood] | | B.5.48 | 2.19 (j) | 343 | B |
| 2-Chloro-N-cyclopropylfuro[3,2-d]pyrimidin-4-amine (Preparation #A.1) | 2,2-Dimethyl-3,4-dihydro-2H-benzo[b][1,4]oxazin-6-amine [Anichem] | | B.5.49 | 1.99 (h) | 352 | B |
| 2-Chloro-N-cyclopropylfuro[3,2-d]pyrimidin-4-amine (Preparation #A.1) | 7-Amino-3-(hydroxymethyl)quinolin-2(1H)-one [US 20100016285, Example 9, Step 2] | | B.5.50 | 1.64 (j) | 364 | B |
| 2-Chloro-N-cyclopropylfuro[3,2-d]pyrimidin-4-amine (Preparation #A.1) | 2,2-Dimethyl-chroman-6-amine [WO 2004020428] | | B.5.51 | 2.20 (h) | 351 | B |
| 2-Chloro-N-cyclopropylfuro[3,2-d]pyrimidin-4-amine (Preparation #A.1) | 7-Amino-2H-chromen-2-one [3B Scientific] | | B.5.52 | 1.81 (m) | 335 | A |
| 2-Chloro-N-cyclopropylfuro[3,2-d]pyrimidin-4-amine (Preparation #A.1) | 2,3-Dihydrobenzo[b][1,4]dioxin-6-amine [Aldrich] | | B.5.53 | No Data | No Data | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| 2-Chloro-N-cyclopropylfuro[3,2-d]pyrimidin-4-amine (Preparation #A.1) | Benzo[d]oxazol-6-amine [ArkPharm] | | B.5.54 | 1.86 (h) | 308 | B |
| 2-Chloro-N-cyclopropylfuro[3,2-d]pyrimidin-4-amine (Preparation #A.1) | 4-(2H-1,2,3-Triazol-2-yl)aniline [Enamine] | | B.5.55 | 2.05 (h) | 334 | B |
| 2-Chloro-N-cyclopropylfuro[3,2-d]pyrimidin-4-amine (Preparation #A.1) | 7-Amino-4,5-dihydro-1H-benzo[b]azepin-2(3H)-one [Alfa Aesar] | | B.5.56 | 1.77 (h) | 350 | A |
| 2-Chloro-N-cyclopropylfuro[3,2-d]pyrimidin-4-amine (Preparation #A.1) | 1-(7-Amino-4,5-dihydro-1H-benzo[d]azepin-3(2H)-yl)ethanone [WO 2008038051, Example 2B] | | B.5.57 | 1.85 (h) | 378 | B |
| 2-Chloro-N-methylfuro[3,2-d]pyrimidin-4-amine (prepared using A from 2,4-dichlorofuro[3,2-d]pyrimidine [ArkPharm] with methylamine) | 6-Amino-2,2-dimethyl-2H-benzo[b][1,4]oxazin-3(4H)-one [ArkPharm] | | B.5.58 | 1.81 (h) | 340 | B |
| 2-Chloro-N-isopropylfuro[3,2-d]pyrimidin-4-amine (prepared using A from 2,4-dichlorofuro[3,2-d]pyrimidine [ArkPharm] with isopropylamine) | 6-Amino-2,2-dimethyl-2H-benzo[b][1,4]oxazin-3(4H)-one [ArkPharm] | | B.5.59 | 1.98 (h) | 368 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| N-((1-(2-Chlorofuro[3,2-d]pyrimidin-4-yl)piperidin-4-yl)methyl)-2,2-difluoroethanamine (Preparation #H.1) | 6-Amino-3,3-dimethylindolin-2-one [Astatech] | | B.5.60 | 1.46 (c) | 471 | A |
| Diexo-3-(2-chlorofuro[3,2-d]pyrimidin-4-ylamino)bicyclo[2.2.1]hept-5-ene-2-carboxamide (prepared using A from 2,4-dichlorofuro[3,2-d]pyrimidine [ArkPharm] with diexo-3-aminobicyclo[2.2.1]hept-5-ene-2-carboxamide [Acros]) | 6-Amino-3,3-dimethylindolin-2-one [Astatech] | | B.5.61 | 1.65 (c) | 445 | A |
| 2,4-Dichlorofuro[3,2-d]pyrimidine [ArkPharm] | 6-Amino-2,2-dimethyl-2H-benzo[b][1,4]oxazin-3(4H)-one [ArkPharm] | | B.5.62 | 2.05 (c) | 502 | B |
| Diexo-3-(2-chlorofuro[3,2-d]pyrimidin-4-ylamino)bicyclo[2.2.1]heptane-2-carboxamide (prepared using A from 2,4-dichlorofuro[3,2-d]pyrimidine [ArkPharm] with diexo-3-aminobicyclo[2.2.1]heptane-2-carboxamide [Acros]) | 6-Amino-2,2-dimethyl-2H-benzo[b][1,4]oxazin-3(4H)-one [ArkPharm] | | B.5.63 | 1.75 (c) | 523 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| 2-Chloro-N-((3-methyloxetan-3-yl)methyl)furo[3,2-d]pyrimidin-4-amine (prepared using A from 2,4-dichlorofuro[3,2-d]pyrimidine [ArkPharm] with (3-methyloxetan-3-yl)methanamine) | 6-Amino-2,2-dimethyl-2H-benzo[b][1,4]oxazin-3(4H)-one [ArkPharm] | | B.5.64 | 1.83 (h) | 410 | B |
| N-((1-(2-Chlorofuro[3,2-d]pyrimidin-4-yl)piperidin-4-yl)methyl)-2-(methylsulfonyl)ethanamine (prepared using H from Preparation #P.1 with 2-(methylsulfonyl)ethanamine hydrochloride [Chem-Impex]) | 6-Amino-2,2-dimethyl-2H-benzo[b][1,4]oxazin-3(4H)-one [ArkPharm] | | B.5.65 | 1.82 (h) | 529 | A |
| 3-(2-Chlorofuro[3,2-d]pyrimidin-4-ylamino)propanamide (prepared using A from 2,4-dichlorofuro[3,2-d]pyrimidine [ArkPharm] with 3-aminopropanamide [J&W PharmLab]) | 6-Amino-2,2-dimethyl-2H-benzo[b][1,4]oxazin-3(4H)-one [ArkPharm] | | B.5.66 | 1.66 (h) | 397 | B |
| 2-Chloro-N-(2,2-difluoroethyl)furo[3,2-d]pyrimidin-4-amine (prepared using A from 2,4-dichlorofuro[3,2-d]pyrimidine [ArkPharm] with 2,2-difluoroethanamine [Matrix]) | 6-Amino-2,2-dimethyl-2H-benzo[b][1,4]oxazin-3(4H)-one [ArkPharm] | | B.5.67 | 1.91 (h) | 390 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| N-((1-(2-Chlorofuro[3,2-d]pyrimidin-4-yl)piperidin-4-yl)methyl)-2-(methylsulfonyl)ethanamine (prepared using H from Preparation #P.1 with 2-(methylsulfonyl)ethanamine hydrochloride [Chem-Impex]) | 6-Amino-3,3-dimethylindolin-2-one [Astatech] | 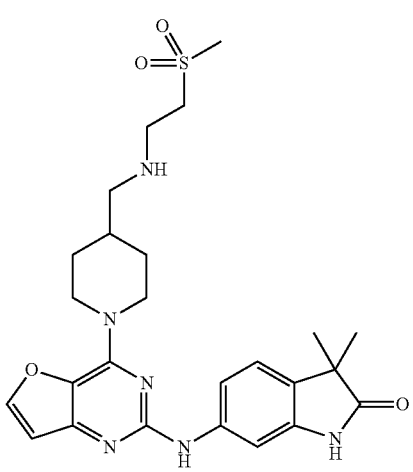 [SMILES: CC1(C)C(=O)Nc2cc(Nc3nc(N4CCC(CNCCS(C)(=O)=O)CC4)c4occc4n3)ccc21] | B.5.68 | 1.78 (h) | 513 | A |
| 2-Chloro-N-(2,2-difluoroethyl)furo[3,2-d]pyrimidin-4-amine (prepared using A from 2,4-dichlorofuro[3,2-d]pyrimidine [ArkPharm] with 2,2-difluoroethanamine [Matrix]) | 7-Amino-3,4-dihydroquinolin-2(1H)-one [Alfa Aesar] | 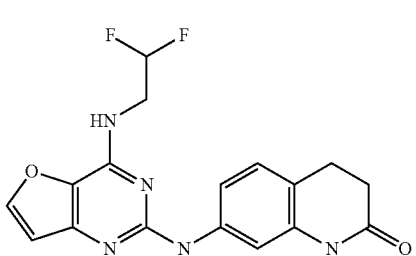 | B.5.69 | 1.77 (h) | 360 | B |
| 2-Chloro-4-(3,4-dihydroisoquinolin-2(1H)-yl)furo[3,2-d]pyrimidine (prepared using A from 2,4-dichlorofuro[3,2-d]pyrimidine [ArkPharm] with 1,2,3,4-tetrahydroisoquinoline) | N-(4-Aminophenyl)-N-methylacetamide | 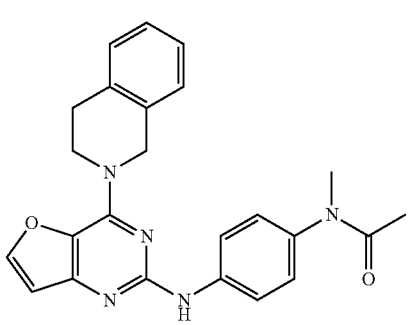 [SMILES: CC(=O)N(C)c1ccc(Nc2nc(N3CCc4ccccc4C3)c3occc3n2)cc1] | B.5.70 | 2.39 (c) | 414 | B |
| 2-Chloro-4-(cyclopropylethynyl)furo[3,2-d]pyrimidine [Preparation #5] | 6-Amino-3,3-dimethylindolin-2-one [Astatech] | 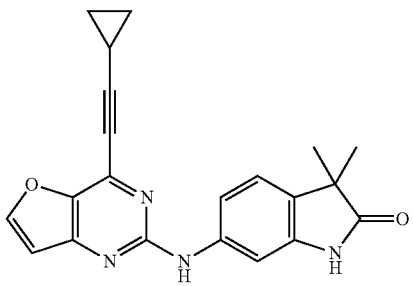 [SMILES: CC1(C)C(=O)Nc2cc(Nc3nc(C#CC4CC4)c4occc4n3)ccc21] | B.5.71 | 2.14 (c) | 359 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)$^+$ | Syk IC$_{50}$ |
|---|---|---|---|---|---|---|
| 2-Chloro-N-(2,2-difluoroethyl)furo[3,2-d]pyrimidin-4-amine (prepared using A from 2,4-dichlorofuro[3,2-d]pyrimidine [ArkPharm] with 2-methylpropan-2-amine) | 6-Amino-2,2-dimethyl-2H-benzo[b][1,4]oxazin-3(4H)-one [ArkPharm] | | B.5.72 | 2.08 (f) | 382 | B |
| 2-Chloro-N,N-diethylfuro[3,2-d]pyrimidin-4-amine (prepared using A from 2,4-dichlorofuro[3,2-d]pyrimidine [ArkPharm] with diethylamine) | 6-Amino-2,2-dimethyl-2H-benzo[b][1,4]oxazin-3(4H)-one [ArkPharm] | | B.5.73 | 2.14 (f) | 382 | B |
| N-((1-(2-Chlorofuro[3,2-d]pyrimidin-4-yl)piperidin-4-yl)methyl)-2,2-difluoroethanamine (Preparation #H.1) | 4-Amino-N-(3-methoxypropyl)benzenesulfonamide [Akos] | | B.5.74 | 2.02 (f) | 539 | B |
| N-((1-(2-Chlorofuro[3,2-d]pyrimidin-4-yl)piperidin-4-yl)methyl)-2,2-difluoroethanamine (Preparation #H.1) | 1-Methyl-1H-indazol-5-amine [ArkPharm] | | B.5.75 | 1.98 (f) | 442 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| N-((1-(2-Chlorofuro[3,2-d]pyrimidin-4-yl)piperidin-4-yl)methyl)-2-fluoroethanamine (prepared using H from Preparation #P.1 with 2-fluoroethanamine) | 6-Amino-2,2-dimethyl-2H-benzo[b][1,4]oxazin-3(4H)-one [ArkPharm] | | B.5.76 | 1.92 (f) | 469 | A |
| N-((1-(2-Chlorofuro[3,2-d]pyrimidin-4-yl)piperidin-4-yl)methyl)-2-fluoroethanamine (prepared using H from Preparation #P.1 with 2-fluoroethanamine) | 6-Amino-3,3-dimethylindolin-2-one [Astatech] | | B.5.77 | 1.87 (f) | 453 | A |
| 1-(2-Chlorofuro[3,2-d]pyrimidin-4-yl)piperidine-3-carboxamide (prepared using A from 2,4-dichlorofuro[3,2-d]pyrimidine [ArkPharm] with piperidine-3-carboxamide) | 6-Amino-2,2-dimethyl-2H-benzo[b][1,4]oxazin-3(4H)-one [ArkPharm] | | B.5.78 | 1.77 (f) | 437 | B |
| N-((1-(2-Chlorofuro[3,2-d]pyrimidin-4-yl)piperidin-4-yl)methyl)-2,2-difluoroethanamine (Preparation #H.1) | 7-Amino-3,4-dihydroquinolin-2(1H)-one [Astatech] | | B.5.79 | 1.94 (f) | 457 | A |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| 2-Chloro-N-isobutylfuro[3,2-d]pyrimidin-4-amine (prepared using A from 2,4-dichlorofuro[3,2-d]pyrimidine [ArkPharm] with 2-methylpropan-1-amine) | 6-Amino-3,3-dimethylindolin-2-one [Astatech] | | B.5.80 | 2.02 (f) | 366 | B |
| 2-Chloro-N-propylfuro[3,2-d]pyrimidin-4-amine (prepared using A from 2,4-dichlorofuro[3,2-d]pyrimidine [ArkPharm] with propan-1-amine) | 6-Amino-3,3-dimethylindolin-2-one [Astatech] | | B.5.81 | 1.95 (f) | 352 | A |
| N-((1-(2-Chlorofuro[3,2-d]pyrimidin-4-yl)piperidin-4-yl)methyl)-2,2-difluoroethanamine (Preparation #H.1) | 7-Aminoquinolin-2(1H)-one [ArkPharm] | | B.5.82 | 1.90 (f) | 455 | A |
| N-((1-(2-Chlorofuro[3,2-d]pyrimidin-4-yl)piperidin-4-yl)methyl)-2,2-difluoroethanamine (Preparation #H.1) | 7-Amino-4-methylquinolin-2(1H)-one | | B.5.83 | 1.94 (f) | 469 | A |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| N-((1-(2-Chlorofuro[3,2-d]pyrimidin-4-yl)piperidin-4-yl)methyl)-2,2-difluoroethanamine (Preparation #H.1) | 6-Amino-2H-benzo[b][1,4]oxazin-3(4H)-one [Bionet] | | B.5.84 | 1.27 (c) | 459 | B |
| N-((1-(2-Chlorofuro[3,2-d]pyrimidin-4-yl)piperidin-4-yl)methyl)-2,2-difluoroethanamine (Preparation #H.1) | 3-Chloro-4-morpholino-aniline [Akos] | | B.5.85 | 2.02 (c) | 507 | A |
| N-((1-(2-Chlorofuro[3,2-d]pyrimidin-4-yl)piperidin-4-yl)methyl)-2,2-difluoroethanamine (Preparation #H.1) | 7-Amino-3,3-dimethyl-3,4-dihydroquinolin-2(1H)-one [*Bioorganic & Medicinal Chemistry* 2000, 8, 393, Compound 16] | | B.5.86 | 2.12 (f) | 485 | A |
| N-((1-(2-Chlorofuro[3,2-d]pyrimidin-4-yl)piperidin-4-yl)methyl)-2,2-difluoroethanamine (Preparation #H.1) | 7-Amino-3-methylquinolin-2(1H)-one [Aurora Fine Chem] | | B.5.87 | 2.00 (f) | 469 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| N-((1-(2-Chlorofuro[3,2-d]pyrimidin-4-yl)piperidin-4-yl)methyl)-2,2-difluoroethanamine (Preparation #H.1) | 6-Amino-2,2-difluoro-2H-benzo[b][1,4]oxazin-3(4H)-one (WO 2008/024634, Intermediate D) | | B.5.88 | 1.76 (c) | 495 | B |
| N-(1-(1-(2-Chlorofuro[3,2-d]pyrimidin-4-yl)piperidin-4-yl)ethyl)-2,2-difluoroethanamine (prepared using A from 2,4-dichlorofuro[3,2-d]pyrimidine [ArkPharm] with 1-(piperidin-4-yl)ethanone and H with 2,2-difluoroethanamine [Matrix]) | 6-Amino-2,2-dimethyl-2H-benzo[b][1,4]oxazin-3(4H)-one [ArkPharm] | | B.5.89 | 2.15 (f) | 501 | B |
| N-(1-(1-(2-Chlorofuro[3,2-d]pyrimidin-4-yl)piperidin-4-yl)ethyl)-2,2-difluoroethanamine (prepared using A from 2,4-dichlorofuro[3,2-d]pyrimidine [ArkPharm] with 1-(piperidin-4-yl)ethanone and H with 2,2-difluoroethanamine [Matrix]) | 6-Amino-3,3-dimethylindolin-2-one [Astatech] | | B.5.90 | 2.10 (f) | 485 | A |
| N-((1-(2-Chlorofuro[3,2-d]pyrimidin-4-yl)piperidin-4-yl)methyl)-2,2-difluoroethanamine (Preparation #H.1) | 3-Fluoro-4-morpholino-aniline [Matrix] | | B.5.91 | 2.14 (f) | 491 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| N-((1-(2-Chlorofuro[3,2-d]pyrimidin-4-yl)piperidin-4-yl)methyl)-2,2-difluoroethanamine (Preparation #H.1) | 7-Amino-3-methyl-3,4-dihydroquinolin-2(1H)-one [Example #6, Step C] | 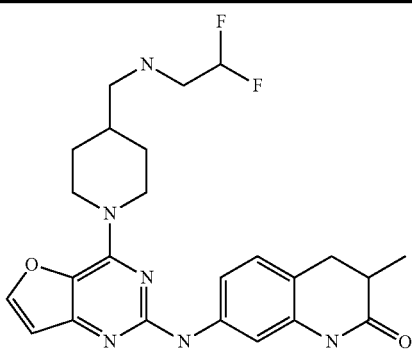 | B.5.92 | 2.02 (f) | 471 | A |
| N-((1-(2-Chlorofuro[3,2-d]pyrimidin-4-yl)-4-methylpiperidin-4-yl)methyl)-2,2-difluoroethanamine (prepared using A from 2,4-dichlorofuro[3,2-d]pyrimidine [ArkPharm] with (4-methylpiperidin-4-yl)methanol [ArkPharm], P and H with 2,2-difluoroethanamine [Matrix]) | 6-Amino-2,2-dimethyl-2H-benzo[b][1,4]oxazin-3(4H)-one [ArkPharm] | 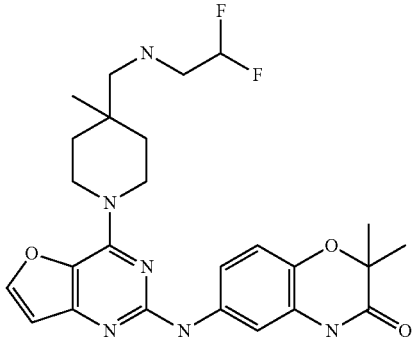 [SMILES: CC1(CNCC(F)F)CCN(c2nc(Nc3ccc4c(c3)NC(=O)C(C)(C)O4)nc3ccoc23)CC1] | B.5.93 | 2.19 (f) | 501 | B |
| 1-(2-Chlorofuro[3,2-d]pyrimidin-4-yl)pyrrolidine-3-carboxamide (prepared using A from 2,4-dichlorofuro[3,2-d]pyrimidine [ArkPharm] with pyrrolidine-3-carboxamide [Enamine]) | 6-Amino-2,2-dimethyl-2H-benzo[b][1,4]oxazin-3(4H)-one [ArkPharm] | 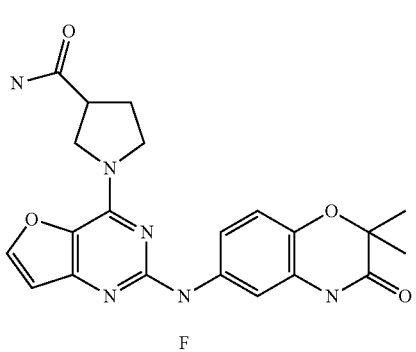 | B.5.94 | 1.71 (f) | 423 | B |
| N-((1-(2-Chlorofuro[3,2-d]pyrimidin-4-yl)piperidin-4-yl)methyl)-2,2-difluoroethanamine (Preparation #H.1) | 6-Amino-2,2-dimethyl-2H-benzo[b][1,4]thiazin-3(4H)-one (*Bioorg. Med. Chem.* 2000, 8, 393, Compound 4) | 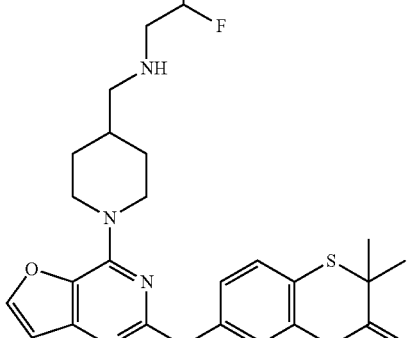 | B.5.95 | 1.89 (c) | 503 | B |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)$^+$ | Syk IC$_{50}$ |
|---|---|---|---|---|---|---|
| 2-Chloro-N-(2-methylcyclopropyl)furo[3,2-d]pyrimidin-4-amine (prepared using A from 2,4-dichlorofuro[3,2-d]pyrimidine [Arkpharm] with 2-methylcyclopropanamine [Ryan]) | 6-Amino-3,3-dimethylindolin-2-one [Astatech] | | B.5.96 | 1.97 (h) | 364 | A |
| 1-(2-Chlorofuro[3,2-d]pyrimidin-4-yl)-4-(2-hydroxyethyl)piperidine-4-carbonitrile (prepared using AF from tert-butyl 4-cyanopiperidine-1-carboxylate with tert-butyl(2-iodoethoxy)dimethylsilane (prepared using AH from 2-iodoethanol with tert-butyldimethylchlorosilane), AD and A with 2,4-dichlorofuro[3,2-d]pyrimidine [ArkPharm]) | 6-Amino-2,2-dimethyl-2H-benzo[b][1,4]oxazin-3(4H)-one [Arkpharm] | | B.5.97 | 1.84 (h) | 463 | B |
| N-((1-(2-Chlorofuro[3,2-d]pyrimidin-4-yl)piperidin-4-yl)methyl)-3,3,3-trifluoropropan-1-amine (prepared using H from Preparation #P.1 with 3,3,3-trifluoropropan-1-amine [Oakwood]) | 6-Amino-2,2-dimethyl-2H-benzo[b][1,4]oxazin-3(4H)-one [Arkpharm] | | B.5.98 | 1.50 (c) | 519 | B |
| 2-Chloro-N-cyclopropylfuro[3,2-d]pyrimidin-4-amine (Preparation #A.1) | 7-Amino-3-methylquinolin-2(1H)-one [Aurora Fine Chem] | | B.5.99 | 1.81 (h) | 348 | A |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk IC$_{50}$ |
|---|---|---|---|---|---|---|
| N-((1-(2-Chlorofuro[3,2-d]pyrimidin-4-yl)pyrrolidin-3-yl)methyl)-2,2-difluoroethanamine (prepared using A from from 2,4-dichlorofuro[3,2-d]pyrimidine [Arkpharm] with pyrrolidin-3-ylmethanol [Chemimpex], P and H with 2,2-difluoroethanamine [Matrix]) | 6-Amino-3,3-dimethylindolin-2-one [Astatech] | | B.5.99 A | 1.60 (c) | 457 | B |
| 2-Chloro-N-(2,2-difluoroethyl)furo[3,2-d]pyrimidin-4-amine (prepared using A from 2,4-dichlorofuro[3,2-d]pyrimidine [ArkPharm] with 2,2-difluoroethanamine [Matrix]) | 3-Methyl-1H-indazol-6-amine [ArkPharm] | | B.5.100 | 1.81 (h) | 345 | B |
| N-((1-(2-Chlorofuro[3,2-d]pyrimidin-4-yl)pyrrolidin-3-yl)methyl)-2,2-difluoroethanamine (prepared using A from 2,4-dichlorofuro[3,2-d]pyrimidine [ArkPharm] with pyrrolidin-3-ylmethanol [Chemimpex]) | 6-Amino-2,2-dimethyl-2H-benzo[b][1,4]oxazin-3(4H)-one [Arkpharm] | | B.5.101 | 1.51(c) | 410 | B |
| N-((1-(2-Chlorofuro[3,2-d]pyrimidin-4-yl)piperidin-4-yl)methyl)-3,3,3-trifluoropropan-1-amine (prepared using H from Preparation #P.1 with 3,3,3-trifluoropropan-1-amine [Oakwood]) | 6-Amino-3,3-dimethylindolin-2-one [Astatech] | | B.5.102 | 1.46 (c) | 503 | A |

TABLE B.5-continued

Examples prepared from a heteroaryl chloride with an aniline using General Procedure B

| Heteroaryl Chloride | Aniline | Product | Example # | $R_t$ min (Table 2, Method) | m/z ESI+ (M + H)+ | Syk $IC_{50}$ |
|---|---|---|---|---|---|---|
| 2-Chloro-N-cyclobutylfuro[3,2-d]pyrimidin-4-amine (prepared using A from from 2,4-dichlorofuro[3,2-d]pyrimidine [Arkpharm] with cyclobutanamine) | 6-Amino-2H-benzo[b][1,4]oxazin-3(4H)-one [Bionet] | | B.5.103 | 1.89 (h) | 352 | B |
| 2-Chloro-4-cyclobutoxyfuro[3,2-d]pyrimidine (Preparation #Y.1) | 8-Amino-4,5-dihydro-1H-benzo[b]azepin-2(3H)-one [Astatech] | | B.5.104 | 2.25 (c) | 365 | B |
| 2-Chloro-4-cyclobutoxyfuro[3,2-d]pyrimidine (Preparation #Y.1) | 7-Amino-3,4-dihydroquinolin-2(1H)-one [Astatech] | | B.5.105 | 2.20 (c) | 351 | B |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 3-Methyl-1H-indazol-6-amine [Advanced ChemBlocks] | | B.5.106 | 1.94 (h) | 335 | A |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 7-Amino-3,4-dihydroquinolin-2(1H)-one [Astatech] | | B.5.107 | 1.91 (h) | 350 | A |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 6-Amino-3,3-dimethylindolin-2-one [Astatech] | | B.5.108 | 1.99 (h) | 364 | A |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 7-Amino-3,3-dimethyl-3,4-dihydroquinolin-2(1H)-one [*Bioorganic & Medicinal Chemistry* 2000, 8, 393, Compound 16] | 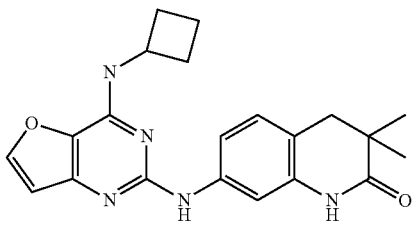 [SMILES: CC1(C)Cc2ccc(Nc3nc(NC4CCC4)c4occc4n3)cc2NC1=O] | B.5.109 | 2.08 (h) | 378 | A |
| 2-Chloro-N-cyclobutylfuro[3,2-d]pyrimidin-4-amine (prepared using A from 2,4-dichlorofuro[3,2-d]pyrimidine [ArkPharm] with cyclobutylamine) | 7-Amino-3-methyl-3,4-dihydroquinolin-2(1H)-one [Example #6, Step C] | 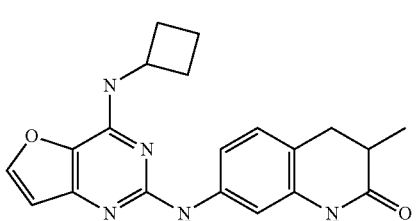 | B.5.110 | 2.00 (h) | 364 | A |
| 2-Chloro-N-isobutylfuro[3,2-d]pyrimidin-4-amine (prepared using A from 2,4-dichlorofuro[3,2-d]pyrimidine [ArkPharm] with 2-methylpropan-1-amine) | 7-Amino-3,4-dihydroquinolin-2(1H)-one [Akos] | 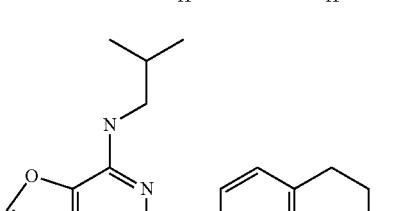 | B.5.111 | 1.95 (h) | 352 | B |
| 2-Chloro-N-propylfuro[3,2-d]pyrimidin-4-amine (prepared using A from from 2,4-dichlorofuro[3,2-d]pyrimidine [ArkPharm] with n-propylamine) | 3-Methyl-1H-indazol-6-amine [Advanced ChemBlocks] | 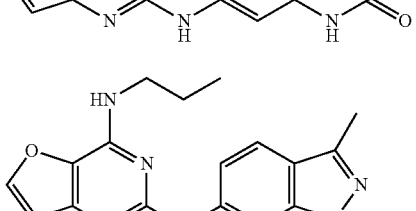 | B.5.112 | 1.91 (h) | 323 | B |
| 2-Chloro-N-propylfuro[3,2-d]pyrimidin-4-amine (prepared using A from from 2,4-dichlorofuro[3,2-d]pyrimidine [ArkPharm] with n-propylamine) | 7-Amino-3,4-dihydroquinolin-2(1H)-one [Akos] | 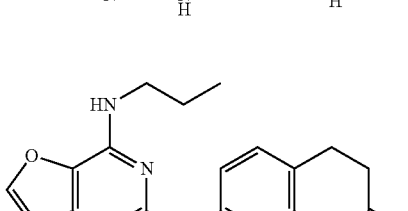 | B.5.113 | 1.86 (h) | 338 | B |
| 2-Chloro-N-propylfuro[3,2-d]pyrimidin-4-amine (prepared using A from from 2,4-dichlorofuro[3,2-d]pyrimidine [ArkPharm] with n-propylamine) | 7-Amino-3,3-dimethyl-3,4-dihydroquinolin-2(1H)-one [*Bioorganic & Medicinal Chemistry* 2000, 8, 393, Compound 16] | 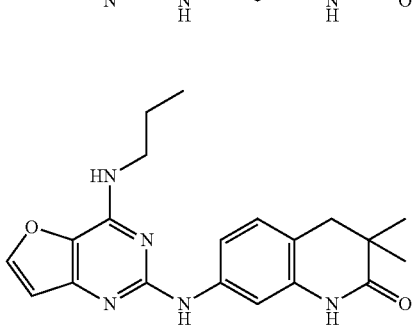 | B.5.114 | 2.04 (h) | 366 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)+ | Syk IC$_{50}$ |
|---|---|---|---|---|---|---|
| 2-Chloro-N-propylfuro[3,2-d]pyrimidin-4-amine (prepared using A from from 2,4-dichlorofuro[3,2-d]pyrimidine [ArkPharm] with n-propylamine) | 8-Amino-4,5-dihydro-1H-benzo[b]azepin-2(3H)-one [Astatech] | 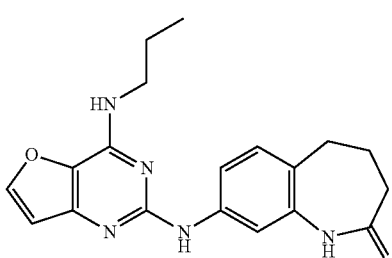 | B.5.115 | 1.91 (h) | 352 | B |
| 2-Chloro-N-propylfuro[3,2-d]pyrimidin-4-amine (prepared using A from from 2,4-dichlorofuro[3,2-d]pyrimidine [ArkPharm] with n-propylamine) | 2-(4-Aminophenyl)-2-methylpropanenitrile [ArkPharm] | 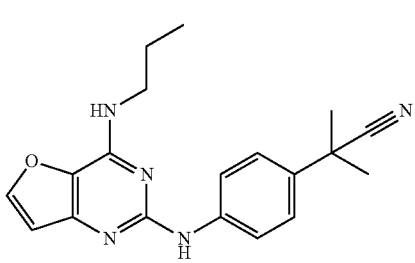 [SMILES: CCCNc1nc(Nc2ccc(C(C)(C)C#N)cc2)nc2ccoc12] | B.5.116 | 2.05 (h) | 336 | B |
| 2-Chloro-N-isobutylfuro[3,2-d]yrimidin-4-amine (prepared using A from 2,4-dichlorofuro[3,2-d]pyrimidine [ArkPharm] with 2-methylpropan-1-amine) | 7-Amino-3,3-dimethyl-3,4-dihydroquinolin-2(1H)-one [*Bioorganic & Medicinal Chemistry* 2000, 8, 393, Compound 16] | 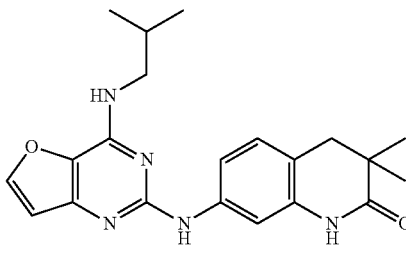 | B.5.117 | 2.11 (h) | 380 | B |
| 2-Chloro-N-isobutylfuro[3,2-d]pyrimidin-4-amine (prepared using A from 2,4-dichlorofuro[3,2-d]pyrimidine [ArkPharm] with 2-methylpropan-1-amine) | 8-Amino-4,5-dihydro-1H-benzo[b]azepin-2(3H)-one [Astatech] | 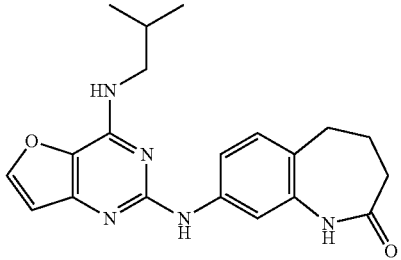 [SMILES: CC(C)CNc1nc(Nc2ccc3c(c2)NC(=O)CCC3)nc2ccoc12] | B.5.118 | 1.97 (h) | 366 | B |
| 2-Chloro-N-isobutylfuro[3,2-d]pyrimidin-4-amine (prepared using A from 2,4-dichlorofuro[3,2-d]pyrimidine [ArkPharm] with 2-methylpropan-1-amine) | 2-(4-Aminophenyl)-2-methylpropanenitrile [ArkPharm] | 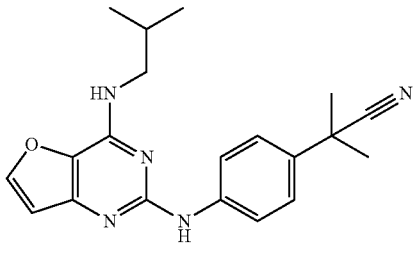 [SMILES: CC(C)CNc1nc(Nc2ccc(C(C)(C)C#N)cc2)nc2ccoc12] | B.5.119 | 2.21 (h) | 350 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 2-Chloro-N-cyclopropylfuro[3,2-d]pyrimidin-4-amine (Preparation #A.1) | 4-(4-(Methylsulfonyl)piperazin-1-yl)aniline [Oakwood] | | B.5.120 | 1.66 (c) | 429 | A |
| 2-Chloro-N-cyclopropylfuro[3,2-d]pyrimidin-4-amine (Preparation #A.1) | 4-(1H-Imidazol-1-yl)aniline | | B.5.121 | 1.49 (c) | 333 | B |
| (1-((2-Chlorofuro[3,2-d]pyrimidin-4-yl)-4-methylpiperidin-4-yl)methanol (prepared using A from 2,4-dichlorofuro[3,2-d]pyrimidine [ArkPharm] with (4-methylpiperidin-4-yl)methanol [ArkPharm]) | 6-Amino-2,2-dimethyl-2H-benzo[b][1,4]oxazin-3(4H)-one [ArkPharm] | | B.5.122 | 1.94 (f) | 438 | B |
| 1-(2-Chlorofuro[3,2-d]pyrimidin-4-yl)-4-methylpiperidin-4-ol (prepared using A from 2,4-dichlorofuro[3,2-d]pyrimidine [ArkPharm] with 4-methylpiperidin-4-ol [MolBridge]) | 6-Amino-2,2-dimethyl-2H-benzo[b][1,4]oxazin-3(4H)-one [ArkPharm] | | B.5.123 | 1.88 (f) | 424 | B |
| 2-(1-(2-Chlorofuro[3,2-d]pyrimidin-4-yl)piperidin-4-yl)ethanol (prepared using A from 2,4-dichlorofuro[3,2-d]pyrimidine [ArkPharm] with 2-(piperidin-4-yl)ethanol) | 6-Amino-2,2-dimethyl-2H-benzo[b][1,4]oxazin-3(4H)-one [ArkPharm] | | B.5.124 | 1.90 (f) | 438 | B |

TABLE B.5-continued

Examples prepared from a heteroaryl chloride with an aniline using General Procedure B

| Heteroaryl Chloride | Aniline | Product | Example # | R$_t$ min (Table 2, Method) | m/z ESI+ (M + H)$^+$ | Syk IC$_{50}$ |
|---|---|---|---|---|---|---|
| 1-(2-Chlorofuro[3,2-d]pyrimidin-4-yl)-4-(hydroxymethyl)piperidin-4-ol (prepared using A from 2,4-dichlorofuro[3,2-d]pyrimidine [ArkPharm] with 4-(hydroxymethyl)piperidin-4-ol [MolBridge]) | 6-Amino-2,2-dimethyl-2H-benzo[b][1,4]oxazin-3(4H)-one [ArkPharm] | | B.5.125 | 1.70 (f) | 440 | B |
| 1-(2-Chlorofuro[3,2-d]pyrimidin-4-yl)piperidin-3-ol (prepared using A from 2,4-dichlorofuro[3,2-d]pyrimidine [ArkPharm] with piperidin-3-ol) | 6-Amino-2,2-dimethyl-2H-benzo[b][1,4]oxazin-3(4H)-one [ArkPharm] | | B.5.126 | 1.85 (f) | 410 | B |
| 2-Chloro-N-cyclopropylfuro[3,2-d]pyrimidin-4-amine (Preparation #A.1) | Benzo[d]isoxazol-6-amine [ArkPharm] | | B.5.127 | 1.87 (f) | 308 | B |
| 2-Chloro-N-cyclopropylfuro[3,2-d]pyrimidin-4-amine (Preparation #A.1) | N$^3$-(Tetrahydro-2H-pyran-4-yl)-1H-indazole-3,6-diamine (prepared using B from 6-bromo-1-(tetrahydro-2H-pyran-2-yl)-N-(tetrahydro-2H-pyran-4-yl)-1H-indazol-3-amine (WO 2010/027500 Intermediate 116 step B) with diphenylmethanimine and AN) | | B.5.128 | 1.74 (h) | 406 | A |

TABLE B.5-continued

Examples prepared from a heteroaryl chloride with an aniline using General Procedure B

| Heteroaryl Chloride | Aniline | Product | Example # | R, min (Table 2, Method) | m/z ESI+ (M + H)+ | Syk IC$_{50}$ |
|---|---|---|---|---|---|---|
| (diexo)-3-(2-Chlorofuro[3,2-d]pyrimidin-4-ylamino)bicyclo[2.2.1]hept-5-ene-2-carboxamide (prepared using A from 2,4-dichlorofuro[3,2-d]pyrimidine [ArkPharm] with diexo-3-aminobicyclo[2.2.1]hept-5-ene-2-carboxamide [Acros]) | 6-Amino-2,2-dimethyl-2H-benzo[b][1,4]oxazin-3(4H)-one [ArkPharm] | | B.5.129 | 1.72 (c) | 461 | A |
| 2-Chloro-N-cyclopropylfuro[3,2-d]pyrimidin-4-amine (Preparation #A.1) | 4-Aminobenzonitrile | | B.5.130 | 2.04 (c) | 292 | B |
| 2-Chloro-N-cyclopropylfuro[3,2-d]pyrimidin-4-amine (Preparation #A.1) | 4-Methoxyaniline | | B.5.131 | 1.77 (c) | 297 | B |
| 1-(2-Chlorofuro[3,2-d]pyrimidin-4-yl)pyrrolidin-3-ol (prepared using A from 2,4-dichlorofuro[3,2-d]pyrimidine [Arkpharm] with pyrrolidin-3-ol) | 6-Amino-2,2-dimethyl-2H-benzo[b][1,4]oxazin-3(4H)-one [Arkpharm] | | B.5.132 | 1.77 (h) | 396 | C |
| 1-(2-Chlorofuro[3,2-d]pyrimidin-4-yl)piperidin-4-ol (prepared using A from 2,4-dichlorofuro[3,2-d]pyrimidine [Arkpharm] with piperidin-4-ol) | 6-Amino-2,2-dimethyl-2H-benzo[b][1,4]oxazin-3(4H)-one [Arkpharm] | | B.5.133 | 1.79 (h) | 410 | A |

TABLE B.5-continued

Examples prepared from a heteroaryl chloride with an aniline using General Procedure B

| Heteroaryl Chloride | Aniline | Product | Example # | R, min (Table 2, Method) | m/z ESI+ (M + H)+ | Syk IC$_{50}$ |
|---|---|---|---|---|---|---|
| 2-Chloro-N-cyclopropylfuro[3,2-d]pyrimidin-4-amine (Preparation #A.1) | 2-(4-Aminophenyl)acetonitrile [Lancaster] | | B.5.134 | 1.85 (c) | 306 | B |
| 2-Chloro-N-cyclopropylfuro[3,2-d]pyrimidin-4-amine (Preparation #A.1) | 4-Amino-N-(pyridin-2-yl)benzenesulfonamide [Matrix] | | B.5.135 | 1.67 (c) | 423 | B |
| 2-Chloro-N-cyclopropylfuro[3,2-d]pyrimidin-4-amine (Preparation #A.1) | 4-(Pyridin-4-yl)aniline [JW PharmLab] | | B.5.136 | 1.86 (c) | 344 | B |

General Procedure C: Removal of a Boc Group from an N-Boc Amine or Heteroaromatic To a solution of an N-Boc amine or heteroaromatic (1 equiv) in an organic solvent (such as DCM, DCE, 1,4-dioxane or MeOH, preferably DCM or 1,4-dioxane) is added an acid (such as TFA or HCl, preferably TFA; 2 to 35 equiv, preferably 15 to 25 equiv). The mixture is stirred at about 0 to 100° C. (preferably about 20 to 60° C.) for about 1 to 24 h (preferably about 1 to 6 h). Optionally, additional acid (2 to 35 equiv, preferably 20 to 25 equiv) may be added and the mixture stirred at about 0 to 100° C. (preferably about 15 to 60° C.) for about 1 to 24 h (preferably about 1 to 6 h). If a solid is present in the mixture, the mixture may be optionally filtered and the solid washed with an organic solvent such as 1,4-dioxane or Et$_2$O. The resulting solid is then optionally dried under reduced pressure to give the targeted compound. Alternatively, the mixture may be optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure C

Example #C.1

4-(4-(4-(Aminomethyl)piperidin-1-yl)furo[3,2-d]pyrimidin-2-ylamino)benzenesulfonamide

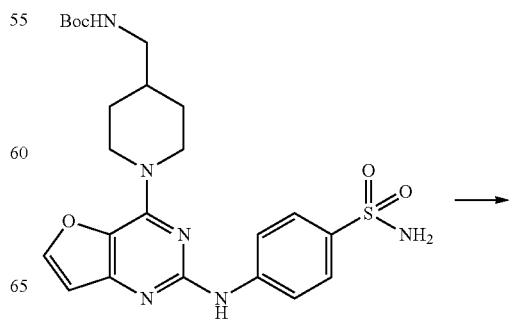

-continued

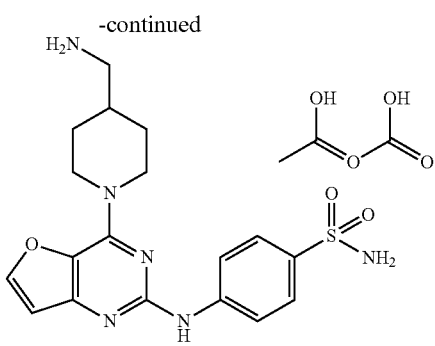

To a flask containing tert-butyl(1-(2-(4-sulfamoylphenylamino)furo[3,2-d]pyrimidin-4-yl)piperidin-4-yl)methylcarbamate (0.215 g, 0.428 mmol, prepared using A from 2,4-dichlorofuro[3,2-d]pyrimidine [ArkPharm] with 4-(tert-butoxycarbonylaminomethyl)piperidine [Tyger] and B with 4-aminobenzenesulfonamide) was slowly added a 20% TFA/DCM (3 mL) solution. The mixture was stirred at rt for about 4 h. The solvent was removed in vacuo and the residue purified by reverse phase preparatory HPLC (Table 2, method b) to provide 4-(4-(4-(aminomethyl)piperidin-1-yl)furo[3,2-d]pyrimidin-2-ylamino)benzenesulfonamide (0.142 g, 63%): LC/MS (Table 2, Method a) $R_t$=0.20 min; MS m/z 403.2 (M+H)$^+$. Syk IC$_{50}$=A

TABLE C.1

Examples for the removal of a Boc protecting group from an N-Boc protected amine or heteroaromatic using General Procedure C

| N-Boc Protected Amine | Product | Example # | $R_t$ min (Table 2, Method) | m/z ESI+ (M + H)$^+$ | Syk IC$_{50}$ |
|---|---|---|---|---|---|
| tert-Butyl 1-(2-(4-sulfamoylphenylamino)furo[3,2-d]pyrimidin-4-yl)pyrrolidin-3-ylcarbamate (prepared using A from 2,4-dichlorofuro[3,2-d]pyrimidine [ArkPharm] with 4-(tert-butyl pyrrolidin-3-ylcarbamate [TIC] and B with 4-aminobenzenesulfonamide) | | C.1.1 | 0.18 (a) | 375 | D |
| tert-Butyl (1-(2-(4-(4-acetylpiperazin-1-yl)phenylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Matrix] and B with 1-(4-(4-aminophenyl)piperazin-1-yl)ethanone [Matrix]) | | C.1.2 | 1.58 (d) | 464 | A |
| tert-Butyl 6-(4-(cyclobutylamino)furo[3,2-d]pyrimidin-2-ylamino)-1H-indazole-1-carboxylate (prepared using A from 2,4-dichlorofuro[3,2-d]pyrimidine [ArkPharm] with cyclobutylamine and B with tert-butyl 6-amino-1H-indazole-1-carboxylate [Frontier]) | | C.1.3 | 1.88 (d) | 321 | A |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl (1-(2-(4-(4-acetylpiperazin-1-yl)phenylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with 1-(4-(4-aminophenyl)piperazin-1-yl)ethanone [Matrix]) | 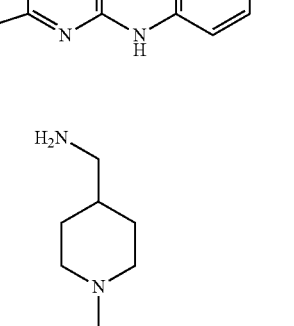 | C.1.4 | 1.26 (e) | 450 | A |
| tert-Butyl (1-(2-(2-oxo-1,2,3,4-tetrahydroquinolin-6-ylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with 6-amino-3,4-dihydroquinolin-2(1H)-one [Akos]) | 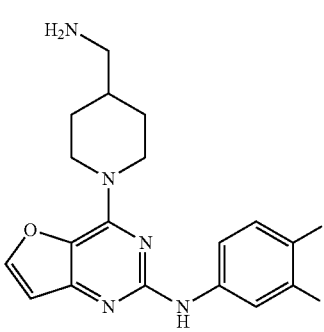 | C.1.5 | 1.52 (d) | 393 | A |
| tert-Butyl (1-(2-(2,2-dimethyl-3-oxo-3,4-dihydro-2H-benzo[b][1,4]oxazin-6-ylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with 6-amino-2,2-dimethyl-2H-benzo[b][1,4]oxazin-3(4H)-one [ArkPharm]) | 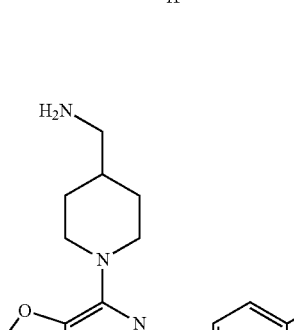 | C.1.6 | 1.70 (d) | 423 | A |
| tert-Butyl (1-(2-(4-(N-methylacetamido)phenyl-amino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with N-(4-aminophenyl)-N-methylacetamide) | 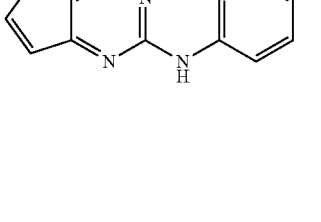 | C.1.7 | 1.58 (d) | 395 | A |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC$_{50}$ |
|---|---|---|---|---|---|
| tert-Butyl (1-(2-(4-butyramidophenylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with Preparation #3) | | C.1.8 | 1.66 (d) | 409 | B |
| tert-Butyl 6-(4-(4-((tert-butoxycarbonylamino)methyl)piperidin-1-yl)furo[3,2-d]pyrimidin-2-ylamino)-1H-indazole-1-carboxylate (prepared using A from 2,4-dichlorofuro[3,2-d]pyrimidine [ArkPharm] with tert-butyl piperidin-4-ylmethylcarbamate [Astatech] and B with tert-butyl 6-amino-1H-indazole-1-carboxylate [Frontier]) | | C.1.9 | 1.54 (h) | 364 | A |
| tert-Butyl 4-((2-(3-chloro-4-morpholinophenylamino)furo[3,2-d]pyrimidin-4-ylamino)methyl)piperidine-1-carboxylate (prepared using A from 2,4-dichlorofuro[3,2-d]pyrimidine [ArkPharm] with tert-butyl 4-(aminomethyl)piperidine-1-carboxylate [Astatech] and B with 3-chloro-4-morpholinoanaline [Akos]) | | C.1.10 | 1.76 (d) | 443 | B |
| tert-Butyl 4-(4-(4-(cyclopropylamino)furo[3,2-d]pyrimidin-2-ylamino)phenyl)piperazine-1-carboxylate (prepared using B from 2-chloro-N-cyclopropylfuro[3,2-d]pyrimidin-4-amine (Preparation #A.1) with tert-butyl 4-(4-aminophenyl)piperazine-1-carboxylate [J&W PharmLab]) | | C.1.11 | 1.63 (h) | 351 | B |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl 4-(4-(4-(cyclopropylamino)furo[3,2-d]pyrimidin-2-ylamino)phenyl)piperzaine-1-carboxylate (prepared using A from 2,4-dichlorofuro[3,2-d]pyrimidine [ArkPharm] with cyclobutylamine and B with tert-butyl 4-(4-aminophenyl)piperazine-1-carboxylate [J&W PharmLab]) | | C.1.12 | 1.35 (i) | 365 | B |
| tert-Butyl (1-(2-(3-chloro-4-morpholinophenylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with 3-chloro-4-morpholinoanaline [Akos]) | | C.1.13 | 1.78 (h) | 443 | A |
| tert-Butyl 6-(4-(4-((2,2-difluoroethylamino)methyl)piperidin-1-yl)furo[3,2-d]pyrimidin-2-ylamino)-1H-indazole-1-carboxylate (prepared using B from Preparation #H.1 with tert-butyl 6-amino-1H-indazole-1-carboxylate [Frontier]) | | C.1.14 | 1.55 (c) | 428 | A |
| tert-Butyl 6-(4-(4-((2-fluoroethylamino)methyl)piperidin-1-yl)furo[3,2-d]pyrimidin-2-ylamino)-1H-indazole-1-carboxylate (prepared using H from Preparation #P.1 with 2-fluoroethanamine and B with tert-butyl 6-amino-1H-indazole-1-carboxylate [Frontier]) | | C.1.15 | 1.41 (c) | 408 | A |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl 6-(4-(4-((oxetan-3-ylamino)methyl)piperidin-1-yl)furo[3,2-d]pyrimidin-2-ylamino)-1H-indazole-1-carboxylate (prepared using H from Preparation #P.1 with oxetan-3-amine and B with tert-butyl 6-amino-1H-indazole-1-carboxylate [Frontier]) | | C.1.16 | 1.42 (c) | 420 | B |
| tert-Butyl (1-(2-(4-(N-(3-methoxypropyl)sulfamoyl)phenylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech]) and B with 4-amino-N-(3-methoxypropyl)benzene-sulfonamide [Akos]) | | C.1.17 | 1.64 (h) | 475 | A |
| tert-Butyl (1-(2-(1-methyl-1H-indazol-5-ylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Astatech] and B with 1-methyl-1H-indazol-5-amine [ArkPharm]) | | C.1.18 | 1.59 (h) | 378 | A |
| tert-Butyl 6-(4-(3-((tert-butoxycarbonyl(methyl)amino)methyl)-5,6-dihydroimidazo[1,5-a]pyrazin-7(8H)-yl)furo[3,2-d]pyrimidin-2-ylamino)-1H-indazole-1-carboxylate (prepared using B from Preparation #L.1 with tert-butyl 6-amino-1H-indazole-1-carboxylate [Frontier]) | | C.1.19 | 1.58 (h) | 416 | B |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ (M + H)+ | Syk IC$_{50}$ |
|---|---|---|---|---|---|
| tert-Butyl 5-(4-(cyclopropylamino)furo[3,2-d]pyrimidin-2-ylamino)-1H-indazole-1-carboxylate (prepared using B from Preparation #A.1 with tert-butyl 5-amino-1H-indazole-1-carboxylate [Frontier]) | | C.1.20 | 1.75 (h) | 307 | A |
| tert-Butyl 6-(4-(4-((2-(methylsulfonyl)ethylamino)methyl)piperidin-1-yl)furo[3,2-d]pyrimidin-2-ylamino)-1H-indazole-1-carboxylate (prepared using H from Preparation #P.1 with 2-(methylsulfonyl)ethanamine [ChemImpex] and b with tert-butyl 6-amino-1H-indazole-1-carboxylate [Frontier]) | | C.1.21 | 1.45 (c) | 470 | B |
| tert-Butyl (1-(2-(2,2-dimethyl-3-oxo-3,4-dihydro-2H-benzo[b][1,4]oxazin-6-ylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Matrix] and B with 6-amino-2,2-dimethyl-2H-benzo[b][1,4]oxazin-3(4H)-one [ArkPharm]) | | C.1.22 | 1.51 (c) | 437 | A |
| tert-Btyl 6-(4-(4-((tert-butoxycarbonyl(methyl)amino)methyl)piperidin-1-yl)furo[3,2-d]pyrimidin-2-ylamino)-1H-indazole-1-carboxylate (prepared using A from 2,4-dichlorofuro[3,2-d]pyrimidine [ArkPharm] with tert-butyl methyl(piperidin-4-ylmethyl)carbamate [Matrix] and B with tert-butyl 6-amino-1H-indazole-1-carboxylate [Frontier]) | | C.1.23 | 1.30 (c) | 436 | A |

TABLE C.1-continued

Examples for the removal of a Boc protecting group from an N-Boc protected amine or heteroaromatic using General Procedure C

| N-Boc Protected Amine | Product | Example # | R<sub>t</sub> min (Table 2, Method) | m/z ESI+ (M + H)<sup>+</sup> | Syk IC<sub>50</sub> |
|---|---|---|---|---|---|
| tert-Butyl 6-(4-(cyclopropylamino)furo[3,2-d]pyrimidin-2-ylamino)-1H-benzo[d]imidazole-1-carboxylate (prepared using B from Preparation #A.1 with tert-butyl 6-amino-1H-benzo[d]imidazole-1-carboxylate (WO 2004/101533, Example 90) | | C.1.24 | 1.47 (c) | 307 | B |
| tert-Butyl 6-(4-(3-((tert-butoxycarbonylamino)methyl)-5,6-dihydro-imidazo[1,5-a]pyrazin-7(8H)-yl)furo[3,2-d]pyrimidin-2-ylamino)-1H-indazole-1-carboxylate (prepared using A from 2,4-dichlorofuro[3,2-d]pyrimidine [ArkPharm] with Preparation #G.1 and B with tert-butyl 6-amino-1H-indazole-1-carboxylate [Frontier]) | | C.1.25 | 1.61 (h) | 393 | B |
| tert-Butyl 6-(4-(cyclopropylamino)furo[3,2-d]pyrimidin-2-ylamino)-3,4-dihydroisoquinoline-2(1H)-carboxylate (prepared using B from Preparation #A.1 with tert-butyl 6-amino-3,4-dihydroisoquinoline-2(1H)-carboxylate [Astatech]) | | C.1.26 | 1.09 (c) | 332 | B |
| tert-Butyl 6-(4-((1R,3S)-3-(tert-butoxycarbonyl-amino)cyclopentylamino)furo[3,2-d]pyrimidin-2-ylamino)-3-methyl-1H-indazole-1-carboxylate (Preparation #M.1.1) | | C.1.27 | 1.55 (h) | 364 | B |
| tert-Butyl 6-(4-((1S,3R)-3-(tert-butoxycarbonyl-amino)cyclopentylamino)furo[3,2-d]pyrimidin-2-ylamino)-3-methyl-1H-indazole-1-carboxylate (Preparation #M.1.2) | | C.1.28 | 1.52 (h) | 364 | B |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ $(M + H)^+$ | Syk $IC_{50}$ |
|---|---|---|---|---|---|
| tert-Butyl 6-(4-(4-(tert-butoxycarbonylamino)azepan-1-yl)furo[3,2-d]pyrimidin-2-ylamino)-3-methyl-1H-indazole-1-carboxylate (prepared using B from Preparation #O.1 with Example #3, Step B) | | C.1.29 | 1.59 (h) | 378 | A |
| tert-Butyl 1-(2-(2,2-dimethyl-3-oxo-3,4-dihydro-2H-benzo[b][1,4]oxazin-6-ylamino)furo[3,2-d]pyrimidin-4-yl)azepan-4-ylcarbamate (prepared using B from Preparation #O.1 with 6-amino-2,2-dimethyl-2H-benzo[b][1,4]oxazin-3(4H)-one [ArkPharm]) | | C.1.30 | 1.67 (h) | 423 | A |
| tert-Butyl 6-(4-(4-((tert-butoxycarbonylamino)methyl)-4-methylpiperidin-1-yl)furo[3,2-d]pyrimidin-2-ylamino)-3-methyl-1H-indazole-1-carboxylate (prepared using A from 2,4-dichlorofuro[3,2-d]pyrimidine [ArkPharm] with tert-butyl (4-methylpiperidin-4-yl)methylcarbamate [A&C Pharmtech] and B with Example #3, Step B) | | C.1.31 | 1.50 (c) | 392 | A |
| tert-Butyl (1-(2-(3,3-dimethyl-2-oxoindolin-6-ylamino)furo[3,2-d]pyrimidin-4-yl)-4-methylpiperidin-4-yl)methylcarbamate (prepared using A from 2,4-dichlorofuro[3,2-d]pyrimidine [ArkPharm] with tert-butyl (4-methylpiperidin-4-yl)methylcarbamate [A&C Pharmtech] and B with 6-amino-3,3-dimethylindolin-2-one [Astatech]) | | C.1.32 | 1.50 (c) | 421 | A |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC$_{50}$ |
|---|---|---|---|---|---|
| tert-Butyl (1-(2-(2,2-dimethyl-3-oxo-3,4-dihydro-2H-benzo[b][1,4]oxazin-6-ylamino)furo[3,2-d]pyrimidin-4-yl)-4-methylpiperidin-4-yl)methylcarbamate (prepared using A from from 2,4-dichlorofuro[3,2-d]pyrimidine [ArkPharm] with tert-butyl (4-methylpiperidin-4-yl)methylcarbamate [A&C Pharmtech] and B with 6-amino-2,2-dimethyl-2H-benzo[b][1,4]oxazin-3(4H)-one [ArkPharm]) | | C.1.33 | 1.54 (c) | 437 | A |
| tert-Butyl 1-(2-(3,3-dimethyl-2-oxoindolin-6-ylamino)furo[3,2-d]pyrimidin-4-yl)acepan-4-ylcarbamate (prepared using A from 2,4-dichlorofuro[3,2-d]pyrimidine [ArkPharm] with azepan-4-one hydrochloride [ArkPharm], H, O with Boc$_2$O and B with 6-amino-3,3-dimethylindolin-2-one [Astatech]) | | C.1.34 | 1.79 (h) | 407 | A |
| tert-Butyl 5-(2-(2,2-dimethyl-3-oxo-3,4-dihydro-2H-benzo[b][1,4]oxazin-6-ylamino)furo[3,2-d]pyrimidin-4-yl)hexahydro-1H-pyrrolo[3,4-c]pyridine-2(3H)-carboxylate (prepared using A from 2,4-dichlorofuro[3,2-d]pyrimidine [ArkPharm] with tert-butyl hexahydro-1H-pyrrolo[3,4-c]pyridine-2(3H)-carboxylate [Milestone], B with 6-amino-2,2-dimethyl-2H-benzo[b][1,4]oxazin-3(4H)-one [ArkPharm]) | | C.1.35 | 1.67 (h) | 435 | B |
| tert-Butyl 2-(2-(2,2-dimethyl-3-oxo-3,4-dihydro-2H-benzo[b][1,4]oxazin-6-ylamino)furo[3,2-d]pyrimidin-4-yl)-2,7-diazaspiro[4.5]decane-7-carboxylate (prepared using A from 2,4-dichlorofuro[3,2-d]pyrimidine [ArkPharm] with tert-butyl 2,7-diazaspiro[4.5]decane-7-carboxylate [ASW MedChem] and B with 6-amino-2,2-dimethyl-2H-benzo[b][1,4]oxazin-3(4H)-one [ArkPharm]) | | C.1.36 | 1.78 (h) | 449 | A |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ $(M + H)^+$ | Syk $IC_{50}$ |
|---|---|---|---|---|---|
| tert-Butyl 9-(2-(3,3-dimethyl-2-oxoindolin-6-ylamino)furo[3,2-d]pyrimidin-4-yl)-2,9-diazaspiro[5.5]undecane-2-carboxylate (prepared using A from 2,4-dichlorofuro[3,2-d]pyrimidine [ArkPharm] with tert-butyl 2,9-diazaspiro[5.5]undecane-2-carboxylate [ASW MedChem] and B with 6-amino-3,3-dimethylindolin-2-one [Astatech]) | | C.1.37 | 1.76 (h) | 447 | A |
| tert-Butyl 8-(2-(3,3-dimethyl-2-oxoindolin-6-ylamino)furo[3,2-d]pyrimidin-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Alfa Aesar] and B with 6-amino-3,3-dimethylindolin-2-one [Astatech]) | | C.1.38 | 1.68 (h) | 433 | A |
| tert-Butyl 9-(2-(3-methoxy-4-morpholinophenylamino)furo[3,2-d]pyrimidin-4-yl)-2,9-diazaspiro[5.5]undecane-2-carboxylate (prepared using A from 2,4-dichlorofuro[3,2-d]pyrimidine [ArkPharm] with tert-butyl 2,9-diazaspiro[5.5]undecane-2-carboxylate [ASW MedChem], B with 3-methoxy-4-morpholinoaniline [Princeton]) | | C.1.39 | 1.77 (h) | 479 | A |
| tert-Butyl 8-(2-(1-methyl-1H-indazol-5-ylamino)furo[3,2-d]pyrimidin-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Alfa] and B with 1-methyl-1H-indazol-5-amine [ArkPharm]) | | C.1.40 | 1.64 (h) | 404 | A |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl 9-(2-(3-chloro-4-morpholinophenylamino)furo[3,2-d]pyrimidin-4-yl)-2,9-diazaspiro[5.5]undecane-2-carboxylate (prepared using A from 2,4-dichlorofuro[3,2-d]pyrimidine [ArkPharm] with tert-butyl 2,9-diazaspiro[5.5]undecane-2-carboxylate [ASW MedChem] and B with 3-chloro-4-morpholinoaniline [Akos]) | | C.1.41 | 1.92 (h) | 484 | A |
| tert-Butyl 9-(2-(3-methyl-4-morpholinophenylamino)furo[3,2-d]pyrimidin-4-yl)-2,9-diazaspiro[5.5]undecane-2-carboxylate (prepared using A from 2,4-dichlorofuro[3,2-d]pyrimidine [ArkPharm] with tert-butyl 2,9-diazaspiro[5.5]undecane-2-carboxylate [ASW MedChem] and B with 3-methyl-4-morpholinoaniline [Matrix]) | | C.1.42 | 1.98 (h) | 463 | A |
| tert-Butyl 9-(2-(1-methyl-1H-indazol-5-ylamino)furo[3,2-d]pyrimidin-4-yl)-2,9-diazaspiro[5.5]undecane-2-carboxylate (prepared using A from from 2,4-dichlorofuro[3,2-d]pyrimidine [ArkPharm] with tert-butyl 2,9-diazaspiro[5.5]undecane-2-carboxylate [ASW MedChem] and B with 1-methyl-1H-indazol-5-amine [ArkPharm]) | | C.1.43 | 1.73 (h) | 418 | A |
| tert-Butyl 8-(2-(3-chloro-4-morpholinophenylamino)furo[3,2-d]pyrimidin-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Alfa] and B with 3-chloro-4-morpholinoaniline [Akos]) | | C.1.44 | 1.91 (h) | 469 | A |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl 8-(2-(3-methoxy-4-morpholinophenylamino)furo[3,2-d]pyrimidine-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Alfa] and B with 3-methoxy-4-morpholinoaniline [Princeton]) | | C.1.45 | 1.70 (h) | 465 | B |
| tert-Butyl 8-(2-(3-methyl-4-morpholinophenylamino)furo[3,2-d]pyrimidin-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Alfa] and B with 3-methyl-4-morpholinoaniline [Matrix]) | | C.1.46 | 1.78 (h) | 449 | A |
| tert-Butyl 6-(4-azetidin-1-yl)furo[3,2-d]pyrimidin-2-ylamino)-3-methyl-1H-indazole-1-carboxylate (prepared using A from 2,4-dichlorofuro[3,2-d]pyrimidine [ArkPharm] with acetidine, B with Example #3, Step B, Step C, J and O with Boc$_2$O) | | C.1.47 | 1.89 (h) | 321 | B |
| tert-Butyl 6-(4-(4-((tert-butoxycarbonyl(methyl)amino)methyl)piperidin-1-yl)furo[3,2-d]pyrimidin-2-ylamino)-3-methyl-1H-indazole-1-carboxylate (prepared using A from 2,4-dichlorofuro[3,2-d]pyrimidine [ArkPharm] with tert-butyl methyl(piperidin-4-ylmethyl)carbamate [Chembridge] and B with Example #3, Step B) | | C.1.48 | 1.40 (c) | 392 | A |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ $(M + H)^+$ | Syk $IC_{50}$ |
|---|---|---|---|---|---|
| tert-Butyl methyl((1-(2-(1-methyl-1H-indazol-5-ylamino)furo[3,2-d]pyrimidin-4-yl)piperidin-4-yl)methyl)carbamate (prepared using A from 2,4-dichlorofuro[3,2-d]pyrimidine [ArkPharm] with tert-butyl methyl(piperidin-4-ylmethyl)carbamate [Chembridge] and B with 1-methyl-1H-indazol-5-amine [ArkPharm]) | 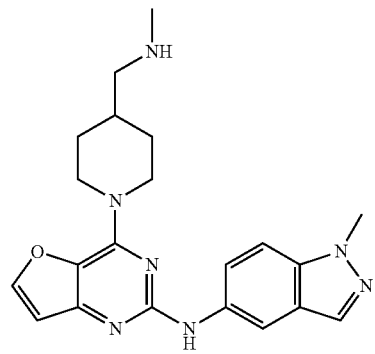 [SMILES: CNCC1CCN(c2nc(Nc3ccc4c(cnn4C)c3)nc3ccoc23)CC1] | C.1.49 | 1.28 (c) | 392 | A |
| tert-Butyl 6-(4-(diexo-3-carbamoylbicyclo[2.2.1]hept-5-en-2-ylamino)furo[3,2-d]pyrimidin-2-ylamino)-1H-indazole-1-carboxylate (prepared using A from 2,4-dichlorofuro[3,2-d]pyrimidine [ArkPharm] and diexo-3-aminobicyclo[2.2.1]hept-5-ene-2-carboxamide [Acros] and B with tert-butyl 6-amino-1H-indazole-1-carboxylate [Frontier]) | 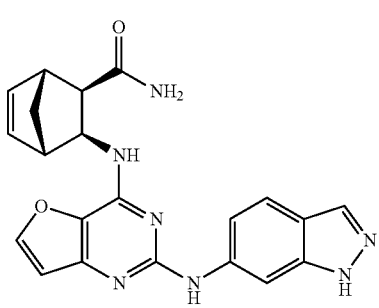 [SMILES: NC(=O)[C@H]1[C@@H](Nc2nc(Nc3ccc4cn[nH]c4c3)nc3ccoc23)[C@@H]2C=C[C@H]1C2] | C.1.50 | 1.61 (c) | 402 | A |
| tert-Butyl (1-(2-(3,3-dimethyl-2-oxoindolin-6-ylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Matrix] and B with 6-amino-3,3-dimethylindolin-2-one [Astatech]) | 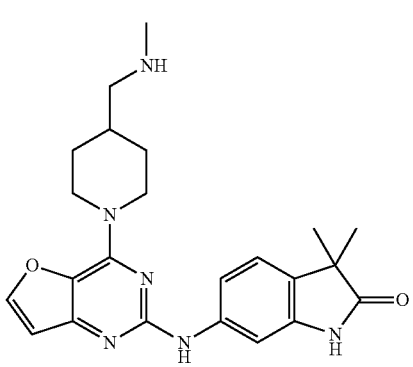 [SMILES: CNCC1CCN(c2nc(Nc3ccc4c(c3)NC(=O)C4(C)C)nc3ccoc23)CC1] | C.1.51 | 1.19 (c) | 421 | A |
| tert-Butyl 6-(4-(diexo-3-carbamoylbicyclo[2.2.1]hept-5-en-2-ylamino)furo[3,2-d]pyrimidin-2-ylamino)-3-methyl-1H-indazole-1-carboxylate (prepared using A from 2,4-dichlorofuro[3,2-d]pyrimidine [ArkPharm] with diexo-3-aminobicyclo[2.2.1]hept-5-ene-2-carboxamide [Acros] and B with Example #3, Step B) | 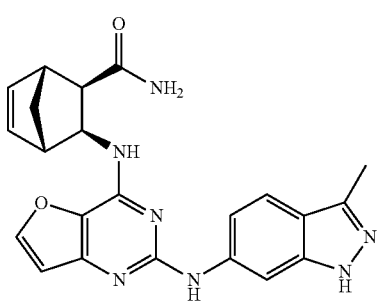 [SMILES: Cc1n[nH]c2cc(Nc3nc(N[C@@H]4[C@H](C(N)=O)[C@H]5C=C[C@@H]4C5)c4occc4n3)ccc12] | C.1.52 | 1.60 (c) | 416 | A |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ $(M + H)^+$ | Syk $IC_{50}$ |
|---|---|---|---|---|---|
| tert-Butyl (1-(2-(2,2-dimethyl-3-oxo-3,4-dihydro-2H-benzo[b][1,4]oxazin-6-ylamino)furo[3,2-d]pyrimidin-4-yl)pyrrolidin-3-yl)methyl(methyl)carbamate (prepared using A from 2,4-dichlorofuro[3,2-d]pyrimidine [ArkPharm] with tert-butyl methyl(pyrrolidin-3-ylmethyl)carbamate [Atlantic SciTech] and B with 6-amino-2,2-dimethyl-2H-benzo[b][1,4]oxazin-3(4H)-one [ArkPharm]) | | C.1.53 | 1.18 (c) | 423 | B |
| tert-Butyl 6-(4-(4-((2,2-difluoroethylamino)methyl)piperidin-1-yl)furo[3,2-d]pyrimidin-2-ylamino)-3-methyl-1H-indazole-1-carboxylate (prepared using B from Preparation #H.1 with Example #3, Step B) | | C.1.54 | 1.72 (c) | 442 | A |
| tert-Butyl 6-(4-(3,4-dihydroisoquinolin-2(1H)-yl)furo[3,2-d]pyrimidin-2-ylamino)-1H-indazole-1-carboxylate (prepared using A from 2,4-dichlorofuro[3,2-d]pyrimidine [ArkPharm] with 1,2,3,4-tetrahydroisoquinoline and B with tert-butyl 6-amino-1H-indazole-1-carboxylate [Frontier]) | | C.1.55 | 2.27 (h) | 383 | B |
| tert-Butyl (1-(2-(4-(N-(3-methoxypropyl)sulfamoyl)phenylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Matrix] and B with 4-amino-N-(3-methoxy-propyl)benzenesulfonamide [Akos]) | | C.1.56 | 1.66 (h) | 489 | A |

TABLE C.1-continued

Examples for the removal of a Boc protecting group from an N-Boc protected amine or heteroaromatic using General Procedure C

| N-Boc Protected Amine | Product | Example # | R$_t$ min (Table 2, Method) | m/z ESI+ (M + H)$^+$ | Syk IC$_{50}$ |
|---|---|---|---|---|---|
| tert-Butyl (1-(2-(4-(2-cyanopropan-2-yl)phenylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Matrix] and B with with 2-(4-aminophenyl)-2-methylpropanenitrile [ArkPharm]) | | C.1.57 | 1.85 (f) | 405 | A |
| tert-Butyl 8-(2-(2,2-dimethyl-3-oxo-3,4-dihydro-2H-benzo[b][1,4]oxazin-6-ylamino)furo[3,2-d]pyrimidin-4-yl)-2,8-diazaspiro[4.5]decane-2-carboxylate (prepared using A from 2,4-dichlorofuro[3,2-d]pyrimidine [ArkPharm] with tert-butyl 2,8-diazaspiro[4.5]decane-2-carboxylate [Tyger] and B with 6-amino-2,2-dimethyl-2H-benzo[b][1,4]oxazin-3(4H)-one [ArkPharm]) | | C.1.58 | 1.43 (c) | 449 | A |
| Tert-butyl 9-(2-(2,2-dimethyl-3-oxo-3,4-dihydro-2H-benzo[b][1,4]oxazin-6-ylamino)furo[3,2-d]pyrimidin-4-yl)-2,9-diazaspiro[5.5]undecane-2-carboxylate prepared using A from 2,4-dichlorofuro[3,2-d]pyrimidine [ArkPharm] with tert-butyl 2,9-diazaspiro[5.5]undecane-2-carboxylate [ASW Medchem] and B with 6-amino-2,2-dimethyl-2H-benzo[b][1,4]oxazin-3(4H)-one[ArkPharm]) | | C.1.59 | 1.57 (c) | 463 | A |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC50 |
|---|---|---|---|---|---|
| tert-Butyl 3-methyl-6-(4-(4-((2-(methylsulfonyl)ethylamino)methyl)piperidin-1-yl)furo[3,2-d]pyrimidin-2-ylamino)-1H-indazole-1-carboxylate (prepared using H from Preparation #P.1 with 2-(methylsulfonyl)ethanamine hydrochloride [Chem-Impex] and B with Example #3, Step B) | | C.1.60 | 1.74 (h) | 484 | A |
| tert-Butyl (1-(2-(2-oxo-1,2,3,4-tetrahydroquinolin-7-ylamino)furo[3,2-d]pyrimidin-4-yl)piperidin-4-yl)methylcarbamate (prepared from using A from 2,4-dichlorofuro[3,2-d]pyrimidine [ArkPharm] with tert-butyl piperidin-4-ylmethylcarbamate [Astatech] and B with 7-amino-3,4-dihydroquinolin-2(1H)-one[Astatech]) | | C.1.61 | 1.63 (h) | 393 | A |
| tert-Butyl 1-(1-(2-(2,2-dimethyl-3-oxo-3,4-dihydro-2H-benzo[b][1,4]oxazin-6-ylamino)furo[3,2-d]pyrimidin-4-yl)piperidin-4-yl)ethylcarbamate (prepared from using A from 2,4-dichlorofuro[3,2-d]pyrimidine [ArkPharm] with tert-butyl 1-(piperidin-4-yl)ethylcarbamate [Ryan Scientific] and B with 6-amino-2,2-dimethyl-2H-benzo[b][1,4]oxazin-3(4H)-one [ArkPharm]) | | C.1.62 | 1.72 (h) | 437 | A |
| tert-Butyl (1-(2-(2-oxo-1,2-dihydroquinolin-7-ylamino)furo[3,2-d]pyrimidin-4-yl)piperidin-4-yl)methylcarbamate (prepared from using A from 2,4-dichlorofuro[3,2-d]pyrimidine [ArkPharm] with tert-butyl piperidin-4-ylmethylcarbamate [Astatech] and B with 7-aminoquinolin-2(1H)-one [ArkPharm]) | | C.1.63 | 1.58 (h) | 391 | A |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC50 |
|---|---|---|---|---|---|
| tert-Butyl (1-(2-(2,2-dimethyl-3-oxo-3,4-dihydro-2H-benzo[b][1,4]oxazin-6-ylamino)furo[3,2-d]pyrimidin-4-yl)-3-methylpyrrolidin-3-yl)methylcarbamate (prepared using A from 2,4-dichlorofuro[3,2-d]pyrimidine [ArkPharm] with tert-butyl (3-methylpyrrolidine-3-yl)methylcarbamate [WO 2006/002047, Example 72 Step B] and B with 6-amino-2,2-dimethyl-2H-benzo[b][1,4]oxazin-3(4H)-one [ArkPharm]) | | C.1.64 | 1.75 (f) | 423 | B |
| tert-Butyl (1-(2-(2,2-dimethyl-3-oxo-3,4-dihydro-2H-benzo[b][1,4]oxazin-6-ylamino)furo[3,2-d]pyrimidin-4-yl)-4-ethylpiperidin-4-yl)methylcarbamate (prepared from using A from 2,4-dichlorofuro[3,2-d]pyrimidine[ArkPharm] with tert-butyl (4-ethylpiperidin-4-yl)methylcarbamate [U.S. Pat. No. 6,140,333, Example 10, Step 3] and B with 6-amino-2,2-dimethyl-2H-benzo[b][1,4]oxazin-3(4H)-one [ArkPharm]) | | C.1.65 | 1.88 (h) | 451 | A |
| tert-Butyl (4-(cyclopropylmethyl)-1-(2-(2,2-dimethyl-3-oxo-3,4-dihydro-2H-benzo[b][1,4]oxazin-6-ylamino)furo[3,2-d]pyrimidin-4-yl)piperidin-4-yl)methylcarbamate (prepared using A from Preparation #K.1 with 2,4-dichlorofuro[3,2-d]pyrimidine[ArkPharm] and B with 6-amino-2,2-dimethyl-2H-benzo[b][1,4]oxazin-3(4H)-one [ArkPharm]) | | C.1.66 | 2.00 (h) | 477 | A |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC$_{50}$ |
|---|---|---|---|---|---|
| tert-Butyl (1-(2-(2,2-dimethyl-3-oxo-3,4-dihydro-2H-benzo[b][1,4]oxazin-6-ylamino)furo[3,2-d]pyrimidin-4-yl)piperidine-4,4-diyl)bis(methylene)dicarbamate (prepared using AE from Preparation #4, O with Boc$_2$O, K, A with 2,4-dichlorofuro[3,2-d]pyrimidine [ArkPharm] and B with 6-amino-2,2-dimethyl-2H-benzo[b][1,4]oxazin-3(4H)-one [ArkPharm]) | | C.1.67 | 0.51 (k) | 452 | A |
| tert-Butyl (1-(2-(2,2-dimethyl-3-oxo-3,4-dihydro-2H-benzo[b][1,4]oxazin-6-ylamino)furo[3,2-d]pyrimidin-4-yl)-4-methylpyrrolidin-3-yl)methylcarbamate (prepared using AE from 1-benzyl-4-methyl-pyrrolidine-3-carbonitrile (Tyger), O with Boc$_2$O, G, A (with 2,4-dichlorofuro[3,2-d]pyrimidine [ArkPharm]) and B (with 6-amino-2,2-dimethyl-2H-benzo[b][1,4]oxazin-3(4H)-one [Matrix]) | | C.1.68 | 1.78 (h) | 423 | B |
| tert-Butyl (1-(2-(2,2-dimethyl-3-oxo-3,4-dihydro-2H-benzo[b][1,4]oxazin-6-ylamino)furo[3,2-d]pyrimidin-4-yl)-4-(hydroxymethyl)piperidin-4-yl)methylcarbamate (prepared using AE from methyl 4-cyano-1-(2-oxo-2-phenylethyl)piperidine-4-carboxylate [U.S. 2004/0072802, Example 24], O with Boc$_2$O, K, A with 2,4-dichlorofuro[3,2-d]pyrimidine [ArkPharm], B with 6-amino-2,2-dimethyl-2H-benzo[b][1,4]oxazin-3(4H)-one [ArkPharm], and W) | | C.1.69 | 1.74 (h) | 453 | A |

TABLE C.1-continued

Examples for the removal of a Boc protecting group from an N-Boc protected amine or heteroaromatic using General Procedure C

| N-Boc Protected Amine | Product | Example # | $R_t$ min (Table 2, Method) | m/z ESI+ $(M + H)^+$ | Syk $IC_{50}$ |
|---|---|---|---|---|---|
| tert-Butyl (1-(2-(4-methyl-2-oxo-1,2-dihydroquinolin-7-ylamino)furo[3,2-d]pyrimidin-4-yl)piperidin-4-yl)methylcarbamate (prepared using A from 2,4-dichlorofuro[3,2-d]pyrimidine [ArkPharm] with tert-butyl piperidin-4-ylmethylcarbamate [Alfa Aesar] and B with 7-amino-4-methylquinolin-2(1H)-one) | 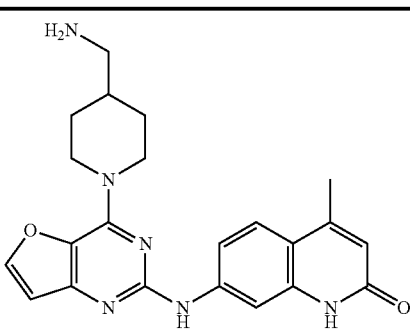 | C.1.70 | 1.62 (f) | 405 | A |
| tert-Butyl (1-(2-(2,2-dimethyl-3-oxo-3,4-dihydro-2H-benzo[b][1,4]thiazin-6-ylamino)furo[3,2-d]pyrimidin-4-yl)piperidin-4-yl)methyl(methyl)carbamate (prepared using A from 2,4-dichlorofuro[3,2-d]pyrimidine [ArkPharm] with tert-butyl methyl(piperidin-4-ylmethyl)carbamate [Chembridge and, B with 6-amino-2,2-dimethyl-2H-benzo[b][1,4]thiazin-3(4H)-one (*Bioorg. Med. Chem.* 2000, 8, 393, Compound 4)) | 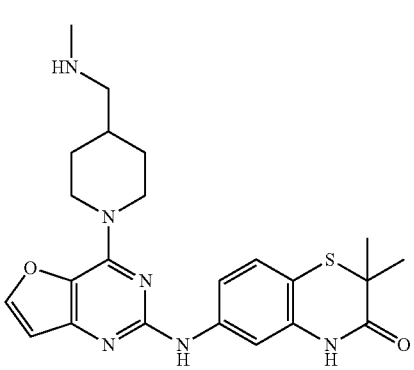 [SMILES: CNCC1CCN(c2nc(Nc3ccc4c(c3)NC(=O)C(C)(C)S4)nc3ccoc23)CC1] | C.1.71 | 1.41 (c) | 453 | A |
| tert-Butyl 6-(4-(4-(2-(tert-butoxycarbonylamino)ethyl)piperidin-1-yl)furo[3,2-d]pyrimidin-2-ylamino)-3-methyl-1H-indazole-1-carboxylate (prepared using A from 2,4-dichlorofuro[3,2-d]pyrimidine [ArkPharm] with tert-butyl 2-(piperidin-4-yl)ethylcarbamate [Tyger] and B with Example #3, Step B) | 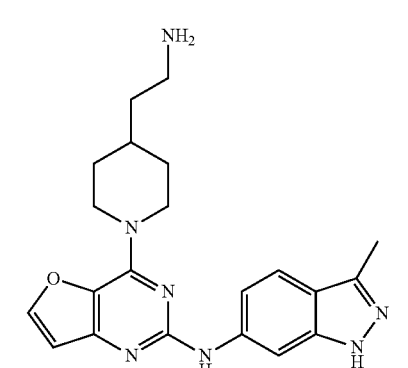 | C.1.72 | 1.23 (c) | 392 | B |
| tert-Butyl 6-(4-(4-(2,2-difluoroethylamino)azepan-1-yl)furo[3,2-d]pyrimidin-2-ylamino)-3-methyl-1H-indazole-1-carboxylate (prepared using A from 2,4-dichlorofuro[3,2-d]pyrimidine [ArkPharm] with azepan-4-one [J&W PharmLab], H with 2,2-difluoroethanamine [Matrix] and B with Example #3, Step B) | 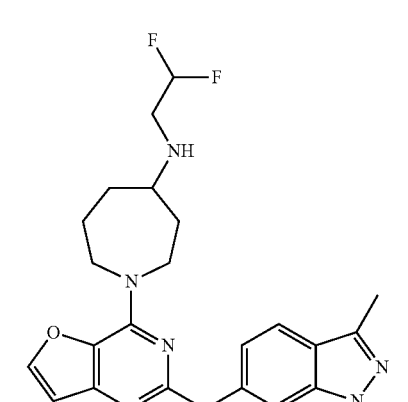 | C.1.73 | 1.41 (c) | 442 | B |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC$_{50}$ |
|---|---|---|---|---|---|
| tert-Butyl 3-methyl-6-(4-(4-((3,3,3-trifluoropropylamino)methyl)piperidin-1-yl)furo[3,2-d]pyrimidin-2-ylamino)-1H-indazole-1-carboxylate (prepared using H from Preparation # P.1 with 3,3,3-trifluoropropan-1-amine [Oakwood] and B with Example #3, Step B) | | C.1.74 | 1.43 (c) | 474 | A |
| tert-Butyl 2-(2-(2,2-dimethyl-3-oxo-3,4-dihydro-2H-benzo[b][1,4]oxazin-6-ylamino)furo[3,2-d]pyrimidin-4-yl)-2,6-diazaspiro[3.5]nonane-6-carboxylate (prepared using A from 2,4-dichlorofuro[3,2-d]pyrimidine [ArkPharm] with 6-(tert-butoxycarbonyl)-2,6-diazaspiro[3.5]nonane [Wuxi] and B with 6-amino-2,2-dimethyl-2H-benzo[b][1,4]oxazin-3(4H)-one [ArkPharm]) | | C.1.75 | 0.40 (s) | 435 | B |
| tert-Butyl 9-(2-(2,2-dimethyl-3-oxo-3,4-dihydro-2H-benzo[b][1,4]oxazin-6-ylamino)furo[3,2-d]pyrimidin-4-yl)-3,9-diazaspiro[5.5]undecane-3-carboxylate (prepared using A from 2,4-dichlorofuro[3,2-d]pyrimidine [ArkPharm] with tert-butyl 3,9-diazaspiro[5.5]undecane-3-carboxylate [Wuxi] and B with 6-amino-2,2-dimethyl-2H-benzo[b][1,4]oxazin-3(4H)-one [ArkPharm] | | C.1.76 | 1.32 (s) | 463 | B |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC50 |
|---|---|---|---|---|---|
| tert-Butyl 7-(2-(2,2-dimethyl-3-oxo-3,4-dihydro-2H-benzo[b][1,4]oxazin-6-ylamino)furo[3,2-d]pyrimidin-4-yl)-2,7-diazaspiro[4.4]nonane-2-carboxylate (prepared using A from 2,4-dichlorofuro[3,2-d]pyrimidine [ArkPharm] with tert-butyl 2,7-diazaspiro[4.4]nonane-2-carboxylate [Wuxi] and B with 6-amino-2,2-dimethyl-2H-benzo[b][1,4]oxazin-3(4H)-one [ArkPharm] | | C.1.77 | 0.42 (s) | 435 | B |
| tert-Butyl 2-(2-(2,2-dimethyl-3-oxo-3,4-dihydro-2H-benzo[b][1,4]oxazin-6-ylamino)furo[3,2-d]pyrimidin-4-yl)-2,8-diazaspiro[4.5]decane-8-carboxylate (prepared using A from 2,4-dichlorofuro[3,2-d]pyrimidine [ArkPharm] with tert-butyl 2,8-diazaspiro[4.5]decane-8-carboxylate [Wuxi] and B with 6-amino-2,2-dimethyl-2H-benzo[b][1,4]oxazin-3(4H)-one [ArkPharm]) | | C.1.78 | 0.43 (s) | 449 | B |
| tert-Butyl 2-(2-(2,2-dimethyl-3-oxo-3,4-dihydro-2H-benzo[b][1,4]oxazin-6-ylamino)furo[3,2-d]pyrimidin-4-yl)-2,7-diazaspiro[4.5]decane-7-carboxylate (prepared using A from 2,4-dichlorofuro[3,2-d]pyrimidine [ArkPharm] with tert-butyl 2,7-diazaspiro[4.5]decane-7-carboxylate [Wuxi] and B with 6-amino-2,2-dimethyl-2H-benzo[b][1,4]oxazin-3(4H)-one [ArkPharm]) | | C.1.79 | 0.44 (s) | 449 | B |
| tert-Butyl 7-(2-(2,2-dimethyl-3-oxo-3,4-dihydro-2H-benzo[b][1,4]oxazin-6-ylamino)furo[3,2-d]pyrimidin-4-yl)-1,7-diazaspiro[3.5]nonane-1-carboxylate (prepared using A from 2,4-dichlorofuro[3,2-d]pyrimidine [ArkPharm] with tert-butyl 1,7-diazaspiro[3.5]nonane-1-carboxylate [Wuxi] and B with 6-amino-2,2-dimethyl-2H-benzo[b][1,4]oxazin-3(4H)-one [ArkPharm]) | | C.1.80 | 0.44 (s) | 435 | B |

TABLE C.1-continued

Examples for the removal of a Boc protecting group from an N-Boc protected amine or heteroaromatic using General Procedure C

| N-Boc Protected Amine | Product | Example # | R, min (Table 2, Method) | m/z ESI+ (M + H)+ | Syk IC50 |
|---|---|---|---|---|---|
| tert-Butyl 6-(4-cyclobutoxyfuro[3,2-d]pyrimidin-2-ylamino)-3-methyl-1H-indazole-1-carboxylate (prepared using B from Preparation #Y.1 with Example #3, Step B) | | C.1.81 | 2.27 (c) | 336 | A |
| tert-Butyl 6-(4-(4-(tert-butoxycarbonylamino)azepan-1-yl)furo[3,2-d]pyrimidin-2-ylamino)-1H-indazole-1-carboxylate (prepared using B from Preparation #O.1 with tert-butyl 6-amino-1H-indazole-1-carboxylate [Frontier]) | | C.1.82 | 1.55 (h) | 364 | B |

General Procedure D: Formation of a Sulfonamide from an Amine and a Sulfonyl Chloride To a flask is added an amine (1.0 equiv), optionally as a hydrochloride salt, a solvent or mixture of solvents (DCM, DCE, EtOAc, THF, 1,4-dioxane or DME, preferably 1:1 pyridine/DCM), and a sulfonyl chloride (0.9 to 2.0 equiv, preferably 1.0 to 1.25 equiv). The mixture is stirred at about 0 to 80° C. (preferably about 15 to 35° C.) for about 1 h to 16 h (preferably 5 to 16 h). The mixture may optionally be concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure D

Preparation #D.1: 2-Chloro-4-(4-(methylsulfonyl)piperazin-1-yl)furo[3,2-d]pyrimidine

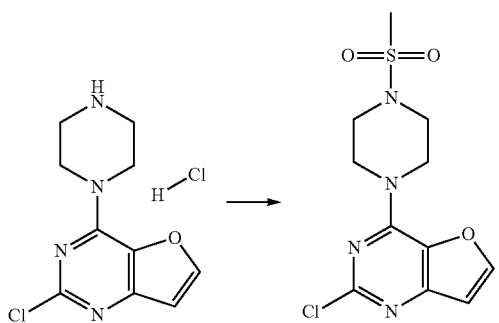

To a flask was added 2-chloro-4-(piperazin-1-yl)furo[3,2-d]pyrimidine, hydrochloride salt (0.325 g, 1.18 mmol, prepared using A from 2,4-dichlorofuro[3,2-d]pyrimidine [Ark Pharm] with piperazine), DCM (7 mL), pyridine (7.00 mL) and MsCl (0.101 mL, 1.29 mmol). The mixture was stirred overnight at rt. The mixture was warmed to about 35° C. and stirred for about 5 h. The solvent was removed in vacuo and the residue dissolved in DCM (20 mL). The organics were washed with water (about 20 mL) and with saturated aqueous NaHCO$_3$ (about 20 mL), dried over MgSO$_4$, filtered and concentrated under reduced pressure. The residue was purified by silica gel chromatography with an elution gradient EtOAc/hexanes (50 to 75%) to give 2-chloro-4-(4-(methylsulfonyl)piperazin-1-yl)furo[3,2-d]pyrimidine (0.162 g, 43%): LC/MS (Table 2, Method a) R$_t$=1.11 min; MS m/z 317.2 (M+H)$^+$.

General Procedure E.1: Formation of an Amide from an Amine and an Acid Halide or Anhydride To a solution of an amine (1 equiv), optionally as a hydrochloride salt, in an organic solvent (such as DCM, DCE, DMF, DMA, NMP, THF, Et$_2$O or 1,4-dioxane, preferably DMF or DCM) is added a base (such as TEA, DIEA or pyridine; 1 to 4 equiv, preferably TEA 1 to 1.5 equiv) and an acid halide or anhydride (1 to 4 equiv, preferably 1 to 2.5 equiv). The mixture is allowed to stir at about 10 to 60° C. (preferably about 25 to 50° C.) for about 5 min to 20 h (preferably about 18 h). The mixture is optionally neutralized with AcOH. The mixture is optionally concentrated in vacuo to give the final compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure E.1

Preparation #E.1.1: 1-(4-(2-Chlorofuro[3,2-d]pyrimidin-4-yl)piperazin-1-yl)ethanone

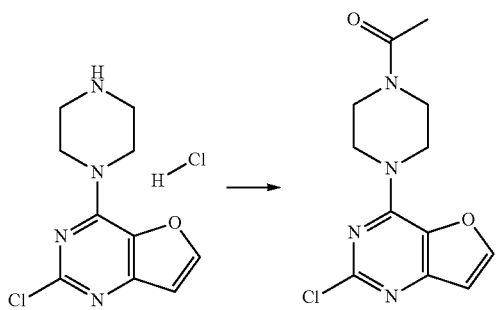

To a flask was added 2-chloro-4-(piperazin-1-yl)furo[3,2-d]pyrimidine, hydrochloride salt (0.325 g, 1.18 mmol, prepared using A from 2,4-dichlorofuro[3,2-d]pyrimidine [Ark Pharm] with piperazine), DMF (10 mL), TEA (0.543 mL, 3.90 mmol) and acetyl chloride (0.185 mL, 2.60 mmol). The mixture was warmed to about 35° C. and stirred overnight. The mixture was cooled to rt and diluted with DCM (50 mL). The organic layer was washed with water (50 mL), saturated aqueous NaHCO$_3$ (50 mL) and brine (50 mL), dried over MgSO$_4$, filtered, concentrated in vacuo and dried in a vacuum oven at about 40° C. to give 1-(4-(2-chlorofuro[3,2-d]pyrimidin-4-yl)piperazin-1-yl)ethanone (0.214 g, 64%): LC/MS (Table 2, Method a) R$_t$=1.04 min; MS m/z 281.4 (M+H)$^+$.

General Procedure E.2: Formation of an Amide from an Amine and a Carboxylic Acid To a flask is added in no particular order, a carboxylic acid or carboxylate salt (1 to 5 equiv, preferably 1.1 to 1.5 equiv) an amine (1 to 5 equiv, preferably 1 to 1.5 equiv), an organic solvent (such as DCM, DCE, THF, or 1,4-dioxane, preferably DCM), a peptide coupling reagent (such as BOP-Cl, IBCF, HATU, DCI or EDC.HCl, preferably HATU; 1 to 10 equiv, preferably 1 to 2 equiv), a base (such as TEA, DIEA, pyridine or DIEA, preferably DIEA; 1 to 20 equiv, preferably 1 to 5 equiv) and optionally HOBt (0 to 5 equiv, preferably 0 to 1 equiv). The mixture is then stirred at about 10 to 60° C. (preferably about 25 to 50° C.) for about 15 min to 48 h (preferably about 15 min to 24 h). Optionally, additional amounts of the reagents above can be added to drive the reaction to completion. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure E.2

Example #E.2.1

N-Cyclopropyl-6-(4-(cyclopropylamino)furo[3,2-d]pyrimidin-2-ylamino)-1H-indazole-3-carboxamide

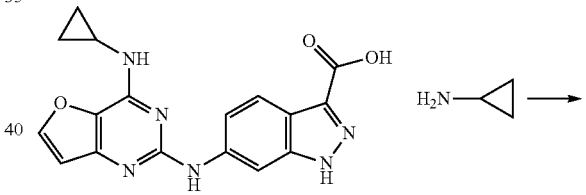

TABLE E.1.1

Examples prepared from an amine and acetyl chloride using General Procedure E

| Amine | Product | Example # | R$_t$ min (Table 2, Method) | m/z ESI+ (M + H)$^+$ | Syk IC$_{50}$ |
|---|---|---|---|---|---|
| 4-(4-(4-(Aminomethyl)piperidin-1-yl)furo[3,2-d]pyrimidin-2-ylamino)benzenesulfonamide (Example #C.1) | | E.1.1.1 | 0.66 (a) | 445 | C |

199

-continued

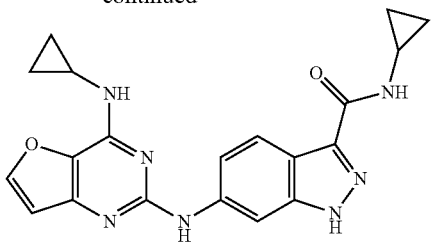

6-(4-(Cyclopropylamino)furo[3,2-d]pyrimidin-2-ylamino)-1H-indazole-3-carboxylic acid (0.13 g, 0.37 mmol, [prepared using I from methyl 6-nitro-1-(2-(trimethylsilyl)ethoxy)methyl)-1H-indazole-3-carboxylate [WO 2010/027500 page 171 intermediate 83 step A], B with Preparation #A.1, J and AI), cyclopropylamine (0.013 mL, 0.18 mmol), and HATU (0.078 g, 0.20 mmol) were combined in DMF (1.9 mL). DIEA (0.081 mL, 0.46 mmol) was added and the mixture was stirred at rt for about 18 h. Additional cyclopropylamine (0.013 mL, 0.19 mmol) was added and the mixture was stirred for about 6 h. HATU (0.04 g, 0.10 mmol) and DIEA (0.1 mL) were added and the mixture was stirred for about 24 h. A solution of 1 M aqueous $Na_2CO_3$ (5 mL) was added. The aqueous layer was separated and extracted with DCM (3×10 mL). The combined organic layers were washed with brine (5 mL), dried over $Na_2SO_4$, filtered, and concentrated under reduced pressure. The residue was dissolved in a mixture of MeOH and DCM and adsorbed onto silica gel (~3 mL). The residue was purified by column chromatography (25 g silica gel) eluting with 2-8% MeOH in DCM to give N-cyclopropyl-6-(4-(cyclopropylamino)furo[3,2-d]pyrimidin-2-ylamino)-1H-indazole-3-carboxamide (0.052 g, 72%) as a white solid on drying under vacuum at about 40° C.: LCMS (Table 2, Method c) $R_t$=1.80 min.; MS m/z: 390 $(M+H)^+$. Syk $IC_{50}$=A

General Procedure F: Reduction of an Azide to an Amine

Method 1:

A phosphine (such as triphenylphospine, tributylphosphine or tert-butylphosphine, preferably triphenylphosphine; 1.0 to 1.05 equiv, preferably 1.0 equiv) and water (3 to 13 equiv, preferably 8 equiv) are added to a solution of an azide (1 equiv) in an organic solvent (such as THF) at about 25° C. The mixture is heated at about 60 to 110° C. (preferably about 100° C.) for about 45 min to 16 h (preferably about 8 to 15 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

200

Method 2:

To an azide (preferably 1 equiv) in an organic solvent such as EtOH, MeOH, EtOAc or THF (preferably MeOH) is added a catalyst such as 20 wt % $Pd(OH)_2$ on carbon or 10% wt Pd/C (preferably 10% wt Pd/C, 0.05 to 0.5 eq., preferably 0.1 to 0.3 equiv). The mixture is then stirred at rt under hydrogen (1 atmosphere pressure) of for about 1 to 48 h, preferably about 4 to 16 h. The catalyst is removed by filtration through a pad of Celite® and the filtrate is concentrated under reduced pressure to yield the targeted compound.

Illustration of General Procedure F

Example #F.1

6-(4-(4-(Aminomethyl)-4-methoxypiperidin-1-yl)furo[3,2-d]pyrimidin-2-ylamino)-2,2-dimethyl-2H-benzo[b][1,4]oxazin-3(4H)-one

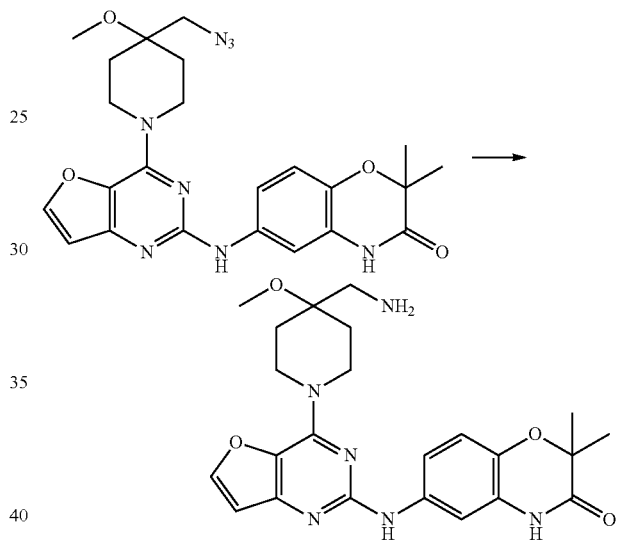

A mixture of 6-(4-(4-(azidomethyl)-4-methoxypiperidin-1-yl)furo[3,2-d]pyrimidin-2-ylamino)-2,2-dimethyl-2H-benzo[b][1,4]oxazin-3(4H)-one (0.030 g, 0.063 mmol, prepared using C from tert-butyl 4-(azidomethyl)-4-methoxypiperidine-1-carboxylate [WO 2010/080864, Example 257], A with 2,4-dichlorofuro[3,2-d]pyrimidine [ArkPharm] and B with 6-amino-2,2-dimethyl-2H-benzo[b][1,4]oxazin-3(4H)-one [ArkPharm]) and triphenylphosphine (0.025 g, 0.094 mmol) in THF (16 mL) and water (2 mL) was stirred at about 100° C. overnight. The organic phase was removed and diluted with water. The aqueous phase was neutralized with aqueous 2 N NaOH and extracted with EtOAc. The combined organic phase was washed with brine and dried over $Na_2SO_4$, filtered, concentrated under vacuum and purified by HPLC (Table 2, Method v) to afford 6-(4-(4-(aminomethyl)-4-methoxypiperidin-1-yl)furo[3,2-d]pyrimidin-2-ylamino)-2,2-dimethyl-2H-benzo[b][1,4]oxazin-3 (4H)-one (0.022 g, 76%). LC/MS (Table 2, method h) $R_t$=1.77 min.; MS m/z: 453 $(M+H)^+$. Syk $IC_{50}$=A

General Procedure G: Removal of a Benzyl Group from an N-Benzyl Amine

To a flask charged with an N-benzyl amine (preferably 1 equiv) are added a Pd catalyst (for example $Pd(OH)_2$ on C or Pd/C; preferably Pd(OH)$_2$ on C) (0.01 to 0.3 equiv, preferably 0.02 to 0.25 equiv) and an organic solvent (such as MeOH or EtOH, preferably MeOH). The mixture is shaken or stirred at about 0 to 60° C. (preferably rt) for about 1 to 96 h (preferably about 6 h) under a H$_2$ atmosphere at about 10 to 60 psi hydrogen (preferably about 10 to 20 psi). The hydrogen source is removed, a nitrogen atmosphere is introduced, and the mixture is filtered through a pad of Celite®. The filtrate is concentrated under reduced pressure to give the desired product. Alternatively, to a vessel charged with an N-benzyl protected amine (preferably 1 equiv) are added a palladium catalyst (for example Pd(OH)$_2$ on C or Pd/C; preferably Pd(OH)$_2$ on C) (0.01 to 0.3 equiv, preferably 0.02 to 0.25 equiv) and an organic solvent (such as MeOH or EtOH, preferably MeOH), formic acid (1 to 10 equiv, preferably 5 equiv), and ammonium formate (10 to 30 equiv, preferably 20 equiv). The mixture is heated to about 50 to 80° C. (preferably about 70° C.) for about 2 to 24 h (preferably about 12 h). The mixture is cooled to rt and filtered. The solvent is removed under reduced pressure and an organic solvent (such as DCM or EtOAc) and optionally an acid (such as HCl) are added. The solution is concentrated under reduced pressure to give the desired product.

Illustration of General Procedure G

Preparation #G.1: tert-Butyl (5,6,7,8-tetrahydroimidazo[1,5-a]pyrazin-3-yl)methylcarbamate

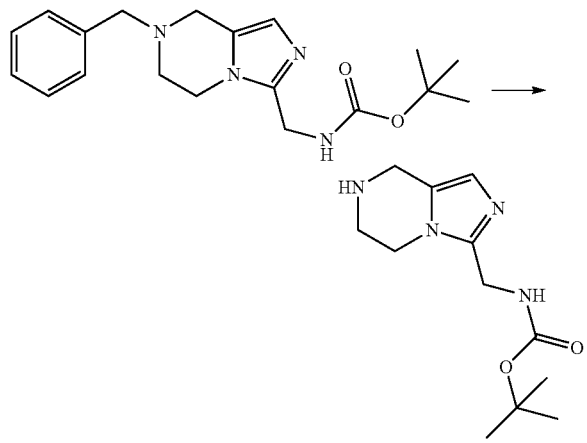

To a flask was added tert-butyl (7-benzyl-5,6,7,8-tetrahydroimidazo[1,5-a]pyrazin-3-yl)methylcarbamate (0.500 g, 1.46 mmol, prepared using O from Preparation #S.1 with Boc$_2$O), MeOH (20 mL) and Pd(OH)$_2$ on carbon (20 wt %, 0.255 g, 0.363 mmol). The mixture was evacuated and purged with N$_2$ three times and a H$_2$ balloon was fitted to the flask. The flask was purged with H$_2$ three times and stirred for about 6 h at rt. The mixture was filtered and the solvent was removed under reduced pressure to give tert-butyl (5,6,7,8-tetrahydroimidazo[1,5-a]pyrazin-3-yl)methylcarbamate (0.40 g, 109%): LC/MS (Table 2, Method e) R$_t$=1.58 min; MS m/z: 253 (M+H)$^+$.

General Procedure H: Reductive Amination of an Aldehyde or Ketone with a Primary or Secondary Amine An aldehyde or ketone (preferably 1.0 equiv) and an amine or amine salt (1.0 to 2.2 equiv) are added in an organic solvent or mixture of organic solvents (such as DCM, DCE or MeOH, or a mixture of DCE and MeOH, preferably DCE) at about rt to 80° C. (preferably about rt). If an amine salt is used, then an amine base (such as TEA or DIEA, 1.0 to 2.2 equiv) is optionally added. AcOH (0.1 equiv to 5.0 equiv) is optionally added. The mixture is stirred at rt for about 0 to 90 min (preferably 5 to 30 min) A reducing agent (such as NaBH(OAc)$_3$, Na(CN)BH$_3$, NaBH$_4$, MP-Cyanoborohydride from Biotage™, 0.5 to 5.0 equiv, preferably 3.0 equiv), is added as a solid or as a solution in an organic solvent (such as DCM, DCE or MeOH, or a mixture of DCE and MeOH). The mixture is stirred at rt for about 30 min to 72 h (preferably 1 to 24 h). The crude mixture may be optionally partitioned between water and an organic solvent (such as EtOAc, Et$_2$O or DCM). The organic layer is isolated and may be optionally washed with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl or Na$_2$SO$_3$). The organic solution may then be optionally dried with a drying agent (such as MgSO$_4$ or Na$_2$SO$_4$), filtered and concentrated in vacuo to give the target compound.

Illustration of General Procedure H

Preparation #H.1: N-((1-(2-Chlorofuro[3,2-d]pyrimidin-4-yl)piperidin-4-yl)methyl)-2,2-difluoroethanamine

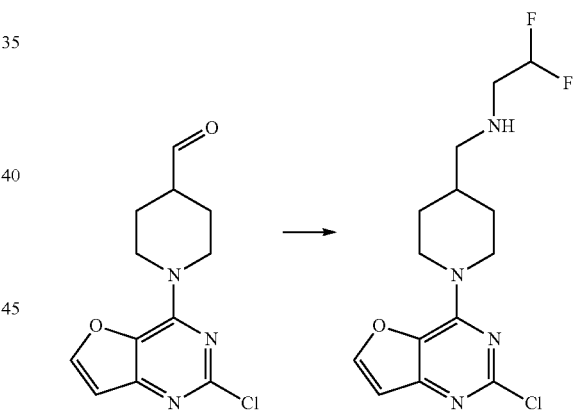

1-(2-Chlorofuro[3,2-d]pyrimidin-4-yl)piperidine-4-carbaldehyde (0.672 g, 2.53 mmol; Preparation #P.1), 2,2-difluoroethanamine (0.226 g, 2.78 mmol, Matrix), and AcOH (0.217 mL, 3.79 mmol) were combined in DCE (25.3 mL) at rt. After about 10 min of stirring, NaBH(OAc)$_3$ (0.804 g, 3.79 mmol) was added in one portion and the mixture was stirred for about 24 h. The mixture was diluted with DCM (50 mL) and saturated aqueous NaHCO$_3$ (50 mL). The layers were separated and the aqueous layer extracted with DCM (3×15 mL). The combined organics were then washed with saturated aqueous NaHCO$_3$ (25 mL), brine (25 mL), dried over Na$_2$SO$_4$, filtered, and concentrated in vacuo. The residue was purified by column chromatography (80 g silica gel, 50-100% EtOAc/heptane) to provide N-((1-(2-chlorofuro[3,2-d]pyrimidin-4-yl)piperidin-4-yl)methyl)-2,2-difluoroethanamine (0.748 g, 89%): LC/MS (Table 2, Method c) Rt=1.52 min.; MS m/z: 331, 333 (M+H)$^+$.

General Procedure I: Reduction of a Nitro Group to an Amine

A flask is charged with a catalyst (such as 10 wt % Pd/C, Pd(OH)$_2$/C, PtO$_2$, RuCl$_2$(PPh$_3$)$_3$, Fe(CO)$_3$(PPh$_3$)$_2$ and Raney Ni etc., preferably 10 wt % Pd/C, 0.005 to 0.05 equiv, preferably 0.02 equiv). The flask is evacuated then flushed with N$_2$ 2 to 5 times (preferably 3 times), then is optionally cooled to about −10 to 30° C. (preferably about 0° C.). To the flask is added an organic solvent or mixture of solvents (such as EtOAc, MeOH, EtOH, MeOH/THF or MeOH/AcOH, preferably EtOAc or MeOH) under a N$_2$ atmosphere. The temperature of the mixture is adjusted to rt and then a nitro-containing compound (1 equiv) is added neat or optionally as a solution in an organic solvent or mixture of solvents (such as EtOAc, MeOH, EtOH, MeOH/THF or MeOH/AcOH, preferably EtOAc or MeOH). The reaction vessel is evacuated and flushed with H$_2$ gas 2 to 5 times (preferably 3 times), and the mixture is stirred under a H$_2$ atmosphere for about 12 to 60 h (preferably about 12 to 24 h). The hydrogen source is then removed, the mixture is bubbled with N$_2$ for about 1 to 20 min (preferably about 5 min), filtered through a pad of Celite®, and the filtrate is concentrated under reduced pressure to give the target compound.

Illustration of General Procedure I.1

Example #I.1

6-Amino-2,2-difluoro-2H-benzo[b][1,4]oxazin-3(4H)-one

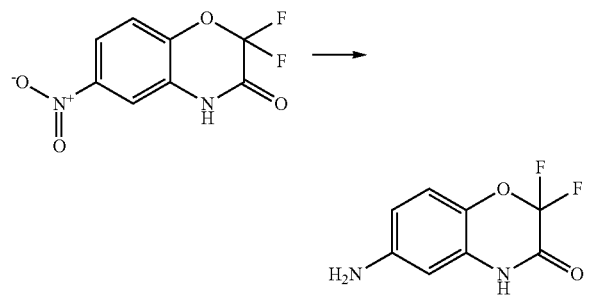

In a flask, 10% Pd/C (0.819 g, 0.769 mmol) was added. The flask was placed under vacuum and purged with N$_2$ three times and then MeOH (25 mL) was added. To the flask was added a solution of 2,2-difluoro-6-nitro-2H-benzo[b][1,4]oxazin-3(4H)-one (5.90 g, 25.6 mmol, WO2008024634A1, Page 161, Intermediate C) in MeOH (20 mL). The mixture was then evacuated, purged with N$_2$ and evacuated again. The mixture was placed under an atmosphere of H$_2$ and stirred at rt for about 16 h. The mixture was placed under vacuum and purged with N$_2$ three times. The mixture was filtered over a Celite Pad®, washed with MeOH (300 mL) and concentrated under reduced pressure to give 6-amino-2,2-difluoro-2H-benzo[b][1,4]oxazin-3(4H)-one (3.4 g, 66%); LC/MS (Table 2, Method c) R$_t$=1.42 min.; MS m/z: 201 (M+H)$^+$.

General Procedure J: Removal of a SEM Group from an N-SEM Heteroaromatic

Method 1:
To a solution of an N-SEM-heteroaromatic (1 equiv) in an organic solvent (such as DMF, 1,4-dioxane, or DCM, preferably DCM) is added an acid (such as TFA or HCl, 5 to 50 equiv, preferably 30 equiv) and the mixture is stirred at about 0 to 100° C. (preferably about 60 to 90° C.) for about 1 to 48 h (preferably about 4 to 1.6 h). Alternatively, additional acid (5 to 20 equiv, preferably 10 equiv) may be added. The mixture is concentrated under reduced pressure then the material is dissolved in an organic solvent (such as MeOH, EtOH, THF or 1,4-dioxane, preferably MeOH or 1,4-dioxane), a base (such as ethylenediamine or NH$_4$OH, preferably NH$_4$OH) is added and the mixture is heated to about 30 to 100° C. (preferably about 50 to 80° C.) for about 0.5 to 10 h (preferably about 1 to 5 h).

Method 2:
To a solution of an N-SEM heteroaromatic (1 equiv) in an organic solvent (such as DMF, 1,4-dioxane, or DCM, preferably DMF) is added TBAF (1 to 10 equiv, preferably 4 equiv), optionally ethylene diamine (5 to 40 equiv, preferably 30 equiv) may be added, and the mixture is stirred at about 30 to 110° C. (preferably about 90° C.) for about 1 to 20 h (preferably about 2 h). Optionally, additional TBAF (1 to 10 equiv, preferably 2 equiv) may be added and the mixture is stirred at about 30 to 110° C. (preferably about 90° C.) for about 1 to 20 h (preferably about 2 h). For either method, the targeted compound may optionally be isolated by cooling the mixture and filtering the precipitate. Alternatively, the mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure J

Example #J.1

6-(4-(Cyclopropylamino)furo[3,2-d]pyrimidin-2-ylamino)-N,N-dimethyl-1H-indazole-3-carboxamide

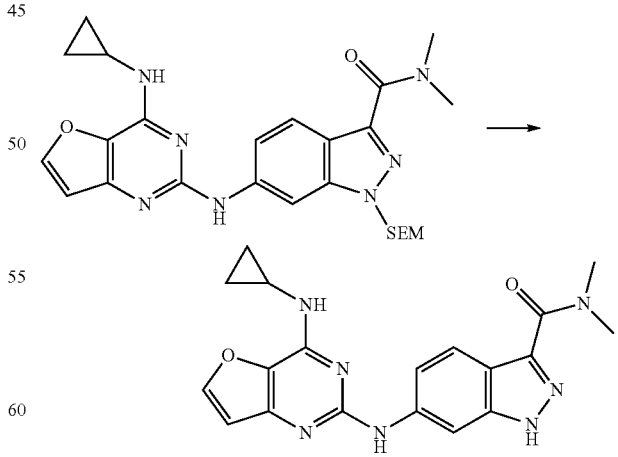

In a vial, 6-(4-(cyclopropylamino)furo[3,2-d]pyrimidin-2-ylamino)-N,N-dimethyl-1-((2-(trimethylsilyl)ethoxy)methyl)-1H-indazole-3-carboxamide (0.94 g, 0.19 mmol, prepared using E.2 from Preparation #AI.1 with dimethylamine) and an aqueous solution of HCl (6 N, 0.401 mL, 2.41 mmol)

in DCE (4 mL) were added. The mixture was heated at about 70° C. for about 15 h. The mixture was concentrated under reduced pressure and 1,4-dioxane (4 mL) and NH$_4$OH (0.956 mL, 7.36 mmol) were added. The mixture was heated at about 75° C. for about 3 h, concentrated under reduced pressure and the residue was suspended in MeOH (1 mL) and filtered. The filtrate was purified by column chromatography eluting with 35 to 85% of 10% MeOH in DCM/DCM (12 g silica gel) to give 6-(4-(cyclopropylamino)furo[3,2-d]pyrimidin-2-ylamino)-N,N-dimethyl-1H-indazole-3-carboxamide (0.029 g, 42%): LC/MS (Table 2 Method c) R$_t$=1.52 min.; MS m/z: 378 (M+H)$^+$. Syk IC$_{50}$=A

TABLE J.1

Examples of the removal of a SEM protecting grou from an N-SEM protected heteroaromatic ring using General Procedure J

| Amine | Product | Example # | R$_t$ min (Table 2, Method) | m/z ESI+ (M + H)$^+$ | Syk IC$_{50}$ |
|---|---|---|---|---|---|
| N-(4-(4-(1-((2-(Trimethylsilyl)ethoxy)methyl)-1H-indazol-6-ylamino)furo[3,2-d]pyrimidin-2-ylamino)phenyl)butyramide (prepared using A from 2,4-dichlorofuro[3,2-d]pyrimidine [ArkPharm] with 1-((2-(trimethylsilyl)ethoxy)methyl)-1H-indazol-6-amine (WO 2010/027500 Intermediate 21, Step C) and B with Preparation #3) | | J.1.1 | 1.84 (h) | 428 | B |
| 4-(3-((Methylamino)methyl)pyrrolidin-1-yl)-N-(1-((2-(trimethylsilyl)ethoxy)methyl)-1H-indazol-6-yl)furo[3,2-d]pyrimidin-2-amine (prepared using L from Preparation #O.1 with iodomethane, C, A with 2,4-dichlorofuro[3,2-d]pyrimidine [ArkPharm], B with 1-((2-(trimethylsilyl)ethoxy)methyl)-1H-indazol-6-amine (WO 2010/027500 Intermediate 21, Step C) and K) | | J.1.2 | 1.60 (h) | 364 | B |
| N$^4$-cyclopropyl-N$^2$-(1-((2-(trimethylsilyl)ethoxy)methyl)-1H-indol-6-yl)furo[3,2-d]pyrimidine-2,4-diamine (prepared using N from 6-nitro-1H-indole [Matrix], I and B with Preparation #A.1) | | J.1.3 | 1.94 (h) | 306 | B |
| N$^4$-Cyclopropyl-N$^4$-methyl-N$^2$-(3-methyl-1-((2-(trimethylsilyl)ethoxy)methyl)-1H-indazol-6-yl)furo[3,2-d]pyrimidine-2,4-diamine (prepared using A from 2,4-dichlorofuro[3,2-d]pyrimidine [ArkPharm] with N-methylcyclopropanamine [J&W PharmLab] and B with Example #5, Step C) | | J.1.4 | 1.99 (h) | 335 | B |

TABLE J.1-continued

Examples of the removal of a SEM protecting grou from an N-SEM protected heteroaromatic ring using General Procedure J

| Amine | Product | Example # | R, min (Table 2, Method) | m/z ESI+ (M + H)+ | Syk IC50 |
|---|---|---|---|---|---|
| N4-(3,3-Difluorocyclobutyl)-N2-(3-methyl-1-((2-(trimethylsilyl)ethoxy)methyl)-1H-indazol-6-yl)furo[3,2-d]pyrimidine-2,4-diamine (prepared using A from 2,4-dichlorofuro[3,2-d]pyrimidine [ArkPharm] with 3,3-difluorocyclobutanamine [Synchem], B with Example #5, Step C) | | J.1.5 | 1.92 (h) | 371 | B |
| N2-(3-Methyl-1-((2-(trimethylsilyl)ethoxy)methyl)-1H-indazol-6-yl)-N4-(2-(trifluoromethyl)cyclopropyl)furo[3,2-d]pyrimidine-2,4-diamine (prepared using A from 2,4-dichlorofuro[3,2-d]pyrimidine [ArkPharm] with 2-(trifluoromethyl)cyclopropanamine [Enamine] and B with Example #5, Step C) | | J.1.6 | 1.96 (h) | 389 | B |
| N4-Cyclopropyl-N2-(3-(pyridin-4-yl)-1-((2-(trimethylsilyl)ethoxy)methyl)-1H-indazol-6-yl)furo[3,2-d]pyrimidine-2,4-diamine (prepared using I from Preparation #Z.1 and B with Preparation #A.1) | | J.1.7 | 1.8 (c) | 384 | A |
| 6-(4-(Cyclopropylamino)furo[3,2-d]pyrimidin-2-ylamino)-1-((2-(trimethylsilyl)ethoxy)methyl)-1H-indazole-3-carbonitrile (prepared using I from Preparation #AA.1 and B with Preparation #A.1) | | J.1.8 | 2.03 (c) | 332 | A |

TABLE J.1-continued

Examples of the removal of a SEM protecting grou from an N-SEM protected heteraromatic ring using General Procedure J

| Amine | Product | Example # | $R_t$ min (Table 2, Method) | m/z ESI+ (M + H)$^+$ | Syk IC$_{50}$ |
|---|---|---|---|---|---|
| N-(3-Methyl-1-((2-((trimethylsilyl)ethoxy)methyl)-1H-indazol-6-yl)-4-(4-((tetrahydro-2H-thiopyran1,1-dioxide-4-ylamino)methyl)piperidin-1-yl)furo[3,2-d]pyrimidin-2-amine (prepared using H from Preparation #P.1 with 4-aminotetrahydro-2H-thiopyran 1,1-dioxide [Alfa Aesar] and B with Example #5, Step C) | 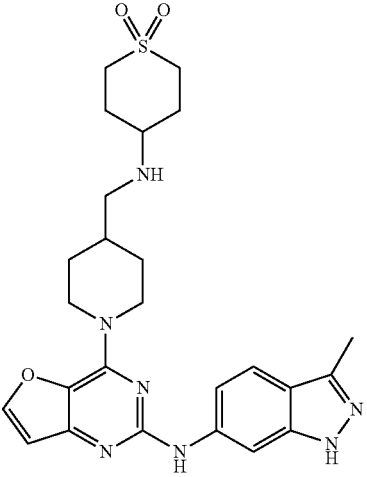 [SMILES: Cc1n[nH]c2cc(Nc3nc(N4CCC(CNC5CCS(=O)(=O)CC5)CC4)c4occc4n3)ccc12] | J.1.9 | 1.8 (h) | 510 | B |
| N-(3-Methyl-1-((2-(trimethylsilyl)ethoxy)methyl)-1H-indazol-6-yl)-4-(4-((tetrahydro-2H-pyran-4-ylamino)methyl)piperidin-1-yl)furo[3,2-d]pyrimidin-2-amine (prepared using H from Preparation #P.1 with tetrahydro-2H-pyran-4-amine and B with Example #5, Step C) | 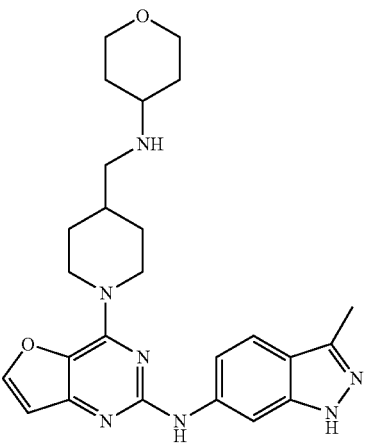 [SMILES: Cc1n[nH]c2cc(Nc3nc(N4CCC(CNC5CCOCC5)CC4)c4occc4n3)ccc12] | J.1.10 | 1.79 (h) | 462 | B |
| N$^4$-Cyclopropyl-N$^4$-methyl-N$^2$-(3-methyl-1-((2-(trimethylsilyl)ethoxy)methyl)-1H-indazol-6-yl)furo[3,2-d]pyrimidine-2,4-diamine (prepared using A from 2,4-dichlorofuro[3,2-d]pyrimidine [ArkPharm] with N-methylcyclopropanamine [J&W PharmLab] and B with Example #5, Step C) | 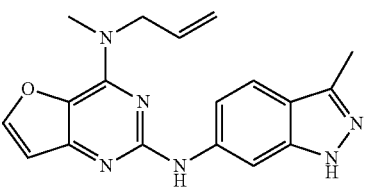 [SMILES: C=CCN(C)c1nc(Nc2ccc3c(C)n[nH]c3c2)nc2ccoc12] | J.1.11 | 1.99 (h) | 335 | B |

TABLE J.1-continued

Examples of the removal of a SEM protecting grou from an N-SEM protected heteroaromatic ring using General Procedure J

| Amine | Product | Example # | $R_t$ min (Table 2, Method) | m/z ESI+ (M + H)$^+$ | Syk IC$_{50}$ |
|---|---|---|---|---|---|
| N$^2$-(3-Methyl-1-((2-(trimethylsilyl)ethoxy)methyl)-1H-indazol-6-yl)-N$^4$-(pyridin-3-ylmethyl)furo[3,2-d]pyrimidine-2,4-diamine (prepared using A from 2,4-dichlorofuro[3,2-d]pyrimidine [ArkPharm] with pyridin-3-ylmethanamine [Alfa Aesar] and B with Example #5, Step C) | 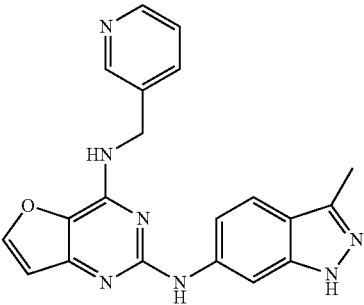 [SMILES: Cc1n[nH]c2cc(Nc3nc(NCc4cccnc4)c4occc4n3)ccc12] | J.1.12 | 1.71 (h) | 372 | B |
| 4-(4-(Aminomethyl)-4-fluoropiperidin-1-yl)-N-(1-((2-(trimethylsilyl)ethoxy)methyl)-1H-indazol-6-yl)furo[3,2-d]pyrimidin-2-amine (Preparation #T.1) | 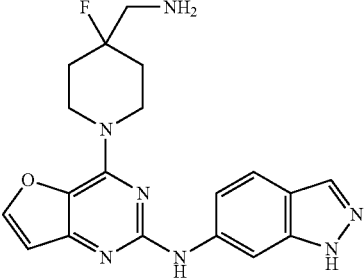 [SMILES: NCC1(F)CCN(c2nc(Nc3ccc4cn[nH]c4c3)nc3ccoc23)CC1] | J.1.13 | 1.55 (h) | 382 | C |
| (6-(4-(Cyclopropylamino)furo[3,2-d]pyrimidin-2-ylamino)-1-((2-(trimethylsilyl)ethoxy)methyl)-1H-indazol-3-yl)(morpholino)methanone (prepared using E.2 from Preparation #AI.1 with morpholine) | 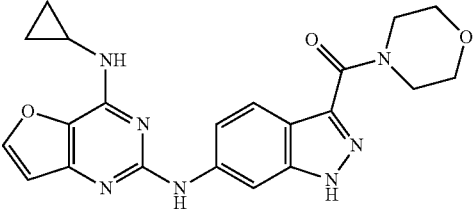 [SMILES: O=C(c1n[nH]c2cc(Nc3nc(NC4CC4)c4occc4n3)ccc12)N1CCOCC1] | J.1.14 | 1.52 (c) | 420 | A |
| 6-(4-(Cyclopropylamino)furo[3,2-d]pyrimidin-2-ylamino)-N-(2-hydroxyethyl)-1-((2-(trimethylsilyl)ethoxy)methyl)-1H-indazole-3-carboxamide (prepared using E.2 from Preparation #AI.1 with 2-aminoethanol) | 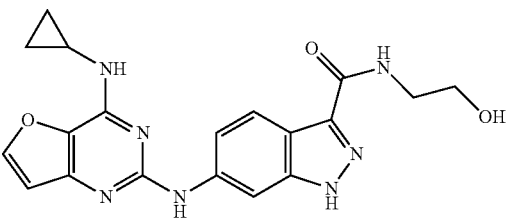 [SMILES: O=C(NCCO)c1n[nH]c2cc(Nc3nc(NC4CC4)c4occc4n3)ccc12] | J.1.15 | 1.35 (c) | 394 | B |

General Procedure K: Removal of a Cbz Group from an N-Cbz Amine

A mixture of an N-Cbz amine (preferably 1 equiv) and 10% Pd on carbon (0.05 to 0.30 equiv, preferably 0.10 equiv) in a protic solvent (such as MeOH, EtOH, AcOH, preferably EtOH) is shaken or stirred under $H_2$ at about 15 to 100 psi (preferably about 60 psi) for about 4 to 48 h (preferably about 4 to 16 h) at rt. The mixture is filtered through Celite® and concentrated in vacuo to dryness under reduced pressure to give the target compound.

Illustration of General Procedure K.1

Preparation #K.1: tert-Butyl (4-(cyclopropylmethyl)piperidin-4-yl)methylcarbamate

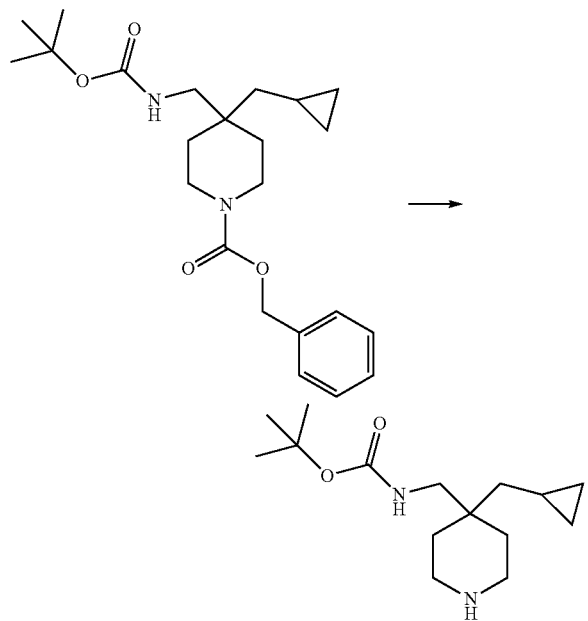

In one portion, 10% Pd/C (0.159 g, 1.491 mmol) was added to a mixture of benzyl 4-((tert-butoxycarbonylamino)methyl)-4-(cyclopropylmethyl)piperidine-1-carboxylate (0.60 g, 1.5 mmol, prepared using AF from benzyl 4-cyanopiperidine-1-carboxylate [Oakwood] with (bromomethyl)cyclopropane, AE, O with $Boc_2O$) in MeOH (50 mL) at rt. The mixture was stirred under $H_2$ at rt overnight. The mixture was filtered and concentrated in vacuo to provide tert-butyl (4-(cyclopropylmethyl)piperidin-4-yl)methylcarbamate (0.40 g, 95%): LC/MS (Table 2, Method i) $R_t$=1.59 min; MS m/z: 269 (M+H)$^+$.

General Procedure L: Alkylation of a Carbamate

To a solution of a carbamate (preferably 1 equiv) in an organic solvent (for example $Et_2O$, 1,4-dioxane, DMF or THF, preferably THF) at about −10° C. to rt (preferably about 0° C.) is added a base (for example LDA, LiHMDS or NaH, preferably NaH, 1 to 5 equiv, preferably about 2 equiv). The mixture is stirred at about 0° C. for about 5 min to 1 h (preferably about 30 min) An alkylating agent (for example an alkyl halide, mesylate or tosylate, preferably an alkyl halide, about 1 to 5 equiv, preferably about 2 equiv) is then added to the mixture is stirred at about −10° C. to rt (preferably about 0° C.) for about 5 min to 24 h (preferably about 30 min). The resulting mixture can be concentrated in vacuo to give the target compound. Alternatively an organic solvent (such as $Et_2O$, EtOAc or DCM) and water or saturated aqueous $NH_4Cl$ (preferably saturated aqueous $NH_4Cl$) are added and the layers are separated. The aqueous layer is extracted with additional organic solvent and the combined organic layers may be optionally washed with brine, dried over anhydrous $Na_2SO_4$ or $MgSO_4$, and then decanted or filtered prior to concentrating under reduced pressure prior to give the target compound.

Illustration of General Procedure L

Preparation #L.1: tert-Butyl (7-(2-chlorofuro[3,2-d]pyrimidin-4-yl)-5,6,7,8-tetrahydroimidazo[1,5-a]pyrazin-3-yl)methyl(methyl)carbamate

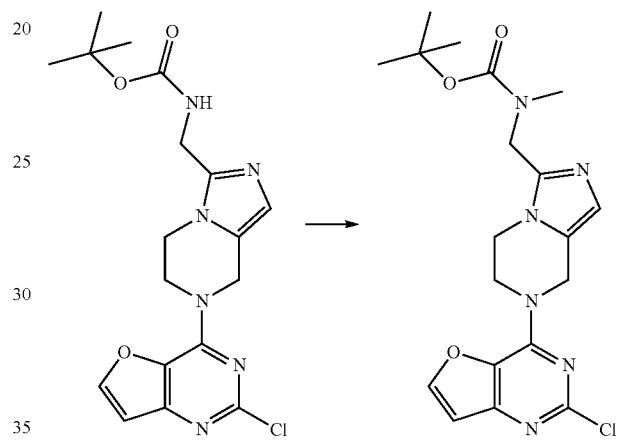

A solution of tert-butyl (7-(2-chlorofuro[3,2-d]pyrimidin-4-yl)-5,6,7,8-tetrahydroimidazo[1,5-a]pyrazin-3-yl)methylcarbamate (0.300 g, 0.741 mmol, prepared using A from 2,4-dichlorofuro[3,2-d]pyrimidine [Arkpharm] with Preparation #G.1) in THF (10 mL) was cooled to about 0° C. To the flask was added NaH (60 wt % dispersion in mineral oil, 0.036 g, 1.5 mmol) and the mixture was stirred for about 0.5 h at about 0° C. To the mixture was added MeI (0.21 g, 1.48 mmol) and the mixture was stirred for about 30 min. Saturated $NH_4Cl$ (15 mL) was added then the mixture was extracted with EtOAc (3×20 mL). The organic extracts were combined then dried over anhydrous $Na_2SO_4$ then filtered. The filtrate was concentrated under reduced pressure to give tert-butyl (7-(2-chlorofuro[3,2-d]pyrimidin-4-yl)-5,6,7,8-tetrahydroimidazo[1,5-a]pyrazin-3-yl)methyl(methyl)carbamate (0.255 g, 82%): LC/MS (Table 2, Method h) $R_t$=1.93 min; MS m/z: 419 (M+H)$^+$.

General Procedure M: Chiral Purification

Chiral purification is performed using a system such as the following: Thar-SFC Prep 80 using a ChiralPak column (preferably particle size 5 μM) with a fraction collector. The detection method is a Gilson UV/VIS-151 wavelength detector. The absolute stereochemistry of the purified compounds was assigned arbitrarily and is drawn as such. Compounds of the invention where the absolute stereochemistry has been determined by the use of a commercially available enantiomerically pure starting material, or a stereochemically defined intermediate, or X-ray diffraction are denoted by an asterisk after the example number.

Illustration of General Procedure M

Preparations #M.1.1 and M.1.2: tert-butyl 6-(4-((1R, 3S)-3-(tert-butoxycarbonylamino)cyclopentylamino) furo[3,2-d]pyrimidin-2-ylamino)-3-methyl-1H-indazole-1-carboxylate and tert-butyl 6-(4-(1S,3R)-3-(tert-butoxycarbonylamino)cyclopentylamino)furo[3,2-d]pyrimidin-2-ylamino)-3-methyl-1H-indazole-1-carboxylate

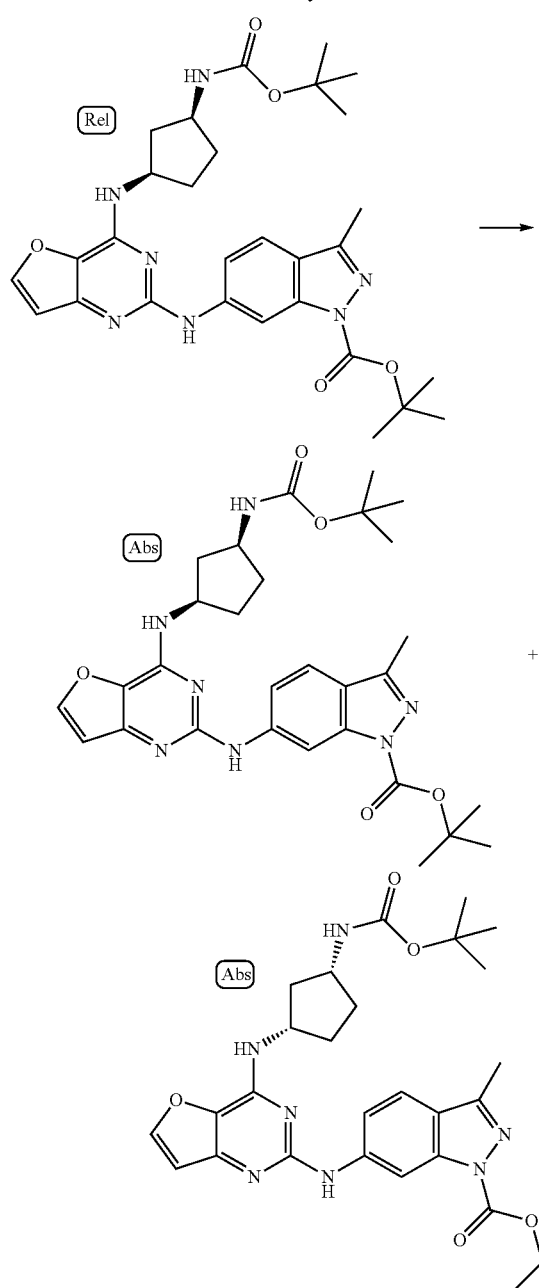

Racemic tert-butyl 6-(4-(cis)-3-(tert-butoxycarbonylamino)cyclopentylamino)furo[3,2-d]pyrimidin-2-ylamino)-3-methyl-1H-indazole-1-carboxylate was separated via chiral SFC (Table 3, Method 1) to afford tert-butyl 6-(4-((1R,3S)-3-(tert-butoxycarbonylamino)cyclopentylamino)furo[3,2-d]pyrimidin-2-ylamino)-3-methyl-1H-indazole-1-carboxylate ($R_f$=2.08 min) (0.23 g, 27%) and tert-butyl 6-(4-((1S,3R)-3-(tert-butoxycarbonylamino)cyclopentylamino)furo[3,2-d]pyrimidin-2-ylamino)-3-methyl-1H-indazole-1-carboxylate ($R_f$=2.69 min) (0.34 g, 35%): LC/MS (Table 2, Method h) $R_t$=2.24 min; MS m/z: 564 (M+H)$^+$.

General Procedure N: Formation of an N-SEM Heteroaromatic

To a mixture of a heteroaromatic ring (1 equiv) at about −30 to 25° C. (preferably about 0° C.) in an organic solvent (such as THF, 1,4-dioxane or DMF, preferably DMF) is added a base (such as NaH, $Cs_2CO_3$ or KOH, preferably NaH; 1 to 3 equiv, preferably 1.2 equiv). The mixture is stirred for about 1 to 60 min (preferably about 1 to 30 min) at about −30 to 25° C. (preferably about 0° C.). SEMCl (1 to 3 equiv, preferably 1.5 equiv) is then added to the mixture. The mixture is stirred at about 0 to 30° C. (preferably about rt) for about 1 min to 72 h (preferably about 1 to 72 h). The mixture is then optionally poured slowly into or diluted with an aqueous solution (such as water, ice water or an aqueous solution of $NH_4Cl$, $NaHCO_3$, or NaCl) and stirred to provide a suspension. The solids are optionally collected by filtration and dried to provide the target compound. Alternatively, the mixture is optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure N

Preparation #N.1: 3-Methyl-6-nitro-1-((2-(trimethylsilyl)ethoxy)methyl)-1H-indazole

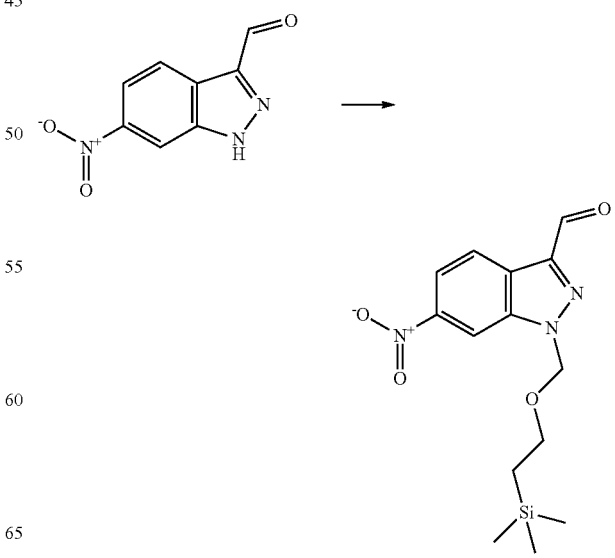

To a flask was added NaH (60% in mineral oil, 0.473 g, 11.8 mmol) and THF (59.1 mL). The mixture was cooled to about 0° C. 6-Nitro-1H-indazole-3-carbaldehyde (2.26 g, 11.8 mmol, ChemPacific) was added in several smaller portions and the mixture was stirred at about 0° C. for about 20 min. SEMCl (2.30 mL, 13.0 mmol) was added dropwise and the mixture was stirred at about 0° C. for about 10 min and then stirred at rt for about 72 h. To the mixture was added saturated aqueous NH$_4$Cl (25 mL) and water (10 mL). The aqueous layer was separated and extracted with DCM (2×50 mL). The combined organic layers were washed with brine (20 mL), dried over MgSO$_4$, filtered, and concentrated under reduced pressure. The residue was purified by column chromatography (80 g silica gel) eluting with 10 to 25% EtOAc/heptane to give 3-methyl-6-nitro-1-((2-(trimethylsilyl)ethoxy)methyl)-1H-indazole (1.915 g, 50%): $^1$H NMR (400 MHz, DMSO) δ 10.24 (s, 1H), 8.94 (d, J=1.5 Hz, 1H), 8.36 (dd, J=6.5, 2.3 Hz, 1H), 8.31-8.13 (m, 1H), 6.08 (s, 2H), 3.58 (s, 2H), 0.83 (s, 2H), −0.12 (s, 9H).

General Procedure O: Formation of a Carbamate from an Amine and Chloroformate or Dicarbonate To a flask charged with an amine or amine salt (preferably 1 equiv) is added an organic solvent (such as THF or 1,4-dioxane, preferably THF). The mixture is optionally cooled to about 0° C. followed by the addition of a chloroformate or dicarbonate (1 to 3 equiv, preferably 1.3 equiv) and a base (such as K$_2$CO$_3$, Na$_2$CO$_3$, NaHCO$_3$, TEA or DIEA, preferably TEA or K$_2$CO$_3$) (1 to 5 equiv, preferably 1.5 equiv). The mixture is stirred at about 0 to 50° C. (preferably rt) for about 1 to 24 h (preferably about 4 h). The mixture is poured into water and the desired product is extracted with an organic solvent (such as DCM or EtOAc). The combined extracts are optionally washed with water and/or brine, dried over anhydrous Na$_2$SO$_4$ or MgSO$_4$, filtered or decanted, and concentrated under reduced pressure. Alternatively, the resulting aqueous solution is acidified by adding an acid such as aqueous NH$_4$Cl or HCl and is then extracted with an organic solvent (such as EtOAc or DCM).

Illustration of General Procedure O

Preparation #O.1: tert-Butyl 1-(2-chlorofuro[3,2-d]pyrimidin-4-yl)azepan-4-ylcarbamate A solution of 1-(2-chlorofuro[3,2-d]pyrimidin-4-yl)azepan-4-amine (1.5 g, 5.6 mmol, prepared using A from 2,4-dichlorofuro[3,2-d]pyrimidine [Arkpharm] with azepan-4-one [Arkpharm], H with NH$_4$OAc) in THF (30 mL) was added TEA (0.784 mL, 5.62 mmol). Then Boc$_2$O (0.818 g, 3.75 mmol) was added to the solution in one portion. Then the mixture was stirred for about 4 h. The mixture was poured into water (30 mL) and extracted with EtOAc (3×30 mL). The combined the organic layers were dried over Na$_2$SO$_4$ and concentrated under reduced pressure to give tert-butyl 1-(2-chlorofuro[3,2-d]pyrimidin-4-yl)azepan-4-ylcarbamate that was used immediately without purification or quantification: LC/MS (Table 2, Method h) R$_t$=2.01 min; MS m/z 367 (M+H)$^+$.

General Procedure P: Oxidation of an Alcohol to an Aldehyde or Ketone

To a solution of an alcohol (preferably 1 equiv) in an organic solvent (such as DCM or DCE, preferably DCM) is added an oxidizing reagent (such as Dess-Martin periodinane, pyridinium dichromate or pyridinium chlorochromate, preferably Dess-Martin periodinane; 1.0 to 1.5 equiv, preferably 1.2 equiv). The mixture is stirred at rt for about 0.5 to 24 h (preferably about 1 to 16 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure P

Preparation #P.1: 1-(2-Chlorofuro[3,2-d]pyrimidin-4-yl)piperidine-4-carbaldehyde

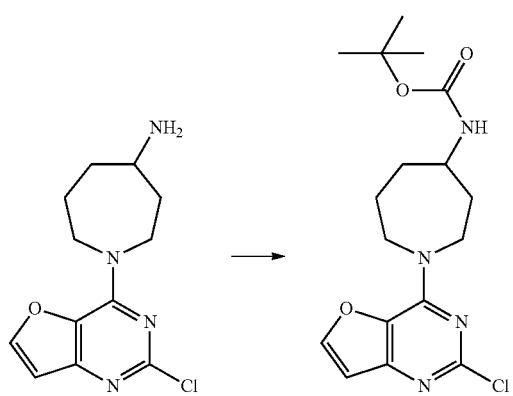 [SMILES: NC1CCCN(c2nc(Cl)nc3ccoc23)CC1 ; CC(C)(C)OC(=O)NC1CCCN(c2nc(Cl)nc3ccoc23)CC1]

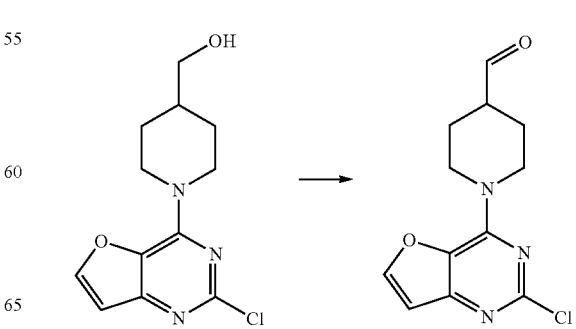

A flask was charged with (1-(2-chlorofuro[3,2-d]pyrimidin-4-yl)piperidin-4-yl)methanol (11.2 g, 41.8 mmol, prepared using A from 2,4-dichlorofuro[3,2-d]pyrimidine [Arkpharm], piperidin-4-ylmethanol), DCM (200 mL) and Dess-Martin periodinane (18.6 g, 43.9 mmol). The mixture was stirred at rt for about 3 h. The mixture was diluted with DCM (100 mL) and washed with an aqueous solution of 1 N Na$_2$CO$_3$ (200 mL). The aqueous layer was extracted with DCM (2×100 mL). The combined extracts were washed with brine, dried over Na$_2$CO$_3$, filtered, and evaporated under vacuum. The residue was purified by column chromatography eluting with 20-80% EtOAc/heptane (120 g silica gel) to provide 1-(2-chlorofuro[3,2-d]pyrimidin-4-yl)piperidine-4-carbaldehyde (10 g, 90%): LC/MS (Table 2, Method u) R$_f$=1.22 min.; MS m/z: 266 (M+H)$^+$.

General Procedure Q: Removal of a Boc Group from an N-Boc Amine or Heteroaromatic and a SEM Group from an N'-SEM Heteroaromatic An acid (such as TFA or HCl, preferably TFA; 5 to 60 equiv, preferably 20 to 50 equiv) is added to a solution of a compound containing an N-Boc amine or heteroaromatic and an N'-SEM heteroaromatic (1 equiv) in an organic solvent (such as DCM) at about 25° C. The mixture is stirred for about 1 to 48 h (preferably about 1 to 24 h) before evaporation of the solvents under reduced pressure. The material is dissolved in an organic solvent (such as MeOH, EtOH, THF or 1,4-dioxane, preferably MeOH or 1,4-dioxane) then the mixture is treated with concentrated aqueous NH$_4$OH (30 to 50 equiv, preferably 45 equiv). The mixture is optionally heated at about 50 to 65° C. (preferably about 60° C.) for about 15 min to 2 h (preferably about 30 min) The mixture is optionally concentrated in vacuo to give the targeted compound. Alternatively, the residue may be purified by HPLC or column chromatography to provide the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure Q

Example Q.1

4-(4-(Aminomethyl)piperidin-1-yl)-N-(3-methyl-1H-indazol-6-yl)furo[3,2-d]pyrimidin-2-amine

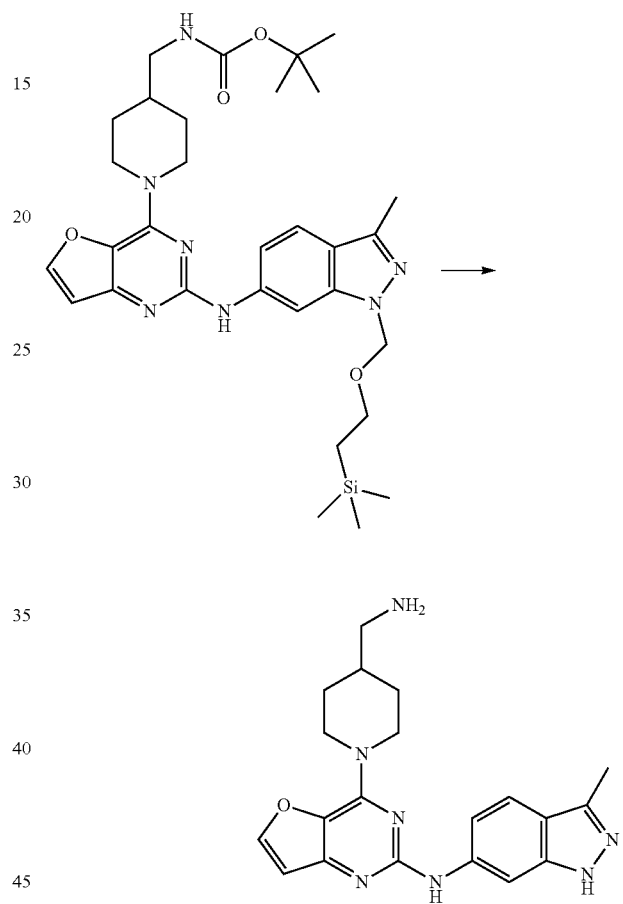

tert-Butyl (1-(2-(3-methyl-1-(2-(trimethylsilyl)ethoxy)methyl)-1H-indazol-6-ylamino)furo[3,2-d]pyrimidin-4-yl)piperidin-4-yl)methylcarbamate (0.62 g, 1.0 mmol, prepared using A from 2,4-dichlorofuro[3,2-d]pyrimidine [ArkPharm] with tert-butyl piperidin-4-ylmethylcarbamate and B with Example #5, Step C) was dissolved in DCM (10 mL). TFA (10 mL, 130 mmol) was added and the resulting mixture was stirred at about 30° C. for about 16 h. The mixture was concentrated in vacuo to give a residue. The residue was diluted with MeOH and NH$_4$OH was added until the pH ~9. The solvents were removed under reduced pressure and the residue was purified by prep-HPLC (Table 2, Method w) to give 4-(4-(aminomethyl)piperidin-1-yl)-N-(3-methyl-1H-indazol-6-yl)furo[3,2-d]pyrimidin-2-amine (0.2 g, 52%): LC/MS (Table 2, Method h) R$_f$=1.56 min; MS m/z: 378 (M+H)$^+$. Syk IC$_{50}$=A

TABLE Q.1

Examples for the one pot removal of a Boc protecting group from an N-Boc protected amine and a SEM protecting group from an N'-SEM protected amine using General Procedure Q

| N-Boc N'-SEM Protected Diamine | Product | Example # | R, min (Table 2, Method) | m/z ESI+ (M + H)+ | Syk IC50 |
|---|---|---|---|---|---|
| tert-Butyl 3-(2-(1-(((trimethylsilyl)methoxy)methyl)-1H-indazol-6-ylamino)furo[3,2-d]pyrimidin-4-ylamino)propylcarbamate (prepared using A from 2,4-dichlorofuro[3,2-d]pyrimidine [ArkPharm] with tert-butyl 3-aminopropylcarbamate and B with 1-((2-(trimethylsilyl)ethoxy)methyl)-1H-indazol-6-amine (WO 2010/027500 Intermediate 21, Step C)) | | Q.1.1 | 1.42 (h) | 324 | B |
| tert-Butyl 4-(2-(1-((2-(trimethylsilyl)ethoxy)methyl)-1H-indazol-6-ylamino)furo[3,2-d]pyrimidin-4-ylamino)butylcarbamate (prepared using A from 2,4-dichlorofuro[3,2-d]pyrimidine [ArkPharm] with tert-butyl 4-aminobutylcarbamate and B with 1-((2-(trimethylsilyl)ethoxy)methyl)-1H-indazol-6-amine (WO 2010/027500 Intermediate 21, Step C)) | | Q.1.2 | 1.44 (h) | 338 | A |
| tert-Butyl 9-(2-(3-methyl-1-((2-(trimethylsilyl)ethoxy)methyl)-1H-indazol-6-ylamino)furo[3,2-d]pyrimidin-4-yl)-2,9-diazaspiro[5.5]undecane-2-carboxylate (prepared using A from 2,4-dichlorofuro[3,2-d]pyrimidine [ArkPharm] with tert-butyl 2,9-diazaspiro[5.5]undecane-2-carboxylate [ASW MedChem] and B with Example #5, Step C) | | Q.1.3 | 1.75 (h) | 418 | A |
| tert-Butyl 9-(2-(3-methyl-1-((2-(trimethylsilyl)ethoxy)methyl)-1H-indazol-6-ylamino)furo[3,2-d]pyrimidin-4-yl)-1-oxa-4,9-diazaspiro[5.5]undecane-4-carboxylate (prepared using A from 2,4-dichlorofuro[3,2-d]pyrimidine [ArkPharm] with tert-butyl 1-oxa-4,9-diazaspiro[5.5]undecane-4-carboxylate [ArkPharm]) and B (Example #5, Step C) | | Q.1.4 | 1.74 (h) | 420 | A |

General Procedure R: Removal of a Silyl Group from an O-Silyl Ether

Method 1:

To a solution of an O-silyl-ether (1 equiv) in an organic solvent (such as DMF, 1,4-dioxane, or DCM, preferably DCM) is added an acid (such as TFA or HCl, 5 to 50 equiv, preferably 30 equiv) and the mixture is stirred at about 0 to 50° C. (preferably about 15 to 25° C.) for about 1 to 48 h (preferably about 4 to 16 h). Alternatively, additional acid (5 to 20 equiv, preferably 10 equiv) may be added and the mixture is heated to about 30 to 100° C. (preferably about 50 to 80° C.) for about 0.5 to 10 h (preferably about 1 to 5 h).

Method 2:

To a solution of an O-silyl ether (1 equiv) in an organic solvent (such as DMF, 1,4-dioxane, or DCM, preferably DMF) is added a fluoride source such as HF, TBAF (1 to 10 equiv, preferably 4 equiv), and the mixture is stirred at about 20 to 110° C. (preferably about 25 to 60° C.) for about 1 to 20 h (preferably about 2 to 8 h).

For either method, the targeted compound may optionally be isolated by cooling the mixture and filtering the precipitate. Alternatively, the mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure R

Example #R.1

6-(4-(4-Amino-3-hydroxyazepan-1-yl)furo[3,2-d]pyrimidin-2-ylamino)-2,2-dimethyl-2H-benzo[b][1,4]oxazin-3(4H)-one

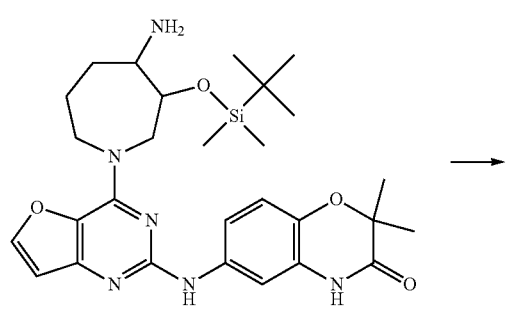

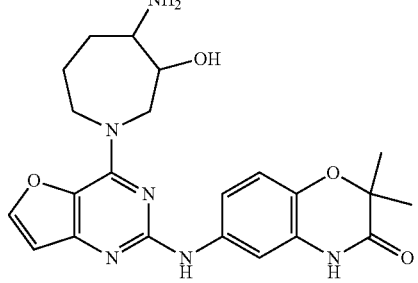

A mixture of 6-(4-(4-amino-3-(tert-butyldimethylsilyloxy)azepan-1-yl)furo[3,2-d]pyrimidin-2-ylamino)-2,2-dimethyl-2H-benzo[b][1,4]oxazin-3(4H)-one (0.400 g, 0.724 mmol, prepared using F from Preparation #AH.1, O with Boc$_2$O, K, A with 2,4-dichlorofuro[3,2-d]pyrimidine [Arkpharm], B with 6-amino-2,2-dimethyl-2H-benzo[b][1,4]oxazin-3(4H)-one [ArkPharm] and C) and TBAF (0.378 g, 1.45 mmol) in THF (10 mL) was stirred at about 25° C. for about 4 h. The mixture was concentrated and purified by preparatory HPLC (Table 2, Method t) to give 6-(4-(4-amino-3-hydroxyazepan-1-yl)furo[3,2-d]pyrimidin-2-ylamino)-2,2-dimethyl-2H-benzo[b][1,4]oxazin-3(4H)-one (0.11 g, 35%): LC/MS (Table 2, Method h) R$_t$=1.69 min.; MS m/z: 439 (M+H)$^+$. Syk IC$_{50}$=B

General Procedure S: Removal of a 2,4-Dimethoxybenzyl Group from a N-2,4-dimethoxybenzylamine To a flask is added a 2,4-dimethoxybenzylamine (preferably 1 equiv), an organic solvent (such as DCM or DCE, preferably DCM) and TFA (about 2:1 ratio of organic solvent to TFA). To the flask is added triethylsilane (1 to 5 equiv, preferably 1.2 equiv) and the mixture is stirred at about 25 to 70° C. (preferably about 55° C.) for about 1 to 24 h (preferably about 6 h). The mixture is concentrated under reduced pressure to give the desired product. Alternatively, the mixture is concentrated under reduced pressure and an organic solvent (such as DCM or EtOAc) is added and the solution is washed with water and/or brine. The layers are separated and the organic solution is dried over anhydrous Na$_2$SO$_4$ or MgSO$_4$, filtered or decanted and concentrated under reduced pressure.

Illustration of General Procedure S

Preparation #S.1: (7-Benzyl-5,6,7,8-tetrahydroimidazo[1,5-a]pyrazin-3-yl)methanamine 2,2,2-trifluoroacetate

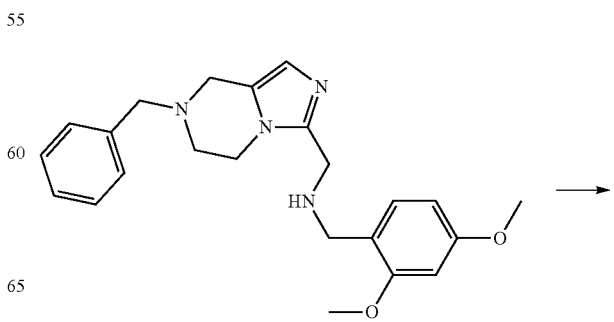

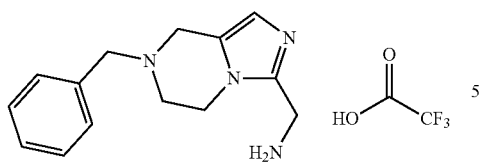

A flask was charged with 1-(7-benzyl-5,6,7,8-tetrahydroimidazo[1,5-a]pyrazin-3-yl)-N-(2,4-dimethoxybenzyl)methanamine (1.0 g, 2.6 mmol, prepared using H from 7-benzyl-5,6,7,8-tetrahydroimidazo[1,5-a]pyrazine-3-carbaldehyde [WO 03/076427, Preparation 138] with 2,4-dimethoxybenzylamine), DCM (20 mL) and TFA (10 mL). To the mixture was added triethylsilane (0.50 mL, 3.1 mmol) and the mixture was heated to about 55° C. for about 6 h. The solvents were removed under reduced pressure to give (7-benzyl-5,6,7,8-tetrahydroimidazo[1,5-a]pyrazin-3-yl)methanamine 2,2,2-trifluoroacetate (1.6 g) as a crude material that was used directly without further purification: LC/MS (Table 2, Method h) $R_t$=1.65 min; MS m/z: 243 (M+H)$^+$.

General Procedure T: Hydrolysis of a Phthalamide to an Amine

To a solution of a phthalamide (1 equiv) at about 0 to 30° C. (preferably rt) in an organic solvent (such as EtOH, 1,4-dioxane or MeOH, preferably MeOH) is added hydrazine or hydrazine hydrate (1 to 10 equiv, preferably 5 equiv). The mixture is stirred for about 1 to 24 h (preferably about 3 to 8 h) at about 25 to 80° C. (preferably about 60 to 70° C.). The mixture is then optionally concentrated in vacuo and the residue is optionally dissolved or suspended in an organic solvent (such as EtOAc, DCM, or DCM/MeOH, preferably 10:1 DCM/MeOH) and filtered. The filtrate is collected and concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure T

Preparation #T.1: 4-(4-(Aminomethyl)-4-fluoropiperidin-1-yl)-N-(1-((2-(trimethylsilyl)ethoxy)methyl)-1H-indazol-6-yl)furo[3,2-d]pyrimidin-2-amine

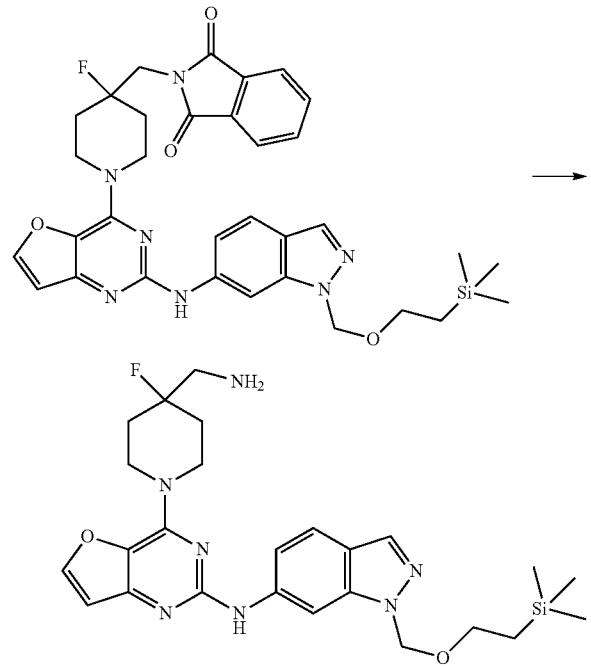

A mixture of 2-((4-fluoro-1-(2-(1-((2-(trimethylsilyl)ethoxy)methyl)-1H-indazol-6-ylamino)furo[3,2-d]pyrimidin-4-yl)piperidin-4-yl)methyl)isoindoline-1,3-dione (0.510 g, 0.795 mmol, prepared using W from Preparation #X.1, V, U with phthalamide, G, A with 2,4-dichlorofuro[3,2-d]pyrimidine [ArkPharm] and B with 1-((2-(trimethylsilyl)ethoxy)methyl)-1H-indazol-6-amine [WO 2010/027500 Intermediate 21, Step C]) in MeOH (20 mL) was treated with hydrazine hydrate (0.190 mL, 2.50 mmol). The mixture was heated at about 70° C. for about 3 h. The mixture was cooled to rt and concentrated in vacuo. The residue was dissolved in DCM/MeOH (10:1) (30 mL) and stirred for about 30 min. The resulting suspension was filtered and the filtrate was concentrated in vacuo to give 4-(4-(aminomethyl)-4-fluoropiperidin-1-yl)-N-(1-((2-(trimethylsilyl)ethoxy)methyl)-1H-indazol-6-yl)furo[3,2-d]pyrimidin-2-amine (0.41 g, 100%). LC/MS (Table 2, Method i) $R_t$=1.60 min; MS m/z 512 (M+H)$^+$.

General Procedure U: Substitution of a Mesylate with an Amine Nucleophile

A flask is charged with an alkyl mesylate (preferably 1 equiv) and an organic solvent such as DMF, DMA, NMP or DMSO (preferably DMF). To the flask are added in no particular order the amine nucleophile (1 to 2 equiv, preferably 1.2 equiv), an optional catalyst such as Bu$_4$NI (0.1 to 1 equiv, preferably 0.5 equiv), a base (such as LiHMDS, NaH, NaHMDS, NaOt-Bu, KHMDS or KOt-Bu, preferably KOt-Bu); 1 to 5 equiv, preferably 2 equiv). The mixture is stirred at about 10 to 100° C. (preferably about 100° C.) for about 1 to 24 h (preferably about 8 to 20 h). Optionally, additional amine nucleophile and/or base may be added used (5-300% of the original amount used, preferably 10% (0.05 to 3.0 equiv, preferably 0.1 equiv) and the mixture is stirred at about 10 to 100° C. (preferably about 100° C.) for about 0.5 to 24 h (preferably about 2 h). The mixture is partitioned between an organic solvent such as EtOAc or DCM (preferably EtOAc) and water. The layers are separated and the organic solution is dried over anhydrous MgSO$_4$ or Na$_2$SO$_4$, filtered, and concentrated under reduced pressure to provide the target compound.

Illustration of General Procedure U

Preparation U.1: 2-((1-Benzyl-4-fluoropiperidin-4-yl)methyl)isoindoline-1,3-dione

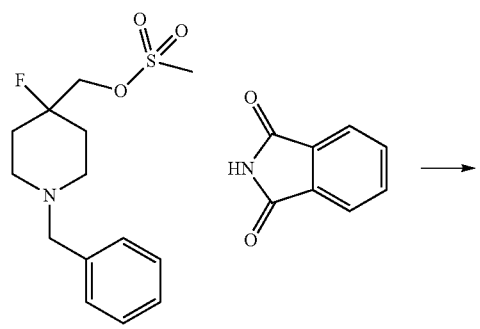

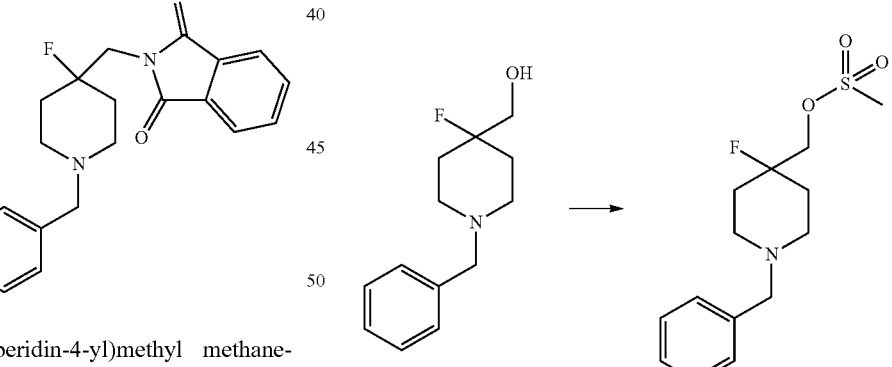

The (1-benzyl-4-fluoropiperidin-4-yl)methyl methanesulfonate (1.82 g, 6.04 mmol, Preparation #V.1) was dissolved in DMF (18 mL) and isoindoline-1,3-dione (1.07 g, 7.25 mmol), Bu$_4$NI (1.12 g, 3.02 mmol) and KOtBu (1.36 g, 12.1 mmol) were added. The resulting mixture was stirred at about 100° C. for about 12 h. The mixture was cooled to rt and concentrated under reduced pressure. The residue was diluted with water (10 mL) and extracted with Et$_2$O (3×10 mL). The combined organic layers were washed with brine (2×20 mL), dried over Na$_2$SO$_4$, filtered, and concentrated under reduced pressure. The residue was purified by silica gel chromatography eluting with a gradient of 0 to 10% MeOH/DCM to afford 2-((1-benzyl-4-fluoropiperidin-4-yl)methyl)isoindoline-1,3-dione (0.8 g, 38%): LC/MS (Table 2, Method f) R$_t$=2.21 min; MS m/z 353 (M+H)$^+$.

General Procedure V: Formation of a Mesylate from an Alcohol

To a solution of an alcohol (preferably 1 equiv) in an organic solvent (such as DCM) is added, in no particular order, an organic base (such as DBU, TEA or DIEA; 1 to 4 equiv, preferably 2 equiv), a mesylating agent such as mesyl chloride or methanesulfonic anhydride (1 to 2 equiv preferably 1.1 equiv) and optionally DMAP (0.1 to 1 equiv) may be used. The mixture is stirred at about 0 to 40° C. (preferably rt). In cases where the mixture is cooled to below rt, it may be stirred at this temperature for about 1 to 3 h (preferably about 2 h) and then optionally warmed to rt while stirring for about 8 to 14 h. The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure V

Preparation #V.1:
(1-Benzyl-4-fluoropiperidin-4-yl)methyl methanesulfonate

A flask was charged with (1-benzyl-4-fluoropiperidin-4-yl)methanol (3.34 g, 14.9 mmol, prepared using W from Preparation #X.1) and DCM (100 mL). To the mixture was added methanesulfonic anhydride (3.91 g, 22.4 mmol), DBU (6.76 mL, 44.9 mmol) and DMAP (0.183 g, 1.496 mmol). The resulting mixture was stirred at rt overnight. The mixture was washed sequentially with an aqueous saturated solution of NH$_4$Cl (50 mL) and NaHCO$_3$ (50 mL). The organic layer was washed with brine, dried over Na$_2$SO$_4$, filtered, and concentrated under reduced pressure. The resulting mixture was deposited onto silica gel purified via column chromatography eluting with 2:1 hexanes/EtOAc to afford the (1-benzyl-4-fluoropiperidin-4-yl)methyl methanesulfonate (4.51 g, 100%). The material obtained was used without characterization.

General Procedure W: Reduction of an Ester to an Alcohol

A reducing agent (such as LAH, DIBAL-H, NaBH₄ or LiBH₄, preferably DIBAL-H, 1.0 to 3.0 equiv, preferably 1.25 equiv), is added either portionwise as a solid or dropwise as a solution in an organic solvent (such as THF, Et₂O, EtOH or MeOH, preferably THF) to a solution of a carbonyl compound (preferably 1 equiv) in an organic solvent (such as THF, Et₂O, EtOH or MeOH, preferably MeOH) at about −40 to 50° C. (preferably rt). The mixture is stirred for about 1 to 20 h (preferably about 4 to 16 h) before adding water or an aqueous salt solution (such as NH₄Cl or NaHCO₃, preferably saturated aqueous NH₄Cl). The mixture is stirred for about 10 min to 3 h (preferably about 20 to 30 min) and then the solution is partitioned with an organic solvent (such as EtOAc, Et₂O or DCM, preferably Et₂O). The organic layer is washed with brine, dried over anhydrous Na₂SO₄ or MgSO₄, filtered, and concentrated under reduced pressure to give the target compound.

Illustration of General Procedure W

Preparation W.1: tert-Butyl 4-(hydroxymethyl)-4-methylpiperidine-1-carboxylate

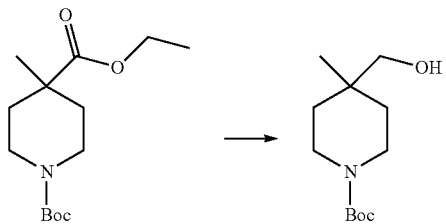 [SMILES: CCOC(=O)C1(C)CCN(C(=O)OC(C)(C)C)CC1 ; CC1(CO)CCN(C(=O)OC(C)(C)C)CC1]

To a mixture of 1-tert-butyl 4-ethyl 4-methylpiperidine-1,4-dicarboxylate (0.10 g, 0.37 mmol) in THF (10 mL) and ethanol (20 mL) was added LiBH₄ (0.032 g, 1.5 mmol). The mixture was stirred for about 8 h at rt. The mixture was diluted with water (20 mL) and extracted with EtOAc (3×20 mL). The EtOAc extracts were combined, dried over anhydrous Na₂SO₄, and concentrated in vacuo to give tert-butyl 4-(hydroxymethyl)-4-methylpiperidine-1-carboxylate (0.067 g, 80%): LC/MS (Table 2, Method i) R$_t$=0.29 min; MS m/z: 130 (M-Boc+H)⁺.

General Procedure X: Nucleophilic Fluorination at the α-Position of an Ester

A flask is charged with a base (such as LDA, LiHMDS, NaHMDS, NaOEt, NaOMe, KOtBu, or NaNH₂, preferably LDA) (1 to 3 equiv, preferably 1.5 equiv) in an organic solvent (such as THF, 1,4-dioxane, Et₂O or DMF, preferably THF). The temperature of the mixture is adjusted to about −78 to −30° C. (preferably about −40° C.) and a solution of an ester (preferably 1 equiv) in an organic solvent (such as 1,4-dioxane, THF, Et₂O, or DMF preferably THF) is added slowly so as to maintain the temperature of the mixture within about +/−10° C. The mixture is stirred at about −40 to 0° C. (preferably about −15 to −10° C.) for about 30 min to 2 h (preferably about 1 h), and is then cooled to about −78 to −40° C. (preferably about −78° C.). To the mixture is slowly added a solution of N-fluoro-N-(phenylsulfonyl)benzenesulfonamide (1-2 equiv, preferably 1.05 equiv) in an organic solvent (such as 1,4-dioxane, THF, Et₂O or DMF, preferably THF) to maintain the temperature of the mixture within about +/−15° C. The resulting mixture is stirred at about −78 to 0° C. (preferably about −78° C.) for about 30 min to 4 h (preferably about 1 h). The mixture is poured into ice water and extracted with an organic solvent (such as DCM or EtOAc). The combined extracts are optionally washed with water and/or brine, dried over anhydrous Na₂SO₄ or MgSO₄, filtered or decanted and concentrated under reduced pressure. The crude material is optionally purified by silica gel chromatography.

Illustration of General Procedure X

Preparation #X.1: Ethyl 1-benzyl-4-fluoropiperidine-4-carboxylate

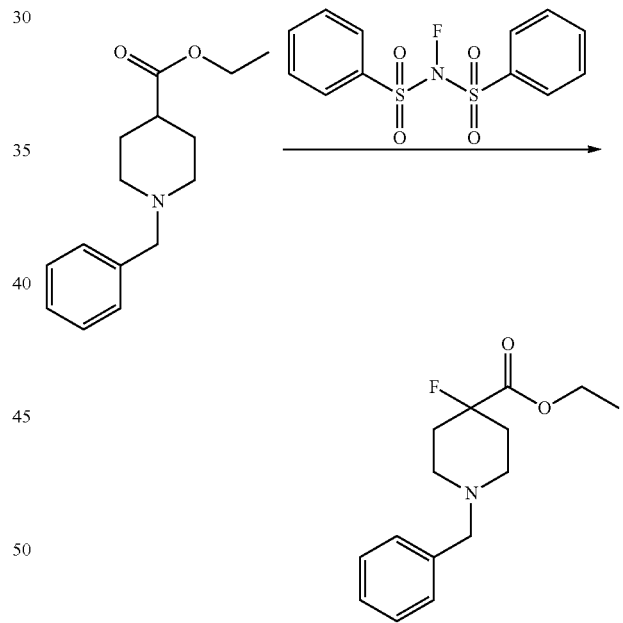

A flask was charged with DIEA (8.64 mL, 60.6 mmol) and THF (100 mL). The mixture was cooled to about −78° C. followed by the addition of n-BuLi (24.3 mL, 60.6 mmol) over about 5 min. The mixture was warmed to about 0° C. and stirred for about 30 min and then cooled to about −40° C. To the mixture was added a solution of ethyl 1-benzylpiperidine-4-carboxylate (10.0 g, 40.4 mmol, Oakwood) in THF (75 mL) over about 10 min such that the solution is kept between −40 to −30° C. The mixture was stirred for about 1 h at about −10° C. before being cooled to about −78° C. A solution of N-fluoro-N-(phenylsulfonyl)benzenesulfonamide (14.0 g, 44.5 mmol) in THF (75 mL) was added over about 20 min while keeping the mixture between about −65 and −78° C. The mixture was then stirred for about 1 h at about −78° C. The mixture was poured into a separatory funnel containing ice water (30 mL) and EtOAc (30 mL) was added. The aqueous layer was extracted with EtOAc (3×25 mL) and the combined organic extracts were washed with brine, dried over anhydrous $Na_2SO_4$, filtered and concentrated under reduced pressure. The resulting mixture was adsorbed onto silica gel and purified by flash silica gel chromatography eluting with hexanes/EtOAc (10:1) to afford ethyl 1-benzyl-4-fluoropiperidine-4-carboxylate (7.13 g, 66%): LC/MS (Table 2, Method h) $R_f$=2.21 min; MS m/z: 266 $(M+H)^+$.

General Procedure Y: Nucleophilic Displacement of an Aryl Halide with an Alcohol To a solution of an aryl halide and an appropriate organic solvent (such as 1,4-dioxane, DME, n-butanol, THF or DMF, preferably 1,4-dioxane) is added an alcohol (1 to 10 equiv, preferably 1 to 5 equiv) and a base (such as NaH, TEA, DIEA, $K_2CO_3$, preferably NaH; 1 to 5 equiv, preferably 1 to 1.5 equiv). The resulting mixture is stirred at about 0 to 150° C. (preferably about 20 to 80° C.) for a period of about 1 h to 24 h (preferably about 4 to 16). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then optionally concentrated in vacuo to give a residue as the target compound. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure Y

Preparation #Y.1:
2-Chloro-4-cyclobutoxyfuro[3,2-d]pyrimidine

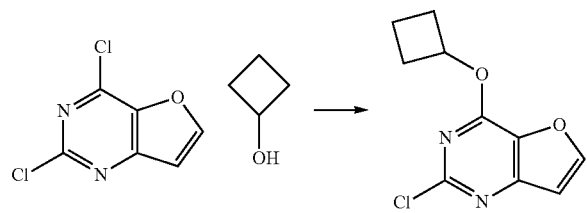

To a flask was added cyclobutanol (0.820 mL, 10.5 mmol), 2-chloro-4-cyclobutoxyfuro[3,2-d]pyrimidine (0.400 g, 2.11 mmol, ArkPharm) and 1,4-dioxane (0.1 mL). To the mixture was added NaH (60% dispersion in mineral oil, 0.102 g, 2.54 mmol). The mixture was stirred at rt overnight. The mixture was extracted with DCM (3×5 mL) and water (5 mL). The organic layer was dried over $Mg_2SO_4$, filtered and concentrated under reduced pressure. Water (20 mL) was added to the residue and the precipitate was collected by filtration and dried in vacuum oven at about 60° C. overnight to give 2-chloro-4-cyclobutoxyfuro[3,2-d]pyrimidine (0.4 g, 91%): LC/MS (Table 2, Method c) $R_f$=2.57 min.; MS m/z: 225 $(M+H)^+$.

General Procedure Z: Suzuki Reaction of an Aryl or Heteroaryl Halide with an Aryl or Heteroaryl Boronic Acid or Boronate To a mixture of an aryl halide (preferably 1 equiv), a boronic acid or boronate ester (1 to 2 equiv, preferably 1.1 equiv), and an inorganic base (such as, KF, $Na_2CO_3$, $K_2CO_3$ or $Cs_2CO_3$, preferably $Cs_2CO_3$) (1.1 to 16 equiv, preferably 2 equiv) in a solvent (such as THF, DME, DMF, 1,4-dioxane, DME/water, 1,4-dioxane/water, toluene/EtOH/water, 1,4-dioxane/EtOH/water or water; preferably 1,4-dioxane) is added a palladium catalyst (for example $Pd_2dba_3$, $Pd(PPh_3)_4$, bis(acetato)triphenylphosphinepalladium(II), polymer-bound FibreCat™ 1032, (1,1'-bis(diphenylphosphino)ferrocene)dichloropalladium(II) complex with DCM, or $Pd(PPh_3)_2Cl_2$; preferably $Pd_2dba_3$, 0.01 to 0.20 equiv, preferably 0.1 equiv) and a ligand (for example tricyclohexylphosphine, tri-tert-butyl-phosphine; preferably tricyclohexylphosphine; 0.01-1.0 equiv, preferably 0.16 equiv) is added optionally. The mixture is heated at about 40 to 120° C. (preferably about 85° C.) for about 1 to 24 h (preferably about 2 h) thermally, or at about 100 to 200° C. (preferably about 120° C.) for about 5 to 60 min (preferably about 20 to 45 min) in a microwave (preferably 5 min ramp time, 300 Watts max power, 250 psi max pressure). The mixture is allowed to cool to rt and is worked up using one of the following methods. Method 1. For reactions containing water, the mixture may be diluted with an organic solvent (such as DCM or EtOAc). The layers are separated, the organic solution is optionally washed with water and/or brine, dried over anhydrous $MgSO_4$ or $Na_2SO_4$, filtered, and the solvent is removed under reduced pressure to give the desired compound. Method 2. The mixture is concentrated under reduced pressure and optionally purified using one or more of the Purification Methods described above to give the desired compound. Method 3. The catalyst is removed by filtration and the filtrate is concentrated under reduced pressure.

Illustration of General Procedure Z

Preparation #Z.1: 6-Nitro-3-(pyridin-4-yl)-1-((2-(trimethylsilyl)ethoxy)methyl)-1H-indazole

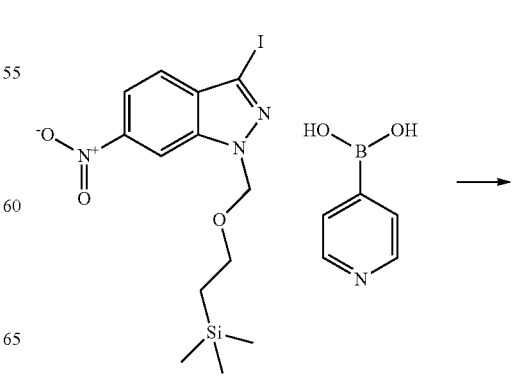

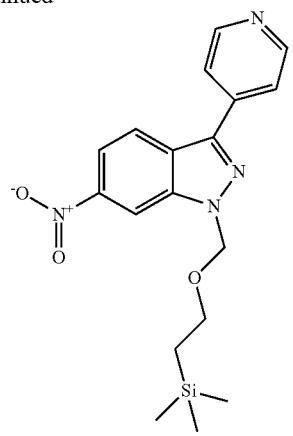

To a microwave vial was added 3-iodo-6-nitro-1-((2-(trimethylsilyl)ethoxy)methyl)-1H-indazole (1.2 g, 2.9 mmol, WO 2010/027500, Intermediate 57, Step B), pyridine-4-boronic acid (0.704 g, 5.72 mmol), and Pd(PPh$_3$)$_4$ (0.165 g, 0.143 mmol), 1,4-dioxane (25 mL) and an aqueous solution of Na$_2$CO$_3$ (2 M, 6.3 mL, 12.6 mmol). The vial was sealed and the mixture was heated in a microwave at about 120° C. for about 40 min. The mixture was diluted with EtOAc (100 mL) and water (25 mL) and the layers separated. The aqueous layer was extracted with EtOAc (15 mL). The combined extracts were washed with brine (20 mL), dried over Na$_2$SO$_4$, filtered, and concentrated under vacuum. The residue was purified by column chromatography (80 g silica gel) eluting with 20 to 80% EtOAc/heptane to provide 6-nitro-3-(pyridin-4-yl)-1-((2-(trimethylsilyl)ethoxy)methyl)-1H-indazole (0.893 g, 84%): LC/MS (Table 2, Method c) R$_f$=3.02 min.; MS m/z: 371 (M+H)$^+$.

General Procedure AA: Conversion of an Aldehyde to a Nitrile

In no particular order a flask is charged with an aldehyde (1 equiv) in an organic solvent such as DCM, THF, DMF (preferably DMF), an amine source (1 to 3 equiv, preferably 1 to 1.5 equiv) such as hydroxylamine hydrochloride, ammonia, hydroxylamine-O-sulfonic acid (preferably hydroxylamine hydrochloride), a base (1 to 3 equiv, preferable 1 to 1.5 equiv) such as pyridine, TEA (preferably TEA) and a dehydrating agent such as hydrogen peroxide, lead tetraacetate, acetic anhydride, 2,2,2-trichloroacetyl chloride or 2,4,6-tripropyl-[1,3,5,2,4,6]trioxatriphosphinane 2,4,6-trioxide (preferably 2,4,6-tripropyl-[1,3,5,2,4,6]trioxatriphosphinane 2,4,6-trioxide). The mixture is stirred at about 40 to 120° C. (preferably about 80 to 110° C.) for about 2 to 15 h (preferably about 4 to 8 h). The mixture is cooled to rt and optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH. LiCl or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AA

Preparation #AA.1: 6-Nitro-1-((2-(trimethylsilyl)ethoxy)methyl)-1H-indazole-3-carbonitrile

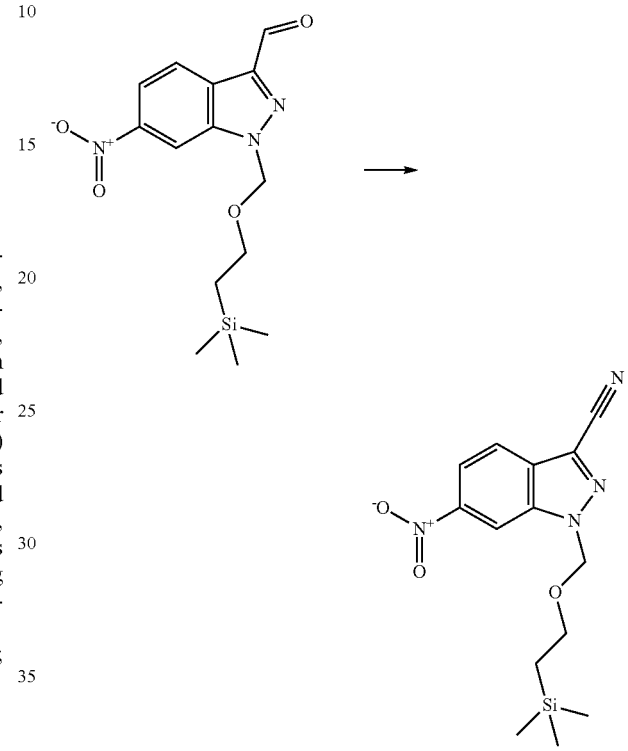

6-Nitro-1-((2-(trimethylsilyl)ethoxy)methyl)-1H-indazole-3-carbaldehyde (0.2 g, 0.622 mmol, prepared using N from 6-nitro-1H-indazole-3-carbaldehyde [Chempacific]), hydroxylamine hydrochloride (0.048 g, 0.68 mmol), and TEA (0.095 mL, 0.68 mmol) were combined in DMF (1.24 mL) in a sealed vial. 2,4,6-Tripropyl-[1,3,5,2,4,6]trioxatriphosphinane 2,4,6-trioxide (50% solution in DMF, 0.400 mL, 0.684 mmol) was added and the mixture was heated at about 100° C. for about 6 h. The mixture was allowed to cool to rt. EtOAc (15 mL) and an aqueous solution of saturated NaHCO$_3$ (5 mL) were added and the layers separated. The aqueous layer was extracted with EtOAc (1×5 mL). The combined extracts were washed with 5% aqueous LiCl (3×10 mL). The combined extracts were washed with brine (10 mL), dried over MgSO$_4$, filtered and evaporated under vacuum. The sample was re-dissolved in DCM and dry loaded onto silica gel (2 mL). The residue was purified by column chromatography (25 g silica gel) eluting with 10 to 25% EtOAc/heptane to provide 6-nitro-1-((2-(trimethylsilyl)ethoxy)methyl)-1H-indazole-3-carbonitrile (0.132 g, 67%): $^1$H NMR (400 MHz, DMSO-d6) δ 9.02 (dd, J=1.5, 1.1 Hz, 1H), 8.22-8.21 (m, 2H), 6.05 (s, 2H), 3.60-3.54 (m, 2H), 0.83-0.78 (m, 2H), −0.12 (s, 9H)

General Procedure AB: Formation of an N-THP Heteroaromatic

A heteroaromatic (1 equiv) and an organic acid (0.01 to 1 equiv, preferably 0.1 equiv) such as p-TSA, H$_2$SO$_4$, TFA, MsOH, PPTS (preferably p-TSA) are dissolved in an organic solvent (such as THF, DCM, Et$_2$O, toluene, CHCl$_3$, CDCl$_3$, EtOAc, or 1,4-dioxane, preferably THF). 3,4-Dihydro-2H-pyran (1 to 10 equiv, preferably 5 equiv) is added and the mixture is heated at about 30 to 100° C. (preferably about 70° C.) for about 1 to 24 h (preferably about 6 h). The mixture is optionally concentrated in vacuo to give the targeted compound. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AB

Preparation #AB.1: 6-Bromo-4-methyl-1-(tetrahydro-2H-pyran-2-yl)-1H-indazole

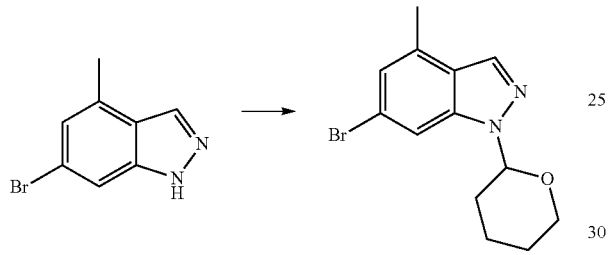

6-Bromo-4-methyl-1H-indazole (1.0 g, 4.7 mmol, J&W PharmLab) and p-TSA (0.082 g, 0.47 mmol) were dissolved in THF (20 mL). 3,4-Dihydro-2H-pyran (1.99 g, 23.7 mmol) was added and the mixture was heated at about 70° C. for about 6 hours. The mixture was concentrated in vacuo and the residue was purified by silica gel chromatography (5:1 hexanes:EtOAc) to give 6-bromo-4-methyl-1-(tetrahydro-2H-pyran-2-yl)-1H-indazole (0.80 g, 41%): LC/MS (Table 2, Method g) R$_t$=2.28 min; MS m/z: 295, 297 (M+H)$^1$.

General Procedure Ac: Removal of a THP Group from an N-THP Heteroaromatic

An N-THP heteroaromatic (preferably 1 equiv) is dissolved in an organic solvent containing an acid (preferably 4 M HCl in 1,4-dioxane, 5-50 equiv, preferably 17 equiv) and stirred at rt to about 70° C. (preferably about 50° C.) for about 0.5 to 10 h (preferably about 2 h). The mixture is concentrated under reduced pressure and optionally purified. Alternatively, the residue is dissolved in an organic solvent (such as DCM or EtOAc) and washed with an aqueous base (such as NaHCO$_3$), water and/or brine. The layers are separated and the organic solution is dried over anhydrous Na$_2$SO$_4$ or MgSO$_4$, filtered or decanted and concentrated under reduced pressure.

Illustration of General Procedure AC

Example #AC.1

N$^4$-Cyclopropyl-N$^2$-(4-methyl-1H-indazol-6-yl)furo[3,2-d]pyrimidine-2,4-<diamine

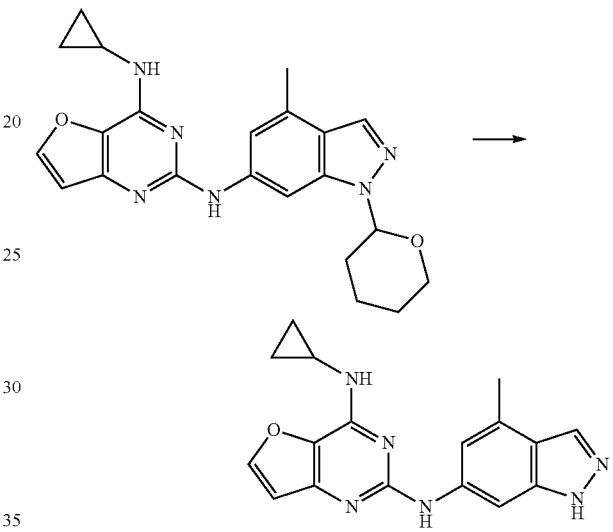

A flask was charged with N$^4$-cyclopropyl-N$^2$-(4-fluoro-3-methyl-1-(tetrahydro-2H-pyran-2-yl)-1H-indazol-6-yl)furo[3,2-d]pyrimidine-2,4-diamine (0.19 g, 0.45 mmol, prepared using B from Preparation #A.1 with Preparation #AN.1) and 4 M HCl in 1,4-dioxane (2 mL). The mixture was stirred at about 50° C. for about 2 h, cooled to rt, concentrated under reduced pressure and purified by reverse phase HPLC (Table 2, Method o) to give N$^4$-cyclopropyl-N$^2$-(4-methyl-1H-indazol-6-yl)furo[3,2-d]pyrimidine-2,4-diamine (0.030, 20%): LC/MS (Table 2, Method h) R$_t$=1.85 min; MS m/z: 321 (M+H)$^+$. Syk IC$_{50}$=A

TABLE AC.1

Example prepared from the removal of a THP protecting group from an aryl nitrogen using General Procedure AC

| N-THP Protected Aryl Nitrogen | Product | Example # | R$_t$ min (Table 2, Method) | m/z ESI+ (M + H)$^+$ | Syk IC$_{50}$ |
|---|---|---|---|---|---|
| N$^4$-Cyclopropyl-N$^2$-(4-fluoro-3-methyl-1-(tetrahydro-2H-pyran-2-yl)-1H-indazol-6-yl)furo[3,2-d]pyrimidine-2,4-diamine (prepared using B from 6-bromo-4-fluoro-3-methyl-1-(tetrahydro-2H-pyran-2-yl)-1H-indazole [WO2010027500 Page 193] and diphenylmethanimine [Alfa], AN and B with 2-chloro-N-cyclopropylfuro[3,2-d]pyrimidin-4-amine | 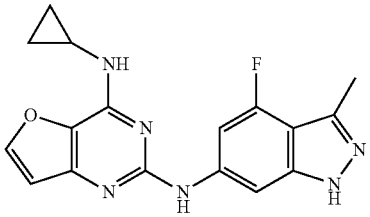 | AC. 1.1 | 1.93 (f) | 339 | A |

General Procedure AD: Removal of a Boc Group from an N-Boc Amine or Heteroaromatic and a Silyl Group from an O-Silyl Ether To a solution of a compound containing an N-Boc amine or heteroaromatic and an O-silyl ether in an organic solvent such as DCM, DMF, THF or 1,4-dioxane (preferably 1,4-dioxane) is added an acid such as TFA or HCl (preferably HCl) (15 to 60 equiv, preferably 30 to 60 equiv) and the mixture is stirred at about 25 to 80° C. (preferably about 25 to 45° C.). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then optionally concentrated in vacuo to give a residue as the target compound. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure AD

Example #AD.1

6-(4-(4-(Aminomethyl)-4-(2-hydroxyethyl)piperidin-1-yl)furo[3,2-d]pyrimidin-2-ylamino)-2,2-dimethyl-2H-benzo[b][1,4]oxazin-3(4H)-one

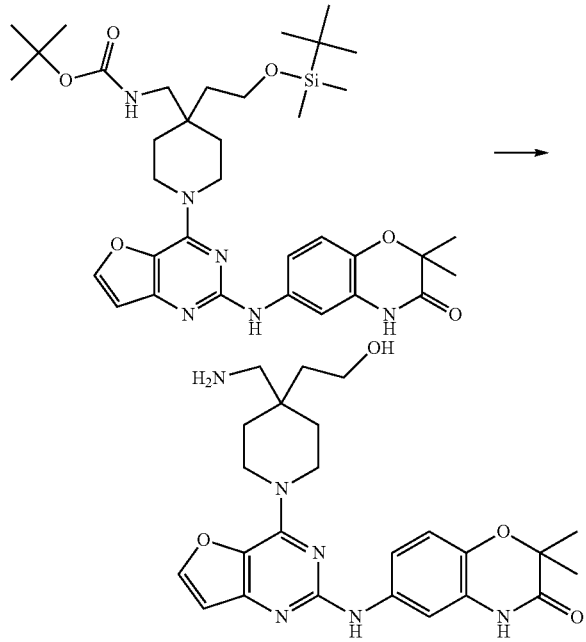

tert-Butyl (4-(2-(tert-butyldimethylsilyloxy)ethyl)-1-(2-(2,2-dimethyl-3-oxo-3,4-dihydro-2H-benzo[b][1,4]oxazin-6-ylamino)furo[3,2-d]pyrimidin-4-yl)piperidin-4-yl)methylcarbamate (0.40 g, 0.587 mmol, prepared using AH from 2-iodoethanol with TBDMSCl, AF with 1-benzylpiperidine-4-carbonitrile [Ryan] with tert-butyl(2-iodoethoxy)dimethylsilane, AE, O with $Boc_2O$, G, A with 2,4-dichlorofuro[3,2-d]pyrimidine [ArkPharm] and B with 6-amino-2,2-dimethyl-2H-benzo[b][1,4]oxazin-3(4H)-one [Arkpharm]) and an aqueous solution of aqueous HCl (4 M, 7.34 mL, 29.4 mmol) were dissolved in 1,4-dioxane (15 mL) and stirred for about 4 h at rt. The mixture was concentrated under vacuum and the residue was purified by Prep-TLC (EtOAc/pet ether 1:2) to give 6-(4-(4-(aminomethyl)-4-(2-hydroxyethyl)piperidin-1-yl)furo[3,2-d]pyrimidin-2-ylamino)-2,2-dimethyl-2H-benzo[b][1,4]oxazin-3 (4H)-one (0.121 g, 43%): LC/MS (Table 2, Method h) $R_t$=1.69 min.; MS m/z: 467 $(M+H)^+$. Syk $IC_{50}$=A

General Procedure AE: Reduction of a Nitrile to an Amine

A flask is charged with a nitrile and an organic solvent such as THF, DCM, 1,4-dioxane, MeOH, toluene (preferably THF), and the mixture may be optionally cooled to about 0 to 10° C. To the mixture is then added a reducing agent (such as LAH, Raney nickel/$H_2$, diborane, tin(II)chloride or cobalt(II) chloride). Optionally, the reducing agent can be added to the solvent followed by the cooling and then the nitrile is added. In cases where Raney nickel/$H_2$ is used, $NH_3$ or $NH_4OH$ may be added and water may be used as co-solvent. The mixture is stirred at about 25 to 80° C. (preferably rt) for about 2 to 20 h (preferably about 4 to 8 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then optionally concentrated in vacuo to give a residue as the target compound. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure AE

Preparation #AE.1
(1-Benzyl-4-methylpyrrolidin-3-yl)methanamine

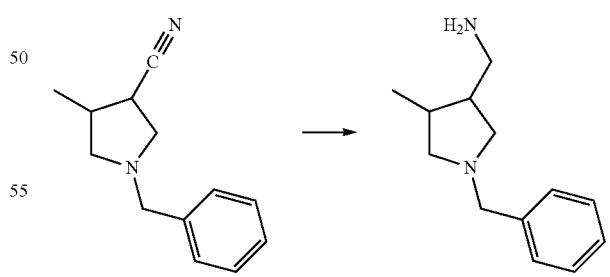

To a mixture of LAH (0.019 g, 0.499 mmol) in THF (5 mL) was added 1-benzyl-4-methylpyrrolidine-3-carbonitrile (0.050 g, 0.250 mmol, Tyger) at about 0° C., then the resulting mixture was stirred at about 25° C. for about 4 h. EtOAc (2 mL) and water (3 mL) were added and the precipitate formed was filtered off. The filtrate was concentrated to give (1-benzyl-4-methylpyrrolidin-3-yl)methanamine (0.05 g, 39%): LCMS (Table 2, Method 1) $R_t$=0.22 min.; MS m/z: 205 $(M+H)^+$.

General Procedure AF: Alkylation α to a Nitrile

A base such as LiHMDS, NaHMDS, KHMDS, LDA, NaH (1 to 5 equiv, preferably 1.5 equiv) is added to a nitrile compound in a suitable organic solvent such as THF, 1,4-dioxane, Et₂O, hexane, DMF, DMA (preferably THF) at about −78° C. to rt (preferably about −78° C. to 0° C.) and stirred for 0.5 to 2 h (preferably about 1 h). An alkylating agent (1 to 5 equiv, preferably 1.5 equiv) is added and the mixture stirred for 30 min to 24 h (preferably about 16 h). To the mixture is added an aqueous salt solution (preferably saturated NH₄Cl) and the mixture is extracted with a suitable organic solvent such as EtOAc, DCM, Et₂O (preferably DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl Na₂SO₃ or Na₂S₂O₃). The organic solution may then be optionally dried with a drying agent (such as anhydrous MgSO₄ or Na₂SO₄), filtered and concentrated in vacuo to give the targeted compound. Alternatively, the residue obtained by concentration of the organic extracts may be purified by HPLC or column chromatography to provide the target compound.

Illustration of General Procedure AF

Preparation #AF.1: Benzyl 4-cyano-4-methylpiperidine-1-carboxylate

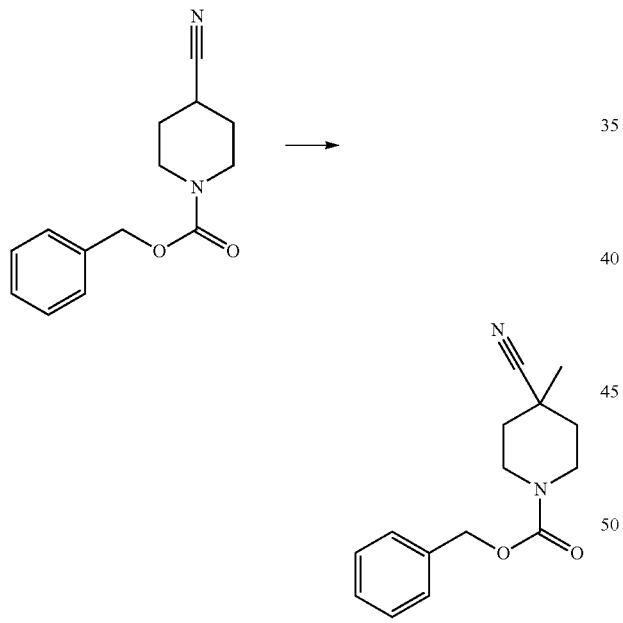

LiHMDS (47.6 mL, 47.6 mmol) was added dropwise via syringe to the mixture of benzyl 4-cyanopiperidine-1-carboxylate (8.00 g, 31.8 mmol, [Oakwood]) in THF (50 mL) at about −78° C. and stirred for about 1 h. MeI (6.76 g, 47.6 mmol) was added dropwise via syringe at about −78° C. and the mixture was stirred overnight at rt. The solution was cooled to 0° C. and saturated aqueous NH₄Cl (200 mL) was added. The mixture was extracted with DCM (3×300 mL). The combined organic extracts were dried over anhydrous Na₂SO₄, filtered and concentrated in vacuo. The sample was deposited onto silica gel and purified by column chromatography eluting with 10:1 pet ether/EtOAc to give benzyl 4-cyano-4-methylpiperidine-1-carboxylate (6.6 g, 74%): LC/MS (Table 2, Method i) $R_t$=2.03 min; MS m/z: 259 (M+H)⁺.

General Procedure Ag: Removal of a Boc Group from an N-Boc Amine or Heteroaromatic and an Acyl Group from an N'-Acyl Amine To a compound containing an N-Boc amine or heteroaromatic and an N'-acyl amine (preferably 1 equiv) are added an organic solvent (such as MeOH or EtOH, preferably MeOH) and an acid (such as TFA or concentrated HCl, preferably concentrated HCl) (preferably as a 1:1 ratio of solvent to acid). The resulting mixture is heated at about 50 to 100° C. (preferably about 90° C.) for about 10 to 48 h (preferably about 32 h). The mixture is cooled to rt and the resulting solid is collected by vacuum filtration and optionally washed with water. The solid is optionally dissolved in an acid (such as aqueous 1 to 6 M HCl) and filtered to remove any undissolved material. The filtrate is neutralized with the addition of a base (such as NaHCO₃, Na₂CO₃, KHCO₃, K₂CO₃, NH₄OH or NaOH, preferably NH₄OH) and the solid is collected by vacuum filtration.

Illustration of General Procedure AG

Example #AG.1

4-(3-(Aminomethyl)pyrrolidin-1-yl)-N-(3-methyl-1H-indazol-6-yl)furo[3,2-d]pyrimidin-2-amine

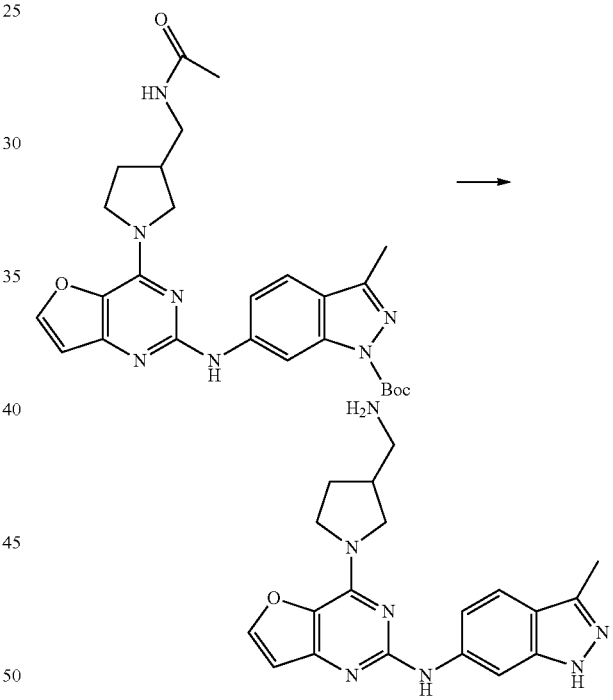

To a solution of tert-butyl 6-(4-(3-(acetamidomethyl)pyrrolidin-1-yl)furo[3,2-d]pyrimidin-2-ylamino)-3-methyl-1H-indazole-1-carboxylate (0.57 g, 1.1 mmol, prepared using E.1 from tert-butyl 3-(aminomethyl)pyrrolidine-1-carboxylate hydrochloride [Astatech] with acetyl chloride, C, A with 2,4-dichlorofuro[3,2-d]pyrimidine [ArkPharm] and B with Example #3, Step B) in MeOH (12 mL) was added concentrated HCl (12 mL). The mixture was stirred for about 32 h at about 90° C. The mixture was cooled to rt, and a white precipitate formed that was collected by vacuum filtration and washed with water. The solid was dissolved in hot aqueous 1 M HCl and the suspension was filtered while hot. To the filtrate was added aqueous NH₄OH to reach a pH~9, and the resulting precipitate was collected to give 4-(3-(aminomethyl)pyrrolidin-1-yl)-N-(3-methyl-1H-indazol-6-yl)furo[3,2-d]pyrimidin-2-amine (0.27 g, 61%): LC/MS (Table 2, Method h) $R_t$=1.61 min; MS m/z: 364 (M+H)⁺. Syk IC₅₀=A

TABLE AG.1

Examples of the removal of a Boc protecting group from an N-Boc protected heteroarmatic ring and an acyl group from an N'-acyl protected amine using General Procedure AG

| Amine | Product | Example # | $R_t$ min (Table 2, Method) | m/z ESI+ $(M + H)^+$ | Syk $IC_{50}$ |
|---|---|---|---|---|---|
| tert-Butyl 6-(4-(3-(acetamidomethyl)pyrrolidin-1-yl)furo[3,2-d]pyrimidin-2-ylamino)-1H-indazole-1-carboxylate (prepared using E.1 from tert-butyl 3-(aminomethyl)pyrrolidine-1-carboxylate [Astatech] with acetyl chloride, C, A with 2,4-dichlorofuro[3,2-d]pyrimidine [ArkPharm] and B with tert-butyl 6-amino-1H-indazole-1-carboxylate [Frontier]) | (structure) | AG.1.1 | 1.58 (h) | 350 | B |

General Procedure AH: Formation of an O-Silyl Ether

To a mixture of an alcohol (1 equiv) in an organic solvent such as DCM, DMF, THF (preferably DMF) is added in no particular order a silylating agent (1 to 5 equiv, preferably 1.2 equiv) such as TMSCl, TESCl, TBDMSCl, TBDMSOTf, hexamethyldisilylamine, (preferably TBDMSCl) a base (1 to 10 equiv, preferably 2.5 equiv) such as TEA, 2,6-lutidine or imidazole (preferably TEA) and optionally an additive such as DMAP (0.1 to 0.6 equiv) may be added. The mixture is stirred at about 10 to 60° C. (preferably rt) for about 1 to 24 h (preferably about 2 to 4 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, EtOH) and then optionally concentrated in vacuo to give a residue as the target compound. Either the residue or the solution may be optionally partitioned between water and an organic solvent (such as EtOAc, Et₂O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl Na₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure AH

Preparation # AH.1: Benzyl 4-azido-3-(tert-butyldimethylsilyloxy)azepane-1-carboxylate

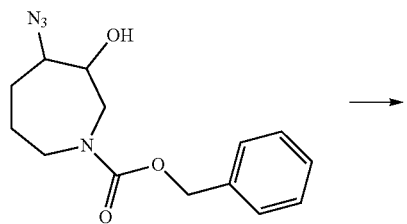

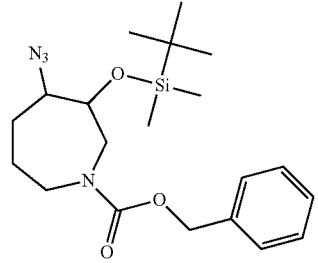

TBDMSOTf (0.010 g, 0.038 mmol) was added drop-wise to the mixture of benzyl 4-azido-3-hydroxyazepane-1-carboxylate (0.010 g, 0.034 mmol, WO 2010/114971, Example 90.5) and TEA (0.0096 mL, 0.069 mmol) in DCM (50 mL). The mixture was stirred at about 25° C. for about 3 h. The mixture was concentrated under reduced pressure and the residue was purified by Prep-TLC (EtOAc/pet ether ¼) to give benzyl 4-azido-3-(tert-butyldimethylsilyloxy)azepane-1-carboxylate (0.005 g, 36%). The material was used without characterization.

General Procedure AI: Hydrolysis of an Ester to a Carboxylic Acid

To a flask containing an ester (preferably 1 equiv) either neat or in an organic solvent (such as 1,4-dioxane, MeOH, or THF/MeOH, preferably MeOH) is added an aqueous base (such as aqueous NaOH or LiOH; 1-10 equiv, preferably 2-6 equiv). The mixture is stirred at about 0 to 100° C. (preferably about 25 to 60° C.) for about 1 to 48 h (preferably about 4 to 24 h). The mixture is then acidified by the addition of a suitable aqueous acid (such as aqueous HCl). The mixture may optionally be concentrated in vacuo to give the target compound as a carboxylate salt. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, EtOH) and then optionally concentrated in vacuo to give a residue as the target compound. Either the residue or the solution may be optionally partitioned between water and an organic solvent (such as EtOAc, Et₂O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AI

Preparation #AI.1: (6-(4-(Cyclopropylamino)furo[3,2-d]pyrimidin-2-ylamino)-1-((2-(trimethylsilyl)ethoxy)methyl)-1H-indazole-3-carboxylic acid

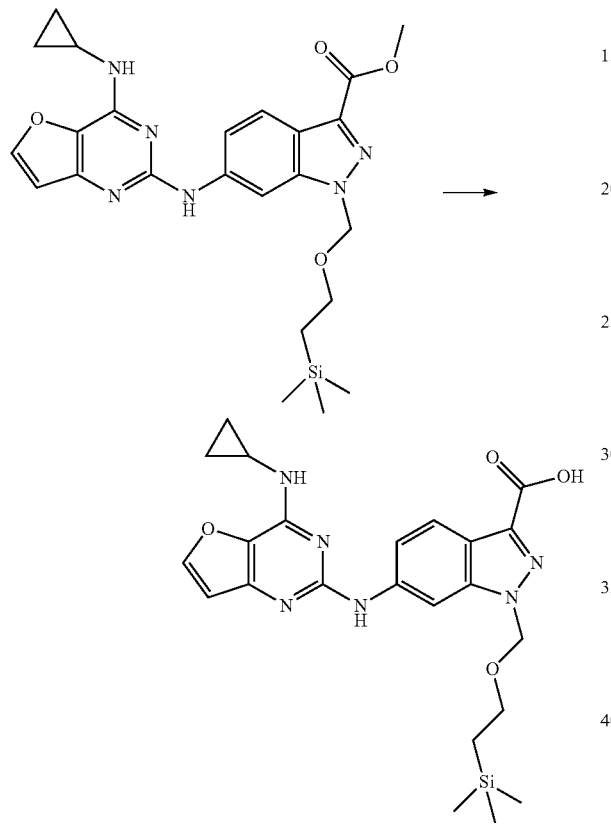

Methyl 6-(4-(cyclopropylamino)furo[3,2-d]pyrimidin-2-ylamino)-1-(2-(trimethylsilyl)ethoxy)methyl)-1H-indazole-3-carboxylate (0.839 g, 1.70 mmol, prepared using I from Preparation #6 and B with Preparation #A.1) was added to MeOH (15.4 mL). A solution of NaOH (0.102 g, 2.54 mmol) in water (1.54 mL) was added in one portion and the mixture stirred at rt for about 18 h. The temperature was increased to about 50° C. After about 18 h mixture was allowed to cool to rt. The solvents were removed under reduced pressure. DCM (30 mL) and water (5 mL) were added. The aqueous layer was acidified with an aqueous solution of 1 N HCl (3 mL). The precipitate was collected by vacuum filtration. The organic layer was concentrated and combined with the solid precipitate. The solid was dissolved in a mixture of 6:3:1 DCM/MeOH/concentrated NH$_4$OH and adsorbed onto silica gel (3 g). The residue was purified by column chromatography (40 g silica gel) eluting with 6:3:1 CHCl$_3$/MeOH/NH$_4$OH. The solvents were removed under reduced pressure. The residue was taken up in a small amount of MeOH and the product was precipitated by the addition of Et$_2$O (30 mL). The resulting solid was collected by vacuum filtration and dried under vacuum at 50° C. over P$_2$O$_5$ to provide (6-(4-(cyclopropylamino)furo[3,2-d]pyrimidin-2-ylamino)-1-((2-(trimethylsilyl)ethoxy)methyl)-1H-indazole-3-carboxylic acid (0.463 g, 57%): LC/MS (Table 2, Method c) R$_t$=2.24 min.; MS m/z: 481 (M+H)$^+$.

General Procedure AJ: Formation of an N-Tosyl Heteroaromatic

A flask that is cooled to about −78 to 0° C. is charged in no particular order with an organic solvent (such as DMF or THF, preferably DMF) and NaH (60% dispersion in mineral oil, 1-2 equiv, preferably 1.2 equiv) and a heteroaryl compound (preferably 1 equiv). The resulting mixture is stirred at about −78 to 0° C. (preferably about 0° C.) for about 15 min to 90 min (preferably about 30 to 90 min) followed by the addition of TsCl (1 to 2 equiv, preferably 1.1 equiv). The mixture is stirred at about −78 to 0° C. (preferably about 0 to 5° C.) for about 0.5 to 2 h (preferably about 1.5 h) and at about 0 to 40° C. (preferably rt) for about 0.5 to 5 h (preferably about 3 to 5 h). To the mixture are added an organic solvent (such as DCM or EtOAc) and water. The layers are separated and the organic solution is optionally washed with water and/or brine, dried over anhydrous Na$_2$SO$_4$ or MgSO$_4$, filtered or decanted and concentrated under reduced pressure.

Illustration of General Procedure AJ

Preparation #AJ.1: tert-Butyl 3-tosyl-6,7-dihydro-3H-imidazo[4,5-c]pyridine-5(4H)-carboxylate

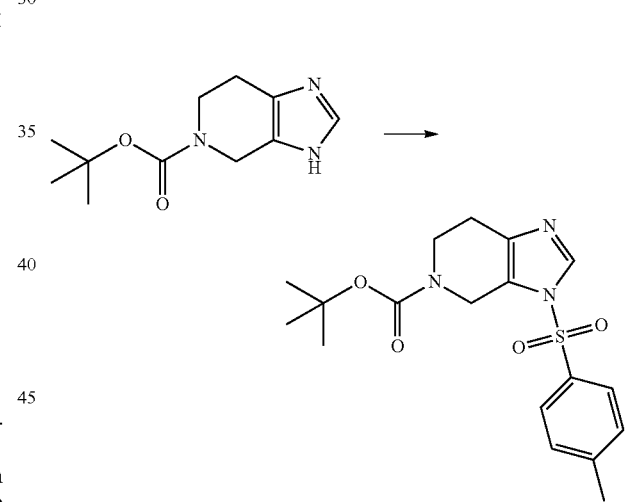

A flask was charged with tert-butyl 6,7-dihydro-3H-imidazo[4,5-c]pyridine-5(4H)-carboxylate (0.44 g, 2.0 mmol, WO2009158394, Example M-In-1) and DMF (10 mL). The mixture was cooled to about 0° C. and NaH (60% dispersion in mineral oil, 0.095 g, 2.4 mmol) was added. The mixture was stirred at about 0° C. for about 20 min followed by the addition of TsCl (0.41 g, 2.2 mmol). The resulting mixture was stirred at about 0° C. for about 90 min and then at about rt for about 3.5 h. The mixture was poured into DCM (40 mL) and water (20 mL) was added. The layers were separated and the organic solution was washed with brine, dried over MgSO$_4$, filtered, and concentrated under reduced pressure. The crude material was purified by silica gel chromatography eluting with a gradient of 0 to 50% EtOAc in DCM to give tert-butyl 3-tosyl-6,7-dihydro-3H-imidazo[4,5-c]pyridine-5(4H)-carboxylate (0.21 g, 28%): LC/MS (Table 2, Method n) R$_t$=2.53 min; MS m/z: 378 (M+H)$^+$.

General Procedure AK: Removal of a Boc Group from an N-Boc Amine or Heteroaromatic and a Tosyl Group from an N'-Tosyl Heteroaromatic To a solution of a compound containing an N-Boc-amine or heteroaromatic and an N'-tosyl-heteroaromatic (preferably 1 equiv) in an organic solvent such as 1,4-dioxane, THF, or DME, preferably 1,4-dioxane) is added an aqueous base such as NaOH, KOH, or $Na_2CO_3$, preferably NaOH (2 to 20 equiv, preferably 3 to 5 equiv). The mixture is stirred at about 25 to 90° C. (preferably about 65° C.) for about 1 to 24 h (preferably about 4.5 h). The temperature is adjusted to rt and an organic solvent (such as DCM or EtOAc) and saturated aqueous $NH_4Cl$ are added. The layers are separated and the organic solution is optionally washed with water and/or brine, dried over anhydrous $MgSO_4$ or $Na_2SO_4$, filtered or decanted and concentrated under reduced pressure. In a case where the product precipitates from the organic solvent, this solid can be collected by vacuum filtration. Alternatively, the mixture can be directly concentrated under reduced pressure and purified.

Illustration of General Procedure AK

Example #AK.1

4-(6,7-Dihydro-3H-imidazo[4,5-c]pyridin-5(4H)-yl)-N-(3-methyl-1H-indazol-6-yl)furo[3,2-d]pyrimidin-2-amine

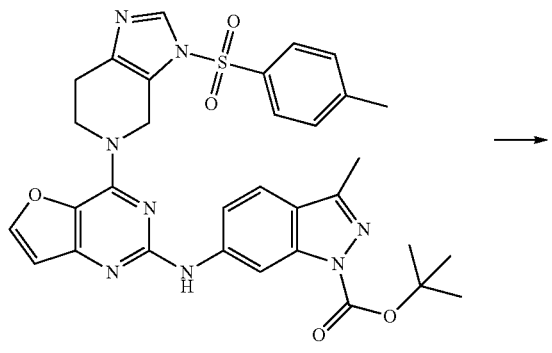

→

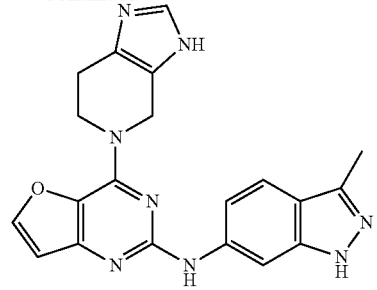

A flask was charged with tert-butyl 3-methyl-6-(4-(3-tosyl-6,7-dihydro-3H-imidazo[4,5-c]pyridin-5 (4H)-yl)furo[3,2-d]pyrimidin-2-ylamino)-1H-indazole-1-carboxylate (0.040 g, 0.062 mmol, prepared using C from Preparation #AJ.1, A with 2,4-dichlorofuro[3,2-d]pyrimidine [ArkPharm] and B with Example #3, Step B) and 1,4-dioxane (1.0 mL). To the mixture was added 2 N aqueous NaOH, (0.094 mL, 0.19 mmol) and the mixture was heated to about 65° C. for about 4.5 h. The mixture was cooled to rt and DCM (10 mL) and saturated aqueous $NH_4Cl$ (3 mL) were added. The layers were separated and a solid remained in the aqueous layer. The solid was collected by vacuum filtration and dried overnight at about 60° C. in a vacuum oven to give 4-(6,7-dihydro-3H-imidazo[4,5-c]pyridin-5 (4H)-yl)-N-(3-methyl-1H-indazol-6-yl)furo[3,2-d]pyrimidin-2-amine (0.008 g, 33%): LC/MS (Table 2, Method c) $R_t$=1.60 min; MS m/z: 387 $(M+H)^+$. Syk $IC_{50}$=A

TABLE AK.1

Examples for the removal of a Boc group from an N-Boc protected amine and a tosyl group from an N'-tosyl protected heteroaromatic ring using General Procedure AK

| N-Boc N'-tosyl Protected Diamine | Product | Example # | $R_t$ min (Table 2, Method) | m/z ESI+ $(M+H)^+$ | Syk $IC_{50}$ |
|---|---|---|---|---|---|
| tert-Butyl 3-methyl-6-(4-(1-tosyl-4,5,6,7-tetrahydro-1H-indazol-6-ylamino)furo[3,2-d]pyrimidin-2-ylamino)-1H-indazole-1-carboxylate (prepared using AJ from tert-butyl 4,5,6,7-tetrahydro-1H-indazol-6-ylcarbamate [A&C Pharmtech], C, A with 2,4-dichlorofuro[3,2-d]pyrimidine [ArkPharm] and B with Example #3, Step B) | | AK.1.1 | 1.66 (c) | 401 | B |

General Procedure AL: Formation of a Cyclic Carbamate from an Aminoalcohol

To a flask containing an aminoalcohol (1 equiv) in an organic solvent such as THF, PhH, DMF, DCM (preferably DMF) is added CDI (1 to 2 equiv, preferably 1 equiv). The mixture is stirred at about 25 to 80° C. (preferably about 60 to 65° C.) for about 0.5 to 20 h (preferably about 0.5 to 2 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AL

Preparation #AL.1: (4aS,8aS)-7-Benzyloctahydro-2H-pyrido[4,3-e][1,3]oxazin-2-one

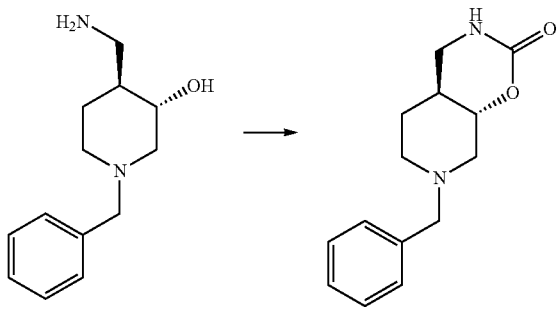 [SMILES: NC[C@@H]1CCN(Cc2ccccc2)C[C@H]1O ; O=C1NC[C@@H]2CCN(Cc3ccccc3)C[C@H]2O1]

In a flask, was added (3S,4S)-4-(aminomethyl)-1-benzylpiperidin-3-ol (1.0 g, 4.5 mmol, Sunshine Labs), DMF (10 mL) and CDI (0.736 g, 4.54 mmol). The mixture was heated to about 65° C. for about 40 min. To the mixture was added EtOAc (20 mL) and washed with water (3×20 mL). The aqueous layers were combined and extracted with DCM (2×20 mL). The organic layers were combined, dried over MgSO$_4$, filtered and concentrated under vacuum to give (4aS,8aS)-7-benzyloctahydro-2H-pyrido[4,3-e][1,3]oxazin-2-one (0.773 g, 69%): LC/MS (Table 2, Method c) R$_t$=1.11 min.; MS m/z: 247 (M+H)$^+$.

General Procedure AM: Hydrolysis of a Cyclic Carbamate to an Aminoalcohol

To a flask containing a cyclic carbamate (preferably 1 equiv) in an organic solvent (such as 1,4-dioxane, MeOH, or THF/MeOH, preferably MeOH) is added an aqueous base (such as aqueous NaOH or LiOH, 5 to 40 equiv, preferably 15 to 25 equiv). The mixture is stirred at about 45 to 150° C. (preferably 75 to 110° C.) for about 0.5 to 20 h (preferably 0.5 to 12 h) either thermally or in a microwave for about 0.5 to 2 h (preferably 0.5 to 1 h), preferably in a microwave. The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AM

Example #AM.1

4-(Aminomethyl)-1-(2-(3-methyl-1H-indazol-6-ylamino)furo[3,2-d]pyrimidin-yl)piperidin-4-ol

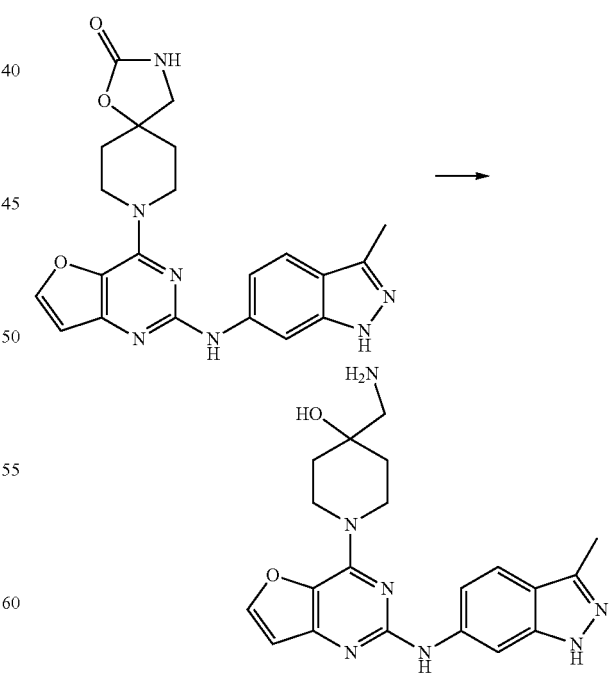

To a vial was added 8-(2-(3-methyl-1H-indazol-6-ylamino)furo[3,2-d]pyrimidin-4-yl)-1-oxa-3,8-diazaspiro[4.5]decan-2-one (0.100 g, 0.238 mmol, prepared using A from 2,4-dichlorofuro[3,2-d]pyrimidine [ArkPharm] with 1-oxa-3,8-diazaspiro[4.5]decan-2-one [Chembridge], B with Example #3, Step B and C) in MeOH (3 mL). Then aqueous NaOH (5 M, 0.715 mL, 3.58 mmol) was added. The mixture was heated in a microwave at about 100° C. for about 30 min (300 psi maximum pressure, 2 min ramp, 250 max watts). Aqueous NaOH (5 M, 0.350 mL, 1.75 mmol) was added. The mixture was heated in a microwave at about 120° C. for about 40 min (300 psi maximum pressure, 2 min ramp, 250 max watts). The mixture was filtered and the filtrate was cooled on ice and the precipitate formed was collected via filtration and dried in a vacuum oven at about 75° C. for about 15 h to give 4-(aminomethyl)-1-(2-(3-methyl-1H-indazol-6-ylamino) furo[3,2-d]pyrimidin-yl)piperidin-4-ol (0.07 g, 75%): LC/MS (Table 2, Method c) $R_t$=1.44 min.; MS m/z: 394 (M+H)$^+$. Syk IC$_{50}$=A General Procedure AN: Removal of a Benzylidine from a Benzophenone Imine To a benzophenone imine (preferably 1 equiv) in an organic solvent (such as MeOH or EtOH) is added a Pd catalyst (for example Pd(OH)$_2$ on C or Pd/C; preferably Pd/C) (0.01 to 0.5 equiv, preferably 0.1 to 0.4 equiv). The mixture is shaken or stirred at about 25 to 60° C. (preferably rt) for about 1 to 96 h (preferably about 16 h) under a H$_2$ atmosphere at about 10 to 60 psi H$_2$ (preferably about 10 to 20 psi). The mixture is adjusted to rt and the H$_2$ source is removed and the flask is charged with N$_2$. The mixture is filtered through a pad of Celite® and the filtrate is concentrated under reduced pressure to give the desired product.

TABLE AM

Examples prepared by the hydrolysis of a cyclic carbamate to an amino-alcohol using General Procedure AM

| Cyclic carbamate | Product | Example # | $R_t$ min (Table 2, Method) | m/z ESI+ (M + H)$^+$ | Syk IC$_{50}$ |
|---|---|---|---|---|---|
| 2,2-Dimethyl-6-(4-(2-oxo-1-oxa-3,8-diazaspiro[4.5]decan-8-yl)furo[3,2-d]pyrimidin-2-ylamino)-2H-benzo[b][1,4]oxazin-3(4H)-one (prepared using A from 2,4-dichlorofuro[3,2-d]pyrimidine [ArkPharm] with 1-oxa-3,8-diazaspiro[4.5]decan-2-one [Chembridge] and B with 6-amino-2,2-dimethyl-2H-benzo[b][1,4]oxazin-3(4H)-one [ArkPharm]) | | AM.1.1 | 1.26 (c) | 439 | A |
| (4aS,8aS)-7-(2-(2,2-Dimethyl-3-oxo-3,4-dihydro-2H-benzo[b][1,4]oxazin-6-ylamino)furo[3,2-d]pyrimidin-4-yl)octahydro-2H-pyrido[4,3-e][1,3]oxazin-2-one (prepared using AL from (3S,4S)-4-(aminomethyl)-1-benzylpiperidin-3-ol [Sunshine Labs], G, A with 2,4-dichlorofuro[3,2-d]pyrimidine[ArkPharm] and B with 6-amino-2,2-dimethyl-2H-benzo[b][1,4]oxazin-3(4H)-one [ArkPharm]) | | AM.1.2 | 1.22 (c) | 439 | A |
| 6-(4-(4-(Aminomethyl)-4-hydroxypiperidin-1-yl)furo[3,2-d]pyrimidin-2-ylamino)-3,3-dimethylindolin-2-one (prepared using A from 2,4-dichlorofuro[3,2-d]pyrimidine [ArkPharm] with 1-oxa-3,8-diazaspiro[4.5]decan-2-one [Chembridge] and B with 6-amino-3,3-dimethylindolin-2-one [Astatech]) | | AM.1.3 | 1.14 (c) | 423 | A |

Illustration of General Procedure AN

Preparation #AN.1: 4-Methyl-1-(tetrahydro-2H-pyran-2-yl)-1H-indazol-6-amine

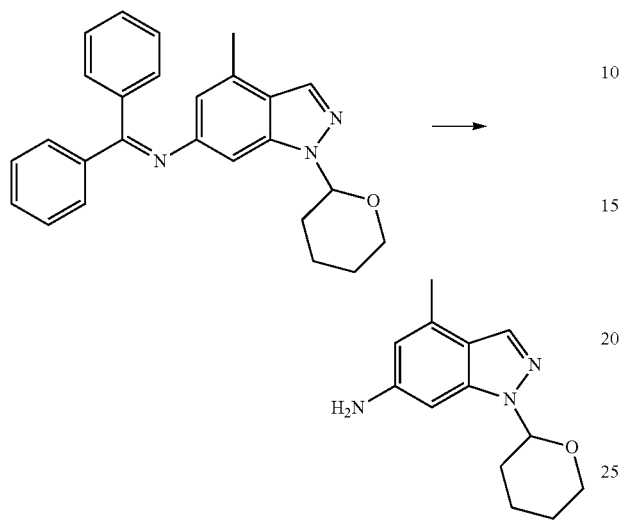

A mixture of N-(diphenylmethylene)-4-methyl-1-(tetrahydro-2H-pyran-2-yl)-1H-indazol-6-amine (0.80 g, 2.0 mmol, prepared using B from Preparation #AB.1 with diphenylmethanimine [Alfa Aesar]) and Pd/C (0.080 g, 0.752 mmol, 10 wt %) in MeOH (10 mL) were stirred at rt for about 16 h under a $H_2$ atmosphere. The mixture was filtered through Celite® and the filter cake was washed with MeOH. The filtrate was concentrated to provide 4-methyl-1-(tetrahydro-2H-pyran-2-yl)-1H-indazol-6-amine (0.45 g, 74%): LC/MS (Table 2, Method h) $R_t$=1.76 min; MS m/z: 232 (M+H)$^+$.

Example #1

$N^4$-Allyl-$N^2$-(4-(methylsulfonyl)phenyl)furo[3,2-d]pyrimidine-2,4-diamine

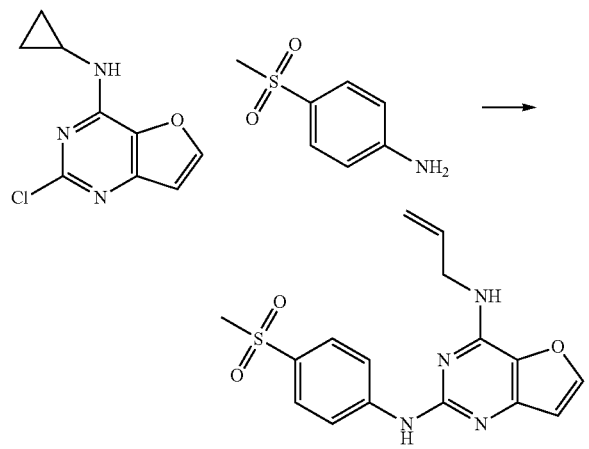

A vial was charged with 2-chloro-N-cyclopropylfuro[3,2-d]pyrimidin-4-amine (0.09 g, 0.429 mmol, Preparation #A.1), 4-(methylsulfonyl)aniline (0.077 g, 0.451 mmol, Oakwood), X-Phos (0.020 g, 0.043 mmol), $Pd_2dba_3$ (0.020 g, 0.021 mmol), $K_2CO_3$ (0.062 g, 0.451 mmol) and t-BuOH (3.5 mL). The vial was purged with argon and heated at about 100° C. overnight. The mixture was diluted with $CHCl_3$ (about 10 mL) passed through a $SiCO_3$ SPE cartridge and concentrated. The crude product was purified by preparative reverse phase HPLC (Table 2, Method a) to provide $N^4$-allyl-$N^2$-(4-(methylsulfonyl)phenyl)furo[3,2-d]pyrimidine-2,4-diamine (0.041 g, 27%): $^1$H NMR (DMSO-$d_6$) δ 9.53 (s, 1H), 8.11 (d, J=2.1 Hz, 1H), 8.02 (m, 3H), 7.72 (d, J=8.9 Hz, 2H), 6.80 (d, J=2.1 Hz, 1H), 6.00 (ddd, J=17.1, 10.2, 5.1 Hz, 1H), 5.22 (dd, J=17.1, 1.6 Hz, 1H), 5.11 (dd, J=10.5, 1.6 Hz, 1H), 4.14 (dd, J=5.1 Hz, 2H), 3.11 (s, 3H). Syk $IC_{50}$=B.

Example #2

$N^2$-Benzyl-$N^4$-(5-cyclopropyl-1H-pyrazol-3-yl)furo[3,2-d]pyrimidine-2,4-diamine

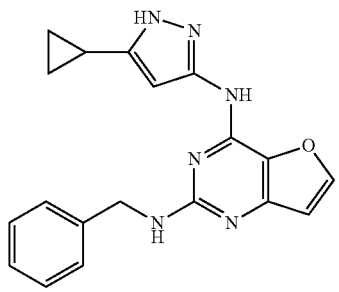 [SMILES: c1ccc(CNc2nc(Nc3cc(C4CC4)[nH]n3)c3occc3n2)cc1]

Step A: 2-Chloro-N-(5-cyclopropyl-1H-pyrazol-3-yl)furo[3,2-d]pyrimidin-4-amine

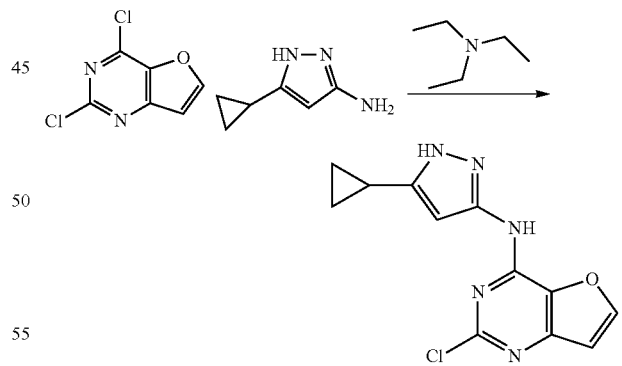

A flask was charged with 2-chloro-N-(5-cyclopropyl-1H-pyrazol-3-yl)furo[3,2-d]pyrimidin-4-amine, TEA (0.286 g, 2.83 mmol), EtOH (5 mL) and 5-cyclopropyl-1H-pyrazol-3-amine (0.174 g, 1.41 mmol, WO 2007/099323 page 134). The mixture was stirred at about 60° C. for about 18 h and concentrated under reduced pressure. The residue was purified by preparative reverse phase HPLC to give 2-chloro-N-(5-cyclopropyl-1H-pyrazol-3-yl)furo[3,2-d]pyrimidin-4-amine (0.042 g, 11%). LC/MS $R_t$=1.31 min; MS m/z 276.4 (M+H)$^+$.

Step B: N²-Benzyl-N⁴-(5-cyclopropyl-1H-pyrazol-3-yl)furo[3,2-d]pyrimidine-2,4-diamine

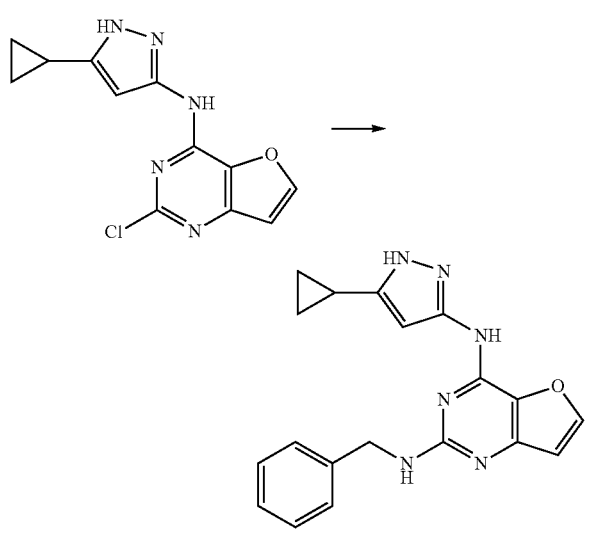

To a vial was added 2-chloro-N-(5-cyclopropyl-1H-pyrazol-3-yl)furo[3,2-d]pyrimidin-4-amine (0.20 g, 0.73 mmol), benzyl amine (0.79 mL, 7.3 mmol), X-Phos (0.02 g, 0.04 mmol) K₂CO₃ (0.50 g, 3.6 mmol), and Pd₂dba₃ (0.04 g, 0.04 mmol). To the vial was added t-BuOH (3.6 mL) and tube was sealed. The tube was evacuated, purged with nitrogen three times and stirred over night at about 100° C. To the mixture was added additional benzyl amine (0.79 mL, 7.3 mmol), X-Phos (0.02 g, 0.04 mmol), and Pd₂dba₃ (0.04 g, 0.04 mmol). The mixture was stirred at about 100° C. for about 26 h. The mixture was filtered, the filter pad was washed with DCM and then the solvent was removed in vacuo. The crude material was added to a silica gel column and was eluted with EtOAc/DCM (50% to 100% gradient) followed by 2.0 M NH₃ in EtOH/DCM (2%) to give N²-benzyl-N⁴-(5-cyclopropyl-1H-pyrazol-3-yl)furo[3,2-d]pyrimidine-2,4-diamine (0.013 g, 5%). LC/MS $R_t$=1.30 min; MS m/z 347.29 (M+H)⁺. Syk IC$_{50}$=B.

Example #3

N⁴-Cyclopropyl-N²-(3-methyl-1H-indazol-6-yl)furo[3,2-d]pyrimidine-2,4-diamine

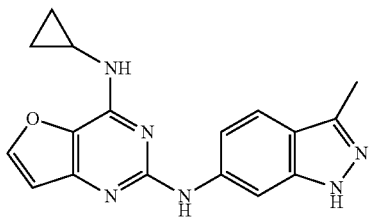 [SMILES: Cc1n[nH]c2cc(Nc3nc(NC4CC4)c4occc4n3)ccc12]

Step A: tert-Butyl 3-methyl-6-nitro-1H-indazole-1-carboxylate

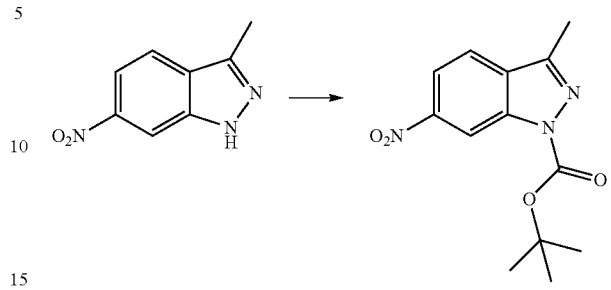

To a flask was added 3-methyl-6-nitro-1H-indazole (5.00 g, 28.2 mmol, ArkPharm), TEA (3.93 mL, 28.2 mmol), DMAP (0.345 g, 2.82 mmol) and DCM (282 mL). Boc₂O (6.47 g, 29.6 mmol) was added and the mixture was stirred at rt for about 8 d. The mixture was washed with 1 N HCl (100 mL) and the layers separated. The aqueous layer was extracted with DCM (20 mL). The combined extracts were washed with brine (50 mL), dried over MgSO₄, filtered, and concentrated under reduced pressure to remove most of the DCM and leave a suspension. Heptane (100 mL) was added and the mixture concentrated to about 50 mL to remove as much of the DCM as possible. The resulting precipitate was collected by vacuum filtration and washed with heptane (15 mL) to provide tert-butyl 3-methyl-6-nitro-1H-indazole-1-carboxylate (7.4 g, 95%): LC/MS (Table 2, Method c) $R_t$=2.62 min.; MS m/z: 278 (M+H)⁺. ¹H NMR (400 MHz, DMSO-d₆) δ 8.82 (d, J=1.5 Hz, 1H), 8.18 (dd, J=8.7, 2.0 Hz, 1H), 8.12-8.08 (m, 1H), 2.58 (s, 3H), 1.65 (s, 9H).

Step B: tert-Butyl 6-amino-3-methyl-1H-indazole-1-carboxylate

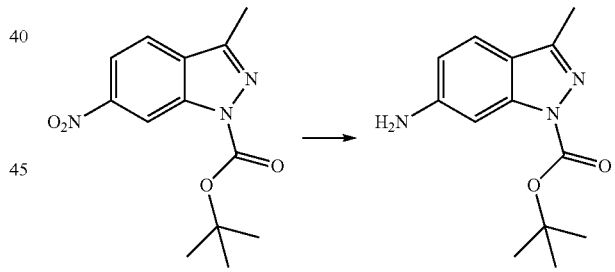

tert-Butyl 3-methyl-6-nitro-1H-indazole-1-carboxylate (7.40 g, 26.7 mmol) was dissolved in EtOH (534 mL). To the solution was added Pd/C (10 wt %, 1.42 g, 1.33 mmol). The mixture was flushed with H₂, and placed under an atmosphere of H₂ at atmospheric pressure at rt for about 6 h. The mixture was filtered through Celite® and washed through with MeOH. The solvents were removed under reduced pressure. The residue was purified by column chromatography (120 g silica gel) eluting with 20-80% EtOAc/heptane to give a solid. The solid redissolved in DCM (20 mL) and heptane (50 mL) was added. The mixture was concentrated to remove the DCM. The resulting precipitate was collected by vacuum filtration and washed with heptane (20 mL) to provide tert-butyl 6-amino-3-methyl-1H-indazole-1-carboxylate (4.57 g, 69%): LCMS (Table 2, Method c) $R_t$=1.81 min.; MS m/z: 248 (M+H)⁺, ¹H NMR (400 MHz, DMSO-d₆) δ 7.36 (d, J=8.5 Hz, 1H), 7.14 (d, J=1.7 Hz, 1H), 6.59 (dd, J=8.5, 1.9 Hz, 1H), 5.71 (d, J=19.5 Hz, 2H), 2.33 (s, 3H), 1.58 (s, 9H).

Step C:
2-Chloro-N-cyclopropylfuro[3,2-d]pyrimidin-4-amine

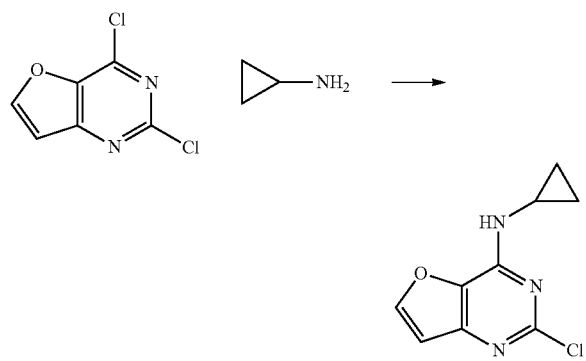

2,4-Dichlorofuro[3,2-d]pyrimidine (30 g, 159 mmol, Ark-Pharm) was stirred in 1,4-dioxane (330 mL). TEA (26.5 mL, 190 mmol) and cyclopropylamine (12.2 mL, 175 mmol) were added and the mixture stirred at rt overnight. The mixture was diluted with EtOAc (500 mL) and washed with saturated aqueous NaHCO$_3$ (400 mL). The aqueous layer was extracted with EtOAc (2×150 mL). The organic layers were combined, dried with anhydrous MgSO$_4$, filtered, and concentrated in vacuo. The residue was suspended in water (400 mL) and allowed to stir at rt for about 1 h. The suspension was filtered and the solid was dried in a vacuum oven at about 70° C. overnight to give 2-chloro-N-cyclopropylfuro[3,2-d]pyrimidin-4-amine (31.9 g, 96%); LC/MS (Table 2, Method c) R$_t$=1.58 min.; MS m/z: 210 (M+H)$^+$, $^1$H NMR (400 MHz, CDCl$_3$) δ 7.77 (d, J=2.1 Hz, 1H), 6.79 (d, J=2.1 Hz, 1H), 5.57-5.50 (m, 1H), 3.12-3.01 (m, 1H), 1.02-0.88 (m, 2H), 0.77-0.65 (m, 2H).

Step D: tert-Butyl 6-(4-(cyclopropylamino)furo[3,2-d]pyrimidin-2-ylamino)-3-methyl-1H-indazole-1-carboxylate

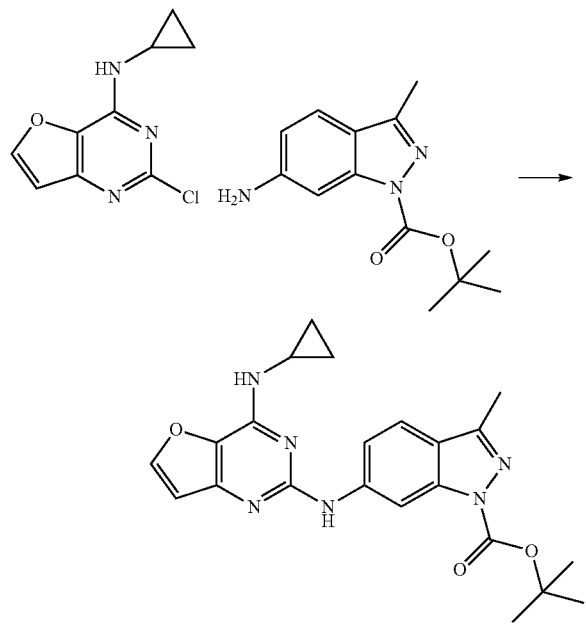

In a flask, RuPhos (3.63 g, 7.79 mmol) and Pd$_2$dba$_3$ (3.56 g, 3.89 mmol) were combined in t-AmOH (100 mL). The mixture was degassed by bubbling N$_2$ into the solution. The mixture was heated to about 60° C. for about 30 min. Then Cs$_2$CO$_3$ (38.3 g, 117 mmol), tert-butyl 6-amino-3-methyl-1H-indazole-1-carboxylate (16.0 g, 64.9 mmol), and 2-chloro-N-cyclopropylfuro[3,2-d]pyrimidin-4-amine (13.6 g, 64.9 mmol) were added in one portion. To the mixture was added t-AmOH (200 mL) and the mixture was placed under vacuum, purged with N$_2$, and then stiffed at about 75° C. for about 15 h. The mixture was filtered through a plug of Celite®. The filtrate was concentrated and redissolved in DCM (50 mL). The mixture was purified by column chromatography (0-2.5% MeOH in DCM over 30 min on 330 g silica gel) to give a solid. The solid was dissolved in DCM (20 mL) and after about 10 min at rt, a thick precipitate formed which was collected via filtration. The solid was washed with DCM (25 mL) and dried in a vacuum oven at about 70° C. for about 12 h to give tert-butyl 6-(4-(cyclopropylamino)furo[3,2-d]pyrimidin-2-ylamino)-3-methyl-1H-indazole-1-carboxylate (12.5 g, 46%); LC/MS (Table 2, Method c) R$_t$=2.29 min.; MS m/z: 421 (M+H)$^+$, $^1$H NMR (400 MHz, CDCl$_3$) δ 8.76 (s, 1H), 7.64 (d, J=2.1 Hz, 1H), 7.50 (d, J=8.6 Hz, 1H), 7.42 (dd, J=8.6, 1.8 Hz, 1H), 7.26 (s, 1H), 6.67 (d, J=2.1 Hz, 1H), 5.29 (s, 1H), 3.20-3.12 (m, 1H), 2.55 (s, 3H), 1.72 (s, 9H), 0.99-0.91 (m, 2H), 0.71-0.64 (m, 2H).

Step E: N$^4$-Cyclopropyl-N$^2$-(3-methyl-1H-indazol-6-yl)furo[3,2-d]pyrimidine-2,4-diamine

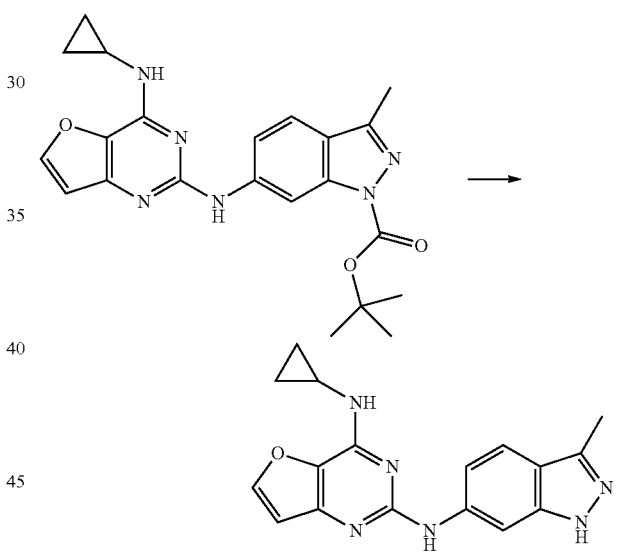

To a flask was added tert-butyl 6-(4-(cyclopropylamino)furo[3,2-d]pyrimidin-2-ylamino)-3-methyl-1H-indazole-1-carboxylate (12.5 g, 29.7 mmol), DCM (270 mL) and TFA (45.8 mL, 595 mmol). The mixture was stirred for about 4 h. The mixture was concentrated and the residue was dissolved in MeOH (100 mL). The resulting solution was added into stirred aqueous NaHCO$_3$ (10 wt %, 1000 mL) and the mixture was allowed to stir for about 1 h. The resultant suspension was filtered. To the solid was added hot water (60° C., 1000 mL) and the mixture was stirred for about 45 min and then filtered. The solid was then added to a mixture of DCM (270 mL) and MeOH (30 mL) in a flask, the mixture was heated to reflux then additional MeOH (25 mL) was added portion wise over a period of about 45 min, until a clear solution formed. The solution was filtered while hot. The filtrate was cooled in an ice bath for about 1 h. The mixture was then filtered to provide the desired product (6 g). The filtrate was combined with silica gel (15 g, 200-400 mesh size) and concentrated to a free flowing powder. The material was purified via column chromatography (0-3% MeOH in DCM over 35 min; 120 g silica gel) to give additional product (2.2 g). The two batches of product were combined to give $N^4$-cyclopropyl-$N^2$-(3-methyl-1H-indazol-6-yl)furo[3,2-d]pyrimidine-2,4-diamine (8.2 g, 86%); LC/MS (Table 2, Method c) $R_t$=1.61 min.; MS m/z: 321 (M+H)$^+$, $^1$H NMR (400 MHz, DMSO-d$_6$) δ 12.24 (s, 1H), 9.04 (s, 1H), 8.44 (s, 1H), 8.06 (d, J=2.1 Hz, 1H), 7.83 (s, 1H), 7.46 (d, J=8.7 Hz, 1H), 7.26 (dd, J=8.8, 1.7 Hz, 1H), 6.75 (d, J=2.1 Hz, 1H), 3.00 (td, J=7.1, 3.6 Hz, 1H), 2.41 (s, 3H), 0.90-0.83 (m, 2H), 0.68-0.61 (m, 2H). Syk IC$_{50}$=A Example #4

(Z)—N'-Hydroxy-1-(2-(3-methyl-1H-indazol-6-ylamino)furo[3,2-d]pyrimidin-4-yl)piperidine-4-carboximidamide

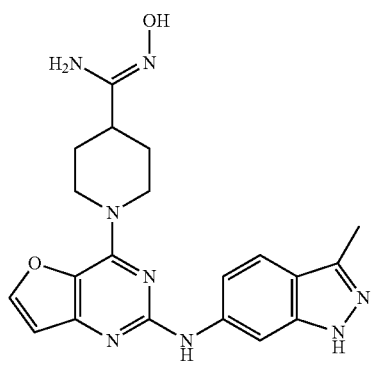 [SMILES: Cc1n[nH]c2cc(Nc3nc(N4CCC(/C(N)=N/O)CC4)c4occc4n3)ccc12]

Step A: 1-(2-Chlorofuro[3,2-d]pyrimidin-4-yl)piperidine-4-carbonitrile

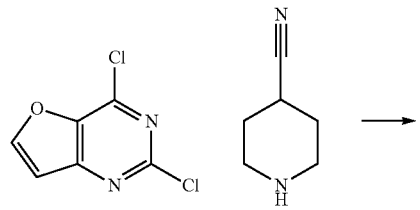

A mixture of 2,4-dichlorofuro[3,2-d]pyrimidine (0.40 g, 2.1 mmol, ArkPharm), piperidine-4-carbonitrile (0.23 g, 2.1 mmol, Oakwood) and TEA (0.59 mL, 4.2 mmol) in 1,4-dioxane (10 mL) was stirred at about 25° C. for about 12 h. The solvent was removed under reduced pressure and water (5 mL) and DCM (10 mL) were added to the residue. The layers were separated and the organic solution was concentrated under reduced pressure to give 1-(2-chlorofuro[3,2-d]pyrimidin-4-yl)piperidine-4-carbonitrile (0.50 g, 90%): LC/MS (Table 2, Method 1) $R_t$=0.76 min; MS m/z: 263 (M+H)$^+$.

Step B: 1-(2-(3-Methyl-1H-indazol-6-ylamino)furo[3,2-d]pyrimidin-4-yl)piperidine-4-carbonitrile

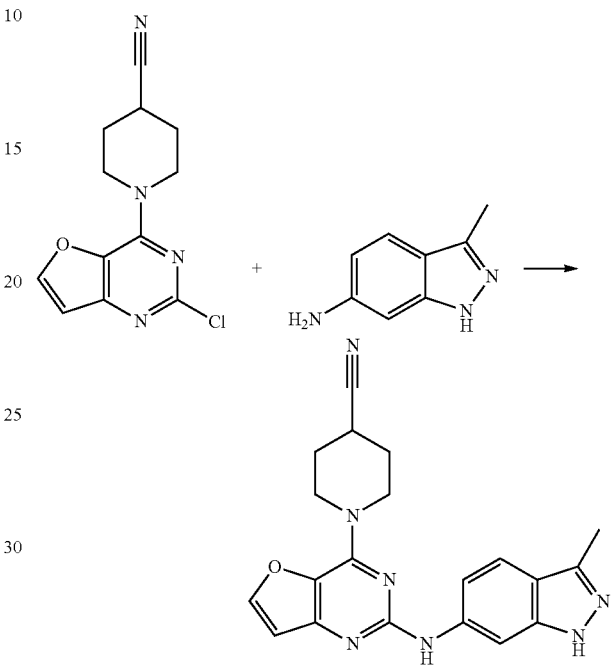

A mixture of K$_2$CO$_3$ (0.052 g, 0.38 mmol), Pd$_2$dba$_3$ (0.017 g, 0.019 mmol), 3-methyl-1H-indazol-6-amine (0.028 g, 0.19 mmol, Advanced ChemBlocks), 1-(2-chlorofuro[3,2-d]pyrimidin-4-yl)piperidine-4-carbonitrile (0.050 g, 0.19 mmol) and X-phos (0.018 g, 0.038 mmol) in 1,4-dioxane (10 mL) was stirred at about 100° C. for about 12 h. The solvent was removed and the residue was purified by Prep-TLC (DCM/MeOH 20:1) to give 1-(2-(3-methyl-1H-indazol-6-ylamino)furo[3,2-d]pyrimidin-4-yl)piperidine-4-carbonitrile (0.020 g, 28%): LC/MS (Table 2, Method 1) $R_t$=0.63 min; MS m/z: 374 (M+H)$^+$.

Step C: N'-Hydroxy-1-(2-(3-methyl-1H-indazol-6-ylamino)furo[3,2-d]pyrimidin-4-yl)piperidine-4-carboximidamide

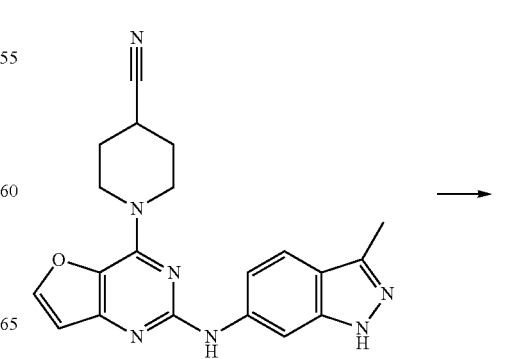

259
-continued

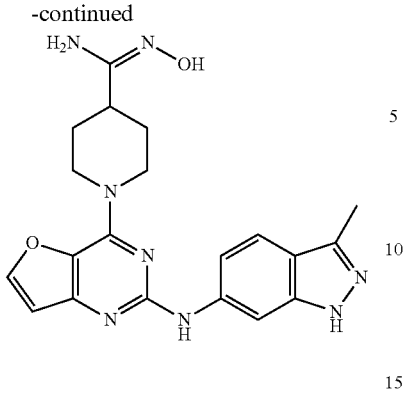

A mixture of 1-(2-(3-methyl-1H-indazol-6-ylamino)furo[3,2-d]pyrimidin-4-yl)piperidine-4-carbonitrile (0.082 g, 0.22 mmol), hydroxylamine hydrochloride (0.061 g, 0.88 mmol) and NaHCO₃ (0.15 g, 1.7 mmol) in MeOH (20 mL) was stirred at about 70° C. for about 120 h. The solvent was removed and the residue was purified by preparative HPLC (Table 2, Method p) to give N'-hydroxy-1-(2-(3-methyl-1H-indazol-6-ylamino)furo[3,2-d]pyrimidin-4-yl)piperidine-4-carboximidamide (0.020 g, 22%): LC/MS (Table 2, Method h) $R_t$=1.66 min; MS m/z: 407 (M+H)⁺. Syk IC₅₀=B Example #5

N-(3-Methyl-1H-indazol-6-yl)-4-(2,8-diazaspiro[4.5]decan-8-yl)furo[3,2-d]pyrimidin-2-amine

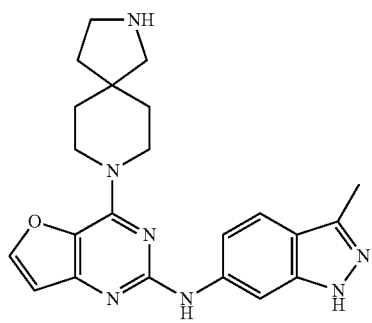 [SMILES: Cc1n[nH]c2cc(Nc3nc(N4CCC5(CCNC5)CC4)c4occc4n3)ccc12]

Step A: tert-Butyl 8-(2-chlorofuro[3,2-d]pyrimidin-4-yl)-2,8-diazaspiro[4.5]decane-2-carboxylate

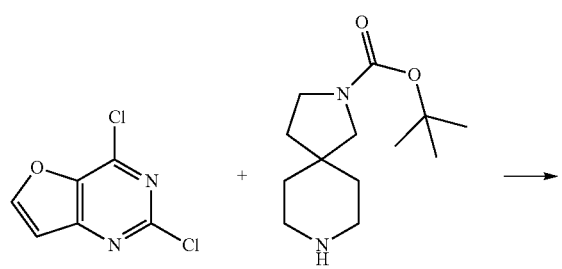

260
-continued

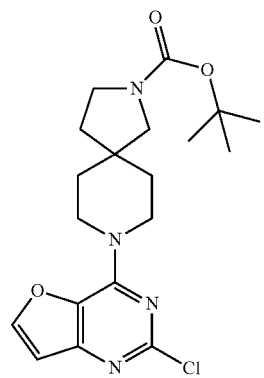

A mixture of tert-butyl 2,8-diazaspiro[4.5]decane-2-carboxylate (0.83 g, 3.4 mmol, Alfa Aesar), 2,4-dichlorofuro[3,2-d]pyrimidine (0.65 g, 3.4 mmol, ArkPharm) and TEA (0.96 mL, 6.9 mmol) in 1,4-dioxane (35 mL) was stirred at about 25° C. for about 12 h. Water (4 mL) and EtOAc (25 mL) were added and the layers were separated. The organic layer was concentrated under reduced pressure to give tert-butyl 8-(2-chlorofuro[3,2-d]pyrimidin-4-yl)-2,8-diazaspiro[4.5]decane-2-carboxylate (1.25 g, 55%): LC/MS (Table 2, Method f) $R_t$=2.12 min; MS m/z: 393 (M+H)⁺.

Step B: 3-Methyl-6-nitro-1-((2-(trimethylsilyl)ethoxy)methyl)-1H-indazole

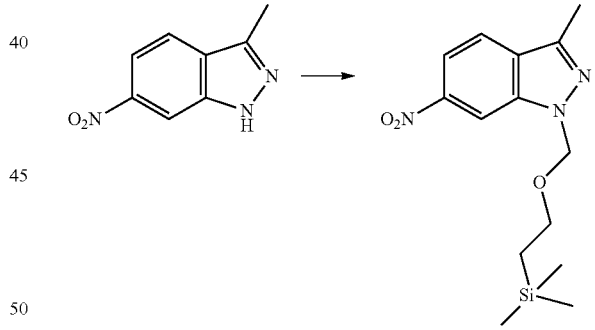

A flask was charged with NaH (60% dispersion in mineral oil, 0.325 g, 13.6 mmol) and THF (40 mL). The mixture was cooled to about 0° C. followed by the addition of 3-methyl-6-nitro-1H-indazole (2.00 g, 11.3 mmol, ArkPharm). The mixture was stirred for about 30 min followed by the addition of SEMCl (2.26 g, 13.6 mmol). The mixture was warmed to rt and stirred for about 12 h. Water (5 mL) and EtOAc (70 mL) were added and the layers were separated. The organic layer was concentrated under reduced pressure to give 3-methyl-6-nitro-1-((2-(trimethylsilyl)ethoxy)methyl)-1H-indazole (3.2 g, 91%): LC/MS (Table 2, Method f) $R_t$=2.18 min; MS m/z: 308 (M+H)⁺.

Step C: 3-Methyl-1-((2-(trimethylsilyl)ethoxy)methyl)-1H-indazol-6-amine

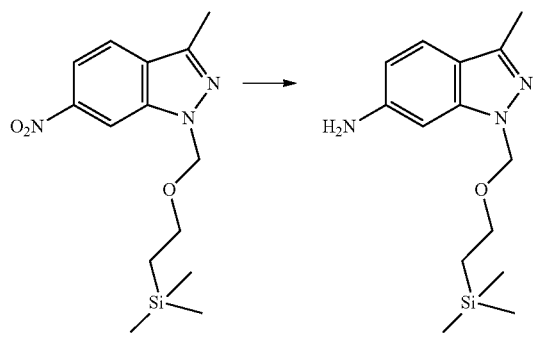 [SMILES: Cc1nn(COCC[Si](C)(C)C)c2cc([N+](=O)[O-])ccc12 ; Cc1nn(COCC[Si](C)(C)C)c2cc(N)ccc12]

A solution of 3-methyl-6-nitro-1-((2-(trimethylsilyl)ethoxy)methyl)-1H-indazole (2.37 g, 7.70 mmol) and Pd/C (10 weight %) (0.082 g, 0.77 mmol) in MeOH (35 mL) was stirred under an atmosphere of $H_2$ at about 25° C. for about 12 h. The hydrogen source was removed and the flask was purged with $N_2$. The catalyst was removed by filtration and the filtrate was concentrated to give 3-methyl-1-((2-(trimethylsilyl)ethoxy)methyl)-1H-indazol-6-amine (1.9 g, 84%): LC/MS (Table 2, Method h) $R_f$=2.09 min; MS m/z: 278 $(M+H)^+$.

Step D: tert-Butyl 8-(2-(3-methyl-1-((2-(trimethylsilyl)ethoxy)methyl)-1H-indazol-6-ylamino)furo[3,2-d]pyrimidin-4-yl)-2,8-diazaspiro[4.5]decane-2-carboxylate

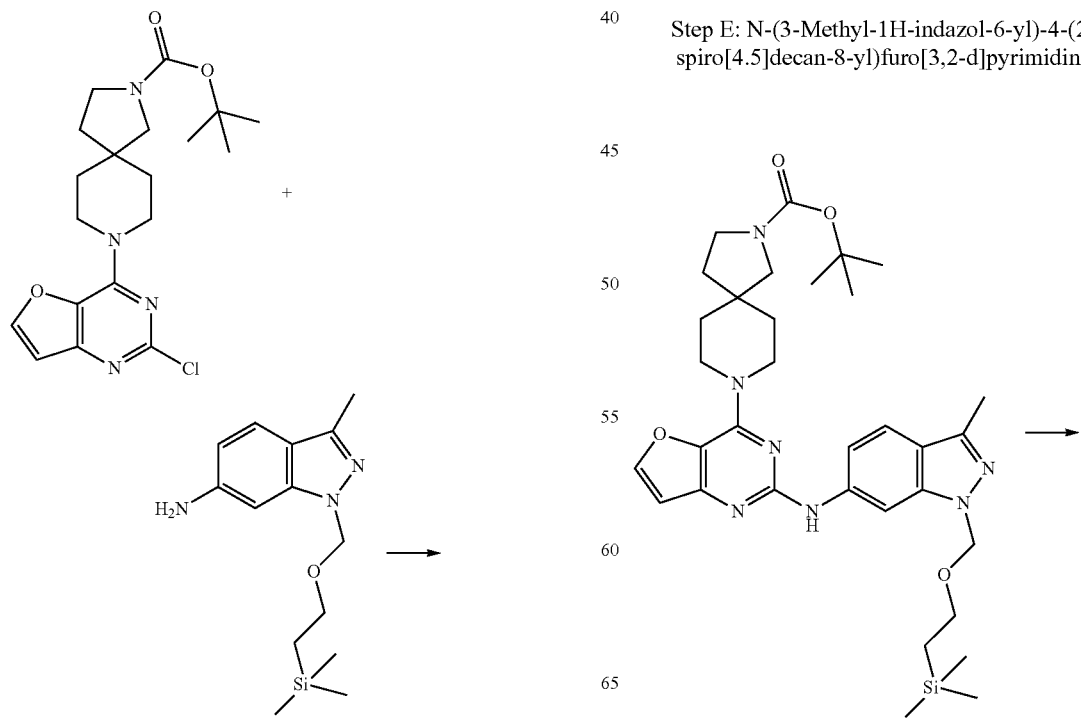

A mixture of tert-butyl 8-(2-chlorofuro[3,2-d]pyrimidin-4-yl)-2,8-diazaspiro[4.5]decane-2-carboxylate (0.20 g, 0.51 mmol), 3-methyl-1-((2-(trimethylsilyl)ethoxy)methyl)-1H-indazol-6-amine (0.21 g, 0.76 mmol), $Pd_2dba_3$ (0.047 g, 0.051 mmol), $K_2CO_3$ (0.14 g, 1.0 mmol) and X-Phos (0.048 g, 0.10 mmol) in 1,4-dioxane (20 mL) was stirred at about 110° C. for about 6 h. The mixture was concentrated under reduced pressure and purified by silica gel chromatography, eluting with DCM/MeOH (20:1) to give tert-butyl 8-(2-(3-methyl-1-((2-(trimethylsilyl)ethoxy)methyl)-1H-indazol-6-ylamino)furo[3,2-d]pyrimidin-4-yl)-2,8-diazaspiro[4.5]decane-2-carboxylate (0.21 g, 65%): LC/MS (Table 2, Method h) $R_f$=2.62 min; MS m/z: 634 $(M+H)^+$.

Step E: N-(3-Methyl-1H-indazol-6-yl)-4-(2,8-diazaspiro[4.5]decan-8-yl)furo[3,2-d]pyrimidin-2-amine

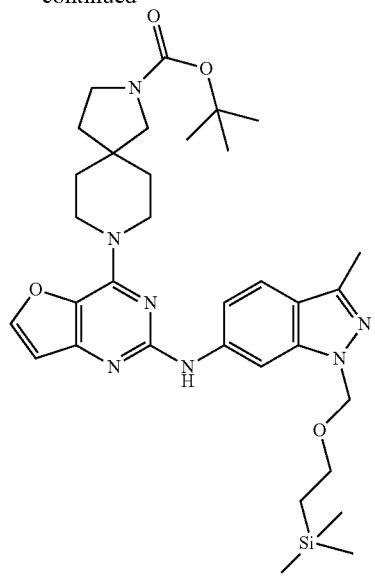

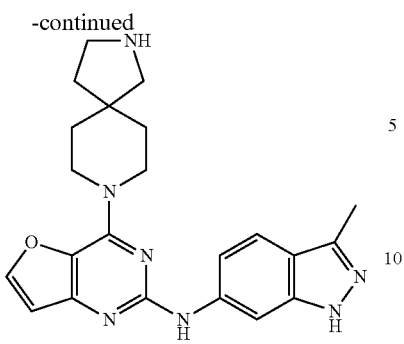

A flask was charged with tert-butyl 8-(2-3-methyl-1-((2-(trimethylsilyl)ethoxy)methyl)-1H-indazol-6-ylamino)furo[3,2-d]pyrimidin-4-yl)-2,8-diazaspiro[4.5]decane-2-carboxylate (0.21 g, 0.33 mmol) and DCM (8 mL). TFA (2 mL) was added and the solution was stirred at rt overnight. The mixture was concentrated under reduced pressure and purified by preparative HPLC (Table 2, Method q) to give N-(3-methyl-1H-indazol-6-yl)-4-(2,8-diazaspiro[4.5]decan-8-yl)furo[3,2-d]pyrimidin-2-amine (0.040 g, 30%): LC/MS (Table 2, Method h) $R_t$=1.61 min; MS m/z: 404 (M+H)$^+$. Syk IC$_{50}$=A Example #6

7-(4-(Cyclopropylamino)furo[3,2-d]pyrimidin-2-ylamino)-3-methyl-3,4-dihydroquinolin-2(1H)-one

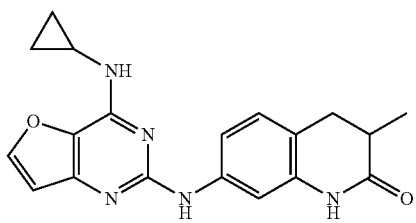 [SMILES: CC1Cc2ccc(Nc3nc(NC4CC4)c4occc4n3)cc2NC1=O]

Step A: 3-(2,4-Dinitrophenyl)-2-methylpropanoic acid

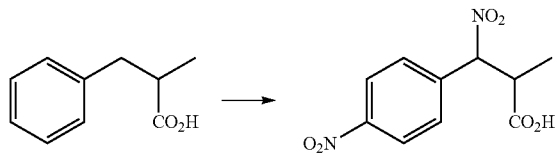 [SMILES: CC(Cc1ccccc1)C(=O)O ; CC(C(=O)O)C(c1ccc([N+](=O)[O-])cc1)[N+](=O)[O-]]

2-Methyl-3-phenylpropanoic acid (1.0 g, 6.1 mmol) was dissolved in H$_2$SO$_4$ (5 mL) and cooled to about −15° C. Concentrated HNO$_3$ (1.00 mL, 15.2 mmol) was added dropwise via syringe maintaining the temperature below −15° C. The mixture was then allowed to warm to rt and was stirred for about 2 h. The mixture was poured into ice water (30 mL) and the product was extracted with EtOAc (3×30 mL). The combined organic extracts were dried over anhydrous Na$_2$SO$_4$, filtered and concentrated under reduced pressure to give 3-(2,4-dinitrophenyl)-2-methylpropanoic acid (1.6 g, 83%): LC/MS (Table 2, Method f) $R_t$=2.10 min; MS m/z: 255 (M−H)$^−$.

Step B: Methyl 3-(2,4-dinitrophenyl)-2-methylpropanoate

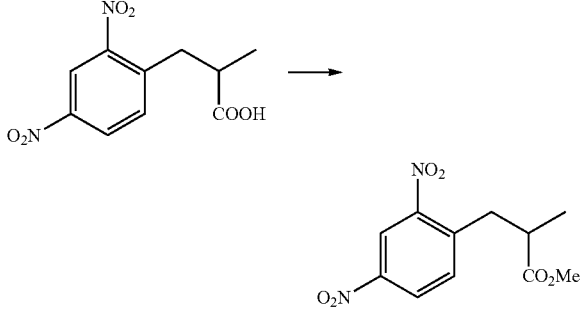

To a solution of 3-(2,4-dinitrophenyl)-2-methylpropanoic acid (1.6 g, 5.0 mmol) in MeOH (10 mL) was added H$_2$SO$_4$ (0.85 mL, 16 mmol) and the mixture was heated to reflux overnight. The solvent was removed under reduced pressure and the residue was dissolved in DCM (100 mL). The organic solution was washed with saturated aqueous NaHCO$_3$ and the layers were separated. The organic solution was dried over anhydrous Na$_2$SO$_4$ and filtered. The organic solution was directly purified by preparative TLC (1.0 mm plate), eluting with 5:1 pet ether/EtOAc to give methyl 3-(2,4-dinitrophenyl)-2-methylpropanoate (1.1 g, 81%): LC/MS (Table 2, Method f) $R_t$=1.95 min; MS m/z: 267 (M−H)$^−$.

Step C: 7-Amino-3-methyl-3,4-dihydroquinolin-2(1H)-one

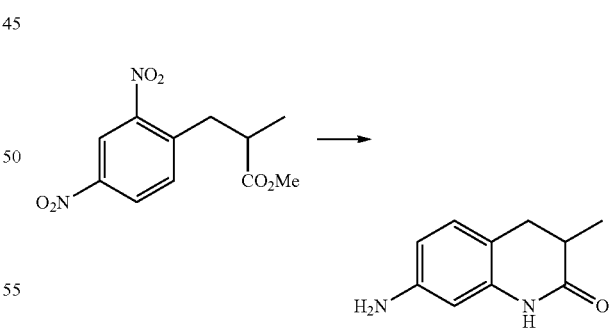

A flask was charged with methyl 3-(2,4-dinitrophenyl)-2-methylpropanoate (1.1 g, 4.1 mmol), 10 wt % Pd on carbon (0.25 g, 2.3 mmol), and t-BuOH (15 mL). The mixture was degassed with H$_2$ three times and was stirred for about 72 h at about 50° C. The mixture was filtered and the filtrate was concentrated under reduced pressure to give 7-amino-3-methyl-3,4-dihydroquinolin-2(1H)-one (0.70 g, 92%): LC/MS (Table 2, Method g) $R_t$=1.04 min; MS m/z: 177 (M+H)$^+$.

Step D: 7-(4-(Cyclopropylamino)furo[3,2-d]pyrimidin-2-ylamino)-3-methyl-3,4-dihydroquinolin-2(1H)-one

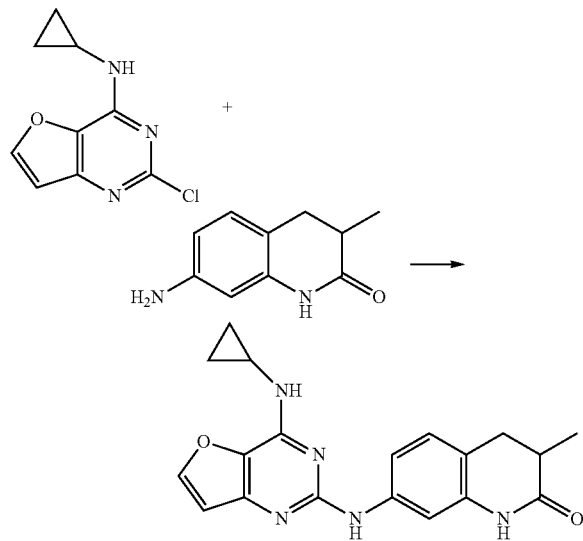

A flask was charged with 2-chloro-N-cyclopropylfuro[3,2-d]pyrimidin-4-amine (0.38 g, 1.8 mmol, Example #3, Step C), 7-amino-3-methyl-3,4-dihydroquinolin-2(1H)-one (0.30 g, 1.7 mmol), $K_2CO_3$ (0.38 g, 2.7 mmol), $Pd_2dba_3$ (0.17 g, 0.18 mmol) and X-Phos (0.17 g, 0.36 mmol) in 1,4-dioxane (20 mL). The flask was evacuated and purged with $N_2$ (3×), and the mixture was heated to about 100° C. overnight. The mixture was cooled to rt and concentrated under reduced pressure to a residue. The residue was purified by preparative TLC (1.0 mm plate), eluting with DCM/MeOH (12:1). The product obtained was further purified by preparative HPLC (Table 2, Method r) to give 7-(4-(cyclopropylamino)furo[3,2-d]pyrimidin-2-ylamino)-3-methyl-3,4-dihydroquinolin-2(1H)-one (0.15 g, 24%): LC/MS (Table 2, Method g) $R_t$=1.04 min; MS m/z: 177 (M+H)$^+$. Syk IC$_{50}$=A

Example #7

7-(4-(Cyclopropylamino)furo[3,2-d]pyrimidin-2-ylamino)-3,4-dihydroquinolin-2(1H)-one

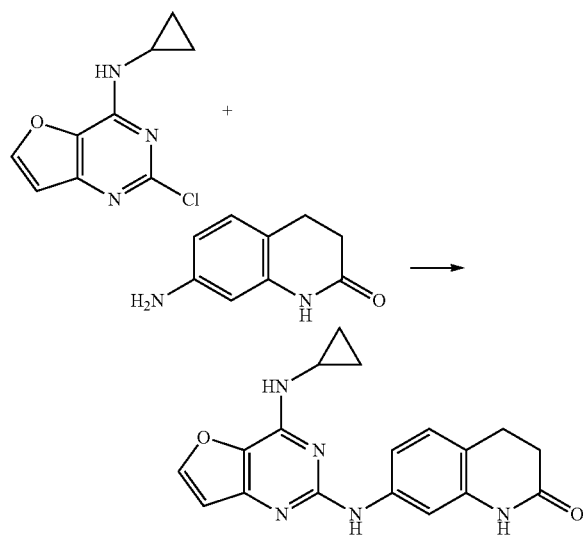

A flask was charged with 2-methyl-2-butanol (140 mL) and the solvent was sparged with $N_2$ for about 15 min. To the solvent were added 2-chloro-N-cyclopropylfuro[3,2-d]pyrimidin-4-amine (6.5 g, 31 mmol, Example #3, Step C), 7-amino-3,4-dihydroquinolin-2(1H)-one (5.03 g, 31.0 mmol, Astatech), and $K_2CO_3$ (8.57 g, 62.0 mmol). The flask was purged with $N_2$ (3×) followed by the addition of X-Phos (2.07 g, 4.34 mmol) and $Pd_2dba_3$ (1.99 g, 2.17 mmol). The flask was again purged with $N_2$ (2×) and the mixture was heated to about 78° C. for about 24 h. The mixture was cooled to rt and filtered through a pad of Celite®. The filter pad was washed with DCM (~900 mL) and the combined filtrates were concentrated under reduced pressure to about ½ the initial volume. The mixture was dissolved in DCM (200 mL) and washed with water (100 mL). The layers were separated and the organic solution was dried over anhydrous $MgSO_4$, filtered and concentrated under reduced pressure to about ⅕ volume. Additional DCM/MeOH (3:1, 100 mL) was added along with silica gel (~25 g, 200-400 Mesh, 60 Å) and the solvents were removed under reduced pressure. The crude material was purified by silica gel chromatography (220 g) eluting with 0.5 to 2.5% MeOH in DCM over about 20 min, 2.5 to 3.5% MeOH in DCM over 15 min, and isocratic at 3.5% MeOH in DCM for about 25 min. The product containing fractions were combined and concentrated under reduced pressure to give a solid that was triturated with MeOH (~30 mL). The solid was collected by vacuum filtration to give 7-(4-(cyclopropylamino)furo[3,2-d]pyrimidin-2-ylamino)-3,4-dihydroquinolin-2(1H)-one (3.2 g, 31%): LC/MS (Table 2, Method c) $R_t$=1.71 min; MS m/z: 336 (M+H)$^+$. Syk IC$_{50}$=A

Example #8

8-(4-(Cyclopropylamino)furo[3,2-d]pyrimidin-2-ylamino)-4,5-dihydro-1H-benzo[b]azepin-2(3H)-one

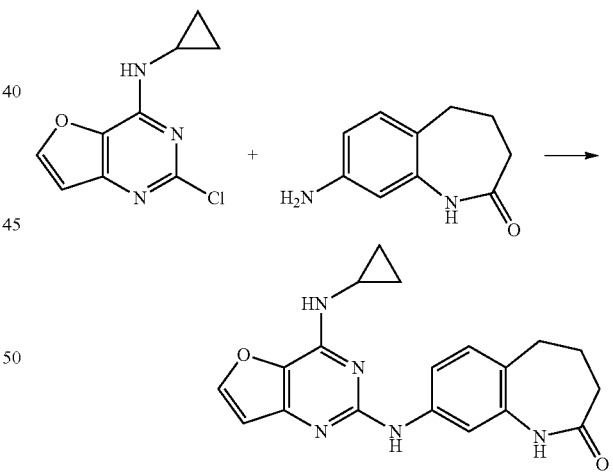

A flask was charged with 2-chloro-N-cyclopropylfuro[3,2-d]pyrimidin-4-amine (0.50 g, 2.385 mmol, Example #3, Step C), 8-amino-4,5-dihydro-1H-benzo[b]azepin-2(3H)-one (0.420 g, 2.385 mmol, Astatech), $K_2CO_3$ (0.989 g, 7.16 mmol) and t-BuOH (9 mL). The flask was purged with $N_2$ for 10 min. $Pd_2dba_3$ (0.153 g, 0.167 mmol) and X-Phos (0.159 g, 0.334 mmol) was added. The flask was again purged with $N_2$ for 5 min and the mixture was heated to about 85° C. for about 18 h. The mixture was cooled to rt. The mixture was partitioned between DCM (200 mL) and water (200 mL) and the aqueous layer was extracted with DCM (3×100 mL). The combined organic layers were concentrated under reduced pressure. The resulting residue was suspended in EtOAc (200 mL) and trituated. The suspension was filtered and the solid was collected and washed with EtOAc (50 mL). The solid was suspended in a mixture solvents of DCM (100 mL) and MeOH (10 mL), filtered to give a gray solid, which was purified by preparative reverse phase HPLC (Table 2, method v). The fractions were collected then most of the MeCN was removed under reduced pressure, the resulting suspension was filtered and the solid was collected to give 8-(4-(cyclopropylamino)furo[3,2-d]pyrimidin-2-ylamino)-4,5-dihydro-1H-benzo[b]azepin-2(3H)-one (0.338 g, 40%): LC/MS (Table 2, Method c) $R_f$=1.80 min; MS m/z: 350 (M+H)$^+$. Syk IC$_{50}$=A Example #9

(3S,4S)-4-(Aminomethyl)-1-(2-(3-methyl-1H-indazol-6-ylamino)furo[3,2-d]pyrimidin-4-yl)piperidin-3-ol

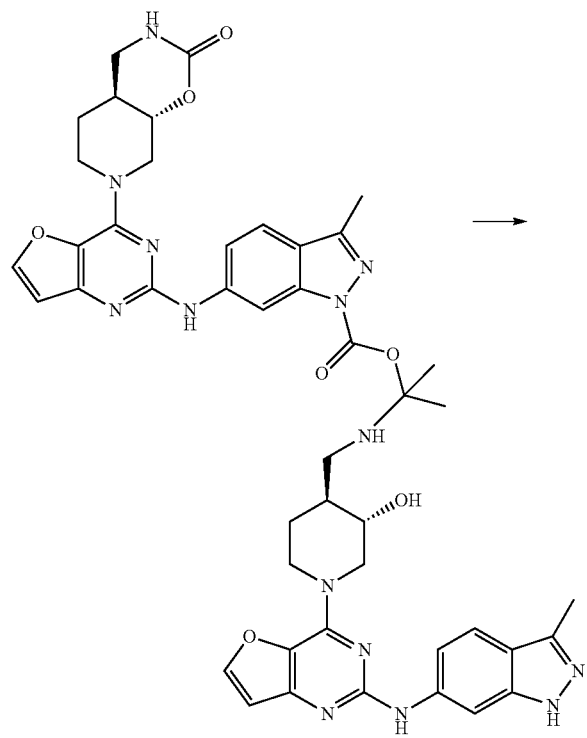

To a vial was added tert-butyl 3-methyl-6-(4-((4aS,8aS)-2-oxotetrahydro-2H-pyrido[4,3-e][1,3]oxazin-7(3H,8H,8aH)-yl)furo[3,2-d]pyrimidin-2-ylamino)-1H-indazole-1-carboxylate (0.367 g, 0.706 mmol, prepared using AL from (3S,4S)-4-(aminomethyl)-1-benzylpiperidin-3-ol [Sunshine Labs], G, A with 2,4-dichlorofuro[3,2-d]pyrimidine [ArkPharm] and B with Example#3, Step B) in MeOH (5 mL). An aqueous solution of NaOH (5 M, 2.83 mL, 14.1 mmol) was added. The mixture was heated at about 80° C. for about 3 h. The resulting suspension was filtered. The precipitate obtained was discarded. Precipitation was observed in the filtrate, the precipitate was collected by filtration and dried to give (3S,4S)-4-(aminomethyl)-1-(2-(3-methyl-1H-indazol-6-ylamino)furo[3,2-d]pyrimidin-4-yl)piperidin-3-ol (0.14 g, 50%): LC/MS (Table 2, Method n) $R_f$=1.16 min.; MS m/z: 394 (M+H)$^+$. Syk IC$_{50}$=A Example #10

6-(4-(Cyclopropylamino)furo[3,2-d]pyrimidin-2-ylamino)-2,2-dimethyl-2H-benzo[b][1,4]oxazin-3(4H)-one

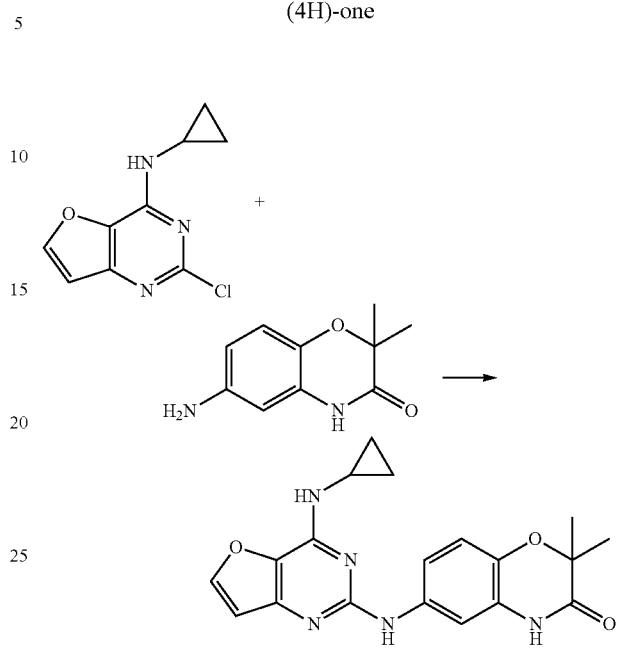

To a flask was added 2-chloro-N-cyclopropylfuro[3,2-d]pyrimidin-4-amine (7.82 g, 37.3 mmol), 6-amino-2,2-dimethyl-2H-benzo[b][1,4]oxazin-3(4H)-one (8.60 g, 44.7 mmol, Example #3, Step C), K$_2$CO$_3$ (6.18 g, 44.7 mmol) and t-BuOH (249 mL). To the mixture was added Pd$_2$dba$_3$ (2.05 g, 2.24 mmol) and X-Phos (2.13 g, 4.47 mmol). The flask was de-gassed and vented with N$_2$ three times. The mixture was heated to about 85° C. and stirred overnight. The mixture was diluted with EtOAc (700 mL) and washed with water (700 mL). The aqueous layer was extracted with EtOAc (2×300 mL). The combined organic layers were dried with MgSO$_4$, filtered through a pad of Celite® and concentrated in vacuo. The material was purified by column chromatography (300 g silica gel) using a gradient of 30 to 100% EtOAc/DCM. The material was suspended in 30% EtOAc/DCM (150 mL) and heated to about 77° C. with stirring. MeOH (20 mL) was added gradually to the hot solution until a clear solution resulted. The mixture was allowed to stir for about 1 h and then cooled to rt. The precipitate formed was collected by filtration to give a solid. The mother liquor was kept in the refrigerator overnight and the resulting precipitate was collected by filtration to yield a second batch of the product. The two solids were combined. The material was then suspended in DCM and filtered. The precipitate was dried in a vacuum oven at about 70° C. for about 18 h. The material was then pulverized using a mortar and pestle and dried in the vacuum oven at about 80° C. for about 16 h. The material was taken up in IPA (200 mL) and the suspension was heated to about 50° C. with stirring for about 2 h. The precipitate was brought to rt and filtered. The precipitate was dried in a vacuum oven at about 80° C. for about 16 h. The material was dissolved in MeOH (200 mL) and evaporated under reduced pressure. The residue was dried in a vacuum oven at about 80° C. for about 16 h. The material was suspended in water (200 mL) and sonicated for about 10 min then stirred vigorously for about 1 h. The mixture was filtered and the precipitate was dried in a vacuum oven at about 80° C. for about 20 h to provide 6-(4-(cyclopropylamino)furo[3,2-d]pyrimidin-2-ylamino)-2,2-dimethyl-2H-benzo[b][1,4]oxazin-3(4H)-one (5.0 g, 37%): LC/MS (Table 2, Method c) $R_f$=1.87 min.; MS m/z: 366 (M+H)$^+$. Syk IC$_{50}$=A

Example #11

6-(4-(Cyclopropylamino)furo[3,2-d]pyrimidin-2-ylamino)-3,3-dimethylindolin-2-one

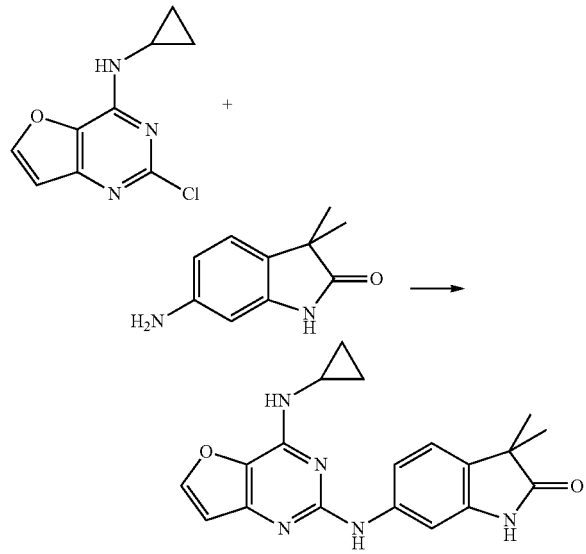

To a flask was added 2-chloro-N-cyclopropylfuro[3,2-d]pyrimidin-4-amine (0.45 g, 2.14 mmol, Example #3, Step C), 6-amino-3,3-dimethylindolin-2-one (0.378 g, 2.14 mmol, Astatech), $K_2CO_3$ (0.89 g, 6.44 mmol) and t-AmOH (5 mL). To the mixture was added $Pd_2dba_3$ (0.118 g, 0.129 mmol) and X-Phos (0.123 g, 0.258 mmol). The mixture was heated to about 100° C. and stirred for about 15 h. The mixture was filtered and the filtrate was directly purified by column chromatography eluting with 0 to 70% of 10% MeOH/DCM (containing 2M 1.5% $NH_3$ in EtOH) and DCM (25 g silica gel)). The material was then dried in a vacuum oven at about 65° C. for about 48 h. The solid was then suspended in $Et_2O$ (5 mL), sonicated for 2 min and filtered. The solid was dried in a vacuum oven at about 80° C. for about 16 h to give 6-(4-(cyclopropylamino)furo[3,2-d]pyrimidin-2-ylamino)-3,3-dimethylindolin-2-one (0.195 g, 26%): LC/MS (Table 2, Method c) $R_t$=1.81 min.; MS m/z: 350 (M+H)$^+$. Syk $IC_{50}$=A

Example #12

4-(4-(Aminomethyl)-4-methylpiperidin-1-yl)-N-(1H-indazol-6-yl)furo[3,2-d]pyrimidin-2-amine

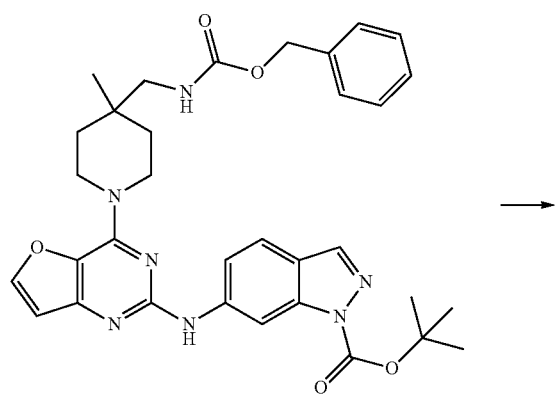

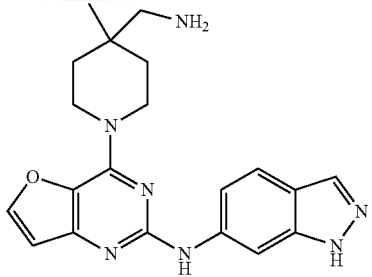

To a mixture of tert-butyl 6-(4-(4-((benzyloxycarbonylamino)methyl)-4-methylpiperidin-1-yl)furo[3,2-d]pyrimidin-2-ylamino)-1H-indazole-1-carboxylate (0.13 g, 0.213 mmol, (prepared using A from 2,4-dichlorofuro[3,2-d]pyrimidine [ArkPharm] with benzyl (4-methylpiperidin-4-yl)methylcarbamate [U.S. Pat. No. 6,140,333 example 3 step 5]), B with tert-butyl 6-amino-1H-indazole-1-carboxylate [Frontier] and C) in AcOH (3 mL) was added HBr (1 mL). The mixture was stirred at about 40° C. for about 8 h. Water (30 mL) was added and the mixture was extracted with DCM (4×20 mL). The mixture was concentrated in vacuo to give 4-(4-(aminomethyl)-4-methylpiperidin-1-yl)-N-(1H-indazol-6-yl)furo[3,2-d]pyrimidin-2-amine (0.015 g, 19%): LC/MS (Table 2, Method h) $R_t$=1.72 min; MS m/z: 378 (M+H)$^+$. Syk $IC_{50}$=A

Example #13

$N^2$-(1H-Indazol-6-yl)-$N^4$-(2,2,2-trifluoroethyl)furo[3,2-d]pyrimidine-2,4-diamine

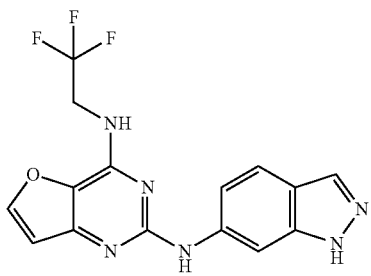 [SMILES: FC(F)(F)CNc1nc(Nc2ccc3cn[nH]c3c2)nc2ccoc12]

Step A: 6-Nitro-1-((2-(trimethylsilyl)ethoxy)methyl)-1H-indazole

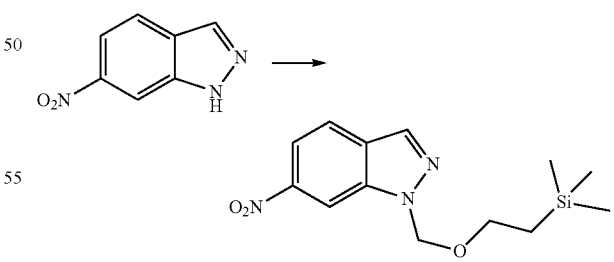

To a flask was added NaH (4.90 g, 123 mmol) (TCI) and THF (100 mL). 6-Nitro-1H-indazole (10 g, 61.3 mmol) was added in one portion with stirring at about 0° C. The mixture was stirred at about 0° C. for about 20 min. SEMCl (13.29 g, 80 mmol) was added slowly to the mixture. The mixture was stirred at about 0° C. for about 1 h and then allowed to warm to rt for about 3 h. The mixture was diluted with saturated aqueous $NH_4Cl$. The aqueous layer was extracted with EtOAc (2×50 mL) and the combined organic layers were washed with brine, dried over Na$_2$SO$_4$, filtered, and concentrated under reduced pressure. The crude material was purified by column chromatography (silica gel, 10:1 hexanes/EtOAc) to afford 6-nitro-1-*(2-(trimethylsilyl)ethoxy)methyl)-1H-indazole (16 g, 89%): LC/MS (Table 2, Method 1) R$_t$=1.03 min.

Step B: 1-((2-(Trimethylsilyl)ethoxy)methyl)-1H-indazol-6-amine

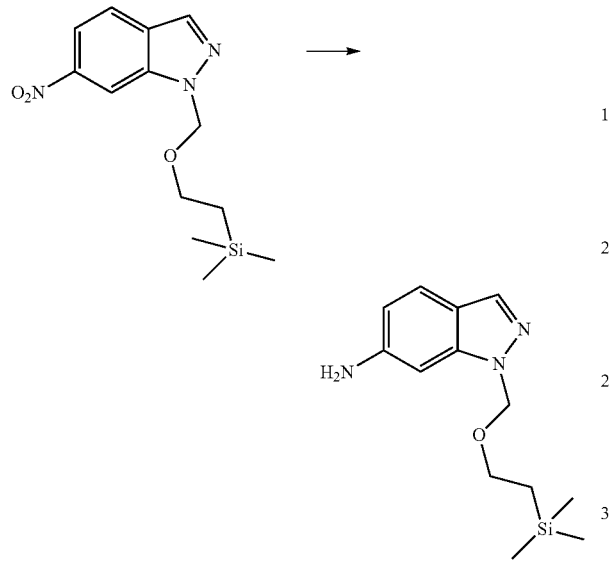

6-Nitro-1-((2-(trimethylsilyl)ethoxy)methyl)-1H-indazole (19.2 g, 65.4 mmol) and Pd\C (10 wt %, 1.920 g) were combined in MeOH (60 mL). The mixture was allowed to stir under an atmosphere of H$_2$ at ambient pressure and at rt for about 18 h. The mixture was filtered and the filtrate was concentrated in vacuo. The residue was purified by column chromatography (silica gel, 10:1 Hex/EtOAc) to give 1-((2-(trimethylsilyl)ethoxy)methyl)-1H-indazol-6-amine (12.3 g, 71%): LC/MS (Table 2, Method h) R$_t$=2.09 min; MS m/z: 264 (M+H)$^+$.

Step C: 2-Chloro-N-(2,2,2-trifluoroethyl)furo[3,2-d]pyrimidin-4-amine

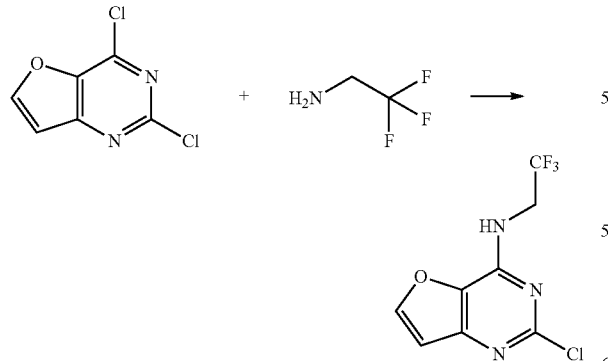

To a flask was added 2,4-dichlorofuro[3,2-d]pyrimidine (0.80 g, 4.23 mmol, ArkPharm) and DMF (3.0 mL). 2,2,2-Trifluoroethanamine (1.05 g, 10.58 mmol, Acros) was added. The mixture was heated in a microwave at about 120° C. for about 15 min. The mixture was diluted with Et$_2$O (100 mL). The mixture was washed with water (3×25 mL). The combined aqueous layer was extracted with Et$_2$O (2×50 mL). The combined organic layers were dried over Na$_2$SO$_4$, filtered, and concentrated in vacuo. The residue was transferred neat and was purified by preparative TLC eluting with 3:1 hexanes/EtOAc to give 2-chloro-N-(2,2,2-trifluoroethyl)furo[3,2-d]pyrimidin-4-amine (0.76 g, 71%): LC/MS (Table 2, Method h) R$_t$=1.85 min; MS m/z: 252, 254 (M+H)$^+$.

Step D: N$^4$-(2,2,2-Trifluoroethyl)-N$^2$-(1-((2-(trimethylsilyl)ethoxy)methyl)-1H-indazol-6-yl)furo[3,2-d]pyrimidine-2,4-diamine

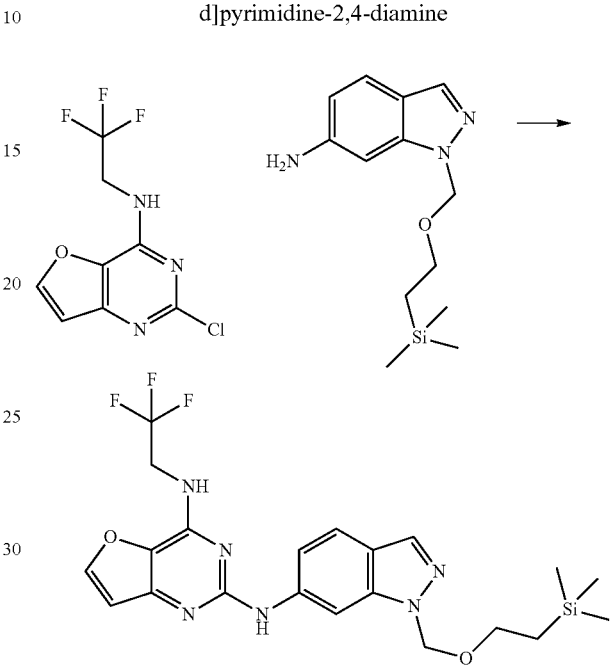

2-Chloro-N-(2,2,2-trifluoroethyl)furo[3,2-d]pyrimidin-4-amine (1.56 g, 6.20 mmol) and 1-((2-(trimethylsilyl)ethoxy)methyl)-1H-indazol-6-amine (1.797 g, 6.82 mmol) were dissolved in 1,4-dioxane (10 mL). RuPhos (0.296 g, 0.620 mmol), Pd$_2$dba$_3$ (0.568 g, 0.620 mmol, Alfa) and K$_2$CO$_3$ (1.714 g, 12.40 mmol) were added. The tube was evacuated and purged with N$_2$ (3×), and the mixture was heated at about 110° C. for about 5 h. The mixture was cooled to rt and filtered. The filter cake was washed with DCM (3×25 mL). The filtrate was washed with saturated aqueous NaCl (3×20 mL). The combined organic layers were dried over Na$_2$SO$_4$, filtered, and concentrated under reduced pressure. The residue was purified by column chromatography (silica gel, 2:1 hexanes/EtOAc) to give N$^4$-(2,2,2-trifluoroethyl)-N$^2$-(1-((2-(trimethylsilyl)ethoxy)methyl)-1H-indazol-6-yl)furo[3,2-d]pyrimidine-2,4-diamine (2.22 g, 75%): LC/MS (Table 2, Method h) R$_t$=2.26 min; MS m/z: 479 (M+H)$^+$.

Step E: N$^2$-(1H-indazol-6-yl)-N$^4$-(2,2,2-trifluoroethyl)furo[3,2-d]pyrimidine-2,4-diamine

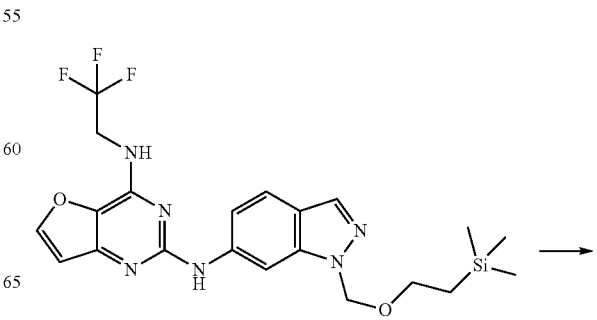

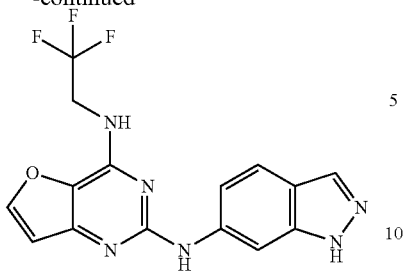

N$^4$-(2,2,2-trifluoroethyl)-N$^2$-(1-((2-(trimethylsilyl)ethoxy)methyl)-1H-indazol-6-yl)furo[3,2-d]pyrimidine-2,4-diamine (1.08 g, 2.257 mmol) was dissolved in DCM (15 mL). TFA (10 mL, 130 mmol) was added. The resulting mixture was stirred at about 30° C. for about 6 h. The mixture was concentrated in vacuo. The residue was diluted with DCM (30 mL) and the pH was adjusted to about pH=9.0 with concentrated NH$_4$OH. The solvents were removed under reduced pressure and the resulting mixture was purified by preparative-HPLC (Table 2, method w) to afford N$^2$-(1H-indazol-6-yl)-N$^4$-(2,2,2-trifluoroethyl)furo[3,2-d]pyrimidine-2,4-diamine (0.15 g, 19%): LC/MS (Table 2, Method h) R$_t$=1.79 min; MS m/z: 349 (M+H)$^+$. Syk IC$_{50}$=A Example #14

Chiral separation of 7-(4-(cyclopropylamino)furo[3,2-d]pyrimidin-2-ylamino)-3-methyl-3,4-dihydroquinolin-2(1H)-one

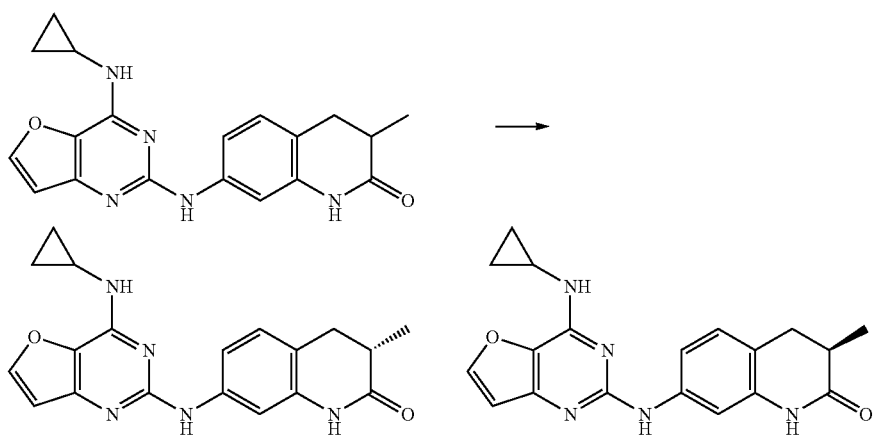

7-(4-(cyclopropylamino)furo[3,2-d]pyrimidin-2-ylamino)-3-methyl-3,4-dihydroquinolin-2(1H)-one as prepared in example 6 was separated into single enantiomers using chiral SFC (Table 3, Method 2) to give (S)-7-(4-(cyclopropylamino)furo[3,2-d]pyrimidin-2-ylamino)-3-methyl-3,4-dihydroquinolin-2(1H)-one (0.128 g, 27%): LC/MS (Table 2, Method h) R$_t$=1.89 min; MS m/z: 350 (M+H); Chiral HPLC (Table 2, Method 3) R$_t$=3.82 min. Syk IC$_{50}$=A. (R)-7-(4-(cyclopropylamino)furo[3,2-d]pyrimidin-2-ylamino)-3-methyl-3,4-dihydroquinolin-2(1H)-one (0.16 g, 36%): LC/MS (Table 2, Method h) R$_t$=1.89 min; MS m/z: 350 (M+H); Chiral HPLC (Table 2, Method 3) R$_t$=4.47 min. Syk IC$_{50}$=A Example #15

N$^4$-Cyclopropyl-N$^2$-(1H-indazol-6-yl)furo[3,2-d]pyrimidine-2,4-diamine

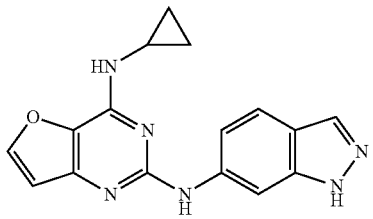 [SMILES: c1cc2nc(Nc3ccc4cn[nH]c4c3)nc(NC3CC3)c2o1]

Step A: tert-Butyl 6-(4-(cyclopropylamino)furo[3,2-d]pyrimidin-2-ylamino)-1H-indazole-1-carboxylate

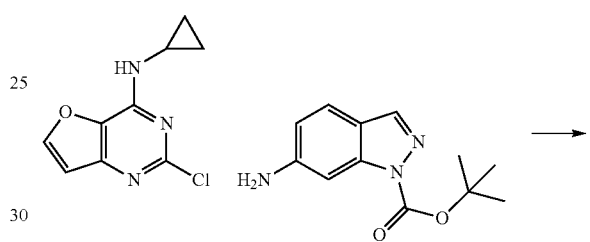

-continued

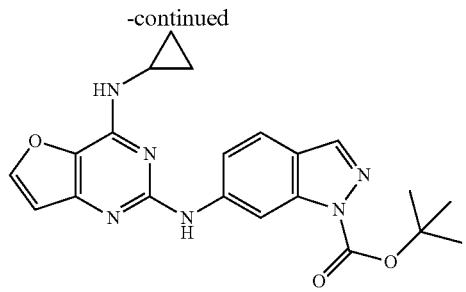

To a flask was added 2-chloro-N-cyclopropylfuro[3,2-d]pyrimidin-4-amine (10.5 g, 50.1 mmol, Example #3, Step C), tert-butyl 6-amino-1H-indazole-1-carboxylate (14.02 g, 60.1 mmol, Frontier), K₂CO₃ (8.31 g, 60.1 mmol) and t-BuOH (334 mL). The reaction vessel was purged under vacuum and vented with N₂ three times. To the mixture was added Pd₂dba₃ (2.75 g, 3.01 mmol) and X-Phos (2.87 g, 6.01 mmol). The reaction vessel was purged under vacuum and vented with N₂. The mixture was heated to about 85° C. for about 3 days. The mixture was diluted with EtOAc (1000 mL) and washed with water (1000 mL). The organic layer was dried with MgSO₄, filtered through a pad of Celite® and concentrated in vacuo. The residue was purified by column chromatography (300 g silica gel, DCM/MeOH 1:0 to 10:1) to give a solid. The material was further purified by column chromatography (300 g silica gel, DCM/EtOAc 1:0 to 0:1) to give tert-butyl 6-(4-(cyclopropylamino)furo[3,2-d]pyrimidin-2-ylamino)-1H-indazole-1-carboxylate (9.78 g, 48%): LC/MS (Table 2, Method u) R$_t$=1.48 min; MS m/z: 407 (M+H)⁺

Step B: N⁴-Cyclopropyl-N²-(1H-indazol-6-yl)furo[3,2-d]pyrimidine-2,4-diamine

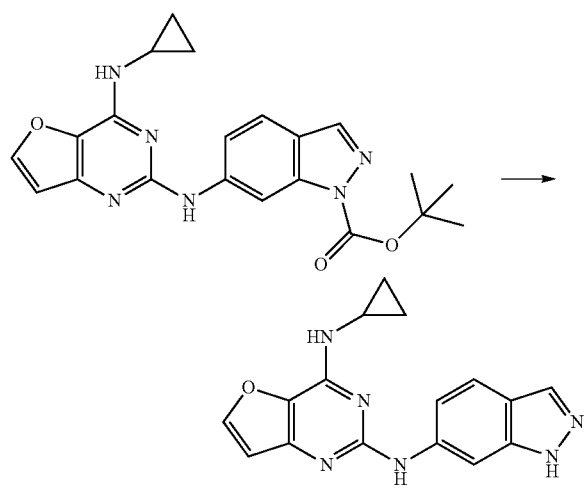

To a flask was added tert-butyl 6-(4-(cyclopropylamino)furo[3,2-d]pyrimidin-2-ylamino)-1H-indazole-1-carboxylate (9.78 g, 24.1 mmol), DCM (120 mL) and TFA (18.5 mL, 241 mmol). The mixture was stirred at rt for about 18 h. The mixture was concentrated in vacuo. The resulting solid was suspended in DCM (100 mL), sonicated, and stirred at rt for about 1 h. The solid was collected by vacuum filtration and dried under vacuum overnight at about 70° C. to give N⁴-cyclopropyl-N²-(1H-indazol-6-yl)furo[3,2-d]pyrimidine-2,4-diamine di-trifluoroacetate salt (4.38 g, 34%) as a solid: LC/MS (Table 2, Method u) R$_t$=1.29 min; MS m/z: 307 (M+H)⁺. Syk IC₅₀=A Example #16

6-(4-(2,2-Difluoroethylamino)furo[3,2-d]pyrimidin-2-ylamino)-3,3-dimethylindolin-2-one

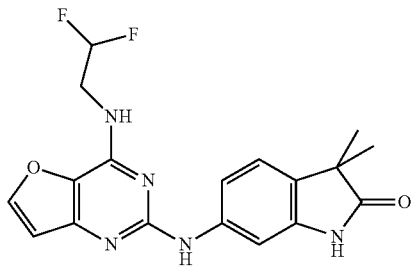 [SMILES: CC1(C)C(=O)Nc2cc(Nc3nc(NCC(F)F)c4occc4n3)ccc21]

Step A: 2-Chloro-N-(2,2-difluoroethyl)furo[3,2-d]pyrimidin-4-amine

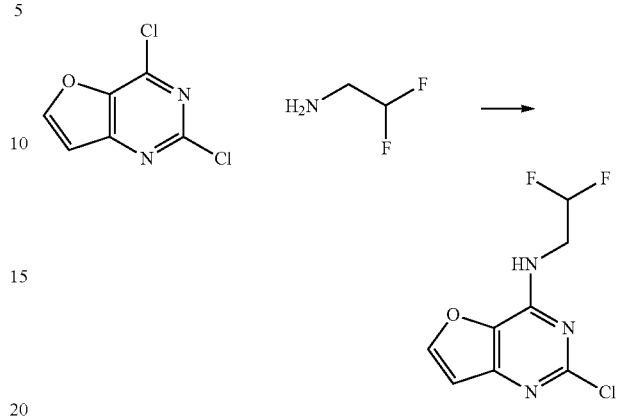

To a flask was added 2,4-dichlorofuro[3,2-d]pyrimidine (2 g, 10.58 mmol, Arkpharm), DCM (20 mL) and TEA (2.95 mL, 21.16 mmol). A solution of 2,2-difluoroethanamine (0.858 g, 10.6 mmol, Matrix) in DCM (5 mL) was added drop-wise and the mixture was stirred at rt overnight. The mixture was concentrated under reduced pressure. To the residue was added 1,4-dioxane (20 mL), TEA (2.95 mL, 21.2 mmol) and a solution of 2,2-difluoroethanamine (0.858 g, 10.58 mmol, Matrix) in 1,4-dioxane (5 mL). The mixture was stirred at rt for about 4 h, and then at about 55° C. overnight. The mixture was concentrated under reduced pressure, and the residue was taken up in EtOAc (120 mL) and water (25 mL). The organic layer was isolated and washed with water (2×25 mL). The combined aqueous layers were washed with EtOAc (2×25 mL). The combined organic layers were washed with brine (25 mL), dried with MgSO₄, filtered, concentrated under reduced pressure, and dried in a vacuum oven at about 70° C. over 2 days to give 2-chloro-N-(2,2-difluoroethyl)furo[3,2-d]pyrimidin-4-amine (2.20 g, 89%): LC/MS (Table 2, Method c) R$_t$=1.69 min.; MS m/z: 234 (M+H)⁺.

Step B: 6-(4-(2,2-Difluoroethylamino)furo[3,2-d]pyrimidin-2-ylamino)-3,3-dimethylindolin-2-one

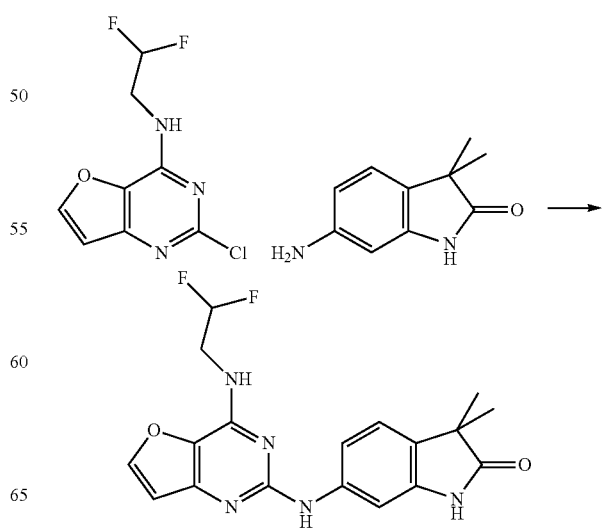

To a vial was added Pd$_2$dba$_3$ (0.235 g, 0.257 mmol), Cs$_2$CO$_3$ (2.37 g, 7.28 mmol) and Ru-Phos (0.240 g, 0.514 mmol) in t-AmOH (8.00 mL). The mixture was evacuated and purged with N$_2$. The mixture was stirred at about 65° C. for about 20 min. 2-Chloro-N-(2,2-difluoroethyl)furo[3,2-d]pyrimidin-4-amine (1.00 g, 4.28 mmol) and 6-amino-3,3-dimethylindolin-2-one (0.754 g, 4.28 mmol, Astatech) were added in one portion. Additional t-AmOH (12.00 mL) was added. The mixture was evacuated and purged with N$_2$. The mixture was stirred at about 70° C. for about 5 h, stirred at about 60° C. for about 15 h and then stirred at about 75° C. for about 2 h. The mixture was cooled to rt and filtered. The precipitate was washed with DCM (20 mL) and MeOH (20 mL). The combined filtrate was concentrated and purified by column chromatography eluting with 25-65% EtOAc/heptane (40 g silica gel) to give a crude material. The material was suspended in Et$_2$O (about 15 mL) and sonicated. The suspension was filtered and washed with Et$_2$O (50 mL), then with DCM (about 30 mL). The precipitate was dissolved in DCM (50 mL), combined with filtrate, concentrated under reduced pressure, dissolved in MeOH (40 mL), and adsorbed onto silica gel (Mesh#200-400, 60A°; 3 g). The material was purified by column chromatography eluting with 0 to 28% of 10% MeOH/DCM and DCM (40 g silica gel) to give a solid. The solid was purified by mass-triggered HPLC (Table 2, Method x) purification to give 6-(4-(2,2-difluoroethylamino)furo[3,2-d]pyrimidin-2-ylamino)-3,3-dimethylindolin-2-one (0.397 g, 25%): LC/MS (Table 2, Method c) R$_t$=1.75 min.; MS m/z: 374 (M+H)$^+$. Syk IC$_{50}$=A

TABLE 4

Efficay of compounds in the Revers Passive Arthus model at a single dose

| Compound | Inhibition @ 10 mg/kg |
|---|---|
| Example #B.5.2 | 55% |
| Example #B.5.8 | 49% |
| Example #B.5.13 | 17% |
| Example #B.5.40 | 3% |
| Example #B.5.41 | 42% |
| Example #B.5.42 | 27% |
| Example #B.5.50 | 0% |
| Example #B.5.52 | 0% |
| Example #B.5.56 | 49% |
| Example #B.5.60 | 10% |
| Example #B.5.61 | 1% |
| Example #B.5.62 | 16% |
| Example #B.5.63 | 15% |
| Example #B.5.65 | 9% |
| Example #B.5.68 | 1% |
| Example #B.5.77 | 20% |
| Example #B.5.80 | 46% |
| Example #B.5.81 | 16% |
| Example #B.5.84 | 38% |
| Example #B.5.85 | 52% |
| Example #B.5.99 | 16% |
| Example #B.5.108 | 56% |
| Example #C.1.2 | −17% |
| Example #C.1.7 | 22% |
| Example #C.1.8 | 0% |
| Example #C.1.23 | −15% |
| Example #C.1.29 | −5% |
| Example #C.1.31 | 0% |
| Example #C.1.32 | 8% |
| Example #C.1.33 | 30% |
| Example #C.1.36 | −31% |
| Example #C.1.37 | −5% |
| Example #C.1.39 | 44% |
| Example #C.1.40 | 40% |
| Example #C.1.41 | 40% |
| Example #C.1.43 | 56% |
| Example #C.1.44 | 54% |
| Example #C.1.48 | 1% |

TABLE 4-continued

Efficay of compounds in the Revers Passive Arthus model at a single dose

| Compound | Inhibition @ 10 mg/kg |
|---|---|
| Example #C.1.49 | −20% |
| Example #C.1.51 | −7% |
| Example #C.1.52 | 8% |
| Example #C.1.57 | 12% |
| Example #C.1.58 | −18% |
| Example #C.1.59 | 20% |
| Example #C.1.60 | 24% |
| Example #C.1.61 | 20% |
| Example #C.1.62 | −6% |
| Example #C.1.71 | 85% |
| Example #E.2.1 | −1% |
| Example #J.1 | −2% |
| Example #J.1.7 | 12% |
| Example #J.1.8 | 9% |
| Example #Q.1.4 | 33% |
| Example #AC.1 | 43% |
| Example #AM.1 | 3% |
| Example #AM.1.1 | 12% |
| Example #AM.1.2 | −16% |
| Example #AM.1.3 | 15% |
| Example #3 | 75% |
| Example #6 | 59% |
| Example #7 | 73% |
| Example #11 | 65% |
| Example #12 | 8% |
| Example #13 | 70% |
| Example #15 | 45% |
| Example #16 | 63% |

What is claimed:
1. A compound of Formula (I)

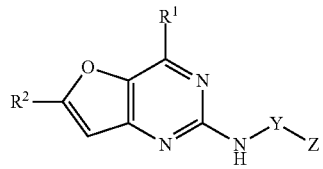

Formula (I)

pharmaceutically acceptable salts, pro-drugs, racemates, enantiomers, diastereomers, solvates and hydrates thereof wherein R$^1$ is N(R$^a$)(R$^b$), —CH(R$^a$)(R$^b$), —C(R$^a$)═CH(R$^b$), —C≡C(R$^b$), —OR$^b$, —C(O)R$^b$, —C(O)N(R$^a$)—R$^b$—, —N(R$^a$)C(O)—R$^b$—, or —SR$^b$; wherein R$^a$ is H, optionally substituted (C$_1$-C$_6$)alkyl, optionally substituted (C$_2$-C$_6$)alkenyl, or optionally substituted (C$_2$-C$_6$)alkynyl; and R$^b$ is optionally substituted (C$_1$-C$_6$)alkyl, optionally substituted (C$_2$-C$_6$)alkenyl, optionally substituted (C$_3$-C$_6$)cycloalkyl, optionally substituted (C$_1$-C$_6$) alkylene-optionally substituted (C$_3$-C$_6$)cycloalkyl, optionally substituted bridged saturated or partially unsaturated (C$_5$-C$_{12}$)cycloalkyl, optionally substituted (C$_6$-C$_{10}$)aryl, optionally substituted saturated or partially unsaturated bridged (C$_2$-C$_{10}$)heterocyclyl, optionally substituted saturated or partially unsaturated (C$_1$-C$_{10}$)heterocyclyl, -optionally substituted (C$_1$-C$_6$)alkylene-optionally substituted saturated or partially unsaturated (C$_1$-C$_{10}$)heterocyclyl, optionally substituted (C$_1$-C$_{10}$)heteroaryl, -optionally substituted (C$_1$-C$_6$)alkylene-optionally substituted (C$_1$-C$_{10}$)heteroaryl; or R$^a$ and R$^b$ together form an optionally substituted saturated or partially unsaturated (C$_3$-C$_{12}$)carbocyclic ring, an optionally substituted saturated or partially unsaturated (C$_2$-C$_{10}$) heterocyclic ring, optionally substituted (C$_1$-C$_{10}$)heteroaryl ring, an optionally substituted saturated or partially unsaturated (C$_5$-C$_{12}$)spirocarbocyclic ring, an optionally substituted saturated or partially unsaturated (C$_5$-C$_{10}$)spiroheterocyclic ring, an optionally substituted saturated or partially unsaturated (C$_5$-C$_{12}$) carbocyclic bridged ring or an optionally substituted saturated or partially unsaturated (C$_2$-C$_{10}$) heterocyclic bridged ring;

R$^2$ is H, deuterium, —N(R$^a$)(R$^b$), halo, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)(R$^b$), —C(O)R$^a$, —N(R$^a$)S(O)$_2$—, —S(O)$_2$N(R$^a$)—, —CF$_3$, —OCF$_3$, optionally substituted —(C$_1$-C$_6$)alkyl, optionally substituted (C$_2$-C$_6$)alkenyl, or optionally substituted —(C$_2$-C$_6$)alkynyl;

Y is optionally substituted (C$_6$-C$_{10}$)arylene, optionally substituted (C$_1$-C$_6$)heterocyclylene, or optionally substituted (C$_1$-C$_{10}$)heteroarylene; and Z is H, halogen, —CN, —C(O)N(R$^c$)(R$^d$), —C(O)R$^d$, —N(R$^c$)(R$^d$), —N(R$^c$)C(O)(R$^d$), —OR$^c$, —S(O)$_2$R$^c$, —S(O)$_2$—N(R$^c$)(R$^d$), optionally substituted (C$_1$-C$_3$) alkyl, -optionally substituted (C$_1$-C$_3$)alkylene-optionally substituted heterocyclyl, optionally substituted (C$_3$-C$_6$)cycloalkyl, optionally substituted (C$_6$-C$_{10}$)aryl, (C$_1$-C$_{10}$)heteroaryl, optionally substituted heterocyclyl or -optionally substituted (C$_1$-C$_3$)alkyl-optionally substituted heterocyclyl;

wherein R$^c$ and R$^d$ are independently H, optionally substituted (C$_1$-C$_6$)alkyl, optionally substituted (C$_3$-C$_6$) cycloalkyl, optionally substituted heterocyclyl or optionally substituted heteroaryl; or R$^c$ and R$^d$, together with the atom to which they are attached, can form an optionally substituted saturated cycloalkyl or optionally substituted saturated heterocyclyl ring.

2. The compound of claim 1 wherein Y is optionally substituted benzo[b]azepinyl, optionally substituted benzo[b][1,4]oxazinyl, optionally substituted benzo[b][1,4]thiazinyl, optionally substituted benzo[d]thiophenyl, optionally substituted benzo[d]imidazolyl, optionally substituted benzo[d] isothiazolyl, optionally substituted benzo[d]isoxazolyl, optionally substituted benzo[d]oxazolyl, optionally substituted benzo[d]thiazolyl, optionally substituted chromanyl, optionally substituted chromenyl, optionally substituted (C$_3$-C$_6$)cycloalkylene, optionally substituted dihydrobenzo[b] azepinyl, optionally substituted dihydrobenzo[b][1,4]dioxinyl, optionally substituted dihydroindenyl, optionally substituted dihydroisoquinolinyl, optionally substituted dihydroquinolinyl, optionally substituted imidazo[1,2-a]pyridinyl, optionally substituted indazolyl, optionally substituted indolinyl, optionally substituted indolyl, optionally substituted isoindolinyl, optionally substituted isoquinolinyl, optionally substituted isothiazolyl, optionally substituted morpholine, optionally substituted naphthalene optionally substituted oxoindolinyl, optionally substituted phenyl, optionally substituted piperazinyl, optionally substituted piperidinyl, optionally substituted pyrrolidinyl, optionally substituted pyrazolyl, optionally substituted pyridinyl, optionally substituted pyrido[3,2-b][1,4]oxazinyl, optionally substituted pyrido[3,2-d][1,4]oxazinyl, optionally substituted quinolinyl, optionally substituted tetrahydrofuran, optionally substituted tetrahydroindole, optionally substituted tetrahydroisoquinolinyl, optionally substituted tetrahydro-1,6-naphthyridinyl, optionally substituted tetrahydroquinolinyl, optionally substituted thiomorpholinyl, optionally substituted tetrahydropyranyl, optionally substituted thiazolyl, optionally substituted thiomorpholinyl or optionally substituted tropanyl.

3. The compound of claim 2 wherein Y is optionally substituted benzo[b]azepinyl, optionally substituted benzo[d] imidazolyl, optionally substituted benzo[b][1,4]oxazinyl, optionally substituted benzo[d]isothiazolyl, optionally substituted benzo[d]oxazolyl, optionally substituted benzo[b][1,4]thiazinyl, optionally substituted benzo[d]thiazolyl, optionally substituted benzo[c]thiophenyl, optionally substituted chromanyl, optionally substituted chromenyl, optionally substituted dihydrobenzo[b]azepinyl, optionally substituted dihydrobenzo[b][1,4]dioxinyl, optionally substituted dihydroisoquinolinyl, optionally substituted dihydroquinolinyl, optionally substituted imidazo[1,2-a]pyridinyl, optionally substituted indazolyl, optionally substituted indolinyl, optionally substituted isoquinolinyl, optionally substituted oxoindolinyl, optionally substituted phenyl, optionally substituted pyrazolyl, optionally substituted pyridinyl, optionally substituted pyrido[3,2-b][1,4]oxazinyl, optionally substituted quinolinyl, optionally substituted tetrahydroisoquinolinyl, or optionally substituted tetrahydro-1,6-naphthyridinyl.

4. The compound of claim 3 wherein Z is H, —CN, —N(R$^c$)(R$^d$), —C(O)N(H)-optionally substituted(C$_1$-C$_3$) alkylene, —C(O)N(H)(C$_3$-C$_6$)cycloalkyl, —C(O)N(CH$_3$)$_2$, —C(O)-optionally substituted(C$_1$-C$_3$)alkyl, —C(O)-morpholinyl, —N(H)morpholinyl, —N(H)C(O)-optionally substituted(C$_1$-C$_3$)alkyl, —N(H)C(O)CH$_2$-morpholinyl, —N(CH$_3$)C(O)-optionally substituted(C$_1$-C$_3$)alkyl, —O-optionally substituted(C$_1$-C$_3$)alkyl, —S(O)$_2$-optionally substituted(C$_1$-C$_3$)alkyl, —S(O)$_2$—N(H)optionally substituted (C$_1$-C$_4$)alkyl, —S(O)$_2$NH$_2$, —S(O)$_2$N(H)-pyridinyl, optionally substituted (C$_1$-C$_3$)alkyl, optionally substituted (C$_3$-C$_6$) cycloalkyl, optionally substituted imidazolyl, optionally substituted morpholinyl, optionally substituted phenyl, optionally substituted piperazinyl, optionally substituted pyridinyl, optionally substituted triazolyl, -optionally substituted (C$_1$-C$_3$)alkylene-optionally substituted azetidinyl, -optionally substituted (C$_1$-C$_3$)alkylene-optionally substituted indolinyl, -optionally substituted (C$_1$-C$_3$)alkylene-optionally substituted isoindolinyl, -optionally substituted (C$_1$-C$_3$)alkylene-optionally substituted morpholinyl, -optionally substituted (C$_1$-C$_3$)alkylene-optionally substituted piperazinyl, -optionally substituted (C$_1$-C$_3$)alkylene-optionally substituted piperidinyl, -optionally substituted (C$_1$-C$_3$)alkylene-optionally substituted pyrrolidinyl, -optionally substituted (C$_1$-C$_3$)alkylene-optionally substituted thiomorpholinyl, -optionally substituted (C$_1$-C$_3$)alkylene-optionally substituted tetrahydropyranyl, -optionally substituted (C$_1$-C$_3$)alkylene-optionally substituted tetrahydrofuranyl, -optionally substituted (C$_1$-C$_3$)alkylene-optionally substituted tetrahydroindolyl, -optionally substituted (C$_1$-C$_3$)alkylene-optionally substituted thiomorpholinyl, -optionally substituted (C$_1$-C$_3$)alkylene-optionally substituted tropanyl, optionally substituted azaindolyl, optionally substituted benzo[b]thienyl, optionally substituted benzo[b][1,4]oxazinyl, optionally substituted benzimidazoly, optionally substituted benzofuranyl, optionally substituted benzoxazolyl, optionally substituted benzothiazolyl, optionally substituted benzothiadiazolyl, optionally substituted benzoxadiazolyl, optionally substituted furanyl, optionally substituted imidazolyl, optionally substituted imidazopyridinyl, optionally substituted indolyl, optionally substituted indazolyl, optionally substituted isoxazolyl, optionally substituted isothiazolyl, optionally substituted oxadiazolyl, optionally substituted oxazolyl, optionally substituted purinyl, optionally substituted pyranyl, optionally substituted pyrazinyl, optionally substituted pyrazolyl, optionally substituted pyridazinyl, optionally substituted pyridinyl, optionally substituted pyrimidinyl, optionally substituted pyrrolyl, optionally substituted pyrrolo[2,3-d]pyrimidinyl, optionally substituted pyrazolo[3,4-d]pyrimidinyl, optionally substituted quinolinyl, optionally substituted quinazolinyl, optionally substituted tetrahydroquinolinyl, optionally substituted triazolyl, optionally substituted thiazolyl, optionally substituted tetrazolyl, optionally substituted thiadiazolyl, or optionally substituted thienyl.

5. The compound of claim 4 wherein Z is H, —CN, —N(R$^c$)(R$^d$), —C(O)N(H)-optionally substituted(C$_1$-C$_3$)alkylene, —C(O)N(H)-optionally substituted(C$_3$-C$_6$)cycloalkylene, —C(O)-optionally substituted(C$_1$-C$_3$)alkyl, —C(O)-morpholinyl, —N(H)C(O)-optionally substituted (C$_1$-C$_3$)alkyl, —N(CH$_3$)C(O)-optionally substituted(C$_1$-C$_3$)alkyl, —OR$^c$, —S(O)$_2$-optionally substituted(C$_1$-C$_3$)alkyl, —S(O)$_2$—N(H)optionally substituted (C$_1$-C$_4$)alkyl, —S(O)$_2$NH$_2$, —S(O)$_2$N(H)-pyridinyl, optionally substituted (C$_1$-C$_3$)alkyl, optionally substituted morpholinyl, optionally substituted piperazinyl, optionally substituted pyridinyl, -optionally substituted (C$_1$-C$_3$)alkylene-optionally substituted morpholinyl, -optionally substituted (C$_1$-C$_3$)alkylene-optionally substituted piperazinyl, optionally substituted imidazolyl, or optionally substituted pyridinyl.

6. The compound of claim 5 wherein Z can be optionally substituted by one or more substituents independently selected from CN, halogen, N(R$^c$)(R$^d$), —OR$^c$, —C(O)R$^c$, —C(O)OR$^S$, —C(O)N(R$^c$)(R$^d$), —N(R$^c$)C(O)(R$^d$), —CF$_3$, —OC(O)R$^c$, —N(R$^c$)S(O)$_2$R$^d$, —OCF$_3$, oxo, S(W), —S(O)(R$^c$), —S(O)$_2$(R$^c$), —S(O)$_2$N(R$^c$)(R$^d$), and optionally substituted —(C$_1$-C$_6$)alkyl.

7. The compound of claim 4 wherein R$^a$ and R$^b$ together form

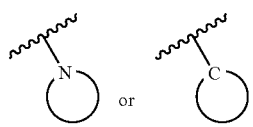

forming an optionally substituted 4 to 10 membered monocyclic, bicyclic or spirocyclic saturated, unsaturated or partially unsaturated ring containing 0 to 4 heteroatoms selected from N, O and S.

8. The compound of claim 7 wherein R$^1$ is optionally substituted azepinyl, optionally substituted azetidinyl, optionally substituted diazaspiro[3.5]nonanyl, optionally substituted diazaspiro[4.5]decanyl, optionally substituted diazaspiro[5.5]undecanyl, optionally substituted dihydroimidazo[1,5-a]pyrazinyl, optionally substituted dihydroimidazo[4,5-c]pyridinyl, optionally substituted dihydroisoquinolinyl, optionally substituted morpholinyl, optionally substituted piperazinyl, optionally substituted piperidinyl, optionally substituted pyrrolidinyl, or tetrahydropyrrolo[3,4-c]pyridinyl.

9. The compound of claim 8 wherein R$^1$ is optionally substituted by one or more substituents selected from halogen, —CN, —C(NH$_2$)(=NOH), —C(O)N(W)(R$^d$), —N(R$^c$)(R$^d$), —OR$^c$, —S(O)$_2$R$^c$, optionally substituted (C$_1$-C$_4$)alkyl, —CH$_2$—NH-optionally substituted heterocyclyl, or optionally substituted heteroaryl.

10. The compound of claim 9 wherein Y is optionally substituted benzo[b][1,4]oxazinyl, optionally substituted benzo[b][1,4]thiazinyl, optionally substituted dihydroisoquinolinyl, optionally substituted dihydroquinolinyl, optionally substituted indazolyl, optionally substituted indolinyl, optionally substituted phenyl, optionally substituted quinolinyl, or optionally substituted tetrahydroquinolinyl.

11. The compound of claim 10 wherein Z is H, F, —N(H)C(O)-optionally substituted(C$_1$-C$_3$)alkyl, —N(CH$_3$)C(O)-optionally substituted(C$_1$-C$_3$)alkyl, —S(O)$_2$-optionally substituted(C$_1$-C$_3$)alkyl, —S(O)$_2$—N(H) optionally substituted (C$_1$-C$_4$)alkyl, —S(O)$_2$NH$_2$, optionally substituted (C$_1$-C$_3$)alkyl, optionally substituted morpholinyl, or optionally substituted piperazinyl.

12. The compound of claim 11 wherein the compound is
4-(4-((2,2-difluoroethylamino)methyl)piperidin-1-yl)-N-(3-methyl-1H-indazol-6-yl)furo[3,2-d]pyrimidin-2-amine;
4-(3,4-dihydroisoquinolin-2(1H)-yl)-N-(1H-indazol-6-yl)furo[3,2-d]pyrimidin-2-amine;
4-(4-(aminomethyl)-4-methylpiperidin-1-yl)-N-(1H-indazol-6-yl)furo[3,2-d]pyrimidin-2-amine;
N-(4-(4-(3,4-dihydroisoquinolin-2(1H)-yl)furo[3,2-d]pyrimidin-2-ylamino)phenyl)-N-methylacetamide;
2,2-dimethyl-6-(4-(4-((2-(methylsulfonyl)ethylamino) methyl)piperidin-1-yl)furo[3,2-d]pyrimidin-2-ylamino)-2H-benzo[b][1,4]oxazin-3(4H)-one;
3,3-dimethyl-6-(4-(4-((2-(methylsulfonyl)ethylamino) methyl)piperidin-1-yl)furo[3,2-d]pyrimidin-2-ylamino)indolin-2-one;
N-(3-methoxypropyl)-4-(4-(4-((methylamino)methyl)piperidin-1-yl)furo[3,2-d]pyrimidin-2-ylamino)benzenesulfonamide;
2-methyl-2-(4-(4-(4-((methylamino)methyl)piperidin-1-yl)furo[3,2-d]pyrimidin-2-ylamino)phenyl)propanenitrile;
6-(4-(2,7-diazaspiro[4.4]nonan-2-yl)furo[3,2-d]pyrimidin-2-ylamino)-2,2-dimethyl-2H-benzo[b][1,4]oxazin-3(4H)-one;
6-(4-(2,8-diazaspiro[4.5]decan-8-yl)furo[3,2-d]pyrimidin-2-ylamino)-2,2-dimethyl-2H-benzo[b][1,4]oxazin-3(4H)-one;
6-(4-(2,7-diazaspiro[4.5]decan-2-yl)furo[3,2-d]pyrimidin-2-ylamino)-2,2-dimethyl-2H-benzo[b][1,4]oxazin-3(4H)-one;
6-(4-(1,7-diazaspiro[3.5]nonan-7-yl)furo[3,2-d]pyrimidin-2-ylamino)-2,2-dimethyl-2H-benzo[b][1,4]oxazin-3(4H)-one;
6-(4-(2,9-diazaspiro[5.5]undecan-9-yl)furo[3,2-d]pyrimidin-2-ylamino)-2,2-dimethyl-2H-benzo[b][1,4]oxazin-3(4H)-one;
6-(4-(4,4-bis(aminomethyl)piperidin-1-yl)furo[3,2-d]pyrimidin-2-ylamino)-2,2-dimethyl-2H-benzo[b][1,4]oxazin-3(4H)-one;
N-(3-methyl-1H-indazol-6-yl)-4-(1-oxa-4,9-diazaspiro [5.5]undecan-9-yl)furo[3,2-d]pyrimidin-2-amine;
N-(3-methyl-1H-indazol-6-yl)-4-(4-((2-(methylsulfonyl) ethylamino)methyl)piperidin-1-yl)furo[3,2-d]pyrimidin-2-amine;
7-(4-(4-(aminomethyl)piperidin-1-yl)furo[3,2-d]pyrimidin-2-ylamino)-3,4-dihydroquinolin-2(1H)-one;
6-(4-(4-(1-aminoethyl)piperidin-1-yl)furo[3,2-d]pyrimidin-2-ylamino)-2,2-dimethyl-2H-benzo[b][1,4]oxazin-3(4H)-one;
7-(4-(4-(aminomethyl)piperidin-1-yl)furo[3,2-d]pyrimidin-2-ylamino)quinolin-2(1H)-one;

6-(4-(3-(aminomethyl)-3-methylpyrrolidin-1-yl)furo[3,2-d]pyrimidin-2-ylamino)-2,2-dimethyl-2H-benzo[b][1,4]oxazin-3(4H)-one;

6-(4-(4-(aminomethyl)-4-ethylpiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-(cyclopropylmethyl)piperidin-1-yl)furo[3,2-d]pyrimidin-2-ylamino)-2,2-dimethyl-2H-benzo[b][1,4]oxazin-3(4H)-one;

(4-{4-[4(4-aminotetrahydro-2H-thiopyrane 1,1-dioxide)-methyl]-piperidin-1-yl}-furo[3,2-d]pyrimidin-2-yl)-(3-methyl-1H-indazol-6-yl)-amine;

N-(3-methyl-1H-indazol-6-yl)-4-(4-((tetrahydro-2H-pyran-4-ylamino)methyl)piperidin-1-yl)furo[3,2-d]pyrimidin-2-amine;

6-(4-(3-(aminomethyl)-4-methylpyrrolidin-1-yl)furo[3,2-d]pyrimidin-2-ylamino)-2,2-dimethyl-2H-benzo[b][1,4]oxazin-3(4H)-one;

6-(4-(4-(aminomethyl)-4-(hydroxymethyl)piperidin-1-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(4-((methylamino)methyl)piperidin-1-yl)furo[3,2-d]pyrimidin-2-amine;

N-(1-methyl-1H-indazol-5-yl)-4-(4-((methylamino)methyl)piperidin-1-yl)furo[3,2-d]pyrimidin-2-amine;

(R)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)piperidine-4-carboxamide;

(S)-1-(2-(4-sulfamoylphenylamino)furo[3,2-d]pyrimidin-4-yl)pyrrolidine-2-carboxamide;

1-(2-(4-sulfamoylphenylamino)furo[3,2-d]pyrimidin-4-yl)piperidine-3-carboxamide;

4-(4-(4-(methylsulfonyl)piperazin-1-yl)furo[3,2-d]pyrimidin-2-ylamino)benzenesulfonamide;

4-(4-(4-(aminomethyl)piperidin-1-yl)furo[3,2-d]pyrimidin-2-ylamino)benzenesulfonamide;

1-(4-(2-(4-(methylsulfonyl)phenylamino)furo[3,2-d]pyrimidin-4-yl)piperazin-1-yl)ethanone;

4-(4-(4-acetylpiperazin-1-yl)furo[3,2-d]pyrimidin-2-ylamino)benzenesulfonamide;

N-((1-(2-(4-sulfamoylphenylamino)furo[3,2-d]pyrimidin-4-yl)piperidin-4-yl)methyl)acetamide;

4-(4-(hydroxymethyl)piperidin-1-yl)furo[3,2-d]pyrimidin-2-ylamino)benzenesulfonamide;

4-(4-(3-aminopyrrolidin-1-yl)furo[3,2-d]pyrimidin-2-ylamino)benzenesulfonamide;

4-(3-(aminomethyl)pyrrolidin-1-yl)-N-(3-methyl-1H-indazol-6-yl)furo[3,2-d]pyrimidin-2-amine;

4-(4-aminoazepan-1-yl)-N-(3-methyl-1H-indazol-6-yl)furo[3,2-d]pyrimidin-2-amine;

6-(4-(4-aminoazepan-1-yl)furo[3,2-d]pyrimidin-2-ylamino)-2,2-dimethyl-2H-benzo[b][1,4]oxazin-3(4H)-one;

4-(4-(aminomethyl)-4-methylpiperidin-1-yl)-N-(3-methyl-1H-indazol-6-yl)furo[3,2-d]pyrimidin-2-amine;

6-(4-(4-(aminomethyl)-4-methylpiperidin-1-yl)furo[3,2-d]pyrimidin-2-ylamino)-3,3-dimethylindolin-2-one;

6-(4-(4-(aminomethyl)-4-methylpiperidin-1-yl)furo[3,2-d]pyrimidin-2-ylamino)-2,2-dimethyl-2H-benzo[b][1,4]oxazin-3(4H)-one;

6-(4-(4-aminoazepan-1-yl)furo[3,2-d]pyrimidin-2-ylamino)-3,3-dimethylindolin-2-one;

(R)-6-(4-(2,7-diazaspiro[4.5]decan-2-yl)furo[3,2-d]pyrimidin-2-ylamino)-2,2-dimethyl-2H-benzo[b][1,4]oxazin-3(4H)-one;

2,2-dimethyl-6-(4-(tetrahydro-1H-pyrrolo[3,4-c]pyridin-5(6H,7H,7aH)-yl)furo[3,2-d]pyrimidin-2-ylamino)-2H-benzo[b][1,4]oxazin-3(4H)-one;

6-(4-(2,9-diazaspiro[5.5]undecan-9-yl)furo[3,2-d]pyrimidin-2-ylamino)-3,3-dimethylindolin-2-one;

6-(4-(2,8-diazaspiro[4.5]decan-8-yl)furo[3,2-d]pyrimidin-2-ylamino)-3,3-dimethylindolin-2-one;

N-(3-methoxy-4-morpholinophenyl)-4-(2,9-diazaspiro[5.5]undecan-9-yl)furo[3,2-d]pyrimidin-2-amine;

N-(1-methyl-1H-indazol-5-yl)-4-(2,8-diazaspiro[4.5]decan-8-yl)furo[3,2-d]pyrimidin-2-amine;

N-(3-chloro-4-morpholinophenyl)-4-(2,9-diazaspiro[5.5]undecan-9-yl)furo[3,2-d]pyrimidin-2-amine;

N-(3-methyl-4-morpholinophenyl)-4-(2,9-diazaspiro[5.5]undecan-9-yl)furo[3,2-d]pyrimidin-2-amine;

N-(1-methyl-1H-indazol-5-yl)-4-(2,9-diazaspiro[5.5]undecan-9-yl)furo[3,2-d]pyrimidin-2-amine;

N-(3-chloro-4-morpholinophenyl)-4-(2,8-diazaspiro[4.5]decan-8-yl)furo[3,2-d]pyrimidin-2-amine;

N-(3-methoxy-4-morpholinophenyl)-4-(2,8-diazaspiro[4.5]decan-8-yl)furo[3,2-d]pyrimidin-2-amine;

N-(3-methyl-1H-indazol-6-yl)-4-(2,9-diazaspiro[5.5]undecan-9-yl)furo[3,2-d]pyrimidin-2-amine;

N-(3-methyl-4-morpholinophenyl)-4-(2,8-diazaspiro[4.5]decan-8-yl)furo[3,2-d]pyrimidin-2-amine;

N-(3-methyl-1H-indazol-6-yl)-4-(2,8-diazaspiro[4.5]decan-8-yl)furo[3,2-d]pyrimidin-2-amine;

4-(azetidin-1-yl)-N-(3-methyl-1H-indazol-6-yl)furo[3,2-d]pyrimidin-2-amine;

(Z)—N'-hydroxy-1-(2-(3-methyl-1H-indazol-6-ylamino)furo[3,2-d]pyrimidin-4-yl)piperidine-4-carboximidamide;

4-(6,7-dihydro-3H-imidazo[4,5-c]pyridin-5(4H)-yl)-N-(3-methyl-1H-indazol-6-yl)furo[3,2-d]pyrimidin-2-amine;

1-(4-(4-(4-(4-((methylamino)methyl)piperidin-1-yl)furo[3,2-d]pyrimidin-2-ylamino)phenyl)piperazin-1-yl)ethanone;

1-(4-(4-(4-(4-(aminomethyl)piperidin-1-yl)furo[3,2-d]pyrimidin-2-ylamino)phenyl)piperazin-1-yl)ethanone;

6-(4-(4-(aminomethyl)piperidin-1-yl)furo[3,2-d]pyrimidin-2-ylamino)-3,4-dihydroquinolin-2(1H)-one;

6-(4-(4-(aminomethyl)piperidin-1-yl)furo[3,2-d]pyrimidin-2-ylamino)-2,2-dimethyl-2H-benzo[b][1,4]oxazin-3(4H)-one;

N-(4-(4-(4-(aminomethyl)piperidin-1-yl)furo[3,2-d]pyrimidin-2-ylamino)phenyl)butyramide;

4-(4-(aminomethyl)piperidin-1-yl)-N-(1H-indazol-6-yl)furo[3,2-d]pyrimidin-2-amine;

N2-(3-chloro-4-morpholinophenyl)-N4-(piperidin-4-ylmethyl)furo[3,2-d]pyrimidine-2,4-diamine;

4-(4-(aminomethyl)piperidin-1-yl)-N-(3-chloro-4-morpholinophenyl)furo[3,2-d]pyrimidin-2-amine;

N-(1H-indazol-6-yl)-4-(3-((methylamino)methyl)pyrrolidin-1-yl)furo[3,2-d]pyrimidin-2-amine;

4-(3-(aminomethyl)pyrrolidin-1-yl)-N-(1H-indazol-6-yl)furo[3,2-d]pyrimidin-2-amine;

4-(3-(aminomethyl)-5,6-dihydroimidazo[1,5-a]pyrazin-7(8H)-yl)-N-(1H-indazol-6-yl)furo[3,2-d]pyrimidin-2-amine;

4-(4-((2,2-difluoroethylamino)methyl)piperidin-1-yl)-N-(1H-indazol-6-yl)furo[3,2-d]pyrimidin-2-amine;

4-(4-((2-fluoroethylamino)methyl)piperidin-1-yl)-N-(1H-indazol-6-yl)furo[3,2-d]pyrimidin-2-amine;

N-(1H-indazol-6-yl)-4-(4-((oxetan-3-ylamino)methyl)piperidin-1-yl)furo[3,2-d]pyrimidin-2-amine;

N-(4-(4-(4-((2,2-difluoroethylamino)methyl)piperidin-1-yl)furo[3,2-d]pyrimidin-2-ylamino)phenyl)-N-methylacetamide;

4-(4-(aminomethyl)piperidin-1-yl)furo[3,2-d]pyrimidin-2-ylamino)-N-(3-methoxypropyl)benzenesulfonamide;

4-(4-(aminomethyl)piperidin-1-yl)-N-(1-methyl-1H-indazol-5-yl)furo[3,2-d]pyrimidin-2-amine;

N-(1H-indazol-6-yl)-4-(3-((methylamino)methyl)-5,6-dihydroimidazo[1,5-a]pyrazin-7(8H)-yl)furo[3,2-d]pyrimidin-2-amine;

6-(4-(4-((2,2-difluoroethylamino)methyl)piperidin-1-yl)furo[3,2-d]pyrimidin-2-ylamino)-2,2-dimethyl-2H-benzo[b][1,4]oxazin-3(4H)-one;

N-(1H-indazol-6-yl)-4-(4-((2-(methylsulfonyl)ethylamino)methyl)piperidin-1-yl)furo[3,2-d]pyrimidin-2-amine;

4-(4-(aminomethyl)piperidin-1-yl)-N-(3-methyl-1H-indazol-6-yl)furo[3,2-d]pyrimidin-2-amine;

6-(4-(3,4-dihydroisoquinolin-2(1H)-yl)furo[3,2-d]pyrimidin-2-ylamino)-2,2-dimethyl-2H-benzo[b][1,4]oxazin-3(4H)-one;

4-(4-aminoazepan-1-yl)-N-(1H-indazol-6-yl)furo[3,2-d]pyrimidin-2-amine;

2,2-dimethyl-6-(4-(4-((methylamino)methyl)piperidin-1-yl)furo[3,2-d]pyrimidin-2-ylamino)-2H-benzo[b][1,4]oxazin-3(4H)-one;

N-(1H-indazol-6-yl)-4-(4-((methylamino)methyl)piperidin-1-yl)furo[3,2-d]pyrimidin-2-amine;

6-(4-(4-((2,2-difluoroethylamino)methyl)piperidin-1-yl)furo[3,2-d]pyrimidin-2-ylamino)-3,3-dimethylindolin-2-one;

3,3-dimethyl-6-(4-(4-((methylamino)methyl)piperidin-1-yl)furo[3,2-d]pyrimidin-2-ylamino)indolin-2-one;

2,2-dimethyl-6-(4-(3-((methylamino)methyl)pyrrolidin-1-yl)furo[3,2-d]pyrimidin-2-ylamino)-2H-benzo[b][1,4]oxazin-3(4H)-one;

4-(4-(aminomethyl)-4-fluoropiperidin-1-yl)-N-(1H-indazol-6-yl)furo[3,2-d]pyrimidin-2-amine;

4-(4-(4-((2,2-difluoroethylamino)methyl)piperidin-1-yl)furo[3,2-d]pyrimidin-2-ylamino)-N-(3-methoxypropyl)benzenesulfonamide;

4-(4-((2,2-difluoroethylamino)methyl)piperidin-1-yl)-N-(1-methyl-1H-indazol-5-yl)furo[3,2-d]pyrimidin-2-amine;

6-(4-(4-((2-fluoroethylamino)methyl)piperidin-1-yl)furo[3,2-d]pyrimidin-2-ylamino)-2,2-dimethyl-2H-benzo[b][1,4]oxazin-3(4H)-one;

6-(4-(4-((2-fluoroethylamino)methyl)piperidin-1-yl)furo[3,2-d]pyrimidin-2-ylamino)-3,3-dimethylindolin-2-one;

1-(2-(2,2-dimethyl-3-oxo-3,4-dihydro-2H-benzo[b][1,4]oxazin-6-ylamino)furo[3,2-d]pyrimidin-4-yl)piperidine-3-carboxamide;

7-(4-(4-(aminomethyl)piperidin-1-yl)furo[3,2-d]pyrimidin-2-ylamino)-4-methylquinolin-2(1H)-one;

7-(4-(4-((2,2-difluoroethylamino)methyl)piperidin-1-yl)furo[3,2-d]pyrimidin-2-ylamino)-3,4-dihydroquinolin-2(1H)-one;

7-(4-(4-((2,2-difluoroethylamino)methyl)piperidin-1-yl)furo[3,2-d]pyrimidin-2-ylamino)quinolin-2(1H)-one;

7-(4-(4-((2,2-difluoroethylamino)methyl)piperidin-1-yl)furo[3,2-d]pyrimidin-2-ylamino)-4-methylquinolin-2(1H)-one;

6-(4-(4-((2,2-difluoroethylamino)methyl)piperidin-1-yl)furo[3,2-d]pyrimidin-2-ylamino)-2H-benzo[b][1,4]oxazin-3(4H)-one;

N-(3-chloro-4-morpholinophenyl)-4-(4-((2,2-difluoroethylamino)methyl)piperidin-1-yl)furo[3,2-d]pyrimidin-2-amine;

7-(4-(4-((2,2-difluoroethylamino)methyl)piperidin-1-yl)furo[3,2-d]pyrimidin-2-ylamino)-3,3-dimethyl-3,4-dihydroquinolin-2(1H)-one;

7-(4-(4-((2,2-difluoroethylamino)methyl)piperidin-1-yl)furo[3,2-d]pyrimidin-2-ylamino)-3-methylquinolin-2(1H)-one;

6-(4-(4-((2,2-difluoroethylamino)methyl)piperidin-1-yl)furo[3,2-d]pyrimidin-2-ylamino)-2,2-difluoro-2H-benzo[b][1,4]oxazin-3(4H)-one;

6-(4-(4-(1-(2,2-difluoroethylamino)ethyl)piperidin-1-yl)furo[3,2-d]pyrimidin-2-ylamino)-2,2-dimethyl-2H-benzo[b][1,4]oxazin-3(4H)-one;

6-(4-(4-(1-(2,2-difluoroethylamino)ethyl)piperidin-1-yl)furo[3,2-d]pyrimidin-2-ylamino)-3,3-dimethylindolin-2-one;

4-(4-((2,2-difluoroethylamino)methyl)piperidin-1-yl)-N-(3-fluoro-4-morpholinophenyl)furo[3,2-d]pyrimidin-2-amine;

7-(4-(4-((2,2-difluoroethylamino)methyl)piperidin-1-yl)furo[3,2-d]pyrimidin-2-ylamino)-3-methyl-3,4-dihydroquinolin-2(1H)-one;

6-(4-(4-((2,2-difluoroethylamino)methyl)-4-methylpiperidin-1-yl)furo[3,2-d]pyrimidin-2-ylamino)-2,2-dimethyl-2H-benzo[b][1,4]oxazin-3(4H)-one;

1-(2-(2,2-dimethyl-3-oxo-3,4-dihydro-2H-benzo[b][1,4]oxazin-6-ylamino)furo[3,2-d]pyrimidin-4-yl)pyrrolidine-3-carboxamide;

6-(4-(4-(hydroxymethyl)-4-methylpiperidin-1-yl)furo[3,2-d]pyrimidin-2-ylamino)-2,2-dimethyl-2H-benzo[b][1,4]oxazin-3(4H)-one;

6-(4-(4-hydroxy-4-methylpiperidin-1-yl)furo[3,2-d]pyrimidin-2-ylamino)-2,2-dimethyl-2H-benzo[b][1,4]oxazin-3(4H)-one;

6-(4-(4-hydroxy-4-(hydroxymethyl)piperidin-1-yl)furo[3,2-d]pyrimidin-2-ylamino)-2,2-dimethyl-2H-benzo[b][1,4]oxazin-3(4H)-one;

6-(4-(3-hydroxypiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-hydroxypiperidin-1-yl)furo[3,2-d]pyrimidin-2-ylamino)-2,2-dimethyl-2H-benzo[b][1,4]oxazin-3(4H)-one;

6-(4-(4-((2,2-difluoroethylamino)methyl)piperidin-1-yl)furo[3,2-d]pyrimidin-2-ylamino)-2,2-dimethyl-2H-benzo[b][1,4]thiazin-3(4H)-one;

4-(aminomethyl)-1-(2-(3-methyl-1H-indazol-6-ylamino)furo[3,2-d]pyrimidin-4-yl)piperidin-4-ol;

6-(4-((3S,4S)-4-(aminomethyl)-3-hydroxypiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-hydroxypiperidin-1-yl)furo[3,2-d]pyrimidin-2-ylamino)-3,3-dimethylindolin-2-one;

2,2-dimethyl-6-(4-(4-((methylamino)methyl)piperidin-1-yl)furo[3,2-d]pyrimidin-2-ylamino)-2H-benzo[b][1,4]thiazin-3(4H)-one;

6-(4-(3,9-diazaspiro[5.5]undecan-3-yl)furo[3,2-d]pyrimidin-2-ylamino)-2,2-dimethyl-2H-benzo[b][1,4]oxazin-3(4H)-one;

4-(4-(2-aminoethyl)piperidin-1-yl)-N-(3-methyl-1H-indazol-6-yl)furo[3,2-d]pyrimidin-2-amine;

4-(4-(2,2-difluoroethylamino)azepan-1-yl)-N-(3-methyl-1H-indazol-6-yl)furo[3,2-d]pyrimidin-2-amine;

1-(2-(2,2-dimethyl-3-oxo-3,4-dihydro-2H-benzo[b][1,4]
oxazin-6-ylamino)furo[3,2-d]pyrimidin-4-yl)-4-(2-hydroxyethyl)piperidine-4-carbonitrile;
2,2-dimethyl-6-(4-(4-(4-((3,3,3-trifluoropropylamino)
methyl)piperidin-1-yl)furo[3,2-d]pyrimidin-2-ylamino)-2H-benzo[b][1,4]oxazin-3(4H)-one;
6-(4-(4-(aminomethyl)-4-methoxypiperidin-1-yl)furo[3,
2-d]pyrimidin-2-ylamino)-2,2-dimethyl-2H-benzo[b]
[1,4]oxazin-3(4H)-one;
6-(4-((3S,4S)-4-amino-3-hydroxyazepan-1-yl)furo[3,2-d]
pyrimidin-2-ylamino)-2,2-dimethyl-2H-benzo[b][1,4]
oxazin-3(4H)-one;
6-(4-(3-((2,2-difluoroethylamino)methyl)pyrrolidin-1-yl)
furo[3,2-d]pyrimidin-2-ylamino)-3,3-dimethylindolin-2-one;
6-(4-(3-(hydroxymethyl)pyrrolidin-1-yl)furo[3,2-d]pyrimidin-2-ylamino)-2,2-dimethyl-2H-benzo[b][1,4]oxazin-3(4H)-one;
3,3-dimethyl-6-(4-(4-((3,3,3-trifluoropropylamino)methyl)piperidin-1-yl)furo[3,2-d]pyrimidin-2-ylamino)
indolin-2-one;
N-(3-methyl-1H-indazol-6-yl)-4-(4-((3,3,3-trifluoropropylamino)methyl)piperidin-1-yl)furo[3,2-d]pyrimidin-2-amine;
6-(4-(4-(aminomethyl)-4-(2-hydroxyethyl)piperidin-1-yl)
furo[3,2-d]pyrimidin-2-ylamino)-2,2-dimethyl-2H-benzo[b][1,4]oxazin-3(4H)-one;
4S)-4-(aminomethyl)-1-(2-(3-methyl-1H-indazol-6-ylamino)furo[3,2-d]pyrimidin-4-yl)piperidin-3-ol;
6-(4-(3-hydroxypyrrolidin-1-yl)furo[3,2-d]pyrimidin-2-ylamino)-2,2-dimethyl-2H-benzo[b][1,4]oxazin-3
(4H)-one;
6-(4-(4-hydroxypiperidin-1-yl)furo[3,2-d]pyrimidin-2-ylamino)-2,2-dimethyl-2H-benzo[b][1,4]oxazin-3
(4H)-one;
1-(4-(4-(4-(((dimethylamino)methyl)piperidin-1-yl)
furo[3,2-d]pyrimidin-2-ylamino)phenyl)piperazin-1-yl)ethanone;
4-(4-(aminomethyl)piperidin-1-yl)-N-(4-(piperazin-1-yl)
phenyl)furo[3,2-d]pyrimidin-2-amine;
1-(4-(4-(4-((dimethylamino)methyl)-4-methylpiperidin-1-yl)furo[3,2-d]pyrimidin-2-ylamino)phenyl)piperazin-1-yl)ethanone;
1-(4-(4-(4-(3-(hydroxymethyl)-5,6-dihydroimidazo[1,5-a]pyrazin-7(8H)-yl)furo[3,2-d]pyrimidin-2-ylamino)
phenyl)piperazin-1-yl)ethanone;
1-(4-(4-(4-(5,6-dihydroimidazo[1,5-a]pyrazin-7(8H)-yl)
furo[3,2-d]pyrimidin-2-ylamino)phenyl)piperazin-1-yl)ethanone;
1-(4-(4-(4-(3-((dimethylamino)methyl)-5,6-dihydroimidazo[1,5-a]pyrazin-7(8H)-yl)furo[3,2-d]pyrimidin-2-ylamino)phenyl)piperazin-1-yl)ethanone;
1-(4-(4-(4-(3-methyl-5,6-dihydroimidazo[1,5-a]pyrazin-7(8H)-yl)furo[3,2-d]pyrimidin-2-ylamino)phenyl)piperazin-1-yl)ethanone;
ethyl 2-(1-(2-(4-(piperazin-1-yl)phenylamino)furo[3,2-d]
pyrimidin-4-yl)piperidin-4-yl)acetate;
ethyl 2-(1-(2-(4-(4-acetylpiperazin-1-yl)phenylamino)
furo[3,2-d]pyrimidin-4-yl)piperidin-4-yl)acetate;
ethyl 2-(1-(2-(4-(N-methylacetamido)phenylamino)furo
[3,2-d]pyrimidin-4-yl)piperidin-4-yl)acetate;
ethyl 2-(1-(2-(4-butyramidophenylamino)furo[3,2-d]pyrimidin-4-yl)piperidin-4-yl)acetate;
1-(4-(4-(4-(4-hydroxy-4-(pyrrolidin-1-ylmethyl)piperidin-1-yl)furo[3,2-d]pyrimidin-2-ylamino)phenyl)piperazin-1-yl)ethanone;
1-(4-(4-(4-(3-((dimethylamino)methyl)pyrrolidin-1-yl)
furo[3,2-d]pyrimidin-2-ylamino)phenyl)piperazin-1-yl)ethanone;
(S)-1-(4-(4-(4-(3-aminopiperidin-1-yl)furo[3,2-d]pyrimidin-2-ylamino)phenyl)piperazin-1-yl)ethanone;
ethyl 2-(1-(2-(2-oxo-1,2,3,4-tetrahydroquinolin-6-ylamino)furo[3,2-d]pyrimidin-4-yl)piperidin-4-yl)acetate;
ethyl 2-(1-(2-(2,2-dimethyl-3-oxo-3,4-dihydro-2H-benzo
[b][1,4]oxazin-6-ylamino)furo[3,2-d]pyrimidin-4-yl)
piperidin-4-yl)acetate;
ethyl 2-(1-(2-(3-chloro-4-morpholinophenylamino)furo
[3,2-d]pyrimidin-4-yl)piperidin-4-yl)acetate;
ethyl 2-(1-(2-(3-oxo-3,4-dihydro-2H-benzo[b][1,4]oxazin-6-ylamino)furo[3,2-d]pyrimidin-4-yl)piperidin-4-yl)acetate;
1-(4-(4-(4-(pyridin-3-yl)piperazin-1-yl)furo[3,2-d]pyrimidin-2-ylamino)phenyl)piperazin-1-yl)ethanone;
ethyl 2-(1-(2-(1H-indazol-6-ylamino)furo[3,2-d]pyrimidin-4-yl)piperidin-4-yl)acetate;
1-(6-(4-(4-(aminomethyl)piperidin-1-yl)furo[3,2-d]pyrimidin-2-ylamino)-5-methoxyindolin-1-yl)-2-(dimethylamino)ethanone;
4-(4-(aminomethyl)piperidin-1-yl)-N-(4-(4-isopropylpiperazin-1-yl)-2-methoxyphenyl)furo[3,2-d]pyrimidin-2-amine;
4-(1-benzylpyrrolidin-3-yl)-N-(1H-indazol-6-yl)furo[3,
2-d]pyrimidin-2-amine;
N-(1H-indazol-6-yl)-4-(piperazin-1-yl)furo[3,2-d]pyrimidin-2-amine;
3-((1-(2-(1H-indazol-6-ylamino)furo[3,2-d]pyrimidin-4-yl)piperidin-4-yl)methyl)oxazolidin-2-one;
N-(1H-indazol-6-yl)-4-(4-((2,2,2-trifluoroethylamino)
methyl)piperidin-1-yl)furo[3,2-d]pyrimidin-2-amine;
4-(3-(2-aminoethyl)azetidin-1-yl)-N-(1H-indazol-6-yl)
furo[3,2-d]pyrimidin-2-amine;
N-(1H-indazol-6-yl)-4-(3-((methylamino)methyl)piperidin-1-yl)furo[3,2-d]pyrimidin-2-amine;
4-(3-(aminomethyl)piperidin-1-yl)-N-(1H-indazol-6-yl)
furo[3,2-d]pyrimidin-2-amine;
4-(3-(2-aminoethyl)piperidin-1-yl)-N-(1H-indazol-6-yl)
furo[3,2-d]pyrimidin-2-amine;
4-(2-(2-aminoethyl)morpholino)-N-(1H-indazol-6-yl)
furo[3,2-d]pyrimidin-2-amine;
4-(2-(aminomethyl)azetidin-1-yl)-N-(1H-indazol-6-yl)
furo[3,2-d]pyrimidin-2-amine;
N-(1H-indazol-6-yl)-4-(4-(((3-methyloxetan-3-yl)methylamino)methyl)piperidin-1-yl)furo[3,2-d]pyrimidin-2-amine;
1-(4-(4-(4-(2-hydroxy-2-methylpropyl)piperazin-1-yl)
furo[3,2-d]pyrimidin-2-ylamino)phenyl)piperazin-1-yl)ethanone;
N-(4-(4-(4-(aminomethyl)piperidin-1-yl)furo[3,2-d]pyrimidin-2-ylamino)phenyl)-N-methylacetamide; or
4-tert-butyl-N-(1-(2-(5-(morpholine-4-carbonyl)pyridin-2-ylamino)furo[3,2-d]pyrimidin-4-yl)piperidin-3-yl)
benzamide bis(2,2,2-trifluoroacetate);
and pharmaceutically acceptable salts thereof.

13. The compound of claim 7 wherein $R^1$ is optionally substituted azepinyl, optionally substituted diazaspiro[4.5]
decanyl, optionally substituted diazaspiro[5.5]undecanyl, optionally substituted 1-oxa-4,9-diazaspiro[5.5]undecanyl, optionally substituted piperidinyl, or optionally substituted pyrrolidinyl.

14. The compound of claim 13 wherein Y is optionally substituted benzo[b][1,4]oxazinyl, optionally substituted benzo[b][1,4]thiazinyl, optionally substituted dihydroquinolinyl, optionally substituted indazolyl, optionally substituted indolinyl, optionally substituted indolyl, optionally substituted phenyl, or optionally substituted quinolinyl.

15. The compound of claim 14 wherein Z is H, —C(O)N(CH$_3$)$_2$, —N(H)C(O)—(C$_1$-C$_3$)alkyl, (C$_1$-C$_3$)alkyl, —S(O)$_2$N(H)optionally substituted (C$_1$-C$_3$)alkyl, optionally substituted morpholinyl, or optionally substituted piperazinyl.

16. The compound of claim 15 wherein the compound is
4-(4-((2,2-difluoroethylamino)methyl)piperidin-1-yl)-N-(3-methyl-1H-indazol-6-yl)furo[3,2-d]pyrimidin-2-amine;
4-(4-(aminomethyl)-4-methylpiperidin-1-yl)-N-(1H-indazol-6-yl)furo[3,2-d]pyrimidin-2-amine;
2,2-dimethyl-6-(4-(4-(2-(methylsulfonyl)ethylamino)methyl)piperidin-1-yl)furo[3,2-d]pyrimidin-2-ylamino)-2H-benzo[b][1,4]oxazin-3(4H)-one;
3,3-dimethyl-6-(4-(4-(2-(methylsulfonyl)ethylamino)methyl)piperidin-1-yl)furo[3,2-d]pyrimidin-2-ylamino)indolin-2-one;
N-(3-methoxypropyl)-4-(4-(4-((methylamino)methyl)piperidin-1-yl)furo[3,2-d]pyrimidin-2-ylamino)benzenesulfonamide;
2-methyl-2-(4-(4-(4-((methylamino)methyl)piperidin-1-yl)furo[3,2-d]pyrimidin-2-ylamino)phenyl)propanenitrile;
6-(4-(2,8-diazaspiro[4.5]decan-8-yl)furo[3,2-d]pyrimidin-2-ylamino)-2,2-dimethyl-2H-benzo[b][1,4]oxazin-3(4H)-one;
6-(4-(2,9-diazaspiro[5.5]undecan-9-yl)furo[3,2-d]pyrimidin-2-ylamino)-2,2-dimethyl-2H-benzo[b][1,4]oxazin-3(4H)-one;
N-(3-methyl-1H-indazol-6-yl)-4-(4-((2-(methylsulfonyl)ethylamino)methyl)piperidin-1-yl)furo[3,2-d]pyrimidin-2-amine;
7-(4-(4-(aminomethyl)piperidin-1-yl)furo[3,2-d]pyrimidin-2-ylamino)-3,4-dihydroquinolin-2(1H)-one;
6-(4-(4-(1-aminoethyl)piperidin-1-yl)furo[3,2-d]pyrimidin-2-ylamino)-2,2-dimethyl-2H-benzo[b][1,4]oxazin-3(4H)-one;
7-(4-(4-(aminomethyl)piperidin-1-yl)furo[3,2-d]pyrimidin-2-ylamino)quinolin-2(1H)-one;
6-(4-(4-(aminomethyl)-4-ethylpiperidin-1-yl)furo[3,2-d]pyrimidin-2-ylamino)-2,2-dimethyl-2H-benzo[b][1,4]oxazin-3(4H)-one;
6-(4-(4-(aminomethyl)-4-(cyclopropylmethyl)piperidin-1-yl)furo[3,2-d]pyrimidin-2-ylamino)-2,2-dimethyl-2H-benzo[b][1,4]oxazin-3(4H)-one;
(4-{4-[(4-aminotetrahydro-2H-thiopyrane 1,1-dioxide)-methyl]-piperidin-1-yl}-furo[3,2-d]pyrimidin-2-yl)-(3-methyl-1H-indazol-6-yl)-amine;
N-(3-methyl-1H-indazol-6-yl)-4-(1-oxa-4,9-diazaspiro[5.5]undecan-9-yl)furo[3,2-d]pyrimidin-2-amine;
N-(3-methyl-1H-indazol-6-yl)-4-(4-((methylamino)methyl)piperidin-1-yl)furo[3,2-d]pyrimidin-2-amine;
N-(1-methyl-1H-indazol-5-yl)-4-(4-((methylamino)methyl)piperidin-1-yl)furo[3,2-d]pyrimidin-2-amine;
4-(4-aminoazepan-1-yl)-N-(3-methyl-1H-indazol-6-yl)furo[3,2-d]pyrimidin-2-amine;
4-(4-(aminomethyl)-4-methylpiperidin-1-yl)-N-(3-methyl-1H-indazol-6-yl)furo[3,2-d]pyrimidin-2-amine;
6-(4-(4-(aminomethyl)-4-methylpiperidin-1-yl)furo[3,2-d]pyrimidin-2-ylamino)-3,3-dimethylindolin-2-one;
6-(4-(4-(aminomethyl)-4-methylpiperidin-1-yl)furo[3,2-d]pyrimidin-2-ylamino)-2,2-dimethyl-2H-benzo[b][1,4]oxazin-3(4H)-one;
(R)-6-(4-(2,7-diazaspiro[4.5]decan-2-yl)furo[3,2-d]pyrimidin-2-ylamino)-2,2-dimethyl-2H-benzo[b][1,4]oxazin-3(4H)-one;
6-(4-(2,9-diazaspiro[5.5]undecan-9-yl)furo[3,2-d]pyrimidin-2-ylamino)-3,3-dimethylindolin-2-one;
6-(4-(2,8-diazaspiro[4.5]decan-8-yl)furo[3,2-d]pyrimidin-2-ylamino)-3,3-dimethylindolin-2-one;
N-(3-methoxy-4-morpholinophenyl)-4-(2,9-diazaspiro[5.5]undecan-9-yl)furo[3,2-d]pyrimidin-2-amine;
N-(1-methyl-1H-indazol-5-yl)-4-(2,8-diazaspiro[4.5]decan-8-yl)furo[3,2-d]pyrimidin-2-amine;
N-(3-chloro-4-morpholinophenyl)-4-(2,9-diazaspiro[5.5]undecan-9-yl)furo[3,2-d]pyrimidin-2-amine;
N-(1-methyl-1H-indazol-5-yl)-4-(2,9-diazaspiro[5.5]undecan-9-yl)furo[3,2-d]pyrimidin-2-amine;
N-(3-chloro-4-morpholinophenyl)-4-(2,8-diazaspiro[4.5]decan-8-yl)furo[3,2-d]pyrimidin-2-amine;
N-(3-methyl-1H-indazol-6-yl)-4-(2,9-diazaspiro[5.5]undecan-9-yl)furo[3,2-d]pyrimidin-2-amine;
N-(3-methyl-4-morpholinophenyl)-4-(2,8-diazaspiro[4.5]decan-8-yl)furo[3,2-d]pyrimidin-2-amine;
N-(3-methyl-1H-indazol-6-yl)-4-(2,8-diazaspiro[4.5]decan-8-yl)furo[3,2-d]pyrimidin-2-amine;
(Z)—N'-hydroxy-1-(2-(3-methyl-1H-indazol-6-ylamino)furo[3,2-d]pyrimidin-4-yl)piperidine-4-carboximidamide;
1-(4-(4-(4-(4-((methylamino)methyl)piperidin-1-yl)furo[3,2-d]pyrimidin-2-ylamino)phenyl)piperazin-1-yl)ethanone;
1-(4-(4-(4-(4-(aminomethyl)piperidin-1-yl)furo[3,2-d]pyrimidin-2-ylamino)phenyl)piperazin-1-yl)ethanone;
6-(4-(4-(aminomethyl)piperidin-1-yl)furo[3,2-d]pyrimidin-2-ylamino)-3,4-dihydroquinolin-2(1H)-one;
N-(4-(4-(4-(aminomethyl)piperidin-1-yl)furo[3,2-d]pyrimidin-2-ylamino)phenyl)butyramide;
4-(4-(aminomethyl)piperidin-1-yl)-N-(1H-indazol-6-yl)furo[3,2-d]pyrimidin-2-amine;
4-(3-(aminomethyl)pyrrolidin-1-yl)-N-(1H-indazol-6-yl)furo[3,2-d]pyrimidin-2-amine;
4-(4-((2,2-difluoroethylamino)methyl)piperidin-1-yl)-N-(1H-indazol-6-yl)furo[3,2-d]pyrimidin-2-amine;
4-(4-((2-fluoroethylamino)methyl)piperidin-1-yl)-N-(1H-indazol-6-yl)furo[3,2-d]pyrimidin-2-amine;
N-(1H-indazol-6-yl)-4-(4-((oxetan-3-ylamino)methyl)piperidin-1-yl)furo[3,2-d]pyrimidin-2-amine;
4-(4-(aminomethyl)piperidin-1-yl)furo[3,2-d]pyrimidin-2-ylamino)-N-(3-methoxypropyl)benzenesulfonamide;
4-(4-(aminomethyl)piperidin-1-yl)-N-(1-methyl-1H-indazol-5-yl)furo[3,2-d]pyrimidin-2-amine;
6-(4-(4-((2,2-difluoroethylamino)methyl)piperidin-1-yl)furo[3,2-d]pyrimidin-2-ylamino)-2,2-dimethyl-2H-benzo[b][1,4]oxazin-3(4H)-one;
N-(1H-indazol-6-yl)-4-(4-((2-(methylsulfonyl)ethylamino)methyl)piperidin-1-yl)furo[3,2-d]pyrimidin-2-amine;
N-(1H-indazol-6-yl)-4-(4-((methylamino)methyl)piperidin-1-yl)furo[3,2-d]pyrimidin-2-amine;
6-(4-(4-((2,2-difluoroethylamino)methyl)piperidin-1-yl)furo[3,2-d]pyrimidin-2-ylamino)-3,3-dimethylindolin-2-one;
(diexo)-3-(2-(3,3-dimethyl-2-oxoindolin-6-ylamino)furo[3,2-d]pyrimidin-4-ylamino)bicyclo[2.2.1]hept-5-ene-2-carboxamide;
3,3-dimethyl-6-(4-(4-((methylamino)methyl)piperidin-1-yl)furo[3,2-d]pyrimidin-2-ylamino)indolin-2-one;

6-(4-(4-((2-fluoroethylamino)methyl)piperidin-1-yl)furo
[3,2-d]pyrimidin-2-ylamino)-2,2-dimethyl-2H-benzo
[b][1,4]oxazin-3(4H)-one;

6-(4-(4-((2-fluoroethylamino)methyl)piperidin-1-yl)furo
[3,2-d]pyrimidin-2-ylamino)-3,3-dimethylindolin-2-
one;

7-(4-(4-((2,2-difluoroethylamino)methyl)piperidin-1-yl)
furo[3,2-d]pyrimidin-2-ylamino)-3,4-dihydroquinolin-
2(1H)-one;

7-(4-(4-((2,2-difluoroethylamino)methyl)piperidin-1-yl)
furo[3,2-d]pyrimidin-2-ylamino)-4-methylquinolin-2
(1H)-one;

6-(4-(4-((2,2-difluoroethylamino)methyl)piperidin-1-yl)
furo[3,2-d]pyrimidin-2-ylamino)-2H-benzo[b][1,4]ox-
azin-3(4H)-one;

N-(3-chloro-4-morpholinophenyl)-4-(44(2,2-difluoroet-
hylamino)methyl)piperidin-1-yl)furo[3,2-d]pyrimidin-
2-amine;

6-(4-(4-(2-hydroxyethyl)piperidin-1-yl)furo[3,2-d]pyri-
midin-2-ylamino)-2,2-dimethyl-2H-benzo[b][1,4]ox-
azin-3(4H)-one;

4-(aminomethyl)-1-(2-(3-methyl-1H-indazol-6-ylamino)
furo[3,2-d]pyrimidin-4-yl)piperidin-4-ol;

6-(4-((3S,4S)-4-(aminomethyl)-3-hydroxypiperidin-1-yl)
furo[3,2-d]pyrimidin-2-ylamino)-2,2-dimethyl-2H-
benzo[b][1,4]oxazin-3(4H)-one;

6-(4-(4-(aminomethyl)-4-hydroxypiperidin-1-yl)furo[3,
2-d]pyrimidin-2-ylamino)-3,3-dimethylindolin-2-one;

2,2-dimethyl-6-(4-(4-((methylamino)methyl)piperidin-1-
yl)furo[3,2-d]pyrimidin-2-ylamino)-2H-benzo[b][1,4]
thiazin-3(4H)-one;

1-(2-(2,2-dimethyl-3-oxo-3,4-dihydro-2H-benzo[b][1,4]
oxazin-6-ylamino)furo[3,2-d]pyrimidin-4-yl)-4-(2-hy-
droxyethyl)piperidine-4-carbonitrile;

6-(4-(4-(aminomethyl)-4-methoxypiperidin-1-yl)furo[3,
2-d]pyrimidin-2-ylamino)-2,2-dimethyl-2H-benzo[b]
[1,4]oxazin-3(4H)-one;

3,3-dimethyl-6-(4-(4-((3,3,3-trifluoropropylamino)me-
thyl)piperidin-1-yl)furo[3,2-d]pyrimidin-2-ylamino)
indolin-2-one;

6-(4-(4-(aminomethyl)-4-(2-hydroxyethyl)piperidin-1-yl)
furo[3,2-d]pyrimidin-2-ylamino)-2,2-dimethyl-2H-
benzo[b][1,4]oxazin-3(4H)-one;

(3S,4S)-4-(aminomethyl)-1-(2-(3-methyl-1H-indazol-6-
ylamino)furo[3,2-d]pyrimidin-4-yl)piperidin-3-ol;

6-(4-(cyclopropylamino)furo[3,2-d]pyrimidin-2-
ylamino)-N,N-dimethyl-1H-indazole-3-carboxamide;

6-(4-(4-hydroxypiperidin-1-yl)furo[3,2-d]pyrimidin-2-
ylamino)-2,2-dimethyl-2H-benzo[b][1,4]oxazin-3
(4H)-one;

N-propyl-4-(4-(2,2,2-trifluoroethylamino)furo[3,2-d]py-
rimidin-2-ylamino)benzamide;

N2-(3-chloro-4-(4-methylpiperazin-1-yl)phenyl)-N4-cy-
clopropylfuro[3,2-d]pyrimidine-2,4-diamine;

N4-allyl-N2-(4-(methylsulfonyl)phenyl)furo[3,2-d]pyri-
midine-2,4-diamine;

N2-(3-chloro-4-morpholinophenyl)-N4-cyclopropylfuro
[3,2-d]pyrimidine-2,4-diamine;

4-(4-(cyclopropylamino)furo[3,2-d]pyrimidin-2-
ylamino)benzenesulfonamide;

4-(4-(cyclopropylamino)furo[3,2-d]pyrimidin-2-
ylamino)benzenesulfonamide bis(2,2,2-trifluoroac-
etate);

4-(4-(cyclopropylamino)furo[3,2-d]pyrimidin-2-
ylamino)-N-propylbenz amide;

N*4*-cyclopropyl-N*2*-(2,2-dioxo-2,3-dihydro-1H-
2lambda*6*-benzo[c]thiophen-5-yl)-furo[3,2-d]pyri-
midine-2,4-diamine;

N4-cyclopropyl-N2-(4-(morpholinomethyl)phenyl)furo
[3,2-d]pyrimidine-2,4-diamine;

1-(4-(4-(4-(cyclopropylamino)furo[3,2-d]pyrimidin-2-
ylamino)phenyl)piperazin-1-yl)ethanone;

N*4*-cyclopropyl-N*2*-(1,1-dioxo-2,3-dihydro-1H-
1lambda*6*-benzo[d]isothiazol-6-yl)-uro[3,2-d]pyri-
midine-2,4-diamine;

6-(4-cyclopropylamino-furo[3,2-d]pyrimidin-2-
ylamino)-1,1-dioxo-1,2-dihydro-1 lambda*6*-benzo
[d]isothiazol-3-one;

N4-cyclopropyl-N2-(1H-indazol-6-yl)furo[3,2-d]pyrimi-
dine-2,4-diamine;

4-(4-(cyclobutylamino)furo[3,2-d]pyrimidin-2-ylamino)
benzenesulfonamide 2,2,2-trifluoroacetate;

N4-cyclopropyl-N2-(1-methyl-1H-pyrazol-4-yl)furo[3,2-
d]pyrimidine-2,4-diamine;

(1R,2S)-2-(2-(4-sulfamoylphenylamino)furo[3,2-d]pyri-
midin-4-ylamino)cyclopentanecarboxamide;

6-(4-(cyclopropylamino)furo[3,2-d]pyrimidin-2-
ylamino)-3,4-dihydroquinolin-2(1H)-one;

(1R,2R,3S,4S)-3-(2-(4-sulfamoylphenylamino)furo[3,2-
d]pyrimidin-4-ylamino)bicyclo[2.2.1]hept-5-ene-2-
carboxamide;

N-(4-(4-(cyclobutylamino)furo[3,2-d]pyrimidin-2-
ylamino)phenyl)-N-methylacetamide;

N-(4-(4-(cyclobutylamino)furo[3,2-d]pyrimidin-2-
ylamino)phenyl)butyramide;

N2-(3-chloro-4-morpholinophenyl)-N4-cyclobutylfuro[3,
2-d]pyrimidine-2,4-diamine;

N4-cyclobutyl-N2-(1H-indazol-6-yl)furo[3,2-d]pyrimi-
dine-2,4-diamine;

6-(4-(cyclopropylamino)furo[3,2-d]pyrimidin-2-
ylamino)-2,2-dimethyl-2H-benzo[b][1,4]oxazin-3
(4H)-one;

N-(4-(4-(cyclopropylamino)furo[3,2-d]pyrimidin-2-
ylamino)phenyl)-N-methylacetamide;

N4-allyl-N2-(quinolin-4-yl)furo[3,2-d]pyrimidine-2,4-di-
amine;

N2-(3-chloro-4-morpholinophenyl)-N4-(piperidin-4-yl-
methyl)furo[3,2-d]pyrimidine-2,4-diamine;

6-(4-(piperidin-4-ylmethylamino)furo[3,2-d]pyrimidin-
2-ylamino)-2H-benzo[b][1,4]oxazin-3(4H)-one;

N-(4-(4-(piperidin-4-ylmethylamino)furo[3,2-d]pyrimi-
din-2-ylamino)phenyl)butyramide;

N4-cyclopropyl-N2-(isoquinolin-1-yl)furo[3,2-d]pyrimi-
dine-2,4-diamine;

6-(4-(cyclobutylamino)furo[3,2-d]pyrimidin-2-ylamino)-
3,4-dihydroquinolin-2(1H)-one;

N4-cyclopropyl-N2-(4-(piperazin-1-yl)phenyl)furo[3,2-
d]pyrimidine-2,4-diamine;

N2-(1H-indazol-6-yl)-N4-(piperidin-4-ylmethyl)furo[3,
2-d]pyrimidine-2,4-diamine;

N4-cyclobutyl-N2-(4-(piperazin-1-yl)phenyl)furo[3,2-d]
pyrimidine-2,4-diamine;

6-(4-(cyclobutylamino)furo[3,2-d]pyrimidin-2-ylamino)-
2,2-dimethyl-2H-benzo[b][1,4]oxazin-3(4H)-one;

6-(4-(cyclopropylamino)furo[3,2-d]pyrimidin-2-
ylamino)-2H-benzo[b][1,4]oxazin-3(4H)-one;

7-(4-(cyclobutylamino)furo[3,2-d]pyrimidin-2-ylamino)-
1H-benzo[d][1,3]oxazin-2(4H)-one;

N4-cyclopropyl-N2-(1-methyl-1H-indazol-5-yl)furo[3,2-
d]pyrimidine-2,4-diamine;

N4-cyclopropyl-N2-(1-methyl-1H-indazol-3-yl)furo[3,2-
d]pyrimidine-2,4-diamine;

4-(4-(cyclopropylamino)furo[3,2-d]pyrimidin-2-ylamino)-N-(3-methoxypropyl)benzamide;
4-(4-(cyclopropylamino)furo[3,2-d]pyrimidin-2-ylamino)-N-(3-methoxypropyl)benzenesulfonamide;
N4-cyclopropyl-N2-(imidazo[1,2-a]pyridin-3-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
2,2-dimethyl-6-(4-(2,2,2-trifluoroethylamino)furo[3,2-d]pyrimidin-2-ylamino)-2H-benzo[b][1,4]oxazin-3(4H)-one;
6-(4-(piperidin-4-ylmethylamino)furo[3,2-d]pyrimidin-2-ylamino)-3,4-dihydroquinolin-2(1H)-one;
2,2-dimethyl-6-(4-(piperidin-4-ylmethylamino)furo[3,2-d]pyrimidin-2-ylamino)-2H-benzo[b][1,4]oxazin-3(4H)-one;
N-methyl-N-(4-(4-(piperidin-4-ylmethylamino)furo[3,2-d]pyrimidin-2-ylamino)phenyl)acetamide;
N4-cyclopropyl-N2-(isoquinolin-4-yl)furo[3,2-d]pyrimidine-2,4-diamine;
N4-cyclopropyl-N2-(quinolin-4-yl)furo[3,2-d]pyrimidine-2,4-diamine;
N4-cyclopropyl-N2-(1-methyl-1H-indazol-6-yl)furo[3,2-d]pyrimidine-2,4-diamine; or
N2-(3-chloro-4-morpholinophenyl)-N4-(2,2,2-trifluoroethyl)furo[3,2-d]pyrimidine-2,4-diamine.

17. The compound of claim 4 wherein $R^1$ is $N(R^a)(R^b)$, —C($R^a$)=CH($R^b$), or —OR$^b$; wherein
$R^a$ is H or optionally substituted ($C_1$-$C_6$)alkyl; and
$R^b$ is optionally substituted ($C_1$-$C_6$)alkyl, optionally substituted ($C_2$-$C_6$)alkenyl, optionally substituted ($C_3$-$C_6$)cycloalkyl, optionally substituted bridged saturated or partially unsaturated ($C_5$-$C_{12}$)cycloalkyl, or optionally substituted ($C_1$-$C_{10}$)heteroaryl.

18. The compound of claim 17 wherein $R^b$ is optionally substituted ($C_1$-$C_6$)alkyl, optionally substituted ($C_2$-$C_6$)alkenyl, optionally substituted cyclopropyl, optionally substituted cyclobutyl, optionally substituted cyclopentyl, optionally substituted cyclohexyl, optionally substituted benzo[b][1,4]oxazinyl, optionally substituted bicyclo[2.2.1]heptanyl, optionally substituted bicyclo[2.2.1]heptenyl, optionally substituted indazolyl, optionally substituted oxetanyl, optionally substituted piperidinyl, —CH$_2$-optionally substituted azetidinyl, —CH$_2$-optionally substituted imidazolyl, —CH$_2$-optionally substituted piperidinyl, or —CH$_2$-optionally substituted pyridinyl.

19. The compound of claim 18 wherein Y is optionally substituted benzo[b]azepinyl, optionally substituted benzo[d]imidazolyl, optionally substituted benzo[b][1,4]oxazinyl, optionally substituted benzo[d]isothiazolyl, optionally substituted benzo[d]oxazolyl, optionally substituted benzo[b][1,4]thiazinyl, optionally substituted benzo[d]thiazolyl, optionally substituted benzo[c]thiophenyl, optionally substituted chromanyl, optionally substituted chromenyl, optionally substituted dihydrobenzo[b]azepinyl, optionally substituted dihydroquinolinyl, optionally substituted imidazo[1,2-a]pyridinyl, optionally substituted indazolyl, optionally substituted indolinyl, optionally substituted isoquinolinyl, optionally substituted phenyl, optionally substituted pyrazolyl, optionally substituted quinolinyl, optionally substituted tetrahydroisoquinolinyl, or optionally substituted tetrahydro-1,6-naphthyridinyl.

20. The compound of claim 19 wherein Z is H, —CN, —N(H)-tetrahydropyranyl, —C(O)N(H)-optionally substituted($C_1$-$C_3$)alkylene, —C(O)N(H)-optionally substituted ($C_3$-$C_6$)cycloalkylene, —C(O)-morpholinyl, —N(H)C(O)-optionally substituted($C_1$-$C_3$)alkyl, —N(CH$_3$)C(O)-optionally substituted($C_1$-$C_3$)alkyl, —O-optionally substituted($C_1$-$C_3$)alkyl, —S(O)$_2$-optionally substituted($C_1$-$C_3$)alkyl, —S(O)$_2$—N(H)optionally substituted ($C_1$-$C_4$)alkyl, —S(O)$_2$NH$_2$, —S(O)$_2$N(H)-pyridinyl, optionally substituted ($C_1$-$C_3$)alkyl, optionally substituted morpholinyl, optionally substituted piperazinyl, optionally substituted pyridinyl, -optionally substituted ($C_1$-$C_3$)alkylene-optionally substituted morpholinyl, or optionally substituted pyridinyl.

21. The compound of claim 20 wherein the compound is
N4-cyclopropyl-N2-(3-methyl-1H-indazol-6-yl)furo[3,2-d]pyrimidine-2,4-diamine;
2,2-dimethyl-6-(4-((3-methyloxetan-3-yl)methylamino)furo[3,2-d]pyrimidin-2-ylamino)-2H-benzo[b][1,4]oxazin-3(4H)-one;
N4-cyclopropyl-N2-(3-(pyridin-4-yl)-1H-indazol-6-yl)furo[3,2-d]pyrimidine-2,4-diamine;
6-(4-(cyclopropylamino)furo[3,2-d]pyrimidin-2-ylamino)-1H-indazole-3-carbonitrile;
N-cyclopropyl-6-(4-(cyclopropylamino)furo[3,2-d]pyrimidin-2-ylamino)-1H-indazole-3-carboxamide;
N4-allyl-N4-methyl-N2-(3-methyl-1H-indazol-6-yl)furo[3,2-d]pyrimidine-2,4-diamine;
7-(4-(2,2-difluoroethylamino)furo[3,2-d]pyrimidin-2-ylamino)-3,4-dihydroquinolin-2(1H)-one;
3-(2-(2,2-dimethyl-3-oxo-3,4-dihydro-2H-benzo[b][1,4]oxazin-6-ylamino)furo[3,2-d]pyrimidin-4-ylamino)propanamide;
6-(4-(2,2-difluoroethylamino)furo[3,2-d]pyrimidin-2-ylamino)-2,2-dimethyl-2H-benzo[b][1,4]oxazin-3(4H)-one;
N4-cyclopropyl-N2-(4-methyl-1H-indazol-6-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
N4-cyclopropyl-N2-(3-(tetrahydro-2H-pyran-4-ylamino)-1H-indazol-6-yl)furo[3,2-d]pyrimidine-2,4-diamine;
(S)-7-(4-(cyclopropylamino)furo[3,2-d]pyrimidin-2-ylamino)-3-methyl-3,4-dihydroquinolin-2(1H)-one;
(R)-7-(4-(cyclopropylamino)furo[3,2-d]pyrimidin-2-ylamino)-3-methyl-3,4-dihydroquinolin-2(1H)-one;
N4-cyclopropyl-N2-(1H-indazol-6-yl)furo[3,2-d]pyrimidine-2,4-diamine 2,2,2-trifluoroacetate;
N-propyl-4-(4-(2,2,2-trifluoroethylamino)furo[3,2-d]pyrimidin-2-ylamino)benzamide;
N2-(3-chloro-4-(4-methylpiperazin-1-yl)phenyl)-N4-cyclopropylfuro[3,2-d]pyrimidine-2,4-diamine;
N4-allyl-N2-(4-(methylsulfonyl)phenyl)furo[3,2-d]pyrimidine-2,4-diamine;
N2-(3-chloro-4-morpholinophenyl)-N4-cyclopropylfuro[3,2-d]pyrimidine-2,4-diamine;
4-(4-(cyclopropylamino)furo[3,2-d]pyrimidin-2-ylamino)benzenesulfonamide;
4-(4-(cyclopropylamino)furo[3,2-d]pyrimidin-2-ylamino)benzenesulfonamide bis(2,2,2-trifluoroacetate);
4-(4-(cyclopropylamino)furo[3,2-d]pyrimidin-2-ylamino)-N-propylbenz amide;
N*4*-cyclopropyl-N*2*-(2,2-dioxo-2,3-dihydro-1H-2lambda*6*-benzo[c]thiophen-5-yl)-furo[3,2-d]pyrimidine-2,4-diamine;
N4-cyclopropyl-N2-(4-(morpholinomethyl)phenyl)furo[3,2-d]pyrimidine-2,4-diamine;
1-(4-(4-(4-(cyclopropylamino)furo[3,2-d]pyrimidin-2-ylamino)phenyl)piperazin-1-yl)ethanone;

N*4*-cyclopropyl-N*2*-(1,1-dioxo-2,3-dihydro-1H-1lambda*6*-benzo[d]isothiazol-6-yl)-uro[3,2-d]pyrimidine-2,4-diamine;
6-(4-cyclopropylamino-furo[3,2-d]pyrimidin-2-ylamino)-1,1-dioxo-1,2-dihydro-1 lambda*6*-benzo[d]isothiazol-3-one;
4-(4-(cyclobutylamino)furo[3,2-d]pyrimidin-2-ylamino)benzenesulfonamide;
N4-cyclopropyl-N2-(1-methyl-1H-pyrazol-4-yl)furo[3,2-d]pyrimidine-2,4-diamine;
(1R,2S)-2-(2-(4-sulfamoylphenylamino)furo[3,2-d]pyrimidin-4-ylamino)cyclopentanecarboxamide;
6-(4-(cyclopropylamino)furo[3,2-d]pyrimidin-2-ylamino)-3,4-dihydroquinolin-2(1H)-one;
(1R,2R,3S,4S)-3-(2-(4-sulfamoylphenylamino)furo[3,2-d]pyrimidin-4-ylamino)bicyclo[2.2.1]hept-5-ene-2-carboxamide;
N4-((1R,3S)-3-aminocyclopentyl)-N2-(3-methyl-1H-indazol-6-yl)furo[3,2-d]pyrimidine-2,4-diamine;
N4-((1S,3R)-3-aminocyclopentyl)-N2-(3-methyl-1H-indazol-6-yl)furo[3,2-d]pyrimidine-2,4-diamine;
2,2-dimethyl-6-(4-(methylamino)furo[3,2-d]pyrimidin-2-ylamino)-2H-benzo[b][1,4]oxazin-3(4H)-one;
6-(4-(isopropylamino)furo[3,2-d]pyrimidin-2-ylamino)-2,2-dimethyl-2H-benzo[b][1,4]oxazin-3(4H)-one;
7-(4-(cyclopropylamino)furo[3,2-d]pyrimidin-2-ylamino)-3,4-dihydroquinolin-2(1H)-one;
7-(4-(cyclopropylamino)furo[3,2-d]pyrimidin-2-ylamino)-3-methyl-3,4-dihydroquinolin-2(1H)-one;
N2-(3-methyl-1H-indazol-6-yl)-N4-(4,5,6,7-tetrahydro-1H-indazol-6-yl)furo[3,2-d]pyrimidine-2,4-diamine;
N4-(3,3-difluorocyclobutyl)-N2-(3-methyl-1H-indazol-6-yl)furo[3,2-d]pyrimidine-2,4-diamine;
N4-(3,3-difluorocyclobutyl)-N2-(3-methyl-1H-indazol-6-yl)furo[3,2-d]pyrimidine-2,4-diamine;
N4-cyclobutyl-N2-(3-methyl-1H-indazol-6-yl)furo[3,2-d]pyrimidine-2,4-diamine;
7-(4-(cyclobutylamino)furo[3,2-d]pyrimidin-2-ylamino)-3,4-dihydroquinolin-2(1H)-one;
6-(4-(cyclobutylamino)furo[3,2-d]pyrimidin-2-ylamino)-3,3-dimethylindolin-2-one;
7-(4-(cyclobutylamino)furo[3,2-d]pyrimidin-2-ylamino)-3,3-dimethyl-3,4-dihydroquinolin-2(1H)-one;
7-(4-(cyclobutylamino)furo[3,2-d]pyrimidin-2-ylamino)-3-methyl-3,4-dihydroquinolin-2(1H)-one;
7-(4-(isobutylamino)furo[3,2-d]pyrimidin-2-ylamino)-3,4-dihydroquinolin-2(1H)-one;
N2-(3-methyl-1H-indazol-6-yl)-N4-propylfuro[3,2-d]pyrimidine-2,4-diamine;
7-(4-(propylamino)furo[3,2-d]pyrimidin-2-ylamino)-3,4-dihydroquinolin-2(1H)-one;
3,3-dimethyl-7-(4-(propylamino)furo[3,2-d]pyrimidin-2-ylamino)-3,4-dihydroquinolin-2(1H)-one;
8-(4-(propylamino)furo[3,2-d]pyrimidin-2-ylamino)-4,5-dihydro-1H-benzo[b]azepin-2(3H)-one;
2-methyl-2-(4-(4-(propylamino)furo[3,2-d]pyrimidin-2-ylamino)phenyl)propanenitrile;
7-(4-(isobutylamino)furo[3,2-d]pyrimidin-2-ylamino)-3,3-dimethyl-3,4-dihydroquinolin-2(1H)-one;
8-(4-(isobutylamino)furo[3,2-d]pyrimidin-2-ylamino)-4,5-dihydro-1H-benzo[b]azepin-2(3H)-one;
2-(4-(4-(isobutylamino)furo[3,2-d]pyrimidin-2-ylamino)phenyl)-2-methylpropanenitrile;
N-(4-(4-(cyclobutylamino)furo[3,2-d]pyrimidin-2-ylamino)phenyl)-N-methylacetamide;
N-(4-(4-(cyclobutylamino)furo[3,2-d]pyrimidin-2-ylamino)phenyl)butyramide;
N2-(3-chloro-4-morpholinophenyl)-N4-cyclobutylfuro[3,2-d]pyrimidine-2,4-diamine;
N4-cyclobutyl-N2-(1H-indazol-6-yl)furo[3,2-d]pyrimidine-2,4-diamine;
N-(4-(4-(cyclopropylamino)furo[3,2-d]pyrimidin-2-ylamino)phenyl)-N-methylacetamide;
6-(4-(cyclobutylamino)furo[3,2-d]pyrimidin-2-ylamino)-3,4-dihydroquinolin-2(1H)-one;
N4-cyclopropyl-N2-(4-(piperazin-1-yl)phenyl)furo[3,2-d]pyrimidine-2,4-diamine;
N4-cyclobutyl-N2-(4-(piperazin-1-yl)phenyl)furo[3,2-d]pyrimidine-2,4-diamine;
6-(4-(cyclobutylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2H-benzo[b][1,4]oxazin-3(4H)-one;
N4-cyclopropyl-N2-(1-methyl-1H-indazol-5-yl)furo[3,2-d]pyrimidine-2,4-diamine;
4-(4-(cyclopropylamino)furo[3,2-d]pyrimidin-2-ylamino)-N-(3-methoxypropyl)benzamide;
4-(4-(cyclopropylamino)furo[3,2-d]pyrimidin-2-ylamino)-N-(3-methoxypropyl)benzenesulfonamide;
2,2-dimethyl-6-(4-(2,2,2-trifluoroethylamino)furo[3,2-d]pyrimidin-2-ylamino)-2H-benzo[b][1,4]oxazin-3(4H)-one;
N4-cyclopropyl-N2-(1-methyl-1H-indazol-6-yl)furo[3,2-d]pyrimidine-2,4-diamine;
N2-(3-chloro-4-morpholinophenyl)-N4-(2,2,2-trifluoroethyl)furo[3,2-d]pyrimidine-2,4-diamine;
N-(4-(4-(1H-indazol-6-ylamino)furo[3,2-d]pyrimidin-2-ylamino)phenyl)butyramide;
N4-cyclopropyl-N2-(1H-indol-6-yl)furo[3,2-d]pyrimidine-2,4-diamine;
N4-(3-aminopropyl)-N2-(1H-indazol-6-yl)furo[3,2-d]pyrimidine-2,4-diamine;
N4-(4-aminobutyl)-N2-(1H-indazol-6-yl)furo[3,2-d]pyrimidine-2,4-diamine;
N4-cyclopropyl-N2-(1H-indazol-5-yl)furo[3,2-d]pyrimidine-2,4-diamine;
N4-cyclopropyl-N2-(1-isopropyl-1H-indazol-5-yl)furo[3,2-d]pyrimidine-2,4-diamine;
6-(4-(cyclopropylamino)furo[3,2-d]pyrimidin-2-ylamino)-2H-benzo[b][1,4]thiazin-3(4H)-one;
N4-cyclopropyl-N2-(4-morpholinophenyl)furo[3,2-d]pyrimidine-2,4-diamine;
6-(4-(cyclopropylamino)furo[3,2-d]pyrimidin-2-ylamino)benzo[d]oxazol-2(3H)-one;
5-(4-(cyclopropylamino)furo[3,2-d]pyrimidin-2-ylamino)-1H-benzo[d]imidazol-2(3H)-one;
5-(4-(cyclopropylamino)furo[3,2-d]pyrimidin-2-ylamino)-2,3-dihydro-1H-inden-1-one;
N-(3-(4-(cyclopropylamino)furo[3,2-d]pyrimidin-2-ylamino)phenyl)acetamide;
3-(4-(cyclopropylamino)furo[3,2-d]pyrimidin-2-ylamino)benzenesulfonamide;
5-(4-(cyclopropylamino)furo[3,2-d]pyrimidin-2-ylamino)benzo[d]oxazol-2(3H)-one;
6-(4-(cyclopropylmethylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-dimethyl-2H-pyrido[3,2-b][1,4]oxazin-3(4H)-one;
6-(4-(cyclopropylamino)furo[3,2-d]pyrimidin-2-ylamino)indolin-2-one;
(3-(4-(cyclopropylamino)furo[3,2-d]pyrimidin-2-ylamino)phenyl)methanol;

N4-cyclopropyl-N2-(6-morpholinopyridin-3-yl)furo[3,2-d]pyrimidine-2,4-diamine;
6-(4-(cyclopropylamino)furo[3,2-d]pyrimidin-2-ylamino)-2,2-dimethyl-2H-benzo[b][1,4]thiazin-3(4H)-one;
N4-cyclopropyl-N2-(4-(thiomorpholine 1,1 dioxide)phenyl)furo[3,2-d]pyrimidine-2,4-diamine;
N2-(1H-benzo[d]imidazol-6-yl)-N4-cyclopropylfuro[3,2-d]pyrimidine-2,4-diamine;
N4-cyclopropyl-N2-(3-fluoro-4-(4-methylpiperazin-1-yl)phenyl)furo[3,2-d]pyrimidine-2,4-diamine;
7-(4-(cyclopropylamino)furo[3,2-d]pyrimidin-2-ylamino)-4-methylquinolin-2(1H)-one;
7-(4-(cyclopropylamino)furo[3,2-d]pyrimidin-2-ylamino)quinolin-2(1H)-one;
2,2-dimethyl-6-(4-(1-methylcyclopropylamino)furo[3,2-d]pyrimidin-2-ylamino)-2H-benzo[b][1,4]oxazin-3(4H)-one;
6-(4-(1-(hydroxymethyl)cyclopropylamino)furo[3,2-d]pyrimidin-2-ylamino)-2,2-dimethyl-2H-benzo[b][1,4]oxazin-3(4H)-one;
6-(4-(ethylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-difluoro-2H-benzo[b][1,4]oxazin-3(4H)-one;
7-(4-(cyclopropylamino)furo[3,2-d]pyrimidin-2-ylamino)-3,3-dimethyl-3,4-dihydroquinolin-2(1H)-one;
2-(4-(4-(cyclopropylamino)furo[3,2-d]pyrimidin-2-ylamino)phenyl)-2-methylpropanenitrile;
N4-cyclopropyl-N2-(1,2,3,4-tetrahydroisoquinolin-6-yl)furo[3,2-d]pyrimidine-2,4-diamine;
N4-cyclopropyl-N2-(4-isopropoxyphenyl)furo[3,2-d]pyrimidine-2,4-diamine;
N4-cyclopropyl-N2-(2-methylbenzo[d]thiazol-6-yl)furo[3,2-d]pyrimidine-2,4-diamine;
N4-cyclopropyl-N2-(2-methylquinolin-6-yl)furo[3,2-d]pyrimidine-2,4-diamine;
N4-cyclopropyl-N2-(4-isopropoxy-3-methylphenyl)furo[3,2-d]pyrimidine-2,4-diamine;
N2-(3-chloro-4-isopropoxyphenyl)-N4-cyclopropylfuro[3,2-d]pyrimidine-2,4-diamine;
N4-cyclopropyl-N2-(3-fluoro-4-isopropoxyphenyl)furo[3,2-d]pyrimidine-2,4-diamine;
7-(4-(cyclopropylamino)furo[3,2-d]pyrimidin-2-ylamino)-3-(hydroxymethyl)quinolin-2(1H)-one;
N4-cyclopropyl-N2-(2,2-dimethylchroman-6-yl)furo[3,2-d]pyrimidine-2,4-diamine;
7-(4-(cyclopropylamino)furo[3,2-d]pyrimidin-2-ylamino)-2H-chromen-2-one;
N4-cyclopropyl-N2-(2,3-dihydrobenzo[b][1,4]dioxin-6-yl)furo[3,2-d]pyrimidine-2,4-diamine;
N2-(benzo[d]oxazol-6-yl)-N4-cyclopropylfuro[3,2-d]pyrimidine-2,4-diamine;
N2-(4-(2H-1,2,3-triazol-2-yl)phenyl)-N4-cyclopropyl-furo[3,2-d]pyrimidine-2,4-diamine;
7-(4-(cyclopropylamino)furo[3,2-d]pyrimidin-2-ylamino)-4,5-dihydro-1H-benzo[b]azepin-2(3H)-one;
1-(7-(4-(cyclopropylamino)furo[3,2-d]pyrimidin-2-ylamino)-4,5-dihydro-1H-benzo[d]azepin-3(2H)-yl)ethanone;
N4-cyclopropyl-N4-methyl-N2-(3-methyl-1H-indazol-6-yl)furo[3,2-d]pyrimidine-2,4-diamine;
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]hept-5-ene-2-carboxamide;
(diexo)-3-(2-(3,3-dimethyl-2-oxoindolin-6-ylamino)furo[3,2-d]pyrimidin-4-ylamino)bicyclo[2.2.1]hept-5-ene-2-carboxamide;
(diexo)-3-(2-(3-methyl-1H-indazol-6-ylamino)furo[3,2-d]pyrimidin-4-ylamino)bicyclo[2.2.1]hept-5-ene-2-carboxamide;
6,6'-(furo[3,2-d]pyrimidine-2,4-diylbis(azanediyl))bis(2,2-dimethyl-2H-benzo[b][1,4]oxazin-3(4H)-one);
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]heptane-2-carboxamide;
6-(4-(tert-butylamino)furo[3,2-d]pyrimidin-2-ylamino)-2,2-dimethyl-2H-benzo[b][1,4]oxazin-3(4H)-one;
6-(4-(diethylamino)furo[3,2-d]pyrimidin-2-ylamino)-2,2-dimethyl-2H-benzo[b][1,4]oxazin-3(4H)-one;
6-(4-(isobutylamino)furo[3,2-d]pyrimidin-2-ylamino)-3,3-dimethylindolin-2-one;
3,3-dimethyl-6-(4-(propylamino)furo[3,2-d]pyrimidin-2-ylamino)indolin-2-one;
8-(4-(cyclopropylamino)furo[3,2-d]pyrimidin-2-ylamino)-4,5-dihydro-1H-benzo[b]azepin-2(3H)-one;
N4-cyclopropyl-N2-(4-fluoro-3-methyl-1H-indazol-6-yl)furo[3,2-d]pyrimidine-2,4-diamine;
N4-cyclopropyl-N2-(4-(4-(methylsulfonyl)piperazin-1-yl)phenyl)furo[3,2-d]pyrimidine-2,4-diamine;
N2-(4-(1H-imidazol-1-yl)phenyl)-N4-cyclopropylfuro[3,2-d]pyrimidine-2,4-diamine;
6-(4-(cyclopropylethynyl)furo[3,2-d]pyrimidin-2-ylamino)-3,3-dimethylindolin-2-one;
N2-(benzo[d]isoxazol-6-yl)-N4-cyclopropylfuro[3,2-d]pyrimidine-2,4-diamine;
7-(4-(cyclopropylamino)furo[3,2-d]pyrimidin-2-ylamino)-3-methylquinolin-2(1H)-one;
6-(4-(cyclopropylamino)furo[3,2-d]pyrimidin-2-ylamino)-2,2-dimethyl-2H-benzo[b][1,4]oxazin-3(4H)-one;
6-(4-(cyclobutylamino)furo[3,2-d]pyrimidin-2-ylamino)-2H-benzo[b][1,4]oxazin-3(4H)-one;
6-(4-(cyclopropylamino)furo[3,2-d]pyrimidin-2-ylamino)-3,3-dimethylindolin-2-one;
3,3-dimethyl-6-(4-(2-methylcyclopropylamino)furo[3,2-d]pyrimidin-2-ylamino)indolin-2-one;
N2-(3-methyl-1H-indazol-6-yl)-N4-(pyridin-3-ylmethyl)furo[3,2-d]pyrimidine-2,4-diamine;
6-(4-(2,2-difluoroethylamino)furo[3,2-d]pyrimidin-2-ylamino)-3,3-dimethylindolin-2-one;
N4-(2,2-difluoroethyl)-N2-(3-methyl-1H-indazol-6-yl)furo[3,2-d]pyrimidine-2,4-diamine;
6-(4-(cyclopropylamino)furo[3,2-d]pyrimidin-2-ylamino)-N,N-dimethyl-1H-indazole-3-carboxamide;
4-(4-(cyclopropylamino)furo[3,2-d]pyrimidin-2-ylamino)benzonitrile;
N4-cyclopropyl-N2-(4-methoxyphenyl)furo[3,2-d]pyrimidine-2,4-diamine;
(6-(4-(cyclopropylamino)furo[3,2-d]pyrimidin-2-ylamino)-1H-indazol-3-yl)(morpholino)methanone;
6-(4-(cyclopropylamino)furo[3,2-d]pyrimidin-2-ylamino)-N-(2-hydroxyethyl)-1H-indazole-3-carboxamide;
2-(4-(4-(cyclopropylamino)furo[3,2-d]pyrimidin-2-ylamino)phenyl)acetonitrile;
4-(4-(cyclopropylamino)furo[3,2-d]pyrimidin-2-ylamino)-N-(pyridin-2-yl)benzenesulfonamide;
N4-cyclopropyl-N2-(4-(pyridin-4-yl)phenyl)furo[3,2-d]pyrimidine-2,4-diamine;
8-(4-cyclobutoxyfuro[3,2-d]pyrimidin-2-ylamino)-4,5-dihydro-1H-benzo[b]azepin-2(3H)-one;

4-cyclobutoxy-N-(3-methyl-1H-indazol-6-yl)furo[3,2-d]pyrimidin-2-amine;
7-(4-cyclobutoxyfuro[3,2-d]pyrimidin-2-ylamino)-3,4-dihydroquinolin-2(1H)-one;
N4-allyl-N2-(quinolin-4-yl)furo[3,2-d]pyrimidine-2,4-diamine;
6-(4-(piperidin-4-ylmethylamino)furo[3,2-d]pyrimidin-2-ylamino)-2H-benzo[b][1,4]oxazin-3(4H)-one;
N-(4-(4-(piperidin-4-ylmethylamino)furo[3,2-d]pyrimidin-2-ylamino)phenyl)butyramide;
N4-cyclopropyl-N2-(isoquinolin-1-yl)furo[3,2-d]pyrimidine-2,4-diamine;
N2-(1H-indazol-6-yl)-N4-(piperidin-4-ylmethyl)furo[3,2-d]pyrimidine-2,4-diamine;
N4-cyclopropyl-N2-(1-methyl-1H-indazol-3-yl)furo[3,2-d]pyrimidine-2,4-diamine;
N4-cyclopropyl-N2-(imidazo[1,2-a]pyridin-3-yl)furo[3,2-d]pyrimidine-2,4-diamine;
6-(4-(piperidin-4-ylmethylamino)furo[3,2-d]pyrimidin-2-ylamino)-3,4-dihydroquinolin-2(1H)-one;
2,2-dimethyl-6-(4-(piperidin-4-ylmethylamino)furo[3,2-d]pyrimidin-2-ylamino)-2H-benzo[b][1,4]oxazin-3(4H)-one;
N-methyl-N-(4-(4-(piperidin-4-ylmethylamino)furo[3,2-d]pyrimidin-2-ylamino)phenyl)acetamide;
N4-cyclopropyl-N2-(isoquinolin-4-yl)furo[3,2-d]pyrimidine-2,4-diamine;
N4-cyclopropyl-N2-(quinolin-4-yl)furo[3,2-d]pyrimidine-2,4-diamine;
1-(4-(4-(4-((1H-imidazol-2-yl)methylamino)furo[3,2-d]pyrimidin-2-ylamino)phenyl)piperazin-1-yl)ethanone;
N4-cyclopropyl-N2-(2-methyl-2H-indazol-6-yl)furo[3,2-d]pyrimidine-2,4-diamine;
N4-cyclopropyl-N2-(3-methyl-1H-indazol-5-yl)furo[3,2-d]pyrimidine-2,4-diamine;
N4-(3-amino-2,2-dimethylpropyl)-N2-(1H-indazol-6-yl)furo[3,2-d]pyrimidine-2,4-diamine;
N4-((1r,4r)-4-aminocyclohexyl)-N2-(3-methyl-1H-indazol-6-yl)furo[3,2-d]pyrimidine-2,4-diamine;
(R)—N2-(3-methyl-1H-indazol-6-yl)-N4-(piperidin-3-yl)furo[3,2-d]pyrimidine-2,4-diamine;
N2-(3-methyl-1H-indazol-6-yl)-N4-(oxetan-3-yl)furo[3,2-d]pyrimidine-2,4-diamine;
6-(4-(cyclopropylamino)furo[3,2-d]pyrimidin-2-ylamino)-4-methyl-2H-benzo[b][1,4]oxazin-3(4H)-one;
N4-cyclopropyl-N2-(3-(pyridin-4-yl)phenyl)furo[3,2-d]pyrimidine-2,4-diamine;
2,2-dimethyl-6-(4-(piperidin-3-ylmethylamino)furo[3,2-d]pyrimidin-2-ylamino)-2H-benzo[b][1,4]oxazin-3(4H)-one;
N4-cyclopropyl-N2-(3-morpholinophenyl)furo[3,2-d]pyrimidine-2,4-diamine;
(S)—N2-(3-methyl-1H-indazol-6-yl)-N4-(piperidin-3-yl)furo[3,2-d]pyrimidine-2,4-diamine;
N4-cyclopropyl-N2-(5,6,7,8-tetrahydro-1,6-naphthyridin-3-yl)furo[3,2-d]pyrimidine-2,4-diamine;
N-(4-(4-(cyclopropylamino)furo[3,2-d]pyrimidin-2-ylamino)-2-methoxyphenyl)-2-morpholinoacetamide; or
6-(4-(cyclopropylamino)furo[3,2-d]pyrimidin-2-ylamino)-2H-pyrido[3,2-b][1,4]oxazin-3(4H)-one.

22. The compound of claim 17 wherein $R^1$ is $N(R^a)(R^b)$, or —$OR^b$; wherein
$R^a$ is H or optionally substituted ($C_1$-$C_6$)alkyl; and
$R^b$ is optionally substituted ($C_1$-$C_6$)alkyl, optionally substituted ($C_3$-$C_6$)cycloalkyl, optionally substituted bridged saturated or partially unsaturated ($C_5$-$C_{12}$)cycloalkyl, or optionally substituted ($C_1$-$C_{10}$)heteroaryl.

23. The compound of claim 22 wherein
$R^a$ is H; and
$R^b$ is optionally substituted ($C_1$-$C_6$)alkyl, optionally substituted cyclopropyl, optionally substituted cyclobutyl, optionally substituted bicycle[2.2.1]heptenyl, optionally substituted bicycle[2.2.1]heptanyl, or optionally substituted indazolyl.

24. The compound of claim 23 wherein Y is optionally substituted benzo[b]azepinyl, optionally substituted benzo[b][1,4]oxazinyl, optionally substituted benzo[b][1,4]thiazinyl, optionally substituted benzo[c]thiophenyl, optionally substituted dihydroquinolinyl, optionally substituted indazolyl, optionally substituted indolinyl, optionally substituted phenyl, optionally substituted quinolinyl, or optionally substituted tetrahydroisoquinolinyl.

25. The compound of claim 24 wherein Z is H, —CN, —C(O)N(H)-optionally substituted cyclopropyl, —C(O)-optionally substituted($C_1$-$C_3$)alkyl, —N(H)C(O)-optionally substituted($C_1$-$C_3$)alkyl, —S(O)$_2$NH$_2$, optionally substituted ($C_1$-$C_3$)alkyl, optionally substituted morpholinyl, optionally substituted piperazinyl, —CH$_2$-optionally substituted morpholinyl, or optionally substituted pyridinyl.

26. The compound of claim 25 wherein the compound is
N4-cyclopropyl-N2-(3-methyl-1H-indazol-6-yl)furo[3,2-d]pyrimidine-2,4-diamine;
N4-cyclopropyl-N2-(3-(pyridin-4-yl)-1H-indazol-6-yl)furo[3,2-d]pyrimidine-2,4-diamine;
6-(4-(cyclopropylamino)furo[3,2-d]pyrimidin-2-ylamino)-1H-indazole-3-carbonitrile;
N-cyclopropyl-6-(4-(cyclopropylamino)furo[3,2-d]pyrimidin-2-ylamino)-1H-indazole-3-carboxamide;
N4-cyclopropyl-N2-(4-methyl-1H-indazol-6-yl)furo[3,2-d]pyrimidine-2,4-diamine;
N2-(1H-indazol-6-yl)-N4-(2,2,2-trifluoroethyl)furo[3,2-d]pyrimidine-2,4-diamine;
(S)-7-(4-(cyclopropylamino)furo[3,2-d]pyrimidin-2-ylamino)-3-methyl-3,4-dihydroquinolin-2(1H)-one;
(R)-7-(4-(cyclopropylamino)furo[3,2-d]pyrimidin-2-ylamino)-3-methyl-3,4-dihydroquinolin-2(1H)-one;
N4-cyclopropyl-N2-(1H-indazol-6-yl)furo[3,2-d]pyrimidine-2,4-diamine 2,2,2-trifluoroacetate;
N2-(3-chloro-4-(4-methylpiperazin-1-yl)phenyl)-N4-cyclopropylfuro[3,2-d]pyrimidine-2,4-diamine;
N2-(3-chloro-4-morpholinophenyl)-N4-cyclopropylfuro[3,2-d]pyrimidine-2,4-diamine;
4-(4-(cyclopropylamino)furo[3,2-d]pyrimidin-2-ylamino)benzenesulfonamide;
4-(4-(cyclopropylamino)furo[3,2-d]pyrimidin-2-ylamino)benzenesulfonamide bis(2,2,2-trifluoroacetate);
N*4*-cyclopropyl-N*2*-(2,2-dioxo-2,3-dihydro-1H-2lambda*6*-benzo[c]thiophen-5-yl)-furo[3,2-d]pyrimidine-2,4-diamine;
(1R,2R,3S,4S)-3-(2-(4-sulfamoylphenylamino)furo[3,2-d]pyrimidin-4-ylamino)bicyclo[2.2.1]hept-5-ene-2-carboxamide;
7-(4-(cyclopropylamino)furo[3,2-d]pyrimidin-2-ylamino)-3,4-dihydroquinolin-2(1H)-one;
7-(4-(cyclopropylamino)furo[3,2-d]pyrimidin-2-ylamino)-3-methyl-3,4-dihydroquinolin-2(1H)-one;
N4-cyclobutyl-N2-(3-methyl-1H-indazol-6-yl)furo[3,2-d]pyrimidine-2,4-diamine;
7-(4-(cyclobutylamino)furo[3,2-d]pyrimidin-2-ylamino)-3,4-dihydroquinolin-2(1H)-one;

6-(4-(cyclobutylamino)furo[3,2-d]pyrimidin-2-ylamino)-3,3-dimethylindolin-2-one;
7-(4-(cyclobutylamino)furo[3,2-d]pyrimidin-2-ylamino)-3-methyl-3,4-dihydroquinolin-2(1H)-one;
N2-(3-methyl-1H-indazol-6-yl)-N4-propylfuro[3,2-d]pyrimidine-2,4-diamine;
7-(4-(propylamino)furo[3,2-d]pyrimidin-2-ylamino)-3,4-dihydroquinolin-2(1H)-one;
2-methyl-2-(4-(4-(propylamino)furo[3,2-d]pyrimidin-2-ylamino)phenyl)propanenitrile;
N2-(3-chloro-4-morpholinophenyl)-N4-cyclobutylfuro[3,2-d]pyrimidine-2,4-diamine;
N4-cyclobutyl-N2-(1H-indazol-6-yl)furo[3,2-d]pyrimidine-2,4-diamine;
N-(4-(4-(4-(aminomethyl)piperidin-1-yl)furo[3,2-d]pyrimidin-2-ylamino)phenyl)-N-methylacetamide;
6-(4-(cyclobutylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2H-benzo[b][1,4]oxazin-3(4H)-one;
N4-cyclopropyl-N2-(1-methyl-1H-indazol-5-yl)furo[3,2-d]pyrimidine-2,4-diamine;
N2-(3-chloro-4-morpholinophenyl)-N4-(2,2,2-trifluoroethyl)furo[3,2-d]pyrimidine-2,4-diamine;
N-(4-(4-(1H-indazol-6-ylamino)furo[3,2-d]pyrimidin-2-ylamino)phenyl)butyramide;
N4-(4-aminobutyl)-N2-(1H-indazol-6-yl)furo[3,2-d]pyrimidine-2,4-diamine;
6-(4-(cyclopropylamino)furo[3,2-d]pyrimidin-2-ylamino)-2H-benzo[b][1,4]thiazin-3(4H)-one;
7-(4-(cyclopropylamino)furo[3,2-d]pyrimidin-2-ylamino)-4-methylquinolin-2(1H)-one;
7-(4-(cyclopropylamino)furo[3,2-d]pyrimidin-2-ylamino)quinolin-2(1H)-one;
6-(4-(ethylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-difluoro-2H-benzo[b][1,4]oxazin-3(4H)-one;
7-(4-(cyclopropylamino)furo[3,2-d]pyrimidin-2-ylamino)-3,3-dimethyl-3,4-dihydroquinolin-2(1H)-one;
2-(4-(4-(cyclopropylamino)furo[3,2-d]pyrimidin-2-ylamino)phenyl)-2-methylpropanenitrile;
2-(4-(4-(cyclopropylamino)furo[3,2-d]pyrimidin-2-ylamino)phenyl)-2-methylpropanenitrile;
7-(4-(cyclopropylamino)furo[3,2-d]pyrimidin-2-ylamino)-3-(hydroxymethyl)quinolin-2(1H)-one;
7-(4-(cyclopropylamino)furo[3,2-d]pyrimidin-2-ylamino)-2H-chromen-2-one;
7-(4-(cyclopropylamino)furo[3,2-d]pyrimidin-2-ylamino)-4,5-dihydro-1H-benzo[b]azepin-2(3H)-one;
1-(7-(4-(cyclopropylamino)furo[3,2-d]pyrimidin-2-ylamino)-4,5-dihydro-1H-benzo[d]azepin-3(2H)-yl)ethanone;
(diexo)-3-(2-(3,3-dimethyl-2-oxoindolin-6-ylamino)furo[3,2-d]pyrimidin-4-ylamino)bicyclo[2.2.1]hept-5-ene-2-carboxamide;
(diexo)-3-(2-(3-methyl-1H-indazol-6-ylamino)furo[3,2-d]pyrimidin-4-ylamino)bicyclo[2.2.1]hept-5-ene-2-carboxamide;
6,6'-(furo[3,2-d]pyrimidine-2,4-diylbis(azanediyl))bis(2,2-dimethyl-2H-benzo[b][1,4]oxazin-3(4H)-one);
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]heptane-2-carboxamide, Acetic Acid;
6-(4-(isobutylamino)furo[3,2-d]pyrimidin-2-ylamino)-3,3-dimethylindolin-2-one;
3,3-dimethyl-6-(4-(propylamino)furo[3,2-d]pyrimidin-2-ylamino)indolin-2-one;
8-(4-(cyclopropylamino)furo[3,2-d]pyrimidin-2-ylamino)-4,5-dihydro-1H-benzo[b]azepin-2(3H)-one;
N4-cyclopropyl-N2-(4-(4-(methylsulfonyl)piperazin-1-yl)phenyl)furo[3,2-d]pyrimidine-2,4-diamine;
N2-(benzo[d]isoxazol-6-yl)-N4-cyclopropylfuro[3,2-d]pyrimidine-2,4-diamine;
7-(4-(cyclopropylamino)furo[3,2-d]pyrimidin-2-ylamino)-3-methylquinolin-2(1H)-one;
6-(4-(cyclopropylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-3,3-dimethylindolin-2-one;
3,3-dimethyl-6-(4-(2-methylcyclopropylamino)furo[3,2-d]pyrimidin-2-ylamino)indolin-2-one;
6-(4-(2,2-difluoroethylamino)furo[3,2-d]pyrimidin-2-ylamino)-3,3-dimethylindolin-2-one;
N4-(2,2-difluoroethyl)-N2-(3-methyl-1H-indazol-6-yl)furo[3,2-d]pyrimidine-2,4-diamine;
6-(4-(cyclopropylamino)furo[3,2-d]pyrimidin-2-ylamino)-N,N-dimethyl-1H-indazole-3-carboxamide;
(6-(4-(cyclopropylamino)furo[3,2-d]pyrimidin-2-ylamino)-1H-indazol-3-yl)(morpholino)methanone;
2-(4-(4-(cyclopropylamino)furo[3,2-d]pyrimidin-2-ylamino)phenyl)acetonitrile;
8-(4-cyclobutoxyfuro[3,2-d]pyrimidin-2-ylamino)-4,5-dihydro-1H-benzo[b]azepin-2(3H)-one;
4-cyclobutoxy-N-(3-methyl-1H-indazol-6-yl)furo[3,2-d]pyrimidin-2-amine; or
7-(4-cyclobutoxyfuro[3,2-d]pyrimidin-2-ylamino)-3,4-dihydroquinolin-2(1H)-one.

27. A pharmaceutical composition comprising a compound of claim 1 and a pharmaceutically acceptable carrier or excipient.

28. A compound of the formula:
(1R,2R,3S,4S)-3-(2-(4-sulfamoylphenylamino)furo[3,2-d]pyrimidin-4-ylamino)bicyclo[2.2.1]hept-5-ene-2-carboxamide;
2S)-2-(2-(4-sulfamoylphenylamino)furo[3,2-d]pyrimidin-4-ylamino)cyclopentanecarboxamide;
6-(4-(3-(aminomethyl)-4-methylpyrrolidin-1-yl)furo[3,2-d]pyrimidin-2-ylamino)-2,2-dimethyl-2H-benzo[b][1,4]oxazin-3(4H)-one;
(3-(4-(cyclopropylamino)furo[3,2-d]pyrimidin-2-ylamino)phenyl)methanol;
(3S,4S)-4-(aminomethyl)-1-(2-(3-methyl-1H-indazol-6-ylamino)furo[3,2-d]pyrimidin-4-yl)piperidin-3-ol;
(4-{4-[(4-aminotetrahydro-2H-thiopyrane 1,1-dioxide)-methyl]-piperidin-1-yl}-furo[3,2-d]pyrimidin-2-yl)-(3-methyl-1H-indazol-6-yl)-amine;
(6-(4-(cyclopropylamino)furo[3,2-d]pyrimidin-2-ylamino)-1H-indazol-3-yl)(morpholino)methanone;
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]hept-5-ene-2-carboxamide;
(diexo)-3-(2-(2,2-dimethyl-3-oxo-3,4-dihydro-2H-benzo[b][1,4]oxazin-6-ylamino)furo[3,2-d]pyrimidin-4-ylamino)bicyclo[2.2.1]heptane-2-carboxamide, Acetic Acid;
(diexo)-3-(2-(3,3-dimethyl-2-oxoindolin-6-ylamino)furo[3,2-d]pyrimidin-4-ylamino)bicyclo[2.2.1]hept-5-ene-2-carboxamide;

(diexo)-3-(2-(3-methyl-1H-indazol-6-ylamino)furo[3,2-d]pyrimidin-4-ylamino)bicyclo[2.2.1]hept-5-ene-2-carboxamide;
6-(4-(2,7-diazaspiro[4.5]decan-2-yl)furo[3,2-d]pyrimidin-2-ylamino)-2,2-dimethyl-2H-benzo[b][1,4]oxazin-3(4H)-one;
(R)-1-(2-(4-sulfamoylphenylamino)furo[3,2-d]pyrimidin-4-yl)pyrrolidine-2-carboxamide;
(R)-6-(4-(2,7-diazaspiro[4.5]decan-2-yl)furo[3,2-d]pyrimidin-2-ylamino)-2,2-dimethyl-2H-benzo[b][1,4]oxazin-3(4H)-one;
(R)-7-(4-(cyclopropylamino)furo[3,2-d]pyrimidin-2-ylamino)-3-methyl-3,4-dihydroquinolin-2(1H)-one;
(R)—N2-(3-methyl-1H-indazol-6-yl)-N4-(piperidin-3-yl)furo[3,2-d]pyrimidine-2,4-diamine;
(S)-1-(2-(4-sulfamoylphenylamino)furo[3,2-d]pyrimidin-4-yl)pyrrolidine-2-carboxamide;
(S)-1-(4-(4-(4-(3-aminopiperidin-1-yl)furo[3,2-d]pyrimidin-2-ylamino)phenyl)piperazin-1-yl)ethanone;
(S)-7-(4-(cyclopropylamino)furo[3,2-d]pyrimidin-2-ylamino)-3-methyl-3,4-dihydroquinolin-2(1H)-one;
(S)—N2-(3-methyl-1H-indazol-6-yl)-N4-(piperidin-3-yl)furo[3,2-d]pyrimidine-2,4-diamine;
(Z)—N'-hydroxy-1-(2-(3-methyl-1H-indazol-6-ylamino)furo[3,2-d]pyrimidin-4-yl)piperidine-4-carboximidamide;
1-(2-(2,2-dimethyl-3-oxo-3,4-dihydro-2H-benzo[b][1,4]oxazin-6-ylamino)furo[3,2-d]pyrimidin-4-yl)piperidine-3-carboxamide;
1-(2-(2,2-dimethyl-3-oxo-3,4-dihydro-2H-benzo[b][1,4]oxazin-6-ylamino)furo[3,2-d]pyrimidin-4-yl)-4-(2-hydroxyethyl)piperidine-4-carbonitrile;
1-(2-(4-sulfamoylphenylamino)furo[3,2-d]pyrimidin-4-yl)piperidine-4-carboxamide;
1-(2-(4-sulfamoylphenylamino)furo[3,2-d]pyrimidin-4-yl)piperidine-3-carboxamide;
1-(4-(2-(4-(methylsulfonyl)phenylamino)furo[3,2-d]pyrimidin-4-yl)piperazin-1-yl)ethanone;
1-(4-(4-(4-((1H-imidazol-2-yl)methylamino)furo[3,2-d]pyrimidin-2-ylamino)phenyl)piperazin-1-yl)ethanone;
1-(4-(4-(4-(3-((dimethylamino)methyl)-5,6-dihydroimidazo[1,5-a]pyrazin-7(8H)-yl)furo[3,2-d]pyrimidin-2-ylamino)phenyl)piperazin-1-yl)ethanone;
1-(4-(4-(4-(3-((dimethylamino)methyl)pyrrolidin-1-yl)furo[3,2-d]pyrimidin-2-ylamino)phenyl)piperazin-1-yl)ethanone;
1-(4-(4-(4-(3-(hydroxymethyl)-5,6-dihydroimidazo[1,5-a]pyrazin-7(8H)-yl)furo[3,2-d]pyrimidin-2-ylamino)phenyl)piperazin-1-yl)ethanone;
1-(4-(4-(4-(3-methyl-5,6-dihydroimidazo[1,5-a]pyrazin-7(8H)-yl)furo[3,2-d]pyrimidin-2-ylamino)phenyl)piperazin-1-yl)ethanone;
1-(4-(4-(4-((dimethylamino)methyl)-4-methylpiperidin-1-yl)furo[3,2-d]pyrimidin-2-ylamino)phenyl)piperazin-1-yl)ethanone;
1-(4-(4-(4-(4-((dimethylamino)methyl)piperidin-1-yl)furo[3,2-d]pyrimidin-2-ylamino)phenyl)piperazin-1-yl)ethanone;
1-(4-(4-(4-(4-((methylamino)methyl)piperidin-1-yl)furo[3,2-d]pyrimidin-2-ylamino)phenyl)piperazin-1-yl)ethanone;
1-(4-(4-(4-(4-(2-hydroxy-2-methylpropyl)piperazin-1-yl)furo[3,2-d]pyrimidin-2-ylamino)phenyl)piperazin-1-yl)ethanone;
1-(4-(4-(4-(4-(aminomethyl)piperidin-1-yl)furo[3,2-d]pyrimidin-2-ylamino)phenyl)piperazin-1-yl)ethanone;
1-(4-(4-(4-(4-(pyridin-3-yl)piperazin-1-yl)furo[3,2-d]pyrimidin-2-ylamino)phenyl)piperazin-1-yl)ethanone;
1-(4-(4-(4-(4-hydroxy-4-(pyrrolidin-1-ylmethyl)piperidin-1-yl)furo[3,2-d]pyrimidin-2-ylamino)phenyl)piperazin-1-yl)ethanone;
1-(4-(4-(4-(5,6-dihydroimidazo[1,5-a]pyrazin-7(8H)-yl)furo[3,2-d]pyrimidin-2-ylamino)phenyl)piperazin-1-yl)ethanone;
1-(4-(4-(4-(cyclopropylamino)furo[3,2-d]pyrimidin-2-ylamino)phenyl)piperazin-1-yl)ethanone;
1-(6-(4-(4-(aminomethyl)piperidin-1-yl)furo[3,2-d]pyrimidin-2-ylamino)-5-methoxyindolin-1-yl)-2-(dimethylamino)ethanone;
1-(7-(4-(cyclopropylamino)furo[3,2-d]pyrimidin-2-ylamino)-4,5-dihydro-1H-benzo[d]azepin-3(2H)-yl)ethanone;
2-(4-(4-(cyclopropylamino)furo[3,2-d]pyrimidin-2-ylamino)phenyl)-2-methylpropanenitrile;
2-(4-(4-(cyclopropylamino)furo[3,2-d]pyrimidin-2-ylamino)phenyl)acetonitrile;
2-(4-(4-(isobutylamino)furo[3,2-d]pyrimidin-2-ylamino)phenyl)-2-methylpropanenitrile;
2,2-dimethyl-6-(4-((3-methyloxetan-3-yl)methylamino)furo[3,2-d]pyrimidin-2-ylamino)-2H-benzo[b][1,4]oxazin-3(4H)-one;
2,2-dimethyl-6-(4-(1-methylcyclopropylamino)furo[3,2-d]pyrimidin-2-ylamino)-2H-benzo[b][1,4]oxazin-3(4H)-one;
2,2-dimethyl-6-(4-(2,2,2-trifluoroethylamino)furo[3,2-d]pyrimidin-2-ylamino)-2H-benzo[b][1,4]oxazin-3(4H)-one;
2,2-dimethyl-6-(4-(3-((methylamino)methyl)pyrrolidin-1-yl)furo[3,2-d]pyrimidin-2-ylamino)-2H-benzo[b][1,4]oxazin-3(4H)-one;
2,2-dimethyl-6-(4-(4-(2-(methylsulfonyl)ethylamino)methyl)piperidin-1-yl)furo[3,2-d]pyrimidin-2-ylamino)-2H-benzo[b][1,4]oxazin-3(4H)-one;
2,2-dimethyl-6-(4-(4-((3,3,3-trifluoropropylamino)methyl)piperidin-1-yl)furo[3,2-d]pyrimidin-2-ylamino)-2H-benzo[b][1,4]oxazin-3(4H)-one;
2,2-dimethyl-6-(4-(4-((methylamino)methyl)piperidin-1-yl)furo[3,2-d]pyrimidin-2-ylamino)-2H-benzo[b][1,4]oxazin-3(4H)-one;
2,2-dimethyl-6-(4-(4-((methylamino)methyl)piperidin-1-yl)furo[3,2-d]pyrimidin-2-ylamino)-2H-benzo[b][1,4]thiazin-3(4H)-one;
2,2-dimethyl-6-(4-(methylamino)furo[3,2-d]pyrimidin-2-ylamino)-2H-benzo[b][1,4]oxazin-3(4H)-one;
4-(3-(aminomethyl)pyrrolidin-1-yl)-N-(1H-indazol-6-yl)furo[3,2-d]pyrimidin-2-amine;
2,2-dimethyl-6-(4-(piperidin-3-ylmethylamino)furo[3,2-d]pyrimidin-2-ylamino)-2H-benzo[b][1,4]oxazin-3(4H)-one;
2,2-dimethyl-6-(4-(piperidin-4-ylmethylamino)furo[3,2-d]pyrimidin-2-ylamino)-2H-benzo[b][1,4]oxazin-3(4H)-one;
2,2-dimethyl-6-(4-(tetrahydro-1H-pyrrolo[3,4-c]pyridin-5(6H,7H,7aH)-yl)furo[3,2-d]pyrimidin-2-ylamino)-2H-benzo[b][1,4]oxazin-3(4H)-one;
2-methyl-2-(4-(4-(4-((methylamino)methyl)piperidin-1-yl)furo[3,2-d]pyrimidin-2-ylamino)phenyl)propanenitrile;
2-methyl-2-(4-(4-(propylamino)furo[3,2-d]pyrimidin-2-ylamino)phenyl)propanenitrile;
3-((1-(2-(1H-indazol-6-ylamino)furo[3,2-d]pyrimidin-4-yl)piperidin-4-yl)methyl)oxazolidin-2-one;

3-(2-(2,2-dimethyl-3-oxo-3,4-dihydro-2H-benzo[b][1,4]
oxazin-6-ylamino)furo[3,2-d]pyrimidin-4-ylamino)
propanamide;
3-(4-(cyclopropylamino)furo[3,2-d]pyrimidin-2-
ylamino)benzenesulfonamide;
3,3-dimethyl-6-(4-(2-methylcyclopropylamino)furo[3,2-
d]pyrimidin-2-ylamino)indolin-2-one;
3,3-dimethyl-6-(4-(4-(2-(methylsulfonyl)ethylamino)me-
thyl)piperidin-1-yl)furo[3,2-d]pyrimidin-2-ylamino)
indolin-2-one;
3,3-dimethyl-6-(4-(4-((3,3,3-trifluoropropylamino)me-
thyl)piperidin-1-yl)furo[3,2-d]pyrimidin-2-ylamino)
indolin-2-one;
3,3-dimethyl-6-(4-(4-((methylamino)methyl)piperidin-1-
yl)furo[3,2-d]pyrimidin-2-ylamino)indolin-2-one;
3,3-dimethyl-6-(4-(propylamino)furo[3,2-d]pyrimidin-2-
ylamino)indolin-2-one;
3,3-dimethyl-7-(4-(propylamino)furo[3,2-d]pyrimidin-2-
ylamino)-3,4-dihydroquinolin-2(1H)-one;
4-(1-benzylpyrrolidin-3-yl)-N-(1H-indazol-6-yl)furo[3,
2-d]pyrimidin-2-amine;
4-(2-(2-aminoethyl)morpholino-N-(1H-indazol-6-yl)
furo[3,2-d]pyrimidin-2-amine;
4-(2-(aminomethyl)azetidin-1-yl)-N-(1H-indazol-6-yl)
furo[3,2-d]pyrimidin-2-amine;
4-(3-(2-aminoethyl)piperidin-1-yl)-N-(1H-indazol-6-yl)
furo[3,2-d]pyrimidin-2-amine;
4-(3-(2-aminoethyl)azetidin-1-yl)-N-(1H-indazol-6-yl)
furo[3,2-d]pyrimidin-2-amine;
4-(3-(aminomethyl)-5,6-dihydroimidazo[1,5-a]pyrazin-7
(8H)-yl)-N-(1H-indazol-6-yl)furo[3,2-d]pyrimidin-2-
amine;
4-(3-(aminomethyl)piperidin-1-yl)-N-(1H-indazol-6-yl)
furo[3,2-d]pyrimidin-2-amine;
4-(3-(aminomethyl)pyrrolidin-1-yl)-N-(3-methyl-1H-in-
dazol-6-yl)furo[3,2-d]pyrimidin-2-amine;
4-(3,4-dihydroisoquinolin-2(1H)-yl)-N-(1H-indazol-6-
yl)furo[3,2-d]pyrimidin-2-amine;
4-(4-((2,2-difluoroethylamino)methyl)piperidin-1-yl)-N-
(1H-indazol-6-yl)furo[3,2-d]pyrimidin-2-amine;
4-(4-((2,2-difluoroethylamino)methyl)piperidin-1-yl)-N-
(1-methyl-1H-indazol-5-yl)furo[3,2-d]pyrimidin-2-
amine;
4-(4-((2,2-difluoroethylamino)methyl)piperidin-1-yl)-N-
(3-fluoro-4-morpholinophenyl)furo[3,2-d]pyrimidin-2-
amine;
4-(4-((2,2-difluoroethylamino)methyl)piperidin-1-yl)-N-
(3-methyl-1H-indazol-6-yl)furo[3,2-d]pyrimidin-2-
amine;
4-(4-((2-fluoroethylamino)methyl)piperidin-1-yl)-N-
(1H-indazol-6-yl)furo[3,2-d]pyrimidin-2-amine;
4-(4-(2,2-difluoroethylamino)azepan-1-yl)-N-(3-methyl-
1H-indazol-6-yl)furo[3,2-d]pyrimidin-2-amine;
4-(4-(2-aminoethyl)piperidin-1-yl)-N-(3-methyl-1H-in-
dazol-6-yl)furo[3,2-d]pyrimidin-2-amine;
4-(4-(3-aminopyrrolidin-1-yl)furo[3,2-d]pyrimidin-2-
ylamino)benzenesulfonamide;
4-(4-(4-((2,2-difluoroethylamino)methyl)piperidin-1-yl)
furo[3,2-d]pyrimidin-2-ylamino)-N-(3-methoxypro-
pyl)benzenesulfonamide;
4-(4-(4-(aminomethyl)piperidin-1-yl)furo[3,2-d]pyrimi-
din-2-ylamino)benzenesulfonamide;
4-(4-(4-(aminomethyl)piperidin-1-yl)furo[3,2-d]pyrimi-
din-2-ylamino)-N-(3-methoxypropyl)benzenesulfona-
mide;
4-(4-(4-(hydroxymethyl)piperidin-1-yl)furo[3,2-d]pyri-
midin-2-ylamino)benzenesulfonamide;
4-(4-(4-(methylsulfonyl)piperazin-1-yl)furo[3,2-d]pyri-
midin-2-ylamino)benzenesulfonamide;
4-(4-(4-acetylpiperazin-1-yl)furo[3,2-d]pyrimidin-2-
ylamino)benzenesulfonamide;
4-(4-(aminomethyl)-4-fluoropiperidin-1-yl)-N-(1H-inda-
zol-6-yl)furo[3,2-d]pyrimidin-2-amine;
4-(4-(aminomethyl)-4-methylpiperidin-1-yl)-N-(1H-in-
dazol-6-yl)furo[3,2-d]pyrimidin-2-amine;
4-(4-(aminomethyl)-4-methylpiperidin-1-yl)-N-(3-me-
thyl-1H-indazol-6-yl)furo[3,2-d]pyrimidin-2-amine;
4-(4-(aminomethyl)piperidin-1-yl)-N-(1H-indazol-6-yl)
furo[3,2-d]pyrimidin-2-amine;
4-(4-(aminomethyl)piperidin-1-yl)-N-(1-methyl-1H-in-
dazol-5-yl)furo[3,2-d]pyrimidin-2-amine;
4-(4-(aminomethyl)piperidin-1-yl)-N-(3-chloro-4-mor-
pholinophenyl)furo[3,2-d]pyrimidin-2-amine;
N-(1H-indazol-6-yl)-4-(3-((methylamino)methyl)pyrroli-
din-1-yl)furo[3,2-d]pyrimidin-2-amine;
4-(4-(aminomethyl)piperidin-1-yl)-N-(3-methyl-1H-in-
dazol-6-yl)furo[3,2-d]pyrimidin-2-amine;
4-(4-(aminomethyl)piperidin-1-yl)-N-(4-(4-isopropylpip-
erazin-1-yl)-2-methoxyphenyl)furo[3,2-d]pyrimidin-2-
amine;
4-(4-(aminomethyl)piperidin-1-yl)-N-(4-(piperazin-1-yl)
phenyl)furo[3,2-d]pyrimidin-2-amine;
4-(4-(cyclobutylamino)furo[3,2-d]pyrimidin-2-ylamino)
benzenesulfonamide 2,2,2-trifluoroacetate;
4-(4-(cyclobutylamino)furo[3,2-d]pyrimidin-2-ylamino)
benzenesulfonamide;
4-(4-(cyclopropylamino)furo[3,2-d]pyrimidin-2-
ylamino)benzenesulfonamide;
4-(4-(cyclopropylamino)furo[3,2-d]pyrimidin-2-
ylamino)benzenesulfonamide bis(2,2,2-trifluoroac-
etate);
4-(4-(cyclopropylamino)furo[3,2-d]pyrimidin-2-
ylamino)benzonitrile;
4-(4-(cyclopropylamino)furo[3,2-d]pyrimidin-2-
ylamino)-N-(3-methoxypropyl)benzamide;
4-(4-(cyclopropylamino)furo[3,2-d]pyrimidin-2-
ylamino)-N-(3-methoxypropyl)benzenesulfonamide;
4-(4-(cyclopropylamino)furo[3,2-d]pyrimidin-2-
ylamino)-N-(pyridin-2-yl)benzenesulfonamide;
N-(4-(4-(4-((2,2-difluoroethylamino)methyl)piperidin-1-
yl)furo[3,2-d]pyrimidin-2-ylamino)phenyl)-N-methy-
lacetamide;
4-(4-(cyclopropylamino)furo[3,2-d]pyrimidin-2-
ylamino)-N-propylbenzamide;
4-(4-aminoazepan-1-yl)-N-(1H-indazol-6-yl)furo[3,2-d]
pyrimidin-2-amine;
4-(4-aminoazepan-1-yl)-N-(3-methyl-1H-indazol-6-yl)
furo[3,2-d]pyrimidin-2-amine;
4-(6,7-dihydro-3H-imidazo[4,5-c]pyridin-5(4H)-yl)-N-
(3-methyl-1H-indazol-6-yl)furo[3,2-d]pyrimidin-2-
amine;
4-(aminomethyl)-1-(2-(3-methyl-1H-indazol-6-ylamino)
furo[3,2-d]pyrimidin-4-yl)piperidin-4-ol;
4-(azetidin-1-yl)-N-(3-methyl-1H-indazol-6-yl)furo[3,2-
d]pyrimidin-2-amine;
4-cyclobutoxy-N-(3-methyl-1H-indazol-6-yl)furo[3,2-d]
pyrimidin-2-amine;
4-tert-butyl-N-(1-(2-(5-(morpholine-4-carbonyl)pyridin-
2-ylamino)furo[3,2-d]pyrimidin-4-yl)piperidin-3-yl)
benzamide bis(2,2,2-trifluoroacetate);
5-(4-(cyclopropylamino)furo[3,2-d]pyrimidin-2-
ylamino)-1H-benzo[d]imidazol-2(3H)-one;
5-(4-(cyclopropylamino)furo[3,2-d]pyrimidin-2-
ylamino)-2,3-dihydro-1H-inden-1-one;

5-(4-(cyclopropylamino)furo[3,2-d]pyrimidin-2-ylamino)benzo[d]oxazol-2(3H)-one;

6-(4-((3S,4S)-4-(aminomethyl)-3-hydroxypiperidin-1-yl)furo[3,2-d]pyrimidin-2-ylamino)-2,2-dimethyl-2H-benzo[b][1,4]oxazin-3(4H)-one;

6-(4-((3S,4S)-4-amino-3-hydroxyazepan-1-yl)furo[3,2-d]pyrimidin-2-ylamino)-2,2-dimethyl-2H-benzo[b][1,4]oxazin-3(4H)-one;

6-(4-(1-(hydroxymethyl)cyclopropylamino)furo[3,2-d]pyrimidin-2-ylamino)-2,2-dimethyl-2H-benzo[b][1,4]oxazin-3(4H)-one;

6-(4-(1,7-diazaspiro[3.5]nonan-7-yl)furo[3,2-d]pyrimidin-2-ylamino)-2,2-dimethyl-2H-benzo[b][1,4]oxazin-3(4H)-one;

6-(4-(2,2-difluoroethylamino)furo[3,2-d]pyrimidin-2-ylamino)-2,2-dimethyl-2H-benzo[b][1,4]oxazin-3(4H)-one;

6-(4-(2,2-difluoroethylamino)furo[3,2-d]pyrimidin-2-ylamino)-3,3-dimethylindolin-2-one;

6-(4-(2,7-diazaspiro[4.4]nonan-2-yl)furo[3,2-d]pyrimidin-2-ylamino)-2,2-dimethyl-2H-benzo[b][1,4]oxazin-3(4H)-one;

6-(4-(2,8-diazaspiro[4.5]decan-8-yl)furo[3,2-d]pyrimidin-2-ylamino)-2,2-dimethyl-2H-benzo[b][1,4]oxazin-3(4H)-one;

6-(4-(2,8-diazaspiro[4.5]decan-8-yl)furo[3,2-d]pyrimidin-2-ylamino)-3,3-dimethylindolin-2-one;

6-(4-(2,9-diazaspiro[5.5]undecan-9-yl)furo[3,2-d]pyrimidin-2-ylamino)-2,2-dimethyl-2H-benzo[b][1,4]oxazin-3(4H)-one;

6-(4-(2,9-diazaspiro[5.5]undecan-9-yl)furo[3,2-d]pyrimidin-2-ylamino)-3,3-dimethylindolin-2-one;

6-(4-(3-((2,2-difluoroethylamino)methyl)pyrrolidin-1-yl)furo[3,2-d]pyrimidin-2-ylamino)-3,3-dimethylindolin-2-one;

6-(4-(3-(aminomethyl)-3-methylpyrrolidin-1-yl)furo[3,2-d]pyrimidin-2-ylamino)-2,2-dimethyl-2H-benzo[b][1,4]oxazin-3(4H)-one;

6-(4-(3-(hydroxymethyl)pyrrolidin-1-yl)furo[3,2-d]pyrimidin-2-ylamino)-2,2-dimethyl-2H-benzo[b][1,4]oxazin-3(4H)-one;

6-(4-(3,4-dihydroisoquinolin-2(1H)-yl)furo[3,2-d]pyrimidin-2-ylamino)-2,2-dimethyl-2H-benzo[b][1,4]oxazin-3(4H)-one;

6-(4-(3,9-diazaspiro[5.5]undecan-3-yl)furo[3,2-d]pyrimidin-2-ylamino)-2,2-dimethyl-2H-benzo[b][1,4]oxazin-3(4H)-one;

6-(4-(3-hydroxypiperidin-1-yl)furo[3,2-d]pyrimidin-2-ylamino)-2,2-dimethyl-2H-benzo[b][1,4]oxazin-3(4H)-one;

6-(4-(4-((2,2-difluoroethylamino)methyl)-4-methylpiperidin-1-yl)furo[3,2-d]pyrimidin-2-ylamino)-2,2-dimethyl-2H-benzo[b][1,4]oxazin-3(4H)-one;

6-(4-(4-((2,2-difluoroethylamino)methyl)piperidin-1-yl)furo[3,2-d]pyrimidin-2-ylamino)-2,2-dimethyl-2H-benzo[b][1,4]oxazin-3(4H)-one;

6-(4-(4-((2,2-difluoroethylamino)methyl)piperidin-1-yl)furo[3,2-d]pyrimidin-2-ylamino)-3,3-dimethylindolin-2-one;

6-(4-(4-((2,2-difluoroethylamino)methyl)piperidin-1-yl)furo[3,2-d]pyrimidin-2-ylamino)-2H-benzo[b][1,4]oxazin-3(4H)-one;

6-(4-(4-((2,2-difluoroethylamino)methyl)piperidin-1-yl)furo[3,2-d]pyrimidin-2-ylamino)-2,2-difluoro-2H-benzo[b][1,4]oxazin-3(4H)-one;

6-(4-(4-((2,2-difluoroethylamino)methyl)piperidin-1-yl)furo[3,2-d]pyrimidin-2-ylamino)-2,2-dimethyl-2H-benzo[b][1,4]thiazin-3(4H)-one;

6-(4-(4-((2-fluoroethylamino)methyl)piperidin-1-yl)furo[3,2-d]pyrimidin-2-ylamino)-2,2-dimethyl-2H-benzo[b][1,4]oxazin-3(4H)-one;

6-(4-(4-((2-fluoroethylamino)methyl)piperidin-1-yl)furo[3,2-d]pyrimidin-2-ylamino)-3,3-dimethylindolin-2-one;

6-(4-(4-(1-(2,2-difluoroethylamino)ethyl)piperidin-1-yl)furo[3,2-d]pyrimidin-2-ylamino)-2,2-dimethyl-2H-benzo[b][1,4]oxazin-3(4H)-one;

6-(4-(4-(1-(2,2-difluoroethylamino)ethyl)piperidin-1-yl)furo[3,2-d]pyrimidin-2-ylamino)-3,3-dimethylindolin-2-one;

6-(4-(4-(1-aminoethyl)piperidin-1-yl)furo[3,2-d]pyrimidin-2-ylamino)-2,2-dimethyl-2H-benzo[b][1,4]oxazin-3(4H)-one;

6-(4-(4-(2-hydroxyethyl)piperidin-1-yl)furo[3,2-d]pyrimidin-2-ylamino)-2,2-dimethyl-2H-benzo[b][1,4]oxazin-3(4H)-one;

6-(4-(4-(aminomethyl)-4-(2-hydroxyethyl)piperidin-1-yl)furo[3,2-d]pyrimidin-2-ylamino)-2,2-dimethyl-2H-benzo[b][1,4]oxazin-3(4H)-one;

6-(4-(4-(aminomethyl)-4-(cyclopropylmethyl)piperidin-1-yl)furo[3,2-d]pyrimidin-2-ylamino)-2,2-dimethyl-2H-benzo[b][1,4]oxazin-3(4H)-one;

6-(4-(4-(aminomethyl)-4-(hydroxymethyl)piperidin-1-yl)furo[3,2-d]pyrimidin-2-ylamino)-2,2-dimethyl-2H-benzo[b][1,4]oxazin-3(4H)-one;

6-(4-(4-(aminomethyl)-4-ethylpiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-hydroxypiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-hydroxypiperidin-1-yl)furo[3,2-d]pyrimidin-2-ylamino)-3,3-dimethylindolin-2-one;

6-(4-(4-(aminomethyl)-4-methoxypiperidin-1-yl)furo[3,2-d]pyrimidin-2-ylamino)-2,2-dimethyl-2H-benzo[b][1,4]oxazin-3(4H)-one;

6-(4-(4-(aminomethyl)-4-methylpiperidin-1-yl)furo[3,2-d]pyrimidin-2-ylamino)-3,3-dimethylindolin-2-one;

6-(4-(4-(aminomethyl)-4-methylpiperidin-1-yl)furo[3,2-d]pyrimidin-2-ylamino)-2,2-dimethyl-2H-benzo[b][1,4]oxazin-3(4H)-one;

6-(4-(4-(aminomethyl)piperidin-1-yl)furo[3,2-d]pyrimidin-2-ylamino)-3,4-dihydroquinolin-2(1H)-one;

6-(4-(4-(aminomethyl)piperidin-1-yl)furo[3,2-d]pyrimidin-2-ylamino)-2,2-dimethyl-2H-benzo[b][1,4]oxazin-3(4H)-one;

6-(4-(4,4-bis(aminomethyl)piperidin-1-yl)furo[3,2-d]pyrimidin-2-ylamino)-2,2-dimethyl-2H-benzo[b][1,4]oxazin-3(4H)-one;

6-(4-(4-aminoazepan-1-yl)furo[3,2-d]pyrimidin-2-ylamino)-2,2-dimethyl-2H-benzo[b][1,4]oxazin-3(4H)-one;

6-(4-(4-aminoazepan-1-yl)furo[3,2-d]pyrimidin-2-ylamino)-3,3-dimethylindolin-2-one;

6-(4-(4-hydroxy-4-(hydroxymethyl)piperidin-1-yl)furo[3,2-d]pyrimidin-2-ylamino)-2,2-dimethyl-2H-benzo[b][1,4]oxazin-3(4H)-one;

6-(4-(4-hydroxy-4-methylpiperidin-1-yl)furo[3,2-d]pyrimidin-2-ylamino)-2,2-dimethyl-2H-benzo[b][1,4]oxazin-3(4H)-one;

6-(4-(4-hydroxypiperidin-1-yl)furo[3,2-d]pyrimidin-2-ylamino)-2,2-dimethyl-2H-benzo[b][1,4]oxazin-3(4H)-one;
6-(4-(cyclobutylamino)furo[3,2-d]pyrimidin-2-ylamino)-2,2-dimethyl-2H-benzo[b][1,4]oxazin-3(4H)-one;
6-(4-(cyclobutylamino)furo[3,2-d]pyrimidin-2-ylamino)-2H-benzo[b][1,4]oxazin-3(4H)-one;
6-(4-(cyclobutylamino)furo[3,2-d]pyrimidin-2-ylamino)-3,3-dimethylindolin-2-one;
6-(4-(cyclobutylamino)furo[3,2-d]pyrimidin-2-ylamino)-3,4-dihydroquinolin-2(1H)-one;
6-(4-(cyclopropylamino)furo[3,2-d]pyrimidin-2-ylamino)-1H-indazole-3-carbonitrile;
6-(4-(cyclopropylamino)furo[3,2-d]pyrimidin-2-ylamino)-2,2-difluoro-2H-benzo[b][1,4]oxazin-3(4H)-one;
6-(4-(cyclopropylamino)furo[3,2-d]pyrimidin-2-ylamino)-2,2-dimethyl-2H-benzo[b][1,4]oxazin-3(4H)-one;
6-(4-(cyclopropylamino)furo[3,2-d]pyrimidin-2-ylamino)-2,2-dimethyl-2H-benzo[b][1,4]thiazin-3(4H)-one;
6-(4-(cyclopropylamino)furo[3,2-d]pyrimidin-2-ylamino)-2H-benzo[b][1,4]oxazin-3(4H)-one;
6-(4-(cyclopropylamino)furo[3,2-d]pyrimidin-2-ylamino)-2H-benzo[b][1,4]thiazin-3(4H)-one;
6-(4-(cyclopropylamino)furo[3,2-d]pyrimidin-2-ylamino)-2H-pyrido[3,2-b][1,4]oxazin-3(4H)-one;
6-(4-(cyclopropylamino)furo[3,2-d]pyrimidin-2-ylamino)-3,3-dimethylindolin-2-one;
6-(4-(cyclopropylamino)furo[3,2-d]pyrimidin-2-ylamino)-3,4-dihydroquinolin-2(1H)-one;
6-(4-(cyclopropylamino)furo[3,2-d]pyrimidin-2-ylamino)-4-methyl-2H-benzo[b][1,4]oxazin-3(4H)-one;
6-(4-(cyclopropylamino)furo[3,2-d]pyrimidin-2-ylamino)benzo[d]oxazol-2(3H)-one;
6-(4-(cyclopropylamino)furo[3,2-d]pyrimidin-2-ylamino)indolin-2-one;
6-(4-(cyclopropylamino)furo[3,2-d]pyrimidin-2-ylamino)-N-(2-hydroxyethyl)-1H-indazole-3-carboxamide;
6-(4-(cyclopropylamino)furo[3,2-d]pyrimidin-2-ylamino)-N,N-dimethyl-1H-indazole-3-carboxamide;
6-(4-(cyclopropylethynyl)furo[3,2-d]pyrimidin-2-ylamino)-3,3-dimethylindolin-2-one;
6-(4-(cyclopropylmethylamino)furo[3,2-d]pyrimidin-2-ylamino)-2,2-dimethyl-2H-benzo[b][1,4]oxazin-3(4H)-one;
6-(4-(diethylamino)furo[3,2-d]pyrimidin-2-ylamino)-2,2-dimethyl-2H-benzo[b][1,4]oxazin-3(4H)-one;
6-(4-(ethylamino)furo[3,2-d]pyrimidin-2-ylamino)-2,2-dimethyl-2H-benzo[b][1,4]oxazin-3(4H)-one;
6-(4-(isobutylamino)furo[3,2-d]pyrimidin-2-ylamino)-3,3-dimethylindolin-2-one;
6-(4-(isopropylamino)furo[3,2-d]pyrimidin-2-ylamino)-2,2-dimethyl-2H-benzo[b][1,4]oxazin-3(4H)-one;
6-(4-(piperidin-4-ylmethylamino)furo[3,2-d]pyrimidin-2-ylamino)-2H-benzo[b][1,4]oxazin-3(4H)-one;
6-(4-(piperidin-4-ylmethylamino)furo[3,2-d]pyrimidin-2-ylamino)-3,4-dihydroquinolin-2(1H)-one;
6-(4-(tert-butylamino)furo[3,2-d]pyrimidin-2-ylamino)-2,2-dimethyl-2H-benzo[b][1,4]oxazin-3(4H)-one;
6-(4-cyclopropylamino-furo[3,2-d]pyrimidin-2-ylamino)-1,1-dioxo-1,2-dihydro-1lambda*6*-benzo[d]isothiazol-3-one;
6,6'-(furo[3,2-d]pyrimidine-2,4-diylbis(azanediyl))bis(2,2-dimethyl-2H-benzo[b][1,4]oxazin-3(4H)-one);
7-(4-(2,2-difluoroethylamino)furo[3,2-d]pyrimidin-2-ylamino)-3,4-dihydroquinolin-2(1H)-one;
7-(4-(4-((2,2-difluoroethylamino)methyl)piperidin-1-yl)furo[3,2-d]pyrimidin-2-ylamino)-3,4-dihydroquinolin-2(1H)-one;
7-(4-(4-((2,2-difluoroethylamino)methyl)piperidin-1-yl)furo[3,2-d]pyrimidin-2-ylamino)quinolin-2(1H)-one;
7-(4-(4-((2,2-difluoroethylamino)methyl)piperidin-1-yl)furo[3,2-d]pyrimidin-2-ylamino)-4-methylquinolin-2(1H)-one;
7-(4-(4-((2,2-difluoroethylamino)methyl)piperidin-1-yl)furo[3,2-d]pyrimidin-2-ylamino)-3,3-dimethyl-3,4-dihydroquinolin-2(1H)-one;
7-(4-(4-((2,2-difluoroethylamino)methyl)piperidin-1-yl)furo[3,2-d]pyrimidin-2-ylamino)-3-methylquinolin-2(1H)-one;
7-(4-(4-((2,2-difluoroethylamino)methyl)piperidin-1-yl)furo[3,2-d]pyrimidin-2-ylamino)-3-methyl-3,4-dihydroquinolin-2(1H)-one;
7-(4-(4-(aminomethyl)piperidin-1-yl)furo[3,2-d]pyrimidin-2-ylamino)-3,4-dihydroquinolin-2(1H)-one;
7-(4-(4-(aminomethyl)piperidin-1-yl)furo[3,2-d]pyrimidin-2-ylamino)quinolin-2(1H)-one;
7-(4-(4-(aminomethyl)piperidin-1-yl)furo[3,2-d]pyrimidin-2-ylamino)-4-methylquinolin-2(1H)-one;
7-(4-(cyclobutylamino)furo[3,2-d]pyrimidin-2-ylamino)-1H-benzo[d][1,3]oxazin-2(4H)-one;
7-(4-(cyclobutylamino)furo[3,2-d]pyrimidin-2-ylamino)-3,3-dimethyl-3,4-dihydroquinolin-2(1H)-one;
7-(4-(cyclobutylamino)furo[3,2-d]pyrimidin-2-ylamino)-3,4-dihydroquinolin-2(1H)-one;
7-(4-(cyclobutylamino)furo[3,2-d]pyrimidin-2-ylamino)-3-methyl-3,4-dihydroquinolin-2(1H)-one;
7-(4-(cyclopropylamino)furo[3,2-d]pyrimidin-2-ylamino)-2H-chromen-2-one;
7-(4-(cyclopropylamino)furo[3,2-d]pyrimidin-2-ylamino)-3-(hydroxymethyl)quinolin-2(1H)-one;
7-(4-(cyclopropylamino)furo[3,2-d]pyrimidin-2-ylamino)-3,3-dimethyl-3,4-dihydroquinolin-2(1H)-one;
7-(4-(cyclopropylamino)furo[3,2-d]pyrimidin-2-ylamino)-3,4-dihydroquinolin-2(1H)-one;
7-(4-(cyclopropylamino)furo[3,2-d]pyrimidin-2-ylamino)-3-methyl-3,4-dihydroquinolin-2(1H)-one;
7-(4-(cyclopropylamino)furo[3,2-d]pyrimidin-2-ylamino)-3-methylquinolin-2(1H)-one;
7-(4-(cyclopropylamino)furo[3,2-d]pyrimidin-2-ylamino)-4,5-dihydro-1H-benzo[b]azepin-2(3H)-one;
7-(4-(cyclopropylamino)furo[3,2-d]pyrimidin-2-ylamino)-4-methylquinolin-2(1H)-one;
7-(4-(cyclopropylamino)furo[3,2-d]pyrimidin-2-ylamino)quinolin-2(1H)-one;
7-(4-(isobutylamino)furo[3,2-d]pyrimidin-2-ylamino)-3,3-dimethyl-3,4-dihydroquinolin-2(1H)-one;
7-(4-(isobutylamino)furo[3,2-d]pyrimidin-2-ylamino)-3,4-dihydroquinolin-2(1H)-one;
7-(4-(propylamino)furo[3,2-d]pyrimidin-2-ylamino)-3,4-dihydroquinolin-2(1H)-one;
7-(4-cyclobutoxyfuro[3,2-d]pyrimidin-2-ylamino)-3,4-dihydroquinolin-2(1H)-one;
8-(4-(cyclopropylamino)furo[3,2-d]pyrimidin-2-ylamino)-4,5-dihydro-1H-benzo[b]azepin-2(3H)-one;
8-(4-(isobutylamino)furo[3,2-d]pyrimidin-2-ylamino)-4,5-dihydro-1H-benzo[b]azepin-2(3H)-one;

8-(4-cyclobutoxyfuro[3,2-d]pyrimidin-2-ylamino)-4,5-dihydro-1H-benzo[b]azepin-2(3H)-one;

ethyl 2-(1-(2-(1H-indazol-6-ylamino)furo[3,2-d]pyrimidin-4-yl)piperidin-4-yl)acetate;

6-(4-(4-(hydroxymethyl)-4-methylpiperidin-1-yl)furo[3,2-d]pyrimidin-2-ylamino)-2,2-dimethyl-2H-benzo[b][1,4]oxazin-3(4H)-one;

ethyl 2-(1-(2-(2,2-dimethyl-3-oxo-3,4-dihydro-2H-benzo[b][1,4]oxazin-6-ylamino)furo[3,2-d]pyrimidin-4-yl)piperidin-4-yl)acetate;

ethyl 2-(1-(2-(2-oxo-1,2,3,4-tetrahydroquinolin-6-ylamino)furo[3,2-d]pyrimidin-4-yl)piperidin-4-yl)acetate;

ethyl 2-(1-(2-(3-chloro-4-morpholinophenylamino)furo[3,2-d]pyrimidin-4-yl)piperidin-4-yl)acetate;

ethyl 2-(1-(2-(3-oxo-3,4-dihydro-2H-benzo[b][1,4]oxazin-6-ylamino)furo[3,2-d]pyrimidin-4-yl)piperidin-4-yl)acetate;

8-(4-(propylamino)furo[3,2-d]pyrimidin-2-ylamino)-4,5-dihydro-1H-benzo[b]azepin-2(3H)-one;

ethyl 2-(1-(2-(4-(4-acetylpiperazin-1-yl)phenylamino)furo[3,2-d]pyrimidin-4-yl)piperidin-4-yl)acetate;

ethyl 2-(1-(2-(4-(N-methylacetamido)phenylamino)furo[3,2-d]pyrimidin-4-yl)piperidin-4-yl)acetate;

ethyl 2-(1-(2-(4-(piperazin-1-yl)phenylamino)furo[3,2-d]pyrimidin-4-yl)piperidin-4-yl)acetate;

ethyl 2-(1-(2-(4-butyramidophenylamino)furo[3,2-d]pyrimidin-4-yl)piperidin-4-yl)acetate;

N-((1-(2-(4-sulfamoylphenylamino)furo[3,2-d]pyrimidin-4-yl)piperidin-4-yl)methyl)acetamide;

N-(1H-indazol-6-yl)-4-(3-((methylamino)methyl)-5,6-dihydroimidazo[1,5-a]pyrazin-7(8H)-yl)furo[3,2-d]pyrimidin-2-amine;

N-(1H-indazol-6-yl)-4-(3-((methylamino)methyl)piperidin-1-yl)furo[3,2-d]pyrimidin-2-amine;

N-(1H-indazol-6-yl)-4-(4-((3-methyloxetan-3-yl)methylamino)methyl)piperidin-1-yl)furo[3,2-d]pyrimidin-2-amine;

N-(1H-indazol-6-yl)-4-(4-(2-(methylsulfonyl)ethylamino)methyl)piperidin-1-yl)furo[3,2-d]pyrimidin-2-amine;

N-(1H-indazol-6-yl)-4-(4-((2,2,2-trifluoroethylamino)methyl)piperidin-1-yl)furo[3,2-d]pyrimidin-2-amine;

N-(1H-indazol-6-yl)-4-(4-((methylamino)methyl)piperidin-1-yl)furo[3,2-d]pyrimidin-2-amine;

N-(1H-indazol-6-yl)-4-(4-((oxetan-3-ylamino)methyl)piperidin-1-yl)furo[3,2-d]pyrimidin-2-amine;

N-(1H-indazol-6-yl)-4-(piperazin-1-yl)furo[3,2-d]pyrimidin-2-amine;

N-(1-methyl-1H-indazol-5-yl)-4-(2,8-diazaspiro[4.5]decan-8-yl)furo[3,2-d]pyrimidin-2-amine;

N-(1-methyl-1H-indazol-5-yl)-4-(2,9-diazaspiro[5.5]undecan-9-yl)furo[3,2-d]pyrimidin-2-amine;

N-(1-methyl-1H-indazol-5-yl)-4-(4-((methylamino)methyl)piperidin-1-yl)furo[3,2-d]pyrimidin-2-amine;

N-(3-(4-(cyclopropylamino)furo[3,2-d]pyrimidin-2-ylamino)phenyl)acetamide;

N-(3-chloro-4-morpholinophenyl)-4-(2,8-diazaspiro[4.5]decan-8-yl)furo[3,2-d]pyrimidin-2-amine;

N-(3-chloro-4-morpholinophenyl)-4-(2,9-diazaspiro[5.5]undecan-9-yl)furo[3,2-d]pyrimidin-2-amine;

N-(3-chloro-4-morpholinophenyl)-4-(44(2,2-difluoroethylamino)methyl)piperidin-1-yl)furo[3,2-d]pyrimidin-2-amine;

N-(3-methoxy-4-morpholinophenyl)-4-(2,8-diazaspiro[4.5]decan-8-yl)furo[3,2-d]pyrimidin-2-amine;

N-(3-methoxy-4-morpholinophenyl)-4-(2,9-diazaspiro[5.5]undecan-9-yl)furo[3,2-d]pyrimidin-2-amine;

N-(3-methoxypropyl)-4-(4-(4-((methylamino)methyl)piperidin-1-yl)furo[3,2-d]pyrimidin-2-ylamino)benzenesulfonamide;

N-(3-methyl-1H-indazol-6-yl)-4-(1-oxa-4,9-diazaspiro[5.5]undecan-9-yl)furo[3,2-d]pyrimidin-2-amine;

N-(3-methyl-1H-indazol-6-yl)-4-(2,8-diazaspiro[4.5]decan-8-yl)furo[3,2-d]pyrimidin-2-amine;

N-(3-methyl-1H-indazol-6-yl)-4-(2,9-diazaspiro[5.5]undecan-9-yl)furo[3,2-d]pyrimidin-2-amine;

6-(4-(3-hydroxypyrrolidin-1-yl)furo[3,2-d]pyrimidin-2-ylamino)-2,2-dimethyl-2H-benzo[b][1,4]oxazin-3(4H)-one;

N-(3-methyl-1H-indazol-6-yl)-4-(4-((2-(methylsulfonyl)ethylamino)methyl)piperidin-1-yl)furo[3,2-d]pyrimidin-2-amine;

N-(3-methyl-1H-indazol-6-yl)-4-(4-((3,3,3-trifluoropropylamino)methyl)piperidin-1-yl)furo[3,2-d]pyrimidin-2-amine;

N-(3-methyl-1H-indazol-6-yl)-4-(4-((methylamino)methyl)piperidin-1-yl)furo[3,2-d]pyrimidin-2-amine;

N-(3-methyl-1H-indazol-6-yl)-4-(4-((tetrahydro-2H-pyran-4-ylamino)methyl)piperidin-1-yl)furo[3,2-d]pyrimidin-2-amine;

N-(3-methyl-4-morpholinophenyl)-4-(2,8-diazaspiro[4.5]decan-8-yl)furo[3,2-d]pyrimidin-2-amine;

N-(3-methyl-4-morpholinophenyl)-4-(2,9-diazaspiro[5.5]undecan-9-yl)furo[3,2-d]pyrimidin-2-amine;

N-(4-(4-(1H-indazol-6-ylamino)furo[3,2-d]pyrimidin-2-ylamino)phenyl)butyramide;

N-(4-(4-(3,4-dihydroisoquinolin-2(1H)-yl)furo[3,2-d]pyrimidin-2-ylamino)phenyl)-N-methylacetamide;

N-(4-(4-(4-(aminomethyl)piperidin-1-yl)furo[3,2-d]pyrimidin-2-ylamino)phenyl)butyramide;

N-(4-(4-(4-(aminomethyl)piperidin-1-yl)furo[3,2-d]pyrimidin-2-ylamino)phenyl)-N-methylacetamide;

N-(4-(4-(cyclobutylamino)furo[3,2-d]pyrimidin-2-ylamino)phenyl)butyramide;

N-(4-(4-(cyclobutylamino)furo[3,2-d]pyrimidin-2-ylamino)phenyl)-N-methylacetamide;

N-(4-(4-(cyclopropylamino)furo[3,2-d]pyrimidin-2-ylamino)-2-methoxyphenyl)-2-morpholinoacetamide;

N-(4-(4-(cyclopropylamino)furo[3,2-d]pyrimidin-2-ylamino)phenyl)-N-methylacetamide;

N-(4-(4-(piperidin-4-ylmethylamino)furo[3,2-d]pyrimidin-2-ylamino)phenyl)butyramide;

N*4*-cyclopropyl-N*2*-(1,1-dioxo-2,3-dihydro-1H-1lambda*6*-benzo[c]isothiazol-6-yl)-uro[3,2-d]pyrimidine-2,4-diamine;

N*4*-cyclopropyl-N*2*-(2,2-dioxo-2,3-dihydro-1H-2lambda*6*-benzo[c]thiophen-5-yl)-furo[3,2-d]pyrimidine-2,4-diamine;

N2-(1H-benzo[d]imidazol-6-yl)-N4-cyclopropylfuro[3,2-d]pyrimidine-2,4-diamine;

N2-(1H-indazol-6-yl)-N4-(2,2,2-trifluoroethyl)furo[3,2-d]pyrimidine-2,4-diamine;

N2-(1H-indazol-6-yl)-N4-(piperidin-4-ylmethyl)furo[3,2-d]pyrimidine-2,4-diamine;

N2-(3-chloro-4-(4-methylpiperazin-1-yl)phenyl)-N4-cyclopropylfuro[3,2-d]pyrimidine-2,4-diamine;

N2-(3-chloro-4-isopropoxyphenyl)-N4-cyclopropylfuro[3,2-d]pyrimidine-2,4-diamine;

N2-(3-chloro-4-morpholinophenyl)-N4-(2,2,2-trifluoroethyl)furo[3,2-d]pyrimidine-2,4-diamine;

N2-(3-chloro-4-morpholinophenyl)-N4-(piperidin-4-ylmethyl)furo[3,2-d]pyrimidine-2,4-diamine;

N2-(3-chloro-4-morpholinophenyl)-N4-cyclobutylfuro[3,2-d]pyrimidine-2,4-diamine;
N2-(3-chloro-4-morpholinophenyl)-N4-cyclopropylfuro[3,2-d]pyrimidine-2,4-diamine;
N2-(3-methyl-1H-indazol-6-yl)-N4-(4,5,6,7-tetrahydro-1H-indazol-6-yl)furo[3,2-d]pyrimidine-2,4-diamine;
N2-(3-methyl-1H-indazol-6-yl)-N4-(oxetan-3-yl)furo[3,2-d]pyrimidine-2,4-diamine;
N2-(3-methyl-1H-indazol-6-yl)-N4-(pyridin-3-ylmethyl)furo[3,2-d]pyrimidine-2,4-diamine;
N2-(3-methyl-1H-indazol-6-yl)-N4-propylfuro[3,2-d]pyrimidine-2,4-diamine;
N2-(4-(1H-imidazol-1-yl)phenyl)-N4-cyclopropylfuro[3,2-d]pyrimidine-2,4-diamine;
N2-(4-(2H-1,2,3-triazol-2-yl)phenyl)-N4-cyclopropylfuro[3,2-d]pyrimidine-2,4-diamine;
N2-(benzo[d]isoxazol-6-yl)-N4-cyclopropylfuro[3,2-d]pyrimidine-2,4-diamine;
1-(2-(2,2-dimethyl-3-oxo-3,4-dihydro-2H-benzo[b][1,4]oxazin-6-ylamino)furo[3,2-d]pyrimidin-4-yl)pyrrolidine-3-carboxamide;
N2-(benzo[d]oxazol-6-yl)-N4-cyclopropylfuro[3,2-d]pyrimidine-2,4-diamine;
N4-((1R,3S)-3-aminocyclopentyl)-N2-(3-methyl-1H-indazol-6-yl)furo[3,2-d]pyrimidine-2,4-diamine;
N4-((1R,4R)-4-aminocyclohexyl)-N2-(3-methyl-1H-indazol-6-yl)furo[3,2-d]pyrimidine-2,4-diamine;
N4-((1S,3R)-3-aminocyclopentyl)-N2-(3-methyl-1H-indazol-6-yl)furo[3,2-d]pyrimidine-2,4-diamine;
N4-(2,2-difluoroethyl)-N2-(3-methyl-1H-indazol-6-yl)furo[3,2-d]pyrimidine-2,4-diamine;
6-(4-(cyclopropylamino)furo[3,2-d]pyrimidin-2-ylamino)-2,2-dimethyl-2H-pyrido[3,2-b][1,4]oxazin-3(4H)-one;
N4-(3,3-difluorocyclobutyl)-N2-(3-methyl-1H-indazol-6-yl)furo[3,2-d]pyrimidine-2,4-diamine;
N4-(3-amino-2,2-dimethylpropyl)-N2-(1H-indazol-6-yl)furo[3,2-d]pyrimidine-2,4-diamine;
N4-(3-aminopropyl)-N2-(1H-indazol-6-yl)furo[3,2-d]pyrimidine-2,4-diamine;
N4-(4-aminobutyl)-N2-(1H-indazol-6-yl)furo[3,2-d]pyrimidine-2,4-diamine;
N4-allyl-N2-(4-(methylsulfonyl)phenyl)furo[3,2-d]pyrimidine-2,4-diamine;
N4-allyl-N2-(quinolin-4-yl)furo[3,2-d]pyrimidine-2,4-diamine;
N4-allyl-N4-methyl-N2-(3-methyl-1H-indazol-6-yl)furo[3,2-d]pyrimidine-2,4-diamine;
N4-cyclobutyl-N2-(1H-indazol-6-yl)furo[3,2-d]pyrimidine-2,4-diamine;
N4-cyclobutyl-N2-(3-methyl-1H-indazol-6-yl)furo[3,2-d]pyrimidine-2,4-diamine;
N4-cyclobutyl-N2-(4-(piperazin-1-yl)phenyl)furo[3,2-d]pyrimidine-2,4-diamine;
N4-cyclopropyl-N2-(1,2,3,4-tetrahydroisoquinolin-6-yl)furo[3,2-d]pyrimidine-2,4-diamine;
N4-cyclopropyl-N2-(1H-indazol-5-yl)furo[3,2-d]pyrimidine-2,4-diamine;
N4-cyclopropyl-N2-(1H-indazol-6-yl)furo[3,2-d]pyrimidine-2,4-diamine 2,2,2-trifluoroacetate;
N4-cyclopropyl-N2-(1H-indol-6-yl)furo[3,2-d]pyrimidine-2,4-diamine;
N4-cyclopropyl-N2-(1-isopropyl-1H-indazol-5-yl)furo[3,2-d]pyrimidine-2,4-diamine;
N4-cyclopropyl-N2-(1-methyl-1H-indazol-3-yl)furo[3,2-d]pyrimidine-2,4-diamine;
N4-cyclopropyl-N2-(1-methyl-1H-indazol-5-yl)furo[3,2-d]pyrimidine-2,4-diamine;
N4-cyclopropyl-N2-(1-methyl-1H-indazol-6-yl)furo[3,2-d]pyrimidine-2,4-diamine;
N4-cyclopropyl-N2-(1-methyl-1H-pyrazol-4-yl)furo[3,2-d]pyrimidine-2,4-diamine;
N4-cyclopropyl-N2-(2,2-dimethylchroman-6-yl)furo[3,2-d]pyrimidine-2,4-diamine;
N4-cyclopropyl-N2-(2,3-dihydrobenzo[b][1,4]dioxin-6-yl)furo[3,2-d]pyrimidine-2,4-diamine;
N4-cyclopropyl-N2-(2-methyl-2H-indazol-6-yl)furo[3,2-d]pyrimidine-2,4-diamine;
N4-cyclopropyl-N2-(2-methylbenzo[d]thiazol-6-yl)furo[3,2-d]pyrimidine-2,4-diamine;
N4-cyclopropyl-N2-(2-methylquinolin-6-yl)furo[3,2-d]pyrimidine-2,4-diamine;
N4-cyclopropyl-N2-(3-(pyridin-4-yl)-1H-indazol-6-yl)furo[3,2-d]pyrimidine-2,4-diamine;
N4-cyclopropyl-N2-(3-(pyridin-4-yl)phenyl)furo[3,2-d]pyrimidine-2,4-diamine;
N4-cyclopropyl-N2-(3-(tetrahydro-2H-pyran-4-ylamino)-1H-indazol-6-yl)furo[3,2-d]pyrimidine-2,4-diamine;
N4-cyclopropyl-N2-(3-fluoro-4-(4-methylpiperazin-1-yl)phenyl)furo[3,2-d]pyrimidine-2,4-diamine;
N4-cyclopropyl-N2-(3-fluoro-4-isopropoxyphenyl)furo[3,2-d]pyrimidine-2,4-diamine;
N4-cyclopropyl-N2-(3-methyl-1H-indazol-5-yl)furo[3,2-d]pyrimidine-2,4-diamine;
N4-cyclopropyl-N2-(3-methyl-1H-indazol-6-yl)furo[3,2-d]pyrimidine-2,4-diamine;
N4-cyclopropyl-N2-(3-morpholinophenyl)furo[3,2-d]pyrimidine-2,4-diamine;
N4-cyclopropyl-N2-(4-(4-(methylsulfonyl)piperazin-1-yl)phenyl)furo[3,2-d]pyrimidine-2,4-diamine;
N4-cyclopropyl-N2-(4-(morpholinomethyl)phenyl)furo[3,2-d]pyrimidine-2,4-diamine;
N4-cyclopropyl-N2-(4-(piperazin-1-yl)phenyl)furo[3,2-d]pyrimidine-2,4-diamine;
N4-cyclopropyl-N2-(4-(pyridin-4-yl)phenyl)furo[3,2-d]pyrimidine-2,4-diamine;
N4-cyclopropyl-N2-(4-(thiomorpholine 1,1 dioxide)phenyl)furo[3,2-d]pyrimidine-2,4-diamine;
N4-cyclopropyl-N2-(4-fluoro-3-methyl-1H-indazol-6-yl)furo[3,2-d]pyrimidine-2,4-diamine;
N4-cyclopropyl-N2-(4-isopropoxy-3-methylphenyl)furo[3,2-d]pyrimidine-2,4-diamine;
N4-cyclopropyl-N2-(4-isopropoxyphenyl)furo[3,2-d]pyrimidine-2,4-diamine;
N4-cyclopropyl-N2-(4-methoxyphenyl)furo[3,2-d]pyrimidine-2,4-diamine;
N4-cyclopropyl-N2-(4-methyl-1H-indazol-6-yl)furo[3,2-d]pyrimidine-2,4-diamine;
N4-cyclopropyl-N2-(4-morpholinophenyl)furo[3,2-d]pyrimidine-2,4-diamine;
N4-cyclopropyl-N2-(5,6,7,8-tetrahydro-1,6-naphthyridin-3-yl)furo[3,2-d]pyrimidine-2,4-diamine;
N4-cyclopropyl-N2-(6-morpholinopyridin-3-yl)furo[3,2-d]pyrimidine-2,4-diamine;
N4-cyclopropyl-N2-(imidazo[1,2-a]pyridin-3-yl)furo[3,2-d]pyrimidine-2,4-diamine;
N4-cyclopropyl-N2-(isoquinolin-1-yl)furo[3,2-d]pyrimidine-2,4-diamine;
N4-cyclopropyl-N2-(isoquinolin-4-yl)furo[3,2-d]pyrimidine-2,4-diamine;
N4-cyclopropyl-N2-(quinolin-4-yl)furo[3,2-d]pyrimidine-2,4-diamine;

N4-cyclopropyl-N4-methyl-N2-(3-methyl-1H-indazol-6-yl)furo[3,2-d]pyrimidine-2,4-diamine;

N-cyclopropyl-6-(4-(cyclopropylamino)furo[3,2-d]pyrimidin-2-ylamino)-1H-indazole-3-carboxamide;

N-methyl-N-(4-(4-(piperidin-4-ylmethylamino)furo[3,2-d]pyrimidin-2-ylamino)phenyl)acetamide; or N-propyl-4-(4-(2,2,2-trifluoroethylamino)furo[3,2-d]pyrimidin-2-ylamino)benzamide;

or a pharmaceutically acceptable salt thereof.

29. A pharmaceutical composition comprising any one of the compounds of claim 28, and a pharmaceutically acceptable carrier or excipient.

* * * * *